US009150880B2

(12) United States Patent
Cooper et al.

(10) Patent No.: US 9,150,880 B2

(45) **Date of Patent: *Oct. 6, 2015**

(54) VECTORS FOR PRODUCTION OF ANTIBODIES

(75) Inventors: Richard K. Cooper, Baton Rouge, LA (US); William C. Fioretti, Addison, TX (US)

(73) Assignee: PROTEOVEC HOLDING, L.L.C., Baton Rouge, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/567,334

(22) Filed: Sep. 25, 2009

(65) Prior Publication Data

US 2010/0099148 A1 Apr. 22, 2010

Related U.S. Application Data

(60) Provisional application No. 61/231,555, filed on Aug. 5, 2009, provisional application No. 61/100,075, filed on Sep. 25, 2008.

(51) Int. Cl.

| | |
|---|---|
| ***C12N 15/63*** | (2006.01) |
| ***C12N 15/85*** | (2006.01) |
| ***C07K 16/00*** | (2006.01) |
| ***C07K 16/30*** | (2006.01) |

(52) U.S. Cl.

CPC ............ *C12N 15/8509* (2013.01); *C07K 16/00* (2013.01); *C07K 16/3076* (2013.01); *A01K 2267/01* (2013.01); *C07K 2317/21* (2013.01); *C07K 2317/23* (2013.01); *C12N 2800/107* (2013.01); *C12N 2800/90* (2013.01)

(58) Field of Classification Search

None

See application file for complete search history.

(56) References Cited

U.S. PATENT DOCUMENTS

| | | | |
|---|---|---|---|
| 4,670,388 | A | 6/1987 | Rubin et al. |
| 4,870,009 | A | 9/1989 | Evans et al. |
| 4,914,025 | A | 4/1990 | Manoil et al. |
| 5,102,797 | A | 4/1992 | Tucker et al. |
| 5,162,215 | A | 11/1992 | Bosselman et al. |
| 5,212,080 | A | 5/1993 | Nag et al. |
| 5,512,483 | A | 4/1996 | Mader et al. |
| 5,556,782 | A | 9/1996 | Cooper et al. |
| 5,565,362 | A | 10/1996 | Rosen |
| 5,645,991 | A | 7/1997 | Berg et al. |
| 5,648,244 | A | 7/1997 | Kuliopulos et al. |
| 5,693,508 | A | 12/1997 | Chang |
| 5,703,055 | A | 12/1997 | Felgner et al. |
| 5,719,055 | A | 2/1998 | Cooper |
| 5,733,779 | A | 3/1998 | Reff |
| 5,753,502 | A | 5/1998 | Kilgannon et al. |
| 5,861,478 | A | 1/1999 | Jaynes |
| 5,869,296 | A | 2/1999 | Nag et al. |
| 5,925,545 | A | 7/1999 | Reznikoff et al. |
| 5,948,622 | A | 9/1999 | Reznikoff et al. |
| 5,958,775 | A | 9/1999 | Wickstrom et al. |
| 5,962,410 | A | 10/1999 | Jaynes et al. |
| 5,965,443 | A | 10/1999 | Reznikoff et al. |
| 5,998,698 | A | 12/1999 | Cooper et al. |
| 6,080,912 | A | 6/2000 | Bremel et al. |
| 6,107,477 | A | 8/2000 | Whitney et al. |
| 6,140,129 | A | 10/2000 | Cox et al. |
| 6,156,568 | A | 12/2000 | Cooper et al. |
| 6,159,730 | A | 12/2000 | Reff |
| 6,159,736 | A | 12/2000 | Reznikoff et al. |
| 6,171,861 | B1 | 1/2001 | Hartley et al. |
| 6,218,185 | B1 | 4/2001 | Shirk et al. |
| 6,255,282 | B1 | 7/2001 | Jaynes |
| 6,258,571 | B1 | 7/2001 | Chumakov et al. |
| 6,261,554 | B1 | 7/2001 | Valerio et al. |
| 6,291,214 | B1 | 9/2001 | Richards et al. |
| 6,291,243 | B1 | 9/2001 | Fogarty et al. |
| 6,291,740 | B1 | 9/2001 | Bremel et al. |
| 6,303,568 | B1 | 10/2001 | Jaynes et al. |
| 6,316,692 | B1 | 11/2001 | Readhead et al. |
| 6,358,710 | B1 | 3/2002 | Graves et al. |
| 6,376,218 | B1 | 4/2002 | Hsu et al. |
| 6,376,743 | B1 | 4/2002 | Yanagimachi |
| 6,475,798 | B2 | 11/2002 | Fogarty et al. |

(Continued)

FOREIGN PATENT DOCUMENTS

| | | |
|---|---|---|
| AU | 2003261096 | 1/2004 |
| EP | 1375654 | 1/2004 |

(Continued)

OTHER PUBLICATIONS

Sarkar et al (BMC Biotechnology, 2006. vol. 6. No. 27, pp. 1-9).*

Kim et al (BioProcess International, 2006. vol. 4 No. 3, Supplement, pp. 24, 26-31).*

Abdel-Salam, H. A. et al., "Expression of mouse anticreatine kinase (MAK33) monoclonal antibody in the yeast *Hansenula polymorpha*", Applied Microbiology and Biotechnology 00/00/2001, Springer Verlag, Berlin, DE, vol. 56, 157-164.

Afanassieff, et al., "Intratesticular Inoculation of Avian Leukosis Virus (ALV) in Chickens—Production of", Avian Diseases Jan. 1, 1996, 841-852.

Alexeyev, M. et al., "Mini-TN10 Transposon Derivatives for Insertion Mutagenesis and Gene Delivery into the Chromosome of Gram-negative Bacteria", Gene 1995, vol. 160, pp. 59-62.

Andra, et al., "Generation and Characterization of Transgenic Mice Expressing Cobra Venom", Molecular Immunology 2002, vol. 39, 357-365.

(Continued)

*Primary Examiner* — Celine Qian

(74) *Attorney, Agent, or Firm* — Kilpatrick Townsend & Stockton LLP

(57) ABSTRACT

Novel compositions for the production of the light and heavy chains of an antibody are provided. These novel compositions are also used to produce germline transgenic birds that can successfully pass the transgene encoding the antibody to their offspring. The compositions comprise components of vectors, such as a vector backbone, a promoter, and a gene of interest that encodes the light or heavy chain of an antibody, and the vectors comprising these components. In certain embodiments, these vectors are transposon-based vectors. Also provided are methods of making these compositions and methods of using these compositions for the production of the light and heavy chains of an antibody. In one embodiment, the antibody is a human monoclonal antibody.

9 Claims, 7 Drawing Sheets

(56) References Cited

U.S. PATENT DOCUMENTS

| | | | |
|---|---|---|---|
| 6,489,458 | B2 | 12/2002 | Hackett et al. |
| 6,492,510 | B2 | 12/2002 | Hasebe et al. |
| 6,503,729 | B1 | 1/2003 | Bult et al. |
| 6,514,728 | B1 | 2/2003 | Kai et al. |
| 6,515,199 | B1 | 2/2003 | Petitte et al. |
| 6,528,699 | B1 | 3/2003 | Meade et al. |
| 6,563,017 | B2 | 5/2003 | Muramatsu et al. |
| 6,602,686 | B1 | 8/2003 | Harrington et al. |
| 6,670,185 | B1 | 12/2003 | Harrington et al. |
| 6,716,823 | B1 | 4/2004 | Tang et al. |
| 6,730,822 | B1 | 5/2004 | Ivarie et al. |
| 6,759,573 | B2 | 7/2004 | Olhoft et al. |
| 6,825,396 | B2 | 11/2004 | MacArthur |
| 6,852,510 | B2 | 2/2005 | Bremel et al. |
| 6,939,959 | B2 | 9/2005 | Hu |
| 7,005,296 | B1 | 2/2006 | Handler |
| 7,019,193 | B2 | 3/2006 | Ditullio et al. |
| 7,034,115 | B1 | 4/2006 | Kawakami |
| 7,083,980 | B2 | 8/2006 | Reznikoff et al. |
| 7,105,343 | B1 | 9/2006 | Frasier, Jr. et al. |
| 7,129,390 | B2 | 10/2006 | Ivarie et al. |
| 7,160,682 | B2 | 1/2007 | Hackett et al. |
| 7,199,279 | B2 | 4/2007 | Rapp |
| 7,294,507 | B2 | 11/2007 | Harvey et al. |
| 7,335,761 | B2 | 2/2008 | Harvey et al. |
| 7,375,258 | B2 | 5/2008 | Harvey et al. |
| 7,381,712 | B2 | 6/2008 | Christman et al. |
| 7,527,966 | B2 | 5/2009 | Cooper et al. |
| 7,597,884 | B2 | 10/2009 | Blatt et al. |
| 7,608,451 | B2 | 10/2009 | Cooper |
| 8,071,364 | B2 | 12/2011 | Cooper et al. |
| 8,236,294 | B2 | 8/2012 | Cooper et al. |
| 8,283,518 | B2 | 10/2012 | Cooper et al. |
| 2001/0044937 | A1 | 11/2001 | Schatten et al. |
| 2002/0007051 | A1 | 1/2002 | Cheo et al. |
| 2002/0013955 | A1 | 1/2002 | Ogden et al. |
| 2002/0016975 | A1 | 2/2002 | Hackett et al. |
| 2002/0028488 | A1 | 3/2002 | Singh et al. |
| 2002/0028513 | A1 | 3/2002 | Fogarty et al. |
| 2002/0042137 | A1 | 4/2002 | Richards et al. |
| 2002/0052047 | A1 | 5/2002 | Hasebe et al. |
| 2002/0053092 | A1 | 5/2002 | Readhead et al. |
| 2002/0055172 | A1 | 5/2002 | Harrington |
| 2002/0056148 | A1 | 5/2002 | Readhead et al. |
| 2002/0072097 | A1 | 6/2002 | delCardayre et al. |
| 2002/0076797 | A1 | 6/2002 | Lin |
| 2002/0083479 | A1 | 6/2002 | Winston et al. |
| 2002/0099015 | A1 | 7/2002 | Barber |
| 2002/0104109 | A1 | 8/2002 | Bremel et al. |
| 2002/0108132 | A1 | 8/2002 | Rapp |
| 2002/0119573 | A1 | 8/2002 | Shaw et al. |
| 2002/0129398 | A1 | 9/2002 | Winston et al. |
| 2002/0132349 | A1 | 9/2002 | Goryshin et al. |
| 2002/0133835 | A1 | 9/2002 | Winston et al. |
| 2002/0138865 | A1 | 9/2002 | Readhead et al. |
| 2002/0148000 | A1 | 10/2002 | Shen |
| 2002/0150577 | A1 | 10/2002 | Lee et al. |
| 2002/0151034 | A1 | 10/2002 | Zhang et al. |
| 2002/0157125 | A1 | 10/2002 | Lee et al. |
| 2002/0160507 | A1 | 10/2002 | Novy et al. |
| 2002/0188105 | A1 | 12/2002 | Craig et al. |
| 2002/0199214 | A1 | 12/2002 | Rapp |
| 2003/0009026 | A1 | 1/2003 | Hasebe et al. |
| 2003/0017534 | A1 | 1/2003 | Buelow et al. |
| 2003/0055017 | A1 | 3/2003 | Schwarz et al. |
| 2003/0056241 | A1 | 3/2003 | Matsuda et al. |
| 2003/0061629 | A1 | 3/2003 | Sutrave |
| 2003/0074680 | A1 | 4/2003 | Lee et al. |
| 2003/0074681 | A1 | 4/2003 | Macarthur |
| 2003/0101472 | A1 | 5/2003 | Baltimore et al. |
| 2003/0115622 | A1 | 6/2003 | Ponce de Leon et al. |
| 2003/0121062 | A1 | 6/2003 | Radcliffe et al. |
| 2003/0126628 | A1 | 7/2003 | Harvey et al. |
| 2003/0126629 | A1 | 7/2003 | Rapp et al. |
| 2003/0138403 | A1 | 7/2003 | Drustrup |
| 2003/0140363 | A1 | 7/2003 | Rapp |
| 2003/0143740 | A1 | 7/2003 | Wooddell et al. |
| 2003/0150006 | A1 | 8/2003 | Petitte et al. |
| 2003/0150007 | A1 | 8/2003 | Savakis et al. |
| 2003/0154502 | A1 | 8/2003 | Wimmer et al. |
| 2003/0167492 | A1 | 9/2003 | Lee et al. |
| 2003/0170888 | A1 | 9/2003 | Van de Lavoir et al. |
| 2003/0172387 | A1 | 9/2003 | Zhu et al. |
| 2003/0177516 | A1 | 9/2003 | Horseman et al. |
| 2003/0182672 | A1 | 9/2003 | Graham et al. |
| 2003/0182675 | A1 | 9/2003 | Etches et al. |
| 2003/0217375 | A1 | 11/2003 | Zcharia et al. |
| 2003/0221206 | A1 | 11/2003 | Schatten et al. |
| 2003/0224519 | A1 | 12/2003 | Harrington et al. |
| 2004/0006776 | A1 | 1/2004 | Meade et al. |
| 2004/0018624 | A1 | 1/2004 | Harrington et al. |
| 2004/0019922 | A1 | 1/2004 | Ivarie et al. |
| 2004/0040052 | A1 | 2/2004 | Radcliffe et al. |
| 2004/0142475 | A1 | 7/2004 | Barman et al. |
| 2004/0158882 | A1 | 8/2004 | Ivarie et al. |
| 2004/0172667 | A1 | 9/2004 | Cooper et al. |
| 2004/0197910 | A1 | 10/2004 | Cooper et al. |
| 2004/0203158 | A1 | 10/2004 | Hackett et al. |
| 2004/0210954 | A1 | 10/2004 | Harvey et al. |
| 2004/0226057 | A1 | 11/2004 | Christmann et al. |
| 2004/0235011 | A1 | 11/2004 | Cooper et al. |
| 2004/0255345 | A1 | 12/2004 | Rapp et al. |
| 2005/0003414 | A1 | 1/2005 | Harvey et al. |
| 2005/0004030 | A1 | 1/2005 | Fischetti et al. |
| 2005/0034186 | A1 | 2/2005 | Harvey et al. |
| 2005/0050581 | A1 | 3/2005 | Harvey et al. |
| 2005/0066383 | A1 | 3/2005 | Harvey |
| 2005/0176047 | A1 | 8/2005 | Harvey et al. |
| 2005/0198700 | A1 | 9/2005 | Christmann et al. |
| 2005/0208038 | A1 | 9/2005 | Fischetti et al. |
| 2005/0273872 | A1 | 12/2005 | Sang et al. |
| 2005/0273873 | A1 | 12/2005 | Christmann et al. |
| 2006/0046248 | A1 | 3/2006 | Rapp et al. |
| 2006/0121509 | A1 | 6/2006 | Hermiston et al. |
| 2006/0123488 | A1 | 6/2006 | Ivarie et al. |
| 2006/0123504 | A1 | 6/2006 | Leavitt et al. |
| 2006/0171921 | A1 | 8/2006 | Ivarie et al. |
| 2006/0185024 | A1 | 8/2006 | Ivarie et al. |
| 2006/0185029 | A1 | 8/2006 | Ivarie et al. |
| 2006/0188478 | A1 | 8/2006 | Ivarie et al. |
| 2006/0210977 | A1 | 9/2006 | Kaminski |
| 2006/0218652 | A1 | 9/2006 | Horn et al. |
| 2006/0236413 | A1 | 10/2006 | Ivics et al. |
| 2006/0258603 | A1 | 11/2006 | Ivics et al. |
| 2007/0009991 | A1 | 1/2007 | Horseman et al. |
| 2007/0022485 | A1 | 1/2007 | Tadeda et al. |
| 2007/0113299 | A1 | 5/2007 | Harvey et al. |
| 2007/0243165 | A1 | 10/2007 | Ivarie et al. |
| 2008/0235813 | A1 | 9/2008 | Cooper et al. |
| 2008/0235815 | A1 | 9/2008 | Cooper et al. |
| 2010/0081789 | A1 | 4/2010 | Cooper et al. |
| 2010/0093036 | A1 | 4/2010 | Cooper et al. |
| 2010/0099148 | A1 | 4/2010 | Cooper et al. |
| 2010/0199366 | A1 | 8/2010 | Cooper et al. |
| 2010/0261227 | A1 | 10/2010 | Cooper et al. |
| 2011/0162096 | A1 | 6/2011 | Cooper et al. |

FOREIGN PATENT DOCUMENTS

| | | | |
|---|---|---|---|
| EP | 1364205 | B1 | 5/2007 |
| EP | 1700914 | A1 | 9/2008 |
| EP | 1539785 | | 5/2009 |
| EP | 1592789 | | 5/2009 |
| EP | 2417263 | | 2/2012 |
| JP | 2000512149 | | 9/2000 |
| JP | 2001513336 | | 9/2001 |
| JP | 2002238559 | | 8/2002 |
| WO | WO-9220316 | | 11/1992 |
| WO | WO-9324626 | | 12/1993 |
| WO | WO-9420608 | | 9/1994 |
| WO | WO-9531566 | | 11/1995 |
| WO | WO-9747739 | | 12/1997 |
| WO | WO-9909817 | | 3/1999 |
| WO | WO-9919472 | | 4/1999 |

(56) References Cited

FOREIGN PATENT DOCUMENTS

| | | |
|---|---|---|
| WO | WO-9940213 | 8/1999 |
| WO | WO-9942569 | 8/1999 |
| WO | WO-0011151 | 3/2000 |
| WO | WO-0023579 | 4/2000 |
| WO | WO-0030437 | 6/2000 |
| WO | WO-0056932 | 9/2000 |
| WO | WO-0114537 | 3/2001 |
| WO | WO-0117344 | 3/2001 |
| WO | WO-0119846 | 3/2001 |
| WO | WO-0123525 | 4/2001 |
| WO | WO-0126455 | 4/2001 |
| WO | WO-0143540 | 6/2001 |
| WO | WO-0171019 | 9/2001 |
| WO | WO-0173094 | 10/2001 |
| WO | WO-0183786 | 11/2001 |
| WO | WO-0185965 | 11/2001 |
| WO | WO 02/02738 A2 | 1/2002 |
| WO | WO-02046430 | 6/2002 |
| WO | WO-02047475 | 6/2002 |
| WO | WO-02063293 | 8/2002 |
| WO | WO-03014344 | 2/2003 |
| WO | WO-03024199 | 3/2003 |
| WO | WO-03025146 | 3/2003 |
| WO | WO-03048364 | 6/2003 |
| WO | WO-03064627 | 8/2003 |
| WO | WO 2004/003157 A2 | 1/2004 |
| WO | WO-2004009792 | 1/2004 |
| WO | WO-2004047531 | 6/2004 |
| WO | 2004067706 | 8/2004 |
| WO | WO-2004065581 | 8/2004 |
| WO | WO-2004067707 | 8/2004 |
| WO | WO-2004067743 | 8/2004 |
| WO | WO-2004080162 | 9/2004 |
| WO | WO-2004092351 | 10/2004 |
| WO | WO-2004110143 | 12/2004 |
| WO | WO2004110143 | 12/2004 |
| WO | WO-2005040215 | 5/2005 |
| WO | WO-2005062881 | 7/2005 |
| WO | WO-2005084430 | 9/2005 |
| WO | WO-2006024867 | 3/2006 |
| WO | WO-2006026238 | 3/2006 |
| WO | WO-2006053245 | 5/2006 |
| WO | WO-2006055040 | 5/2006 |
| WO | WO-2006055931 | 5/2006 |
| WO | WO-2006065821 | 6/2006 |
| WO | WO-2006093847 | 9/2006 |
| WO | 2007092537 | 8/2007 |
| WO | 2007110231 | 10/2007 |
| WO | WO 2010/036976 A2 | 4/2010 |
| WO | WO 2010/036978 A2 | 4/2010 |
| WO | WO 2010/036979 A2 | 4/2010 |
| WO | WO 2010/118360 A1 | 10/2010 |
| WO | 2012051615 | 4/2012 |

OTHER PUBLICATIONS

Araki, et al., "Site-Specific Recombination of a Transgene in Fertilized Eggs by Transient", Proc. Natl. Acad. Sci. USA Jan. 1, 1995, vol. 92, 160-164.

Argaud, et al., "Regulation of Rat Liver Glucose-6-Phosphatase Gene Expression in Different", Diabetes Nov. 1, 1996, 1563-1571.

Awade, et al., "Comparison of Three Liquid Chromatographic Methods for Egg-White Protein", Journal of Chromatography B. Jan. 1, 1999, vol. 723, 69-74.

Awade, A. C., "On Hen Egg Fractionation: Applications of Liquid Chromatography to the Isolation and", Z Lebensm Unters Forsch Jan. 1, 1996, vol. 202, 1-14.

Beardsley, T., "Gene Therapy Setback: A Tragic Death Clouds the Future of an Innovative Treatment", Scientific American Jun. 11, 2001, No. 2.

Bell, et al., "Nucleotide Sequence of a cDNA Clone Encoding Human Preproinsulin", Nature Nov. 29, 1979 , vol. 282, 525-527.

Bolli, et al., "Insulin Analogues and Their Potential in the Management of Diabetes Mellitus", Diabetologia Jan. 1, 1999, vol. 42, 1151-1167.

Brinster, R. L., "Germline Stem Cell Transplantation and Transgenesis", Science Jun. 21, 2002, vol. 296, 2174-2176.

Chatterjee, et al., "Retrofitting High Molecular Weight DNA Cloned in P1: Introduction of Reporter", Genetic Analysis: Biomolecular Jan. 1, 1996, vol. 13, 33-42.

Ciampi, M. S. et al., "Transposon Tn10 Provides a Promoter for Transcription of Adjacent Sequences", Proc Natl Acad Sci USA Aug. 1, 1982, vol. 79, No. 16, 5016-5020.

Ciftci, et al., "Applications of Genetic Engineering in Veterinary Medicine", Advanced Drug Delivery Reviews Jan. 1, 2000, vol. 43, 57-64.

Cochet, M et al., "Organisation and sequence studies of the 17-piece chicken conalbumin gene", Nature Dec. 6, 1979, vol. 282; 567-574.

Davis, C. G., "The Many Faces of Epidermal Growth Factor Repeats", New Biologist May 1990, 2(5), 410-419.

Davis, M. A. et al., "Tn10 Protects Itself at two levels from fortuitous activation by external promoters", Cell Nov. 11, 1985, vol. 43, No. 1, 379-387.

Dematteo, et al., "Engineering Tissue-Specific Expression of a Recombinant Adenovirus: Selective", Journal of Surgical Research Jan. 1, 1997 , vol. 72, 155-161.

Desert, C. et al., "Comparisons of Different Electrophoretic Separations of Hen Egg White Proteins", J. Agric. Food Chem. Jan. 1, 2001, vol. 49, 4553-4561.

Dierich, A. et al., "Cell-Specificity of the Chicken ovalbumin and conalbumin promoters", EMBO. Journal 1987, 6(8), 2305-2312.

Dobeli, H. et al., "Recombinant Fusion Proteins for the Industrial Production of Disulfide Bridge Containing Peptides: Purification, Oxidation without Concatamer Formation, and Selective Cleavage", Protein Expression and Purification 1998, 12, 404-414.

Dong, et al., "Hepatic Insulin Production Type-1 Diabetes", Trends in Endocrinology & Dec. 1, 2001, vol. 12, 441-446.

Dunham, Rex A. et al., "Enhanced Bacterial Disease Resistance of Transgenic Channel Catfish Ictalurus punctatus Possessing Cecropin Genes", Marine Biotechnology 06/00/2002, Springer Verlag, New York, NY, US, vol. 4, No. 3, 38-344.

Dupuy, A. et al., "Mammalian Germ-like Transgenesis by Transposition", PNAS Apr. 2, 2002, vol. 99, 4495-4499.

Ebara, et al., "In Vivo Gene Transfer into Chicken Embryos via Primordial Germ Cells Using Green", Journal of Reproduction and Jan. 1, 2000, vol. 46, 79-83.

Ebara, et al., "Possible Abnormalities of Chimeric Chicken Caused by the Introduction of", Asian-Aus. J. Anim. Sci. Jan. 1, 2000, vol. 13, 1514-1517.

Eggleston, et al., "A Sensitive and Rapid Assay for Homologous Recombination in Mosquito Cells:", BMC Genetics Dec. 17, 2001, vol. 2, No. 21, 1-9.

Etches, et al., "Gene Transfer: Overcoming the Avian Problems (Abstract Provided)", Proceedings, 5th World Congress Aug. 1, 1994, vol. 20, 97-101.

Etches, et al., "Manipulation of the Avian Genome", Jan. 1, 1993, pp. 15-28, 81-101, 103-119, 121-133, 165-184, 205-222, 223-230.

Etches, R. J. et al., "Strategies for the Production of Transgenic Chicken", Methods in Molecular Biology Jan. 1, 1997, vol. 62, 433-450.

Falqui, et al., "Reversal of Diabetes in Mice by Implantation of Human Fibroblasts Genetically Engineered to release matures Human Insulin", Human Gene Therapy Jul. 20, 1999, vol. 10, 1753-1762.

Fischer, R. et al., "Antibody production by molecular farming in plants", Journal of Biological Regulators and Hoeostatic Agents 04/00/2000, Wichtig Editore, Milan, IT, vol. 14, No. 2, 83-92.

Fischer, S. et al., "Regulated Transposition of a Fish Transposon in the Mouse Germ Line", Proc. Natl. Acad. Sci. USA Jan. 1, 2001, vol. 98, No. 12, 6759-6764.

Fisher, et al., "Induction of Terminal Differentiation in Cancer Cells as a Therapeutic Modality for Suppressing Tumor Growth: Studies Employing Human Melanoma", Anticancer Research 1988, vol. 8 (5B), 1057.

Fong, K. P. et al., "The genes for benzene catabolism in Pseudomonas putida ML2 are flanked by two", Plasmid Mar. 1, 2000, vol. 43, No. 2, 103-110.

(56) References Cited

OTHER PUBLICATIONS

Gaub, Marie-Pierre et al., "The Chicken ovalbumin promoter is under negative control which is relieved by steroid hormones", EMBO. Journal 1987, 6(8), 2313-2320.
Ghosh, et al., "Liver-Directed Gene Therapy: Promises, Problems and Prospects at the Turn of the", Journal of Hepatology Jan. 1, 2000, vol. 32, 238-252.
Gibbins, A. M., "Chickens as Bioreactors—Harvesting Commercially-Valuable Proteins from the Egg", Agri-food Research in Ontario Jan. 1, 1996, 39-41.
Gibbins, et al., "Exploring the Product Possibilities Arising from Transgenic Poultry Technology", Kungl. Skogs-och Jan. 1, 1997, vol. 136, 57-68.
Gibbins, et al., "Genetically-Engineered Poultry", Lohmann Information Jan. 1, 1997, No. 21, 3-6.
Gibbins, A. M. V., "The Chicken, the Egg, and the Ancient Mariner", Nat. Biotechnol. Jan. 1, 1998, vol. 16, 1013-1014.
Gibbins, A. M. V., "Transgenic Poultry Technology and Food Production", Animal Biotechnology Jan. 1, 1998, vol. 9, No. 3, 173-179.
Giddings, Glynis, "Transgenic plants as protein factories", Current Opinion in Biotechnology, London, GB 10/00/2001, vol. 12, No. 5, 450-454.
Ginsberg, et al., "The Road Ahead for Biologics Manufacturing", Equity Research Jan. 1, 2002, 1-23.
Hackett, P. B. et al., "Development of Genetic Tools for Transgenic Animals", Transgenic Animals in Agriculture Jan. 1, 1999, 19-35.
Han, et al., "Gene Transfer by Manipulation of Primordial Germ Cells in the Chicken", AJAS Jan. 1, 1994, vol. 7, No. 3, 427-434.
Harvey, A. et al., "Expression of Exogenous Protein in the White Egg of Transgenic Chickens", Nature Biotechnology Apr. 1, 2002, vol. 19, 396-399.
Heilig, R. et al., "NCBI Accession No. V00437-Gallus Gallus Fragment of Ovalbumin Gene Coding for the First Leader Exon", 1997.
Heilig, R. et al., "The Ovalbumin Gene Family, The 5' End Region of the X and Y Genes", J. Mol. Bio 1982, vol. 156, No. 1, pp. 1-19.
Hermann, et al., "Lipoprotein Receptors in Extraembryonic Tissues of the Chicken", J. Biol. Chem. Jun. 2, 2000, vol. 275, 16837-16844.
Herrero, M. et al., "Transposon Vectors containing Non-Antibiotic Resistance Selection Markers for Cloning and Stable Chromosomal Insertion of Foreign Genes in Gram-Negative Bacteria", Journal of Bacteriology 1990, vol. 172, No. 11, pp. 6557-6567.
Hillel, et al., "Strategies for the Rapid Introgression of a Specific Gene Modification into a", Poultry Science Jan. 1, 1993, vol. 72, 1197-1211.
Hong, et al., "Improved Transfection Efficiency of Chicken Gonadal Primordial Germ Cells for the", Transgenic Research Jan. 1, 1998, vol. 7, 247-252.
Horn, et al., "A Versatile Vector Set for Animal Transgenesis", Development Genes and Evolution 2000, vol. 210, No. 12, 630-637.
Houdebine, L. M., "The Methods to Generate Transgenic Animals and to Control Transgene Expression", J. Biotechnol. Sep. 25, 2002, vol. 98, 145-160.
Houdebine, L. M., "Transgenic Animal Bioreactors", Transgenic Research Oct. 1, 2000, vol. 9, No. 4-5, 305-320.
Ivarie, et al., "Avian Transgenesis: Progress Towards the Promise", TRENDS in Biotech Jan. 1, 2003, vol. 21, No. 1, 14-19.
Izsvak, et al., "Sleeping Beauty, A Wide Host-Range Transposon Vector for Genetic Transformation", J. Mol. Biol. Jan. 1, 2000, vol. 302, 93-102.
Jarvis, et al., "Influence of Different Signal Peptides and Prosequences on Expression and", The Journal of Biological Chemistry Aug. 5, 1993, vol. 268, No. 22, 16754-16762.
Jeltsch, et al., "The Complete Nucleotide Sequence of the Chicken Ovotransferrin mRNA", Eur.J. Biochem 1982, 122, 291-295.
Kaminski, et al., "Design of a Nonviral Vector for Site-Selective, Efficient Integration into the Human", The FASEB Journal Aug. 1, 2002, vol. 16, 1242-1247.
Kanda, et al., "Genetic Fusion of an a-Subunit Gene to the Follicle-Stimulating Hormone and", Molecular Endocrinology Nov. 1, 1999, vol. 13, No. 11, 1873-1881.
Kay, Mark A. et al., "Viral vectors for gene therapy: the art of turning infectious agents into vehicles of therapeutics", Nature Medicine Jan. 2001, vol. 7 No. 1, 33-40.
Kleckner, N. et al., "Transposon Tn10: genetic organization, regulation and insertion specificity", Fed Proc Aug. 1, 1982, vol. 41, No. 10, 2649-2652.
Kluin, PH. M. et al., "Proliferation of Spermatogonia and Sertoli Cells in Maturing Mice", Anat. Embryol. Jan. 1, 1984, vol. 169, 73-78.
Koga, et al., "The Medaka Fish To12 Transposable Element can Undergo Excision in Human and", J Hum Genet Mar. 28, 2003, vol. 48, No. 5, 231-235.
Kousteni, et al., "Reversal of Bone Loss in Mice by Nongenotypic Signaling of Sex Steroids", Science Oct. 25, 2002, vol. 298, 843-846.
Kozak, M, "At Least Six Nucleotides Preceding the AUG Initiator Codon Enhance Translation in", J. Mol. Biol. 1987, vol. 196, 947-950.
Kozak, M., "Initiation of translation in prokaryotes and eukaryotes", Gene 1999, vol. 234, 187-208.
Kumaran, J. D. S. et al., "The Normal Development of the Testes in the White Plymouth Rock", Testis Development in White Jan. 1, 1948, 511-519.
Lampe, D. et al., "Hyperactive transposase mutants of the Himarl mariner transposon", Proc. Natl. Acad. Sci. USA Sep. 1, 1999, vol. 96, 11428-11433.
Lillico, et al., "Transgenic Chickens as Bioreactors for Protein-Based Drugs", Drug Discovery Today Feb. 2005, vol. 10, No. 3, pp. 191-196.
Marshak, S. et al., "Purification of the Beta-Cell Glucose-sentitive factor that Transactivates the Insulin", Proc. Natl. Acad. Sci. USA Dec. 1, 1996, vol. 93, 15057-15062.
Massoud, et al., "The Deleterious Effects of Human Erythropoietin Gene Driven by the Rabbit Whey Acidic Protein Gene Promoter in Transgenic Rabbits", Reprod Nutr Dev 1996, 36(5), 555-563.
Mather, et al., "The Mariner Transposable Element: A Potential Vector for Improved Integration of", British Poulty Science Sep. 1, 2000, vol. 41, S27-S28.
Meiss, et al., "Vectors for Dual Expression of Target Genes in Bacterial and Mammalian Cells", BioTechniques 2000, vol. 29, No. 3, 476, 478, 480.
Mohammed, et al., "Deposition of Genetically Egineered Human Antibodies into the Egg Yolk of Hens", Immunotechnology 1998, vol. 4, 115-125.
Monroe, D. et al., "The COUP-Adjacent Repressor (CAR) Element Participates in the Tissue-Specific", Biochemica et Biophysica Acta Jan. 1, 2000, vol. 1517, 27-32.
Mozdziak, et al., "Status of Transgenic Chicken Models for Developmental Biology", Developmental Dynamics 2004, 229:414-421.
Muramatsu, T. et al., "Regulation of Ovalbumin Gene Expression", Poultry and Avian Biology Jan. 1, 1995, vol. 6, No. 2, 107-123.
Muzzin, et al., "Hepatic Insulin Gene Expressions as Treatment for aType 1 Diabetes Mellitus in Rats", Mol Endo Jan. 1, 1997, vol. 11, 833-837.
Nicklin, et al., "Analysis of Cell-Specific Promoters for Viral Gene Therapy Targeted at the Vascular", Hypertension Jan. 1, 2001, vol. 38, 65-70.
Oakberg, E., "Duration of Spermatogenesis in the Mouse and Timing of Stages of the Cycle of the", Duration of Spermatogenesis, 507-516.
Ochiai, H. et al., "Synthesis of Human Erythropoietin in Vivo in the Oviduct of Laying Hens by", Poultry Science 1998, vol. 77, No. 2, 299-302.
Ono, T. et al., "Gene Transfer into Circulating Primorial Germ Cells of Quail Embryos", Exp. Anim. Jan. 1, 1995, vol. 4, No. 4, 275-278.
Osborne, et al., "A System for Insertional Mutagenesis and Chromosomal Rearrangement Using the", Plant J. Apr. 1, 1995, vol. 7, No. 4, 687-701.
Pain, B. et al., "Chicken Embryonic Stem Cells and Transgenic Strategies", Cell Tissues Organs 1999, vol. 165, 212-219.
Park, H., "COUP-TF Plays a Dual Role in the Regulation of the Ovalbumin Gene", Biochemistry Jan. 1, 2000, vol. 39, 8537-8545.

(56) References Cited

OTHER PUBLICATIONS

Phan, J. et al., "Structural Basis for the Substrate Specificity of Tobacco Etch Virus Protease", Journal of Biological Chemistry Dec. 27, 2002, vol. 277, 50564-50572.
Pieper, et al., "Restoration of Vascular Endothelial Function in Diabetes", Diabetes Res. Clin. Pract. Suppl. 1996, S157-S162.
Platon, D. et al., "A Shortage of Monoclonal Antibody Manufacturing Capacity", Pharmaceutical Fine Chemicals and BioMolecule Manufacturing Report 2002.
Prudhomme, M. et al., "Diversity of Tn4001 transposition products: the flanking IS256 elements can form", J Bacteriol Jan. 1, 2002, vol. 184, No. 2, 433-443.
Qiu, Y., "Spatiotemporal Expression Patterns of Chicken Ovalbumin Upstream Promoter-", Proc. Natl. Acad. Sci. Jan. 1, 1994, vol. 91, 4451-4455.
Richardson, P. D., "Gene Repair and Transposon-Mediated Gene Therapy", Stem Cells 2002, vol. 20, 112-115.
Sakai, J. et al., "Two classes of Tn10 transposase mutants that suppress mutations in the Tn10", Genetics Nov. 1, 1996, vol. 144, No. 3, 861-870.
Sang, et al., "Prospects for Transgenesis in the Chick", Mech. Dev. 2004, 121(9): 1179-86.
Sarmasik, Aliye et al., "Transgenic live-bearing fish and crustaceans produced by transforming immature", Marine Biotechnology 00/00/2001, vol. 3, No. 5, 470-477.
Sasakawa, C. et al., "Control of transposon Tn5 transposition in *Escherichia coli*", Prod Natl Acad Sci USA Dec. 1, 1982, vol. 79, No. 23, 7450-7454.
Schillberg, Stefan et al., "Apoplastic and cytosolic expression of full-size antibodies and antibody fragments in Nicotiana tabacum", Transgenic Research 08/00/1999, vol. 8, No. 4, 255-263.
Schillberg, S. et al., "Molecular farming of recombinant antibodies in plants", CMLS Cellular and Molecular Life Sciences 03/00/2003, Birkhauser Verlag, Heidelberg, DE, vol. 60, No. 3, 433-445.
Schlenstedt, et al., "Structural Requirements for Transport of PreprocecropinA and Related Presecretory", The Journal of Biological Chemistry Dec. 5, 1992, vol. 236, No. 34, 24328-24332.
Schneider, et al., "An Epitope Tagged Mammalian / Prokaryotic Expression Vector with Positive", Gene: An International Journal on 1997, vol. 197, 337-341.
Schultz, et al., "Translation Initiation of IS50R Read-through Transcripts", J. Mol. Biol 1991, vol. 221, 65-80.
Seal, et al., "Mutational Studies Reveal a Complex Set of Positive and Negative Control Elements", Mol. Cell Biol. May 1, 1991, vol. 11, 2704-2717.
Sekine, Y. et al., "DNA Sequences required for translational frameshifting in production of the", Mol Gen Genet Nov. 1, 1992, vol. 235, No. 2-3, 325-332.
Sekine, Y. et al., "Identification of the site of translational frameshifting required for production of the", Mol Gen Genet Nov. 1, 1992, vol. 235, No. 2-3, 317-324.
Sharma, S. et al., "Pancreatic Islet Expression of the Homeobox Factor STF-1 Relies on and E-box", Journal of Biological Chemistry Jan. 26, 1996, vol. 271, 2294-2299.
Sherman, et al., "Transposition of the Drosophila Element Mariner into the Chicken Germ Line", Nature Biotechnology Nov. 1998, vol. 16, 1050-1053.
Sherratt, D., "Tn3 and Related Transposable Elements: Site-Specific Recombination and", Mobile DNA Jan. 1, 1989, 163-184.
Simons, R. W. et al., "Translational Control of IS10 Transposition", Cell Sep. 1, 1983, vol. 34, No. 2, 683-691.
Skolnick, J. et al., "From Genes to Protein structure and function: novel applications of computational approaches in the genomic era", Trends in Biotech. 2000, 18:34-39.
Slowinski, et al., "Pattern of Prepo-Endothelin-1 Expression Revealed by Reporter-Gene Activity in", Clinical Science, vol. 103, No. 48, 445-475.
Telmer, et al., "Epitope Tagging Genomic DNA Using a CD-Tagging Tn10 Minitransposon", Bio Techniques, 2002, vol. 32, No. 2, 422-430.
Vilen, et al., "Construction of Gene-Targeting Vectors: a Rapid Mu in vitro DNA Transposition-", Transgenic Research Jan. 1, 2001, vol. 10, 69-80.
Von Specht, M., "English translation of Dissertation entitled Expression of a recombinant human protein in vitro and in vivo in oviduct cells of chickens, with human erythroprotein (hrEPO) as an example", 2002, pp. 49-68.
Von Specht, M., "Expression eines rekombinanten humanen Proteins in vitro and in vivo in", Dissertation 2002, 49-68.
Wallace, et al., Biology the Science of Life 1986, vol. 2, 235.
Wang, A. et al., "Activation of silent genes by transposons Tn5 and Tn10.", Genetics Dec. 1, 1988, vol. 120, No. 4, 875-885.
Williamson, et al., "Expression of the Lysostaphin Gene of *Staphyloccoccus simulans* in a Eukaryotic System", Appl. Environ. Microbil. Mar. 1994, 60(3), 771-776.
Xanthopoulos, et al., "The structure of the gene for cecropin B, an antibacterial immune protein from", European Journal of Biochemistry 1988 , vol. 172, 371-376.
Zagoraiou, L., "In vivo Transposition of Minos, a Drosophila Mobile Element, in Mammalian Tissues", Proc. Natl. Acad. Sci. USA Jan. 1, 2001, vol. 98, No. 20, 11474-11478.
Zhukova, et al., "Expression of the Human Insulin Gene in the Gastric G Cells of Transgenic Mice", Transgenic Research 2001, vol. 10, 329-338.
JP 2004-518011 Final Decision of Rejection dated Mar. 2, 2010.
GEYERet al., "Protecting against promiscuity: The regulatory role of insulators," CMLS Cellular and Molecular Life Sciences, Dec. 2002, pp. 2112-2127.
Largaespada, "Generating and manipulating transgenic animals using transposable elements," Reproductive Biology and Endocrinology, vol. 1, No. 1, Nov. 7, 2003, p. 80-89.
Maksimenko, "Insulators of Higher Eukaryotes: Properties, Mechanisms of Action, and Role in Transcriptional Regulation," Russian Journal of Genetics, 42(8), Aug. 2006, pp. 845-857.
Maksimenko et al., "Insulators of higher eukaryotes: properties, mechanisms of action, and role in transcriptional regulation", Genetika vol. 42, No. 8, Aug. 2006, Abstract only.
International Search Report and Written Opinion of the International Searching Authority of PCT/US2009/058494, dated Apr. 14, 2010, 15 pages.
International Search Report and Written Opinion of the International Searching Authority of PCT/US2009/058497, dated Apr. 14, 2010, 14 pages.
Blatt et al., "Human variant interferon-alpha 2b protein Seq ID No. 1440", Database Geneseq [Online] Derwent: XP002601423-424, Dec. 13, 2007, 2 Pages.
Kwaks et al., "Employing epigenetics to augment the expression of therapeutic proteins in mammalian cells", Trends in Biotechnology, Elsevier Publications, vol. 24, No. 3, Mar. 2006, pp. 137-142.
International Application No. PCT/US2009/058498, International Search Report and Written Opinion mailed on Oct. 6, 2010, 16 Pages.
International Application No. PCT/US2010/030589, International Search Report and Written Opinion, mailed on Sep. 24, 2010, 26 Pages.
Australian Patent Application No. 2003261096, Examiner's First Report, dated Jun. 7, 2007.
Australian Patent Application No. 2003261096, Response to Examiner's First Report, dated May 12, 2008.
Australian Patent Application No. 2003261096, Examiner's Second Report, dated Jun. 6, 2008.
Australian Patent Application No. 2003261096, Response to Examiner's Second Report, dated Sep. 8, 2008.
Australian Patent Application No. 2003261096, Notice of Acceptance, dated Sep. 25, 2008.
Canadian Patent Application No. 2,490,693, Office Action, mailed Oct. 5, 2009.
Canadian Patent Application No. 2,490,693, Response to Office Action, filed Apr. 1, 2010.
Canadian Patent Application No. 2,490,693, Response to Office Action, filed Nov. 4, 2010.
Canadian Patent Application No. 2,490,693, Office Action, dated Dec. 30, 2010 (2 pages).

(56) References Cited

OTHER PUBLICATIONS

Canadian Patent Application No. 2,490,693, Response to Office Action, filed Mar. 7, 2011.
Canadian Patent Application No. 2,490,693, Notice of Allowance, mailed Mar. 24, 2011.
European Patent Application No. 037621729, Supplementary Search Report, mailed Feb. 15, 2006.
European Patent Application No. 037621729, First Office Action, mailed Jun. 9, 2006.
European Patent Application No. 037621729, Response to First Office Action, filed Oct. 18, 2006.
European Patent Application No. 037621729, Second Office Action, mailed Nov. 23, 2006.
European Patent Application No. 037621729, Response to Second Office Action, filed Apr. 2, 2007.
European Patent Application No. 037621729, Third Office Action, mailed Apr. 24, 2007.
European Patent Application No. 037621729, Response to Third Office Action, filed Aug. 31, 2007.
European Patent Application No. 037621729, Fourth Office Action, mailed Oct. 10, 2007.
European Patent Application No. 037621729, Response to Fourth Office Action, filed Feb. 11, 2008.
European Patent Application No. 037621729, Fifth Office Action, mailed Feb. 26, 2008.
European Patent Application No. 037621729, Response to Fifth Office Action, filed Jul. 4, 2008.
European Patent Application No. 037621729, Communication Under Rule 71(3) EPC, mailed Nov. 11, 2008.
European Patent Application No. 038002259, Supplementary Partial Search Report, mailed May 26, 2006.
European Patent Application No. 038002259, Second Office Action, mailed Jun. 14, 2007.
European Patent Application No. 038002259, Response to Second Office Action, filed Oct. 23, 2007.
European Patent Application No. 038002259, Third Office Action, mailed Nov. 7, 2007.
European Patent Application No. 038002259, Response to Third Office Action, filed Mar. 17, 2008.
European Patent Application No. 038002259, Fourth Office Action, mailed Mar. 31, 2008.
European Patent Application No. 038002259, Response to Fourth Office Action, filed May 30, 2008.
European Patent Application No. 038002259, Communication Under Rule 71(3) EPC, mailed Aug. 19, 2008.
European Patent Application No. 038085635, First Office Action, mailed Oct. 5, 2005.
European Patent Application No. 038085635, Response to First Office Action, filed Oct. 18, 2005.
European Patent Application No. 038085635, Search Report, mailed Jan. 23, 2007.
European Patent Application No. 038085635, Search Report, mailed Apr. 12, 2007.
European Patent Application No. 038085635, Second Office Action, mailed May 2, 2007.
European Patent Application No. 09815462.8, Communication Under Rule 161(1) and 162, mailed May 17, 2011.
Indian Patent Application No. 99/KOLNP/2005, First Official Action, mailed Jun. 17, 2006.
International Patent Application No. PCT/US2003/020389, International Search Report, mailed Apr. 2, 2004.
International Patent Application No. PCT/US2003/020389, Written Opinion, mailed Jun. 17, 2004.
International Patent Application No. PCT/US2003/041261, International Search Report, mailed Nov. 3, 2004.
International Patent Application No. PCT/US2003/041269, International Search Report, mailed May 18, 2004.
International Patent Application No. PCT/US2003/041335, International Search Report, mailed Nov. 3, 2004.
International Patent Application No. PCT/US2004/043092, International Search Report and Written Opinion, mailed May 11, 2006.
International Patent Application No. PCT/US2009/058494, International Preliminary Report on Patentability, mailed Apr. 7, 2011 (7 pages).
International Patent Application No. PCT/US2009/058497, International Preliminary Report on Patentability, mailed Apr. 7, 2011 (7 pages).
International Patent Application No. PCT/US2009/058498, International Preliminary Report on Patentability, mailed Apr. 7, 2011 (7 pages).
International Patent Application No. PCT/US2010/030589, International Preliminary Report on Patentability, mailed Oct. 20, 2011 (15 pages).
Japanese Patent Application No. 2004518011, First Office Action, mailed Sep. 8, 2009.
Japanese Patent Application No. 2004567449, First Office Action, mailed Dec. 1, 2009.
U.S. Appl. No. 10/583,812, Office Action, mailed Feb. 3, 2011 (11 pages).
U.S. Appl. No. 10/583,812, Notice of Allowance, mailed Oct. 11, 2011 (37 pages).
U.S. Appl. No. 10/609,019, Office Action, mailed Dec. 27, 2005 (15 pages).
U.S. Appl. No. 10/609,019, Office Action, mailed Jun. 26, 2006 (13 pages).
U.S. Appl. No. 10/609,019, Office Action, mailed Nov. 7, 2006 (11 pages).
U.S. Appl. No. 10/609,019, Office Action, mailed May 4. 2007 (12 pages).
U.S. Appl. No. 10/609,019, Office Action, mailed Oct. 17, 2007 (18 pages).
U.S. Appl. No. 10/609,019, Office Action, mailed Feb. 12, 2008 (26 pages).
U.S. Appl. No. 10/609,019, Notice of Allowance, mailed Jan. 9, 2009 (9 pages).
U.S. Appl. No. 10/746,149, Office Action, mailed Aug. 9, 2006 (38 pages).
U.S. Appl. No. 10/746,149, Office Action, mailed Feb. 28, 2007 (29 pages).
U.S. Appl. No. 10/746,149, Office Action, mailed Oct. 18, 2007 (21 pages).
U.S. Appl. No. 10/746,149, Office Action, mailed Feb. 8, 2008 (25 pages).
U.S. Appl. No. 10/746,149, Office Action, mailed Aug. 20, 2008 (32 pages).
U.S. Appl. No. 10/746,149, Office Action, mailed Feb. 3, 2009 (22 pages).
U.S. Appl. No. 11/981,574, Office Action, mailed Jan. 7, 2009 (19 pages).
U.S. Appl. No. 11/981,574, Office Action, mailed Jun. 24, 2009 (8 pages).
U.S. Appl. No. 11/981,574, Notice of Allowance, mailed Aug. 10, 2009 (7 pages).
U.S. Appl. No. 11/981,629, Office Action, mailed Feb. 5, 2009 (36 pages).
U.S. Appl. No. 11/981,629, Response to Non-Final Office Action, filed Aug. 5, 2009.
U.S. Appl. No. 11/981,629, Office Action, mailed Dec. 10, 2009 (23 pages).
U.S. Appl. No. 11/981,629, Response to Final Office Action, filed Feb. 10, 2010.
U.S. Appl. No. 11/981,629, Advisory Action, mailed Feb. 24, 2010.
U.S. Appl. No. 11/981,629, Request for Continued Examination and Amendment, filed May 10, 2010.
U.S. Appl. No. 11/981,629, Office Action, mailed Dec. 27, 2010 (19 pages).
U.S. Appl. No. 11/981,629, Response to Non-Final Office Action, filed May 17, 2011.
U.S. Appl. No. 11/981,629, Office Action, mailed Aug. 10, 2011 (15 pages).
U.S. Appl. No. 11/981,629, Response to Non-Final Office Action, filed Sep. 30, 2011.

(56) References Cited

OTHER PUBLICATIONS

U.S. Appl. No. 11/981,629, Office Action, mailed Dec. 30, 2011 (9 pages).
U.S. Appl. No. 12/567,513, Office Action, mailed Apr. 14, 2011 (12 pages).
U.S. Appl. No. 12/567,513, Office Action, mailed Nov. 4, 2011 (14 pages).
U.S. Appl. No. 12/757,591, Office Action, mailed Sep. 13, 2011 (4 pages).
U.S. Appl. No. 12/941,448, Office Action, mailed Oct. 19, 2011 (8 pages).
U.S. Appl. No. 11/981,629, "Response to Interview Summary" filed Mar. 19, 2012.
U.S. Appl. No. 12/567,214, "Office Action" mailed Apr. 2, 2012.
U.S. Appl. No. 12/567,513, "Request for Continued Examination and Response to Office Action" filed Apr. 3, 2012.
U.S. Appl. No. 12/567,513, "Response to Office Action" filed Feb. 6, 2012.
U.S. Appl. No. 12/567,513, "Response to Office Action" filed Jul. 13, 2011.
U.S. Appl. No. 12/941,448, "Response to Office Action", filed Feb. 23, 2012.
U.S. Appl. No. 12/941,448, "Supplemental Response to Office Action" filed Apr. 4, 2012.
European Application No. EP09815462.8, "Response to Office Action" filed Nov. 16, 2011.
European Application No. EP10715625.9, "Office Action" mailed Nov. 17, 2011.
European Application No. EP10715625.9, "Response to Office Action" filed Mar. 7, 2012.
U.S. Appl. No. 11/981,629 , "Notice of Allowance", Jul. 11, 2012, 6 pages.
U.S. Appl. No. 12/567,214 , "Office Action", Dec. 7, 2012, 19 pages.
U.S. Appl. No. 12/567,214 , "Response to Non-Final Office Action", Oct. 1, 2012, 9 pages.
U.S. Appl. No. 12/757,591 , "Office Action", Dec. 28, 2012, 17 pages.
U.S. Appl. No. 12/757,591 , "Response to Non-Final Office Action", Oct. 2, 2012, 10 pages.
European Patent Application No. EP10715625.9 , "Office Action", Jul. 20, 2012, 6 pages.
European Patent Application No. EP10715625.9 , "Office Action", Jan. 28, 2014, 7 pages.
U.S. Appl. No. 12/757,591, Office Action mailed Apr. 6, 2012 (12 pages).
U.S. Appl. No. 12/941,448, Notice of Allowance mailed Apr. 17, 2012 (13 pages).
U.S. Appl. No. 12/941,448, "Office Action", Nov. 25, 2011, 28.
Canadian Patent Application No. 2,490,693, "Office Action", mailed May 4, 2010.
International Patent Application No. PCT/US2011/056562, "International Search Report and Written Opinion", mailed Jan. 27, 2012 (13 pages).
Schubeler, et al., "Scaffold/Matrix-Attached Regions Act upon Transcription in a Context-Dependent Manner", Biochemistry, 1996, 35: 11160-11169.
U.S. Appl. No. 12/567,513 , "Non Final Office Action", Sep. 15, 2014, 18 pages.
U.S. Appl. No. 12/757,591 , "Non Final Office Action", Oct. 8, 2014, 16 pages.
European Patent Application No. EP10715625.9 , Office Action mailed Sep. 10, 2014.

* cited by examiner

| ChOval Promoter | CMV enhancer –promoter |
|---|---|

B.

| Ch SDRE | CMV anh | Ch NRE | CMV Promoter |
|---|---|---|---|

A.

B.

| | T5 LMH mAb HC | T6 2A's mAb HC | | T5 LMH mAb LC | T6 2A's mAb LC |
|---|---|---|---|---|---|
| M1 | 341.4 | 152.2 | | 311.6 | 141.0 |
| M2 | 687.5 | 239.4 | | 597.7 | 201.4 |
| M3 | 62.6 | 10.4 | | 41.4 | 6.9 |
| M4 | 15.1 | 3.9 | | 9.7 | 0.8 |

LMH = First and third rows
LMH 2A's = Second and fourth rows

| | T7 | T8 | T9 | | T19 | T20 | T21 |
|---|---|---|---|---|---|---|---|
| M1 | 122.0 | 154.9 | 176.3 | | 61.9 | 60.2 | 62.2 |
| M2 | 125.7 | 138.4 | 136.1 | | 38.5 | 33.4 | 30.0 |
| M3 | 15.6 | 17.6 | 14.3 | | 3.8 | 3.3 | 2.4 |

| | T7 | T8 | T9 | | T19 | T20 | T21 |
|---|---|---|---|---|---|---|---|
| M1 | 112.7 | 141.7 | 159.4 | | 57.8 | 53.5 | 56.2 |
| M2 | 100.8 | 108.9 | 108.9 | | 33.1 | 28.6 | 24.3 |
| M3 | 11.3 | 12.9 | 10.9 | | 3.6 | 3.2 | 3.6 |

| | LMH-273 | LMH2A-273 | LMH-275 | LMH2A-275 | | LMH-273 | LMH2A-273 | LMH-275 | LMH2A-275 |
|---|---|---|---|---|---|---|---|---|---|
| M1 | 500.5 | 216.0 | 777.6 | 299.9 | | 483.8 | 195.5 | 754.8 | 270.1 |
| M2 | 385.7 | 114.2 | 576.1 | 167.1 | | 331.7 | 115.6 | 507.3 | 157.5 |
| M3 | 86.4 | 18.2 | 109.5 | 21.0 | | 70.1 | 13.7 | 98.5 | 16.5 |

VECTORS FOR PRODUCTION OF ANTIBODIES

PRIOR RELATED APPLICATIONS

The present application claims the benefit of priority to U.S. Provisional Application No. 61/100,075 filed Sep. 25, 2008 and to U.S. Provisional Application No. 61/231,555 filed Aug. 5, 2009, both of which are hereby incorporated by reference in their entirety.

FIELD OF THE INVENTION

The present disclosure relates to compositions and methods for the production of an antibody, for example, a monoclonal antibody (mAb). In particular, the disclosure relates to transposon based vectors and their use in methods for the efficient expression of an antibody, for example, a monoclonal antibody.

BACKGROUND OF THE INVENTION

Antibodies, or immunoglobulins, are proteins produced by cells of the immune system to identify and neutralize foreign substances, such as bacteria, viruses, or improperly proliferating native cells. An antibody consists of two larger "heavy" chain polypeptides and two smaller "light" chain polypeptides. Both the heavy and the light chain polypeptides contain a constant region and a variable region. It is the variable region that allows each antibody to specifically recognize a different target (i.e., antigen). The recognition of a foreign antigen by a specific antibody allows other parts of the immune system to recognize and attack the foreign antigen. In addition, an antibody can directly neutralize a bacterial or viral cell by binding to a part of the bacterial or viral cell that is needed for infection.

Antibodies are useful both for therapeutic and diagnostic functions. For example, anti-Rhesus factor D (anti-RhD) antibodies are regularly given as a prenatal therapy to mothers who are Rhesus factor negative ($Rh^-$) to prevent the mother's body from attacking the Rhesus factor positive ($Rh^+$) cells of a baby that she is carrying. Antibodies also are currently being used for a number of other therapeutic applications, such as for the treatment of rheumatoid arthritis, multiple sclerosis, psoriasis, transplant rejection, cardiovascular disease, inflammatory diseases (e.g., autoimmune-related disorders), respiratory syncytial virus infections, macular degeneration, and many forms of cancer including non-Hodgkin's lymphoma, colorectal cancer, head and neck cancer, chronic lymphocytic leukemia, and breast cancer. Some immune deficiencies, such as X-linked agammaglobulinemia and hypogammaglobulinemia also are treated with antibodies. In addition, antibodies are used to detect bacterial or viral infections or to detect which particular allele of a protein is being produced by a patient.

The manufacture of therapeutic and/or diagnostic proteins such as antibodies, is an expensive process. Companies using recombinant techniques to manufacture these proteins are working at capacity and usually have a long waiting list to access their fermentation facilities. What is needed, therefore, is a new, efficient, and economical approach to make antibodies in vitro or in vivo.

SUMMARY

The present invention addresses these needs by providing novel compositions which can be used to transfect cells for production of antibodies in vivo and in vitro, and which can be used for the production of transgenic animals that can transmit the gene encoding an antibody to their offspring. These novel compositions include components of vectors such as a vector backbone (SEQ ID NOs:1-13), a novel promoter (SEQ ID NOs:14-15), and a gene of interest that encodes for the light chain and/or heavy chain protein subunits of an antibody. The present vectors comprise an insulator element located between the transposon insertion sequences and the multicloning site on the vector. In one embodiment, the insulator element is selected from the group consisting of an HS4 element, a lysozyme replicator element, a combination of a lysozyme replicator element and an HS4 element, and a matrix attachment region element. The vectors comprising each of these components are shown in SEQ ID NOs:17-27. In one embodiment, the gene of interest encodes a kappa chain or a lambda chain of an antibody. In one embodiment, the disclosed vectors are transposon-based vectors. The present invention also provides methods of making these compositions and methods of using these compositions for the production of antibodies. In certain embodiments, the antibody is a human monoclonal antibody. In one embodiment, the antibody is a human RM2 monoclonal antibody or herceptin. Some of these vectors have been used to transfect germline cells of birds through cardiac injection. The transgene in these vectors has been successfully passed through two generations of offspring, demonstrating stable integration and inheritance of the transgene.

It is to be understood that different cells may be transfected in vitro with one of the presently disclosed compositions, provided the cells contain protein synthetic biochemical pathways for the expression of the gene of interest. For example, both prokaryotic cells and eukaryotic cells may be transfected with one of the disclosed compositions. In certain embodiments, animal or plant cells are transfected. Animal cells are preferred cells and include, for example, mammalian cells and avian cells. Animal cells that may be transfected include, but are not limited to, Chinese hamster ovary (CHO) cells, CHO-K1 cells, chicken embryonic fibroblasts, HeLa cells, Vero cells, FAO (liver cells), human 3T3 cells, A20 cells, EL4 cells, HepG2 cells, J744A cells, Jurkat cells, P388D1 cells, RC-4B/c cells, SK-N-SH cells, Sp2/mIL-6 cells, SW480 cells, 3T6 Swiss cells, human ARPT-19 (human pigmented retinal epithelial) cells, LMH cells, LMH2a cells, tubular gland cells, or hybridomas.

In one embodiment, avian cells are transfected with one of the disclosed compositions. In a specific embodiment, avian hepatocytes, hepatocyte-related cells, or tubular gland cells are transfected. In certain embodiments, chicken cells are transfected with one of the disclosed compositions. In one embodiment, chicken tubular gland cells, chicken embryonic fibroblasts, chicken LMH2A cells, or chicken LMH cells are transfected with one of the disclosed compositions. Chicken LMH and LMH2A cells are chicken hepatoma cell lines; LMH2A cells have been transformed to express estrogen receptors on their cell surface.

In other embodiments, mammalian cells are transfected with one of the disclosed compositions. In one embodiment, Chinese hamster ovary (CHO) cells, ARPT-19 cells, chicken embryonic fibroblasts, HeLa cells, Vero cells, FAO (liver cells), human 3T3 cells, or hybridomas are transfected for antibody production. In a specific embodiment, CHO-K1 cells or ARPT-19 cells are transfected with one of the disclosed compositions.

The present invention provides compositions and methods for efficient production of antibodies. These methods enable production of large quantities of bioactive antibodies. In some embodiments, the antibodies are produced at a level of between about 25 g protein/month and about 4 kg protein/month.

These vectors may also be used in vivo to transfect germline cells in animals such as birds which can be bred and which then pass the antibody transgene through several generations. These vectors also may be used for the production of antibodies in vivo, for example, for deposition in an egg.

BRIEF DESCRIPTION OF THE FIGURES

Figure 1:
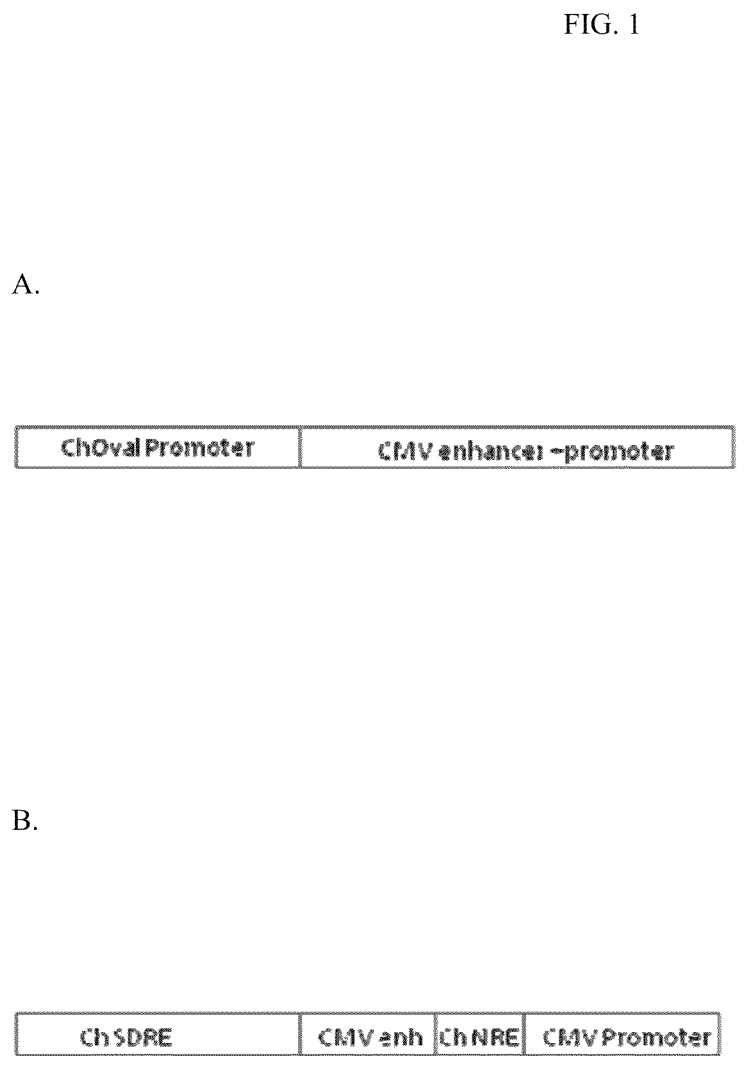

FIG. 1 shows the structure of two different hybrid promoters. FIG. 1A is a schematic of the Version 1 CMV/Oval promoter 1 (ChOvp/CMVenh/CMVp; SEQ ID NO:14). FIG. 1B is a schematic of the Version 2 CMV/Oval promoter (SEQ ID NO:15; ChSDRE/CMVenh/ChNRE/CMVp).

DETAILED DESCRIPTION OF PREFERRED EMBODIMENTS OF THE INVENTION

Figure 2:
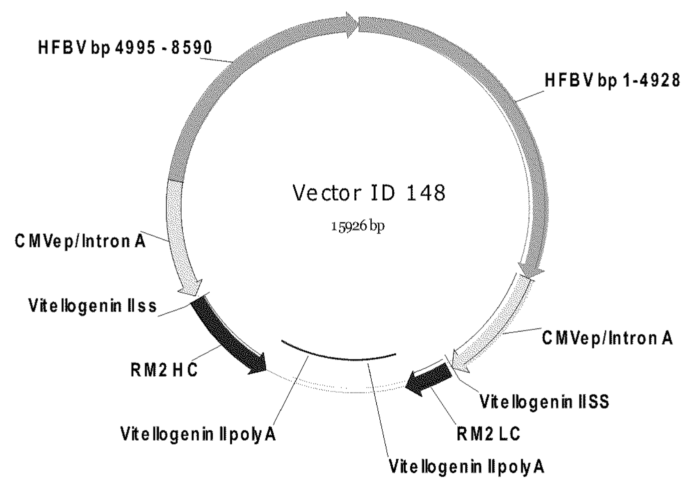
FIG. 2 is a schematic showing vector #148 (SEQ ID NO:17) used for expression of an RM2 monoclonal antibody.
Figure 3:
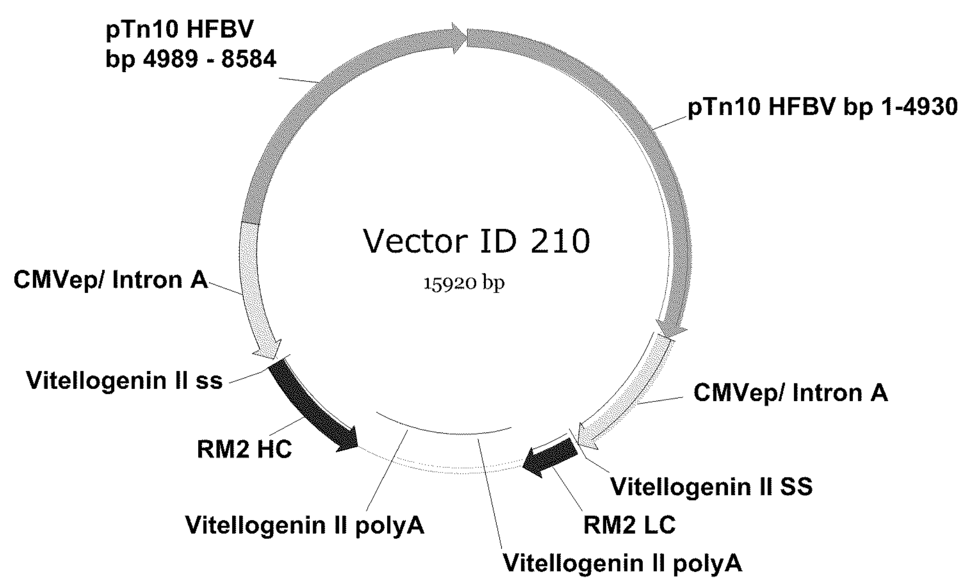
FIG. 3 is a schematic showing vector #210 (SEQ ID NO:18) used for expression of an RM2 monoclonal antibody.
Figure 4:
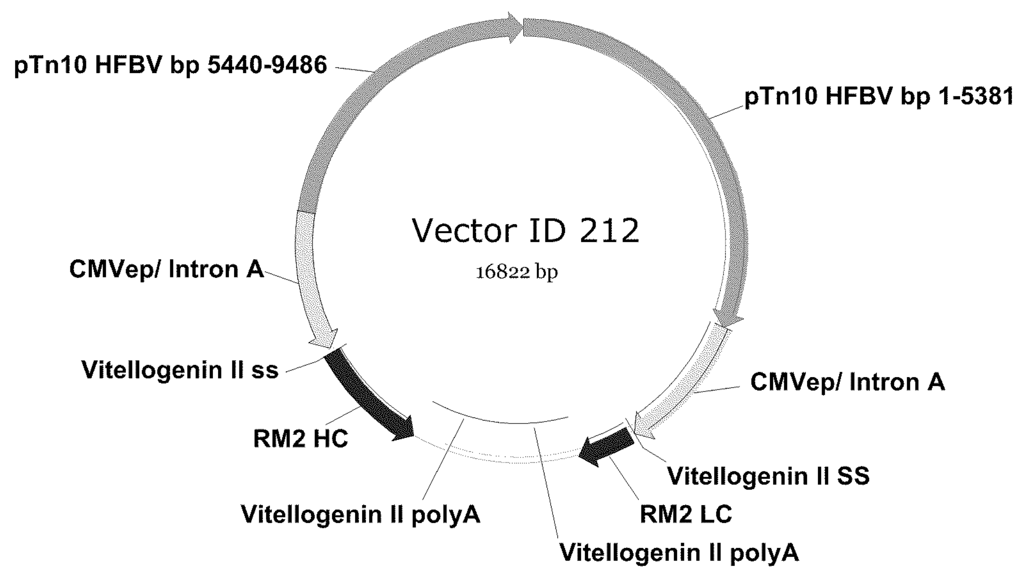
FIG. 4 is a schematic showing vector #212 (SEQ ID NO:19) used for expression of an RM2 monoclonal antibody.
Figure 5:
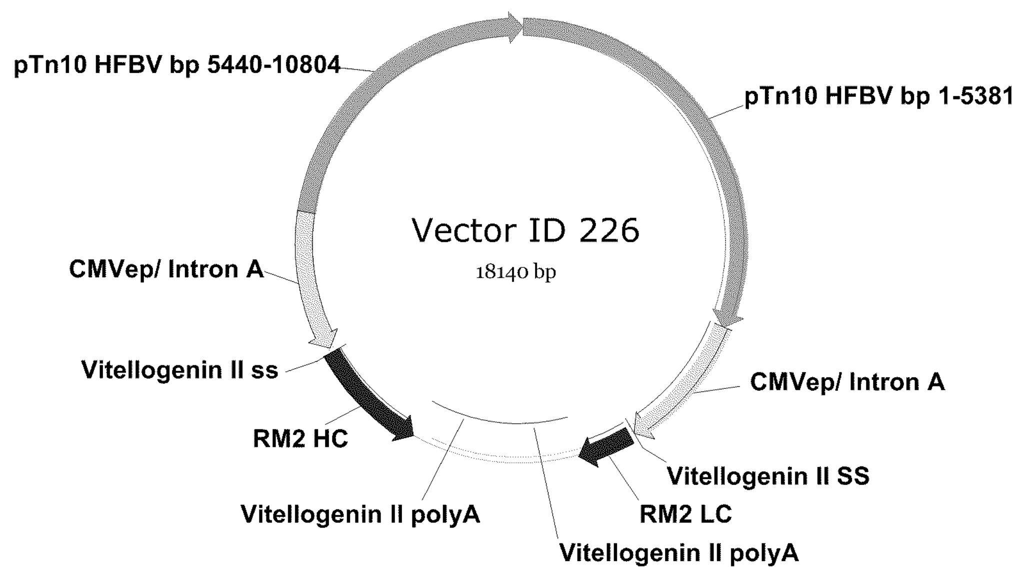
FIG. 5 is a schematic showing vector #226 (SEQ ID NO:20) used for expression of an RM2 monoclonal antibody.

The present invention provides novel vectors and vector components for use in antibody production. In one embodiment, the vectors are used for transfecting cells for antibody production in vitro. In another embodiment, the vectors are used for transfecting cells for antibody production in vivo. The present invention provides methods to make these vector components, methods to make the vectors themselves, and methods for using these vectors to transfect cells such that the transfected cells produce antibodies in vitro. These vectors also may be used in vivo to transfect germline cells in animals, such as birds, which can be bred and which then pass the transgene through several generations. These vectors may be used in vivo to transfect cells such as secretory cells in birds which may produce the antibodies, for example, for deposition into an egg of the bird.

It is to be understood that different cells may be transfected in vitro with one of the presently disclosed compositions, provided the cells contain protein synthetic biochemical pathways for the expression of the gene of interest. For example, both prokaryotic cells and eukaryotic cells may be transfected with one of the disclosed compositions. In certain embodiments, animal or plant cells are transfected. Animal cells are preferred cells and include, for example, mammalian cells and avian cells. Animal cells that may be transfected include, but are not limited to, Chinese hamster ovary (CHO) cells, CHO-K1 cells, chicken embryonic fibroblasts, HeLa cells, Vero cells, FAO (liver cells), human 3T3 cells, A20 cells, EL4 cells, HepG2 cells, J744A cells, Jurkat cells, P388D1 cells, RC-4B/c cells, SK-N-SH cells, Sp2/mIL-6 cells, SW480 cells, 3T6 Swiss cells, human ARPT-19 (human pigmented retinal epithelial) cells, LMH cells, LMH2a cells, tubular gland cells, or hybridomas. Avian cells include, but are not limited to, LMH, LMH2a cells, chicken embryonic fibroblasts, and tubular gland cells. In one embodiment, avian cells are transfected with one of the disclosed compositions. In a specific embodiment, avian hepatocytes, hepatocyte-related cells, or tubular gland cells are transfected. In certain embodiments, chicken cells are transfected with one of the disclosed compositions. In one embodiment, chicken tubular gland cells, chicken embryonic fibroblasts, chicken LMH2A or chicken LMH cells are transfected with one of the disclosed compositions. Chicken LMH and LMH2A cells are chicken hepatoma cell lines; LMH2A cells have been transformed to express estrogen receptors on their cell surface.

In other embodiments, mammalian cells are transfected with one of the disclosed compositions. In one embodiment, Chinese hamster ovary (CHO) cells, ARPT-19 cells, HeLa cells, Vero cells, FAO (liver cells), human 3T3 cells, or hybridomas are transfected for antibody production. In a specific embodiment, CHO-K1 cells or ARPT-19 cells are transfected with one of the disclosed compositions.

As used herein, the terms "antibody" or "antibodies" refer to a light chain and heavy chain protein of an antibody that are encoded by a gene or genes that are either a naturally occurring gene or a codon-optimized gene. As used herein, the term "codon-optimized" means that the DNA sequence has been changed such that where several different codons code for the same amino acid residue, the sequence selected for the gene is the one that is most often utilized by the cell in which the gene is being expressed. For example, in some embodiments, the antibody light and heavy chain genes are expressed in LMH2A cells and include codon sequences that are preferred in that cell type. In certain embodiments, the antibody light chain and heavy chain genes are human antibody light chain and heavy chain genes. In certain embodiments, the light chain is either a kappa chain or a lambda chain.

In one embodiment, the genes encode RM2 monoclonal antibody heavy and light chain subunits and are shown at nucleotides 9274-10644 and 6623-7270 of SEQ ID NO:17, nucleotides 9268-10638 and 6617-7264 of SEQ ID NO:18, nucleotides 9719-11089 and 7068-7715 of SEQ ID NO:19, nucleotides 9719-11089 and 7068-7715 of SEQ ID NO:20, and nucleotides 11766-13133 and 7918-8565 of SEQ ID NO:21, respectively.

In one embodiment, the vectors contain a gene of interest encoding an antibody, for the production of such antibody by transfected cells in vitro. In one embodiment, the vectors of the present invention contain a gene encoding a heavy chain of an antibody for the production of such protein by transfected cells in vitro. In another embodiment, the vectors contain a gene encoding a light chain of an antibody for the production of such protein by transfected cells in vitro. In another embodiment, the vectors contain a gene encoding a monoclonal antibody for the production of such protein by transfected cells in vitro.

Immunoglobulins are one class of desired globulin molecules and include, but are not limited to, IgG, IgM, IgA, IgD, IgE, IgY, lambda chains, kappa chains and fragments thereof; bi-specific antibodies, and fragments thereof; scFv fragments, Fc fragments, and Fab fragments as well as dimeric, trimeric and oligomeric forms of antibody fragments. Desired antibodies include, but are not limited to, naturally occurring antibodies, animal-specific antibodies, human antibodies, humanized antibodies, autoantibodies and hybrid antibodies. Genes encoding modified versions of naturally occurring antibodies or fragments thereof and genes encoding artificially designed antibodies or fragments thereof may be incorporated into the transposon-based vectors of the present invention. Desired antibodies also include antibodies with the ability to bind specific ligands, for example, antibodies against proteins associated with cancer-related molecules, such as anti-her 2, or anti-CA125. Accordingly, the present invention encompasses a transposon-based vector containing one or more genes encoding a heavy immunoglobulin (Ig) chain and a light Ig chain. Further, more than one gene encoding for more than one antibody may be administered in one or more transposon-based vectors of the present invention. Such administration may be in vivo or in vitro to transfect cultured cells. In this manner, antibodies may be made in liver cells or another cell selected for transfection, such as fibroblasts and released in vitro, or released locally, or gain access to the circulation in vivo. In one embodiment, a transposon-based vector contains a heavy Ig chain and a light Ig chain, both operably linked to a promoter.

Antibodies used as therapeutic reagents include but are not limited to antibodies for use in cancer immunotherapy against specific antigens, or for providing passive immunity to an animal against an infectious disease or a toxic agent. Antibodies may be made by the animal receiving the transposon-based vectors to facilitate the animal's immune response to a selected antigen.

Antibodies that may be made with the practice of the present invention include, but are not limited to primary antibodies, secondary antibodies, designer antibodies, anti-protein antibodies, anti-peptide antibodies, anti-DNA antibodies, anti-RNA antibodies, anti-hormone antibodies, anti-hypophysiotropic peptides, antibodies against non-natural antigens, anti-anterior pituitary hormone antibodies, anti-posterior pituitary hormone antibodies, anti-venom antibodies, anti-tumor marker antibodies, antibodies directed against epitopes associated with infectious disease, including, anti-viral, anti-bacterial, anti-protozoal, anti-fungal, anti-parasitic, anti-receptor, anti-lipid, anti-phospholipid, anti-growth factor, anti-cytokine, anti-monokine, anti-idiotype, and anti-accessory (presentation) protein antibodies. Antibodies made with the present invention, as well as light chains or heavy chains, may also be used to inhibit enzyme activity.

Antibodies that may be produced using the present invention include, but are not limited to, antibodies made against the following proteins: Bovine γ-Globulin, Serum; Bovine IgG, Plasma; Chicken γ-Globulin, Serum; Human γ-Globulin, Serum; Human IgA, Plasma; Human $IgA_1$, Myeloma; Human $IgA_2$, Myeloma; Human $IgA_2$, Plasma; Human IgD, Plasma; Human IgE, Myeloma; Human IgG, Plasma; Human IgG, Fab Fragment, Plasma; Human IgG, $F(ab')_2$ Fragment, Plasma; Human IgG, Fc Fragment, Plasma; Human $IgG_1$, Myeloma; Human $IgG_2$, Myeloma; Human $IgG_3$, Myeloma; Human $IgG_4$, Myeloma; Human IgM, Myeloma; Human IgM, Plasma; Human Immunoglobulin, Light Chain κ, Urine; Human Immunoglobulin, Light Chains κ and λ, Plasma; Mouse γ-Globulin, Serum; Mouse IgG, Serum; Mouse IgM, Myeloma; Rabbit γ-Globulin, Serum; Rabbit IgG, Plasma; and Rat γ-Globulin, Serum. In one embodiment, the transposon-based vector comprises the coding sequence of light and heavy chains of a murine monoclonal antibody that shows specificity for human seminoprotein (GenBank Accession numbers AY129006 and AY129304 for the light and heavy chains, respectively).

A further non-limiting list of antibodies that recognize other antibodies is as follows: Anti-Chicken IgG, heavy (H) & light (L) Chain Specific (Sheep); Anti-Goat γ-Globulin (Donkey); Anti-Goat IgG, Fc Fragment Specific (Rabbit); Anti-Guinea Pig γ-Globulin (Goat); Anti-Human Ig, Light Chain, Type κ Specific; Anti-Human Ig, Light Chain, Type λ Specific; Anti-Human IgA, α-Chain Specific (Goat); Anti-Human IgA, Fab Fragment Specific; Anti-Human IgA, Fc Fragment Specific; Anti-Human IgA, Secretory; Anti-Human IgE, ϵ-Chain Specific (Goat); Anti-Human IgE, Fc Fragment Specific; Anti-Human IgG, Fc Fragment Specific (Goat); Anti-Human IgG, γ-Chain Specific (Goat); Anti-Human IgG, Fc Fragment Specific; Anti-Human IgG, Fd Fragment Specific; Anti-Human IgG, H & L Chain Specific (Goat); Anti-Human $IgG_1$, Fc Fragment Specific; Anti-Human $IgG_2$, Fc Fragment Specific; Anti-Human $IgG_2$, Fd Fragment Specific; Anti-Human $IgG_3$, Hinge Specific; Anti-Human $IgG_4$, Fc Fragment Specific; Anti-Human IgM, Fc Fragment Specific; Anti-Human IgM, μ-Chain Specific; Anti-Mouse IgE, ϵ-Chain Specific; Anti-Mouse γ-Globulin (Goat); Anti-Mouse IgG, γ-Chain Specific (Goat); Anti-Mouse IgG, γ-Chain Specific (Goat) $F(ab')_2$ Fragment; Anti-Mouse IgG, H & L Chain Specific (Goat); Anti-Mouse IgM, μ-Chain Specific (Goat); Anti-Mouse IgM, H & L Chain Specific (Goat); Anti-Rabbit γ-Globulin (Goat); Anti-Rabbit IgG, Fc Fragment Specific (Goat); Anti-Rabbit IgG, H & L Chain Specific (Goat); Anti-Rat γ-Globulin (Goat); Anti-Rat IgG, H & L Chain Specific; Anti-Rhesus Monkey γ-Globulin (Goat); and, Anti-Sheep IgG, H & L Chain Specific.

Another non-limiting list of the antibodies that may be produced using the present invention is provided in product catalogs of companies such as Phoenix Pharmaceuticals, Inc. (Burlingame, Calif.), Peninsula Labs (San Carlos Calif.), SIGMA (St. Louis, Mo.), Cappel ICN (Irvine, Calif.), and Calbiochem (La Jolla, Calif.), which are all incorporated herein by reference in their entirety. The polynucleotide sequences encoding these antibodies may be obtained from the scientific literature, from patents, and from databases such as GenBank. Alternatively, one of ordinary skill in the art may design the polynucleotide sequence to be incorporated into the genome by choosing the codons that encode for each amino acid in the desired antibody. Antibodies made by the transgenic animals in vivo or transfected cells in vitro of the present invention include antibodies that may be used as therapeutic reagents, diagnostic reagents or laboratory reagents. Some of these antibodies include, but are not limited to, antibodies which bind the following ligands: adrenomedulin, amylin, calcitonin, amyloid, calcitonin gene-related peptide, cholecystokinin, gastrin, gastric inhibitory peptide, gastrin releasing peptide, interleukin, interferon, cortistatin, somatostatin, endothelin, sarafotoxin, glucagon, glucagon-like peptide, insulin, atrial natriuretic peptide, BNP, CNP, neurokinin, substance P, leptin, neuropeptide Y, melanin concentrating hormone, melanocyte stimulating hormone, orphanin, endorphin, dynorphin, enkephalin, enkephalin, leumorphin, peptide F, PACAP, PACAP-related peptide, parathyroid hormone, urocortin, corticotrophin releasing hormone, PHM, PHI, vasoactive intestinal polypeptide, secretin, ACTH, angiotensin, angiostatin, bombesin, endostatin, bradykinin, FMRF amide, galanin, gonadotropin releasing hormone (GnRH) associated peptide, GnRH, growth hormone releasing hormone, inhibin, granulocyte-macrophage colony stimulating factor (GM-CSF), motilin, neurotensin, oxytocin, vasopressin, osteocalcin, pancreastatin, pancreatic polypeptide, peptide YY, proopiomelanocortin, transforming growth factor, vascular endothelial growth factor, vesicular monoamine transporter, vesicular acetylcholine transporter, ghrelin, NPW, NPB, C3d, prokinetican, thyroid stimulating hormone, luteinizing hormone, follicle stimulating hormone, prolactin, growth hormone, beta-lipotropin, melatonin, kallikriens, kinins, prostaglandins, erythropoietin, p146, estrogen, testosterone, corticosteroids, mineralocorticoids, thyroid hormone, thymic hormones, connective tissue proteins, nuclear proteins, actin, avidin, activin, agrin, albumin, and prohormones, propeptides, splice variants, fragments and analogs thereof.

The following is yet another non-limiting list of antibodies that can be produced by the methods of present invention: abciximab (ReoPro), abciximab anti-platelet aggregation monoclonal antibody, anti-CD11a (hu1124), anti-CD18 antibody, anti-CD20 antibody, anti-cytomegalovirus (CMV) antibody, anti-digoxin antibody, anti-hepatitis B antibody, anti-HER-2 antibody, anti-idiotype antibody to GD3 glycolipid, anti-IgE antibody, anti-IL-2R antibody, antimetastatic cancer antibody (mAb 17-1A), anti-rabies antibody, anti-respiratory syncytial virus (RSV) antibody, anti-Rh antibody, anti-TCR, anti-TNF antibody, anti-VEGF antibody and Fab fragment thereof, rattlesnake venom antibody, black widow spider venom antibody, coral snake venom antibody, antibody against very late antigen-4 (VLA-4), C225 humanized antibody to EGF receptor, chimeric (human & mouse) antibody against TNFα, antibody directed against GPIIb/IIIa receptor on human platelets, gamma globulin, anti-hepatitis B immunoglobulin, human anti-D immunoglobulin, human antibodies against *S aureus*, human tetanus immunoglobulin, humanized antibody against the epidermal growth receptor-2, humanized antibody against the α subunit of the interleukin-2 receptor, humanized antibody CTLA4IG, humanized antibody to the IL-2 R α-chain, humanized anti-CD40-ligand monoclonal antibody (5c8), humanized mAb against the epidermal growth receptor-2, humanized mAb to rous sarcoma virus, humanized recombinant antibody (IgG1k) against respiratory syncytial virus (RSV), lymphocyte immunoglobulin (anti-thymocyte antibody), lymphocyte immunoglobulin, mAb against factor VII, MDX-210 bi-specific antibody against HER-2, MDX-22, MDX-220 bi-specific antibody against TAG-72 on tumors, MDX-33 antibody to FcγR1 receptor, MDX-447 bi-specific antibody against EGF receptor, MDX-447 bispecific humanized antibody to EGF receptor, MDX-RA immunotoxin (ricin A linked) antibody, Medi-507 antibody (humanized form of BTI-322) against CD2 receptor on T-cells, monoclonal antibody LDP-02, muromonab-CD3(OKT3) antibody, OKT3 ("muromomab-CD3") antibody, PRO 542 antibody, ReoPro ("abciximab") antibody, and TNF-IgG fusion protein. It is to be understood that wherever the term "humanized" appears in the present patent application with regard to an antibody or molecule, that an antibody or molecule may be designed to be specific for any animal using selected polynucleotide sequences in the gene of interest included in the transposon-based vectors. Antibodies may be made against any selected antigen known to one of ordinary skill in the art.

The antibodies prepared using the methods of the present invention may also be designed to possess specific labels that may be detected through means known to one of ordinary skill in the art so that their location and distribution can be assessed following gene therapy and expression of the antibodies. The antibodies may also be designed to possess specific sequences useful for purification through means known to one of ordinary skill in the art. Specialty antibodies designed for binding specific antigens may also be made in transgenic animals using the transposon-based vectors of the present invention.

As used herein, the proteins referred to herein encompass a protein that is encoded by a gene that is either a naturally occurring or a codon-optimized gene. As used herein, the term "codon-optimized" means that the DNA sequence has been changed such that where several different codons code for the same amino acid residue, the sequence selected for the gene is the one that is most often utilized by the cell in which the gene is being expressed. For example, in some embodiments, the gene of interest is expressed in LMH or LMH2A cells and includes codon sequences that are preferred in that cell type.

In one embodiment, the vectors of the present invention contain a gene or genes (called a gene(s) of interest) encoding for a protein or protein of interest for the production of such protein by transfected cells in vitro. As used herein, the "protein of interest" is an antibody or antibody light chain or heavy chain. In one embodiment, the vectors of the present invention contain a gene encoding a heavy chain of an antibody for the production of such protein by transfected cells in vitro. In one embodiment, the vectors of the present invention contain a gene encoding a light chain of an antibody for the production of such protein by transfected cells in vitro. In one embodiment, the vectors of the present invention contain a gene encoding a monoclonal antibody for the production of such protein by transfected cells in vitro.

A. Vectors & Vector Components

The following paragraphs describe the novel vector components and vectors employed in the present invention.

1. Backbone Vectors

The backbone vectors provide the vector components minus the genes of interest (GOIs) that encode for the light and heavy chains of an antibody. In one embodiment, transposon-based vectors are used. The present vectors comprise an insulator element located between the transposon insertion sequences and the multicloning site on the vector. In one embodiment, the insulator element is selected from the group consisting of an HS4 element, a lysozyme replicator element, a combination of a lysozyme replicator element and an HS4 element, and a matrix attachment region element.

a. Transposon-Based Vector Tn-MCS #5001 (p5001) (SEQ ID NO:1)

Linear sequences were amplified using plasmid DNA from pBluescriptII sk(−) (Stratagene, La Jolla, Calif.), pGWIZ (Gene Therapy Systems, San Diego, Calif.), pNK2859 (Dr. Nancy Kleckner, Department of Biochemistry and Molecular Biology, Harvard University), and synthetic linear DNA constructed from specifically designed DNA Oligonucleotides (Integrated DNA Technologies, Coralville, Iowa). PCR was set up using the above referenced DNA as template, electrophoresed on a 1% agarose gel, stained with ethidium bromide, and visualized on an ultraviolet transilluminator. DNA bands corresponding to the expected size were excised from the gel and purified from the agarose using Zymo Research's Clean Gel Recovery Kit (Orange, Calif.). The resulting products were cloned into the Invitrogen's PCR Blunt II Topo plasmid (Carlsbad, Calif.) according to the manufacturer's protocol.

After sequence verification, subsequent clones were selected and digested from the PCR Blunt II Topo Vector (Invitrogen Life Technologies, Carlsbad, Calif.) with corresponding enzymes (New England Biolabs, Beverly, Mass.) according to the manufacturer's protocol. The linear pieces were ligated together using Stratagene's T4 Ligase Kit (La Jolla, Calif.) according to the manufacturer's protocol. Ligated products were transformed into *E. coli* Top10 cells (Invitrogen Life Technologies, Carlsbad, Calif.) using chemical transformation according to the manufacturer's protocol. Transformed bacterial cells were incubated in 1 ml of SOC (GIBCO BRL, CAT#15544-042) for 1 hour at 37° C. then spread to LB (Luria-Bertani) agar plates supplemented with 100 μg/ml ampicillin (LB/amp plates). These plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on a U.V. transilluminator after ethidium bromide staining Colonies producing a plasmid of the expected size were cultured in a minimum of 250 ml of LB/amp broth. Plasmid DNA was harvested using Qiagen's Maxi-Prep Kit according to the manufacturer's protocol (Chatsworth, Calif.). The DNA was used as a sequencing template to verify that the pieces were ligated together accurately to form the desired vector sequence. All sequencing was performed using Beckman Coulter's CEQ 8000 Genetic Analysis System. Once a clone was identified that consisted of the desired sequence, the DNA was isolated for use in cloning in specific genes of interest.

b. Preparation of Transposon-Based Vector TnX-MCS #5005 (p5005)

This vector (SEQ ID NO:2) is a modification of p5001 (SEQ ID NO:1) described above in section 1.a. The MCS extension was designed to add unique restriction sites to the multiple cloning site of the pTn-MCS vector (SEQ ID NO:1), creating pTnX-MCS (SEQ ID NO:2), in order to increase the ligation efficiency of constructed cassettes into the backbone vector. The first step was to create a list of all non-cutting enzymes for the current pTn-MCS DNA sequence (SEQ ID NO:1). A linear sequence was designed using the list of enzymes and compressing the restriction site sequences together. Necessary restriction site sequences for XhoI and PspOMI (New England Biolabs, Beverly, Mass.) were then added to each end of this sequence for use in splicing this MCS extension into the pTn-MCS backbone (SEQ ID NO:1). The resulting sequence of 108 bases is SEQ ID NO:16 shown in the Appendix. A subset of these bases within this 108 base pair sequence corresponds to bases 4917-5012 in SEQ ID NO:4 (discussed below).

For construction, the sequence was split at the NarI restriction site and divided into two sections. Both 5' forward and 3' reverse oligonucleotides (Integrated DNA Technologies, San Diego, Calif.) were synthesized for each of the two sections. The 5' and 3' oligonucleotides for each section were annealed together, and the resulting synthetic DNA sections were digested with NarI then subsequently ligated together to form the 108 bp MCS extension (SEQ ID NO:16). PCR was set up on the ligation, electrophoresed on a 1% agarose gel, stained with ethidium bromide, and visualized on an ultraviolet transilluminator. DNA bands corresponding to the expected size were excised from the gel and purified from the agarose using a Zymo Clean Gel Recovery Kit (Zymo Research, Orange, Calif.). The resulting product was cloned into the PCR Blunt II Topo Vector (Invitrogen Life Technologies, Carlsbad, Calif.) according to the manufacturer's protocol.

After sequence verification of the MCS extension sequence (SEQ ID NO:16), a clone was selected and digested from the PCR Blunt II Topo Vector (Invitrogen Life Technologies, Carlsbad, Calif.) with XhoI and PspoMI (New England Biolabs, Beverly, Mass.) according to the manufacturer's protocol. The pTn-MCS vector (SEQ ID NO:1) also was digested with XhoI and PspOMI (New England Biolabs, Beverly, Mass.) according to the manufacturer's protocol, purified as described above, and the two pieces were ligated together using Stratagene's T4 Ligase Kit (La Jolla, Calif.) according to the manufacturer's protocol. Ligated product was transformed into *E. coli* Top10 cells (Invitrogen Life Technologies, Carlsbad, Calif.) using chemical transformation according the manufacturer's protocol. Transformed bacterial cells were incubated in 1 ml of SOC (GIBCO BRL, CAT#15544-042) for 1 hour at 37° C. then spread onto LB agar plates supplemented with 100 μg/ml ampicillin (LB/amp plates). All plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in a minimum of 250 mls of LB/amp broth. Plasmid DNA was harvested using a Qiagen Maxi-Prep Kit (column purification) according to the manufacturer's protocol (Qiagen, Inc., Chatsworth, Calif.). The DNA was then used as a sequencing template to verify that the changes made in the vector were the desired changes and that no further changes or mutations occurred. All sequencing was performed using Beckman Coulter's CEQ 8000 Genetic Analysis System. Once a clone was identified that contained the multiple cloning site extension, the DNA was isolated and used for cloning specific genes of interest.

c. Preparation of Transposon-Based Vector TnHS4FBV #5006 (p5006)

This vector (SEQ ID NO:3) is a modification of p5005 (SEQ ID NO:2) described above in section 1.b. The modification includes insertion of the HS4 βeta globin insulator element on both the 5' and 3' ends of the multiple cloning site. The 1241 bp HS4 element was isolated from chicken genomic DNA and amplified through polymerase chain reaction (PCR) using conditions known to one skilled in the art. The PCR product was electrophoresed on a 1% agarose gel, stained with ethidium bromide, and visualized on an ultraviolet transilluminator. DNA bands corresponding to the expected size of the HS4 βeta globin insulator element were excised from the agarose gel and purified using a Zymo Clean Gel Recovery Kit (Zymo Research, Orange, Calif.).

Purified HS4 DNA was digested with restriction enzymes NotI, XhoI, PspOMI, and MluI (New England Biolabs, Beverly, Mass.) according to the manufacturer's protocol. The digested DNA was then purified using a Zymo DNA Clean and Concentrator kit (Orange, Calif.). To insert the 5' HS4 element into the MCS of the p5005 vector (SEQ ID NO:2), HS4 DNA and vector p5005 (SEQ ID NO:2) were digested with NotI and XhoI restriction enzymes, purified as described above, and ligated using Stratagene's T4 Ligase Kit (La Jolla, Calif.) according to the manufacturer's protocol. To insert the 3' HS4 element into the MCS of the p5005 vector (SEQ ID NO:2), HS4 and vector p5005 DNA (SEQ ID NO:2) were digested with PspOMI and MluI, purified, and ligated as described above. Ligated product was transformed into *E. coli* Top10 cells (Invitrogen Life Technologies, Carlsbad, Calif.) using chemical transformation according to the manufacturer's protocol. Transformed bacterial cells were incubated in 1 ml of SOC (GIBCO BRL, CAT#15544-042) for 1 hour at 37° C. then spread onto LB agar plates supplemented with 100 μg/ml ampicillin (LB/amp plates). These plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in at least 250 mls of LB/amp broth and plasmid DNA was harvested using a Qiagen Maxi-Prep Kit according to the manufacturer's protocol (Qiagen, Inc., Chatsworth, Calif.). The DNA was then used as sequencing template to verify that any changes made in the vector were the desired changes and that no further changes or mutations occurred. All sequencing was performed using Beckman Coulter's CEQ 8000 Genetic Analysis System. Once a clone was identified that contained both HS4 elements, the DNA was isolated and used for cloning in specific genes of interest.

All plasmid DNA was isolated by standard procedures. Briefly, *E. coli* bacteria containing the plasmid of interest were grown in 500 ml of LB broth (supplemented with an appropriate antibiotic) at 37° C. overnight in a shaking incubator. Plasmid DNA was isolated from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

d. Preparation of Transposon-Based Vector pTn10 HS4FBV #5012

This vector (SEQ ID NO:4) is a modification of p5006 (SEQ ID NO:3) described above under section 1.c. The modification includes a base pair substitution in the transposase gene at base pair 1998 of p5006. The corrected transposase gene was amplified by PCR from template DNA, using PCR conditions known to one skilled in the art. PCR product of the corrected transposase was electrophoresed on a 1% agarose gel, stained with ethidium bromide, and visualized on an ultraviolet transilluminator. DNA bands corresponding to the expected size were excised from the gel and purified from the agarose using a Zymo Clean Gel Recovery Kit (Zymo Research, Orange, Calif.).

Purified transposase DNA was digested with restriction enzymes NruI and StuI (New England Biolabs, Beverly, Mass.) according to the manufacturer's protocol. Digested DNA was purified from restriction digests using a Zymo DNA Clean and Concentrator kit (Zymo Research). To insert the corrected transposase sequence into the MCS of the p5006 vector (SEQ ID NO:3), the transposase DNA and the p5006 vector (SEQ ID NO:3) were digested with NruI and StuI, purified as described above, and ligated using a Stratagene's T4 Ligase Kit (La Jolla, Calif.) according to the manufacturer's protocol. Ligated product was transformed into *E. coli* Top10 cells (Invitrogen Life Technologies, Carlsbad, Calif.) using chemical transformation according to the manufacturer's protocol. Transformed cells were incubated in 1 ml of SOC (GIBCO BRL, CAT#15544-042) for 1 hour at 37° C. before spreading onto LB agar plates supplemented with 100 μg/ml ampicillin (LB/amp plates). All plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in at least 250 ml of LB/amp broth. The plasmid DNA was harvested using a Qiagen Maxi-Prep Kit according to the manufacturer's protocol (Qiagen, Inc., Chatsworth, Calif.). The DNA was then used as a sequencing template to verify that the changes made in the vector were desired changes and that no further changes or mutations occurred. All sequencing was performed using a Beckman Coulter CEQ 8000 Genetic Analysis System. Once a clone was identified that contained the corrected transposase sequence, the DNA was isolated and used for cloning in specific genes of interest.

All plasmid DNA was isolated by standard procedures. Briefly, *E. coli* bacteria containing the plasmid of interest was grown in 500 mL of LB broth (supplemented with an appropriate antibiotic) at 37° C. overnight in a shaking incubator. Plasmid DNA was isolated from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

e. Preparation of Transposon-Based Vector pTn-10 MARFBV #5018

This vector (SEQ ID NO:5) is a modification of p5012 (SEQ ID NO:4) described above under section 1.d. The modification includes insertion of the chicken 5' Matrix Attachment Region (MAR) on both the 5' and 3' ends of the multiple cloning site. To accomplish this, the 1.7 kb MAR element was isolated from chicken genomic DNA and amplified by PCR. PCR product was electrophoresed on a 1% agarose gel, stained with ethidium bromide, and visualized on an ultraviolet transilluminator. DNA bands corresponding to the expected size were excised from the gel and purified from the agarose using a Zymo Clean Gel Recovery Kit (Zymo Research, Orange, Calif.).

Purified MAR DNA was digested with restriction enzymes NotI, XhoI, PspOMI, and MluI (New England Biolabs, Beverly, Mass.) according to the manufacturer's protocol. Digested DNA was purified from agarose using a Zymo DNA Clean and Concentrator kit (Zymo Research, Orange Calif.). To insert the 5' MAR element into the MCS of p5012, the purified MAR DNA and p5012 were digested with Not I and Xho I, purified as described above, and ligated using Stratagene's T4 Ligase Kit (La Jolla, Calif.) according to the manufacturer's protocol. To insert the 3' MAR element into the MCS of p5012, the purified MAR DNA and p5012 were digested with PspOMI and MluI, purified, and ligated as described above. Ligated product was transformed into *E. coli* Top10 cells (Invitrogen Life Technologies, Carlsbad, Calif.) using chemical transformation according to the manufacturer's protocol. Transformed cells were incubated in 1 ml of SOC (GIBCO BRL, CAT#15544-042) for 1 hour at 37° C. and then spread onto LB agar plates supplemented with 100 μg/ml ampicillin (LB/amp plates). All plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in a minimum of 250 ml of LB/amp broth, and plasmid DNA was harvested using a Qiagen Maxi-Prep Kit according to the manufacturer's protocol (Qiagen, Inc., Chatsworth, Calif.). Column purified DNA was used as a sequencing template to verify that the changes made in the vector were the desired changes and that no further changes or mutations occurred. All sequencing was performed using a Beckman Coulter CEQ 8000 Genetic Analysis System. Once a clone was identified that contained both MAR elements, the DNA was isolated and used for cloning in specific genes of interest.

All plasmid DNA was isolated by standard procedures. Briefly, *E. coli* bacteria containing the plasmid of interest were grown in 500 mL of LB broth (supplemented with an appropriate antibiotic) at 37° C. in a shaking incubator. Plasmid DNA was isolated from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

f. Preparation of Transposon-Based Vector TnLysRep #5020

The vector (SEQ ID NO:6) included the chicken lysozyme replicator (LysRep or LR2) insulator elements to prevent gene silencing. Each LysRep element was ligated 3' to the insertion sequences (IS) of the vector. To accomplish this ligation, a 930 bp fragment of the chicken LysRep element (GenBank # NW 060235) was amplified using PCR conditions known to one skilled in the art. Amplified PCR product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.).

Purified LysRep DNA was sequentially digested with restriction enzymes Not I and Xho I (5'end) and Mlu I and Apa I (3'end) (New England Biolabs, Beverly, Mass.) according to the manufacturer's protocol. Digested DNA was purified from restriction enzymes using a Zymo DNA Clean and Concentrator kit (Zymo Research). To insert the LysRep elements between the IS left and the MCS in pTnX-MCS (SEQ ID NO:2), the purified LysRep DNA and pTnX-MCS were digested with Not I and Xho I, purified as described above, and ligated using a Stratagene T4 Ligase Kit (Stratagene, Inc. La Jolla, Calif.) according to the manufacturer's protocol. Ligated product was transformed into *E. coli* Top10 competent cells (Invitrogen Life Technologies, Carlsbad, Calif.) using chemical transformation according to Invitrogen's protocol. Transformed bacteria were incubated in 1 ml of SOC (GIBCO BRL, CAT#15544-042) medium for 1 hour at 37° C. before being spread to LB media (broth or agar) plates supplemented with 100 μg/ml ampicillin (LB/amp plates). These plates were incubated overnight at 37° C., and resulting colonies picked to LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in at least 250 ml of LB/amp broth and plasmid DNA harvested using a Qiagen Maxi-Prep Kit (column purification) according to the manufacturer's protocol (Qiagen, Inc., Chatsworth, Calif.). Column purified DNA was used as template for sequencing to verify the changes made in the vector were the desired changes and no further changes or mutations occurred. All sequencing was done on a Beckman Coulter CEQ 8000 Genetic Analysis System. Once a clone was identified that contained the 5' LysRep DNA, the vector was digested with Mlu I and Apa I as was the purified LysRep DNA. The same procedures described above were used to ligate the LysRep DNA into the backbone and verify that it was correct. Once a clone was identified that contained both LysRep elements, the DNA was isolated for use in cloning in specific genes of interest.

All plasmid DNA was isolated by standard procedures. Briefly, *E. coli* containing the plasmid were grown in 500 mL aliquots of LB broth (supplemented with an appropriate antibiotic) at 37° C. overnight with shaking. Plasmid DNA was recovered from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

g. Preparation of Transposon-Based Vector TnPuro #5019 (p5019)

This vector (SEQ ID NO:7) is a modification of p5012 (SEQ ID NO:4) described above in section 1.d. The modification includes insertion of the puromycin gene in the multiple cloning site adjacent to one of the HS4 insulator elements. To accomplish this ligation, the 602 bp puromycin gene was isolated from the vector pMOD Puro (Invivogen, Inc.) using PCR conditions known to one skilled in the art. Amplified PCR product was electrophoresed on a 1% agarose gel, stained with ethidium bromide, and visualized on a U.V. transilluminator. A band corresponding to the expected size was excised from the gel and purified from the agarose using a Zymo Clean Gel Recovery Kit (Zymo Research, Orange, Calif.).

Purified Puro DNA was digested with restriction enzyme Kas I (New England Biolabs, Beverly, Mass.) according to the manufacturer's protocol. Digested DNA was purified from restriction enzymes using a Zymo DNA Clean and Concentrator kit (Zymo Research). To insert the Puro gene into the MCS of p5012, the purified Puro DNA and p5012 were digested with Kas I, purified as described above, and ligated using a Stratagene T4 Ligase Kit (Stratagene, Inc. La Jolla, Calif.) according to the manufacturer's protocol. Ligated product was transformed into *E. coli* Top10 competent cells (Invitrogen Life Technologies, Carlsbad, Calif.) using chemical transformation according to Invitrogen's protocol. Transformed bacteria were incubated in 1 ml of SOC (GIBCO BRL, CAT#15544-042) medium for 1 hour at 37° C. before being spread to LB (broth or agar) plates supplemented with 100 μg/ml ampicillin (LB/amp plates). These plates were incubated overnight at 37° C. and resulting colonies picked to LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in at least 250 ml of LB/amp broth and plasmid DNA harvested using a Qiagen Maxi-Prep Kit (column purification) according to the manufacturer's protocol (Qiagen, Inc., Chatsworth, Calif.). Column purified DNA was used as template for sequencing to verify the changes made in the vector were the desired changes and no further changes or mutations occurred. All sequencing was done on a Beckman Coulter CEQ 8000 Genetic Analysis System. Once a clone was identified that contained both Puro gene, the DNA was isolated for use in cloning in specific genes of interest.

All plasmid DNA was isolated by standard procedures. Briefly, *E. coli* containing the plasmid were grown in 500 mL aliquots of LB broth (supplemented with an appropriate antibiotic) at 37° C. overnight with shaking. Plasmid DNA was recovered from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

h. Preparation of Transposon-Based Vector pTn-10 PuroMAR #5021 (p5021)

This vector (SEQ ID NO:8) is a modification of p5018 (SEQ ID NO:5) described above in section i.e. The modification includes insertion of the puromycin (puro) gene into the multiple cloning site adjacent to one of the MAR insulator elements. To accomplish this, the 602 bp puromycin gene was amplified by PCR from the vector pMOD Puro (Invitrogen Life Technologies, Carlsbad, Calif.). Amplified PCR product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.).

Purified DNA from the puromycin gene was digested with the restriction enzymes BsiWI and MluI (New England Biolabs, Beverly, Mass.) according to the manufacturer's protocol. Digested DNA was purified from agarose using a Zymo DNA Clean and Concentrator kit (Zymo Research). To insert the puro gene into the MCS of p5018, puro and p5018 were digested with BsiWI and MluI, purified as described above, and ligated using Stratagene's T4 Ligase Kit (La Jolla, Calif.) according to the manufacturer's protocol. Ligated product was transformed into *E. coli* Top10 cells (Invitrogen Life Technologies, Carlsbad, Calif.) using chemical transformation according to the manufacturer's protocol. Transformed cells were incubated in 1 ml of SOC (GIBCO BRL, CAT#15544-042) for 1 hour at 37° C. then spread onto LB agar plates supplemented with 100 μg/ml ampicillin (LB/amp plates). These plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in a minimum of 250 ml of LB/amp broth. The plasmid DNA was harvested using a Qiagen Maxi-Prep Kit according to the manufacturer's protocol (Qiagen, Inc., Chatsworth, Calif.). The DNA was used as a sequencing template to verify that the changes made in the vector were desired changes and that no further changes or mutations occurred. All sequencing was performed using Beckman Coulter's CEQ 8000 Genetic Analysis System. Once a clone was identified that contained the puro gene, the DNA was isolated and used for cloning in specific genes of interest.

All plasmid DNA was isolated by standard procedures. Briefly, *E. coli* containing the plasmid of interest was grown in 500 ml of LB broth (supplemented with an appropriate antibiotic) at 37° C. overnight in a shaking incubator. Plasmid DNA was isolated from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

i. Preparation of Transposon-Based Vector TnGenMAR #5022 (p5022)

This vector (SEQ ID NO:9) is a modification of p5021 (SEQ ID NO:8) described above under section 1.h. The modification includes insertion of the gentamycin gene in the multiple cloning site adjacent to one of the MAR insulator elements. To accomplish this ligation, the 1251 bp gentamycin gene was isolated from the vector pS65T-C1 (ClonTech Laboratories, using PCR conditions known to one skilled in the art. Amplified PCR product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.).

Purified gentamycin DNA was digested with restriction enzyme BsiW I and Mlu I (New England Biolabs, Beverly, Mass.) according to the manufacturer's protocol. Digested DNA was purified from restriction enzymes using a Zymo DNA Clean and Concentrator kit (Zymo Research). To insert the gentamycin gene into the MCS of p5018, the purified gentamycin DNA and p5018 were digested with BsiW I and Mlu I, purified as described above, and ligated using a Stratagene T4 Ligase Kit (Stratagene, Inc. La Jolla, Calif.) according to the manufacturer's protocol. Ligated product was transformed into *E. coli* Top10 competent cells (Invitrogen Life Technologies, Carlsbad, Calif.) using chemical transformation according to Invitrogen's protocol. Transformed bacteria were incubated in 1 ml of SOC (GIBCO BRL, CAT#15544-042) medium for 1 hour at 37° C. before being spread to LB (broth or agar) plates supplemented with 100 μg/ml ampicillin (LB/amp plates). These plates were incubated overnight at 37° C., and resulting colonies picked to LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining Colonies producing a plasmid of the expected size were cultured in at least 250 ml of LB/amp broth and plasmid DNA harvested using a Qiagen Maxi-Prep Kit (column purification) according to the manufacturer's protocol (Qiagen, Inc., Chatsworth, Calif.). Column purified DNA was used as template for sequencing to verify that the changes made in the vector were the desired changes and that no further changes or mutations occurred. All sequencing was done on a Beckman Coulter CEQ 8000 Genetic Analysis System. Once a clone was identified that contained both Puro gene, the DNA was isolated for use in cloning in specific genes of interest.

All plasmid DNA was isolated by standard procedures. Briefly, *E. coli* containing the plasmid were grown in 500 mL aliquots of LB broth (supplemented with an appropriate antibiotic) at 37° C. overnight with shaking. Plasmid DNA was recovered from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

j. Preparation of Low Expression CMV Tn PuroMAR Flanked Backbone #5024 (p5024)

This vector (SEQ ID NO:10) is a modification of p5018 (SEQ ID NO:5), which includes the deletion of the CMV Enhancer region of the transposase cassette. The CMV enhancer was removed from p5018 by digesting the backbone with MscI and AfeI restriction enzymes (New England Biolabs, Beverly, Mass.). The digested product was electrophoresed, stained with Syber Safe DNA Gel Stain (Invitrogen Life Technologies, Carlsbad, Calif.), and visualized on a Visi-Blue transilluminator (UVP Laboratory Products, Upland, Calif.). A band corresponding to the expected size of the backbone without the enhancer region was excised from the gel and purified from the agarose using a Zymo Clean Gel Recovery Kit (Zymo Research, Orange, Calif.).

Backbone DNA from above was re-circularized using an Epicentre Fast Ligase Kit (Epicentre Biotechnologies, Madison, Wis.) according to the manufacturer's protocol. The ligation was transformed into *E. coli* Top10 cells (Invitrogen Life Technologies, Carlsbad, Calif.) using chemical transformation according to the manufacturer's protocol. Transformed cells were incubated in 250 ml of SOC (GIBCO BRL, CAT#15544-042) for 1 hour at 37° C. then spread onto LB agar plates supplemented with 100 μg/ml ampicillin (LB/amp plates). All plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining Colonies producing a plasmid of the expected size were cultured in 5 ml of LB/amp broth. Plasmid DNA was harvested using Fermentas' Gene Jet Plasmid Miniprep Kit according to the manufacturer's protocol (Glen Burnie, Md.). The DNA was then used as a sequencing template to verify that any changes made in the vector were desired changes and that no further changes or mutations occurred. All sequencing was performed using Beckman Coulter's CEQ 8000 Genetic Analysis System. Once a clone was identified containing the replacement promoter fragment, the DNA was isolated and used for cloning in specific genes of interest.

All plasmid DNA was isolated by standard procedures. Briefly, *E. coli* bacteria containing the plasmid of interest were grown in a minimum of 500 ml of LB broth (supplemented with an appropriate antibiotic) at 37° C. overnight in a shaking incubator. Plasmid DNA was isolated from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

k. Preparation of Low Expression CMV Tn PuroMAR Flanked Backbone #5025 (p5025)

This vector (SEQ ID NO:11) is a modification of p5021 (SEQ ID NO:8), which includes the deletion of the CMV Enhancer of on the transposase cassette. The CMV enhancer was removed from p5021 by digesting the backbone with MscI and AfeI restriction enzymes (New England Biolabs, Beverly, Mass.). The digested product was electrophoresed, stained with Syber Safe DNA Gel Stain (Invitrogen Life Technologies, Carlsbad, Calif.), and visualized on a Visi-Blue transilluminator (UVP Laboratory Products, Upland, Calif.). A band corresponding to the expected size of the backbone without the enhancer region was excised from the gel and purified from the agarose using a Zymo Clean Gel Recovery Kit (Zymo Research, Orange, Calif.).

Backbone DNA from above was re-circularized using an Epicentre Fast Ligase Kit (Epicentre Biotechnologies, Madison, Wis.) according to the manufacturer's protocol. The ligation was transformed into *E. coli* Top10 cells (Invitrogen Life Technologies, Carlsbad, Calif.) using chemical transformation according to the manufacturer's protocol. Transformed cells were incubated in 250 ml of SOC (GIBCO BRL, CAT#15544-042) for 1 hour at 37° C. then spread onto LB (Luria-Bertani) agar plates supplemented with 100 μg/ml ampicillin (LB/amp plates). All plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining Colonies producing a plasmid of the expected size were cultured in 5 ml of LB/amp broth. Plasmid DNA was harvested using Fermentas' Gene Jet Plasmid Miniprep Kit according to the manufacturer's protocol (Glen Burnie, Md.). The DNA was then used as a sequencing template to verify that any changes made in the vector were desired changes and that no further changes or mutations occurred. All sequencing was performed using Beckman Coulter's CEQ 8000 Genetic Analysis System. Once a clone was identified containing the replacement promoter fragment, the DNA was isolated and used for cloning in specific genes of interest.

All plasmid DNA was isolated by standard procedures. Briefly, *E. coli* bacteria containing the plasmid of interest were grown in a minimum of 500 ml of LB broth (supplemented with an appropriate antibiotic) at 37° C. overnight in a shaking incubator. Plasmid DNA was isolated from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

l. Preparation of Low Expression SV40 Promoter Tn PuroMAR Flanked Backbone #5026 (p5026)

This vector (SEQ ID NO:12) is a modification of p5018 (SEQ ID NO:5), which includes the replacement of the CMV Enhanced promoter of the transposase cassette, with the SV40 promoter from pS65T-C1 (Clontech, Mountainview, Calif.). The CMV enhanced promoter was removed from p5018 by digesting the backbone with MscI and AfeI restriction enzymes. (New England Biolabs, Beverly, Mass.). The digested product was electrophoresed, stained with Syber Safe DNA Gel Stain (Invitrogen Life Technologies, Carlsbad, Calif.), and visualized on a Visi-Blue transilluminator (UVP Laboratory Products, Upland, Calif.). A band corresponding to the expected size was excised from the gel and purified from the agarose using a Zymo Clean Gel Recovery Kit (Zymo Research, Orange, Calif.). The SV40 promoter fragment was amplified to add the 5' and 3' cut sites, MscI and AscI, respectively. The PCR product was then cloned into pTopo Blunt II backbone (Invitrogen Life Technologies, Carlsbad, Calif.). Sequence verified DNA was then digested out of the pTopo Blunt II backbone (Invitrogen Life Technologies, Carlsbad, Calif.), with MscI and AfeI restriction enzymes (New England Biolabs, Beverly, Mass.). The digested product was electrophoresed, stained with Syber Safe DNA Gel Stain (Invitrogen Life Technologies, Carlsbad, Calif.), and visualized on a Visi-Blue transilluminator (UVP Laboratory Products, Upland, Calif.). A band corresponding to the expected size was excised from the gel and purified from the agarose using a Zymo Clean Gel Recovery Kit (Zymo Research, Orange, Calif.).

Purified digestion product was ligated into the excised backbone DNA using Epicentre's Fast Ligase Kit (Madison, Wis.) according to the manufacturer's protocol. The ligation product was transformed into *E. coli* Top10 cells (Invitrogen Life Technologies, Carlsbad, Calif.) using chemical transformation according to the manufacturer's protocol. Transformed cells were incubated in 250 ml of SOC (GIBCO BRL, CAT#15544-042) for 1 hour at 37° C. before then spread onto LB agar plates supplemented with 100 μg/ml ampicillin (LB/amp plates). All plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in 5 ml of LB/amp broth. The plasmid DNA was harvested using a Fermentas' Gene Jet Plasmid Miniprep Kit according to the manufacturer's protocol (Glen Burnie, Md.). The DNA was then used as sequencing template to verify that any changes made in the vector were desired changes and that no further changes or mutations occurred. All sequencing was performed using Beckman Coulter's CEQ 8000 Genetic Analysis System. Once a clone was identified that contained the replacement promoter fragment, the DNA was isolated for use in cloning in specific genes of interest.

All plasmid DNA was isolated by standard procedures. Briefly, *E. coli* bacteria containing the plasmid of interest were grown in a minimum of 500 mL of LB broth (supplemented with an appropriate antibiotic) at 37° C. overnight in a shaking incubator. Plasmid DNA was isolated from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

m. Preparation of Low Expression SV40 Promoter Tn PuroMAR Flanked Backbone #5027 (p5027)

This vector (SEQ ID NO:13) is a modification of p5021 (SEQ ID NO:8), which includes the replacement of the CMV Enhanced promoter of the transposase cassette, with the SV40 promoter from pS65T-C1 (Clontech, Mountainview, Calif.). The CMV enhanced promoter was removed from p5021 by digesting the backbone with MscI and AfeI restriction enzymes (New England Biolabs, Beverly, Mass.). The digested product was electrophoresed, stained with Syber Safe DNA Gel Stain (Invitrogen Life Technologies, Carlsbad, Calif.), and visualized on a Visi-Blue transilluminator (UVP Laboratory Products, Upland, Calif.). A band corresponding to the expected size was excised from the gel and purified from the agarose using a Zymo Clean Gel Recovery Kit (Zymo Research, Orange, Calif.). The SV40 promoter fragment was amplified to add the 5' and 3' cut sites, MscI and AscI, respectively. The PCR product was then cloned into pTopo Blunt II backbone (Invitrogen Life Technologies, Carlsbad, Calif.). Sequence verified DNA was then digested out of the pTopo Blunt II backbone (Invitrogen Life Technologies, Carlsbad, Calif.), with MscI and AfeI restriction enzymes (New England Biolabs, Beverly, Mass.). The digested product was electrophoresed, stained with Syber Safe DNA Gel Stain (Invitrogen Life Technologies, Carlsbad, Calif.), and visualized on a Visi-Blue transilluminator (UVP Laboratory Products, Upland, Calif.). A band corresponding to the expected size was excised from the gel and purified from the agarose using a Zymo Clean Gel Recovery Kit (Zymo Research, Orange, Calif.).

Purified digestion product was ligated into the excised backbone DNA using Epicentre's Fast Ligase Kit (Madison, Wis.) according to the manufacturer's protocol. The ligation product was transformed into *E. coli* Top10 cells (Invitrogen Life Technologies, Carlsbad, Calif.) using chemical transformation according to the manufacturer's protocol. Transformed cells were incubated in 250 μl of SOC (GIBCO BRL, CAT#15544-042) for 1 hour at 37° C. before being spread onto LB agar plates supplemented with 100 μg/ml ampicillin (LB/amp plates). All plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on an ultraviolet transilluminator after ethidium bromide staining. Colonies producing a plasmid of the expected size were cultured in 5 ml of LB/amp broth. The plasmid DNA was harvested using a Fermentas' Gene Jet Plasmid Miniprep Kit according to the manufacturer's protocol (Glen Burnie, Md.). The DNA was then used as sequencing template to verify that any changes made in the vector were desired changes and that no further changes or mutations occurred. All sequencing was performed using Beckman Coulter's CEQ 8000 Genetic Analysis System. Once a clone was identified that contained the replacement promoter fragment, the DNA was isolated for use in cloning in specific genes of interest.

All plasmid DNA was isolated by standard procedures. Briefly, *E. coli* bacteria containing the plasmid of interest were grown in a minimum of 500 mL of LB broth (supplemented with an appropriate antibiotic) at 37° C. overnight in a shaking incubator. Plasmid DNA was isolated from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

2. Promoters

A second embodiment of this invention are hybrid promoters that consist of elements from the constitutive CMV promoter and the estrogen inducible ovalbumin promoter. The goal of designing these promoters was to couple the high rate of expression associated with the CMV promoter with the estrogen inducible function of the ovalbumin promoter. To accomplish this goal, two hybrid promoters, designated versions 1 and 2 (SEQ ID NOs:14 and 15, respectively) (FIG. 1), were designed, built, and tested in cell culture. Both versions 1 and 2 provided high rates of expression.

a. Version 1 CMV/Oval Promoter 1=ChOvp/CMVenh/CMVp

Hybrid promoter version 1 (SEQ ID NO:14) was constructed by ligating the chicken ovalbumin promoter regulatory elements to the 5' end of the CMV enhancer and promoter. A schematic is shown in FIG. 1A.

Hybrid promoter version 1 was made by PCR amplifying nucleotides 1090 to 1929 of the ovalbumin promoter (GenBank #J00895) from the chicken genome and cloning this DNA fragment into the pTopo vector (Invitrogen, Carlsbad, Calif.). Likewise, nucleotides 245-918 of the CMV promoter and enhancer were removed from the pgWiz vector (Clon-Tech, Mountain View, Calif.) and cloned into the pTopo vector. By cloning each fragment into the multiple cloning site of the pTopo vector, an array of restriction enzyme sites were available on each end of the DNA fragments which greatly facilitated cloning without PCR amplification. Each fragment was sequenced to verify it was the correct DNA sequence. Once sequence verified, the pTopo clone containing the ovalbumin promoter fragment was digested with Xho I and EcoR I, and the product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.). The pTopo clone containing the CMV promoter was treated in the same manner to open up the plasmid 5' to the CMV promoter; these restriction enzymes also allowed directional cloning of the ovalbumin promoter fragment upstream of CMV.

All plasmid DNA was isolated by standard procedures. Briefly, *E. coli* containing the plasmid were grown in 500 mL aliquots of LB broth (supplemented with an appropriate antibiotic) at 37° C. overnight with shaking. Plasmid DNA was recovered from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

b. Version 2 CMV/Oval Promoter=ChSDRE/CMVenh/ChNRE/CMVp

Hybrid promoter version 2 (SEQ ID NO:15) consisted of the steroid dependent response element (SDRE) ligated 5' to the CMV enhancer (enh) and the CMV enhancer and promoter separated by the chicken ovalbumin negative response element (NRE).

A schematic is shown in FIG. 1B. Hybrid promoter version 2 was made by PCR amplifying the steroid dependent response element (SDRE), nucleotides 1100 to 1389, and nucleotides 1640 to 1909 of the negative response element (NRE) of the ovalbumin promoter (GenBank #J00895) from the chicken genome and cloning each DNA fragment into the pTopo vector. Likewise, nucleotides 245-843 of the CMV enhancer and nucleotides 844-915 of the CMV promoter were removed from the pgWiz vector and each cloned into the pTopo vector. By cloning each piece into the multiple cloning site of the pTopo vector, an array of restriction enzyme sites were available on each end of the DNA fragments which greatly facilitated cloning without PCR amplification.

Each fragment was sequenced to verify it was the correct DNA sequence. Once sequence verified, the pTopo clone containing the ovalbumin SDRE fragment was digested with Xho I and EcoR I to remove the SDRE, and the product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.). The pTopo clone containing the CMV enhancer was treated in the same manner to open up the plasmid 5' to the CMV enhancer; these restriction enzymes also allowed directional cloning of the ovalbumin SDRE fragment upstream of CMV. The ovalbumin NRE was removed from pTopo using NgoM IV and Kpn I; the same restriction enzymes were used to digest the pTopo clone containing the CMV promoter to allow directional cloning of the NRE.

The DNA fragments were purified as described above. The new pTopo vectors containing the ovalbumin SDRE/CMV enhancer and the NRE/CMV promoter were sequence verified for the correct DNA sequence. Once sequence verified, the pTopo clone containing the ovalbumin SDRE/CMV enhancer fragment was digested with Xho I and NgoM IV to remove the SDRE/CMV Enhancer, and the product was electrophoresed on a 1% agarose gel, stained with ethidium bromide, and visualized on an ultraviolet transilluminator. A band corresponding to the expected size was excised from the gel and purified from the agarose using a Zymo Clean Gel Recovery Kit (Zymo Research, Orange, Calif.). The pTopo clone containing the NRE/CMVpromoter was treated in the same manner to open up the plasmid 5' to the CMV enhancer. These restriction enzymes also allowed directional cloning of the ovalbumin SDRE fragment upstream of CMV. The resulting promoter hybrid was sequence verified to insure that it was correct.

All plasmid DNA was isolated by standard procedures. Briefly, *E. coli* containing the plasmid were grown in 500 mL aliquots of LB broth (supplemented with an appropriate antibiotic) at 37° C. overnight with shaking. Plasmid DNA was recovered from the bacteria using a Qiagen Maxi-Prep kit (Qiagen, Inc., Chatsworth, Calif.) according to the manufacturer's protocol. Plasmid DNA was resuspended in 500 μL of PCR-grade water and stored at −20° C. until needed.

3. Transposases and Insertion Sequences

In a further embodiment of the present invention, the transposase found in the transposase-based vector is an altered target site (ATS) transposase and the insertion sequences are those recognized by the ATS transposase. However, the transposase located in the transposase-based vectors is not limited to a modified ATS transposase and can be derived from any transposase. Transposases known in the prior art include those found in AC7, Tn5SEQ1, Tn916, Tn951, Tn1721, Tn 2410, Tn1681, Tn1, Tn2, Tn3, Tn4, Tn5, Tn6, Tn9, Tn10, Tn30, Tn101, Tn903, Tn501, Tn1000 (γδ), Tn1681, Tn2901, AC transposons, Mp transposons, Spm transposons, En transposons, Dotted transposons, Mu transposons, Ds transposons, dSpm transposons and I transposons. According to the present invention, these transposases and their regulatory sequences are modified for improved functioning as follows: a) the addition one or more modified Kozak sequences comprising any one of SEQ ID NOs:28 to 37 at the 3' end of the promoter operably-linked to the transposase; b) a change of the codons for the first several amino acids of the transposase, wherein the third base of each codon was changed to an A or a T without changing the corresponding amino acid; c) the addition of one or more stop codons to enhance the termination of transposase synthesis; and/or, d) the addition of an effective polyA sequence operably-linked to the transposase to further enhance expression of the transposase gene.

Although not wanting to be bound by the following statement, it is believed that the modifications of the first several N-terminal codons of the transposase gene increase transcription of the transposase gene, in part, by increasing strand dissociation. It is preferable that between approximately 1 and 20, more preferably 3 and 15, and most preferably between 4 and 12 of the first N-terminal codons of the transposase are modified such that the third base of each codon is changed to an A or a T without changing the encoded amino acid. In one embodiment, the first ten N-terminal codons of the transposase gene are modified in this manner. It is also preferred that the transposase contain mutations that make it less specific for preferred insertion sites and thus increases the rate of transgene insertion as discussed in U.S. Pat. No. 5,719,055.

In some embodiments, the transposon-based vectors are optimized for expression in a particular host by changing the methylation patterns of the vector DNA. For example, prokaryotic methylation may be reduced by using a methylation deficient organism for production of the transposon-based vector. The transposon-based vectors may also be methylated to resemble eukaryotic DNA for expression in a eukaryotic host.

Transposases and insertion sequences from other analogous eukaryotic transposon-based vectors that can also be modified and used are, for example, the *Drosophila* P element derived vectors disclosed in U.S. Pat. No. 6,291,243; the *Drosophila* mariner element described in Sherman et al. (1998); or the sleeping beauty transposon. See also Hackett et al. (1999); D. Lampe et al., 1999. Proc. Natl. Acad. Sci. USA, 96:11428-11433; S. Fischer et al., 2001. Proc. Natl. Acad. Sci. USA, 98:6759-6764; L. Zagoraiou et al., 2001. Proc. Natl. Acad. Sci. USA, 98:11474-11478; and D. Berg et al. (Eds.), Mobile DNA, Amer. Soc. Microbiol. (Washington, D.C., 1989). However, it should be noted that bacterial transposon-based elements are preferred, as there is less likelihood that a eukaryotic transposase in the recipient species will recognize prokaryotic insertion sequences bracketing the transgene.

Many transposases recognize different insertion sequences, and therefore, it is to be understood that a transposase-based vector will contain insertion sequences recognized by the particular transposase also found in the transposase-based vector. In a preferred embodiment of the invention, the insertion sequences have been shortened to about 70 base pairs in length as compared to those found in wild-type transposons that typically contain insertion sequences of well over 100 base pairs.

While the examples provided below incorporate a "cut and insert" Tn10 based vector that is destroyed following the insertion event, the present invention also encompasses the use of a "rolling replication" type transposon-based vector. Use of a rolling replication type transposon allows multiple copies of the transposon/transgene to be made from a single transgene construct and the copies inserted. This type of transposon-based system thereby provides for insertion of multiple copies of a transgene into a single genome. A rolling replication type transposon-based vector may be preferred when the promoter operably-linked to gene of interest is endogenous to the host cell and present in a high copy number or highly expressed. However, use of a rolling replication system may require tight control to limit the insertion events to non-lethal levels. Tn1, Tn2, Tn3, Tn4, Tn5, Tn9, Tn21, Tn501, Tn551, Tn951, Tn1721, Tn2410 and Tn2603 are examples of a rolling replication type transposon, although Tn5 could be both a rolling replication and a cut and insert type transposon.

4. Other Promoters and Enhancers

The first promoter operably-linked to the transposase gene and the second promoter operably-linked to the gene of interest can be a constitutive promoter or an inducible promoter. Constitutive promoters include, but are not limited to, immediate early cytomegalovirus (CMV) promoter, herpes simplex virus 1 (HSV1) immediate early promoter, SV40 promoter, lysozyme promoter, early and late CMV promoters, early and late HSV promoters, β-actin promoter, tubulin promoter, Rous-Sarcoma virus (RSV) promoter, and heat-shock protein (HSP) promoter. Inducible promoters include tissue-specific promoters, developmentally-regulated promoters and chemically inducible promoters. Examples of tissue-specific promoters include the glucose-6-phosphatase (G6P) promoter, vitellogenin promoter, ovalbumin promoter, ovomucoid promoter, conalbumin promoter, ovotransferrin promoter, prolactin promoter, kidney uromodulin promoter, and placental lactogen promoter. The G6P promoter sequence may be deduced from a rat G6P gene untranslated upstream region provided in GenBank accession number U57552.1. Examples of developmentally-regulated promoters include the homeobox promoters and several hormone induced promoters. Examples of chemically inducible promoters include reproductive hormone induced promoters and antibiotic inducible promoters such as the tetracycline inducible promoter and the zinc-inducible metallothionine promoter.

Other inducible promoter systems include the Lac operator repressor system inducible by IPTG (isopropyl beta-D-thiogalactoside) (Cronin, A. et al. 2001. Genes and Development, v. 15), ecdysone-based inducible systems (Hoppe, U. C. et al. 2000. Mol. Ther. 1:159-164); estrogen-based inducible systems (Braselmann, S. et al. 1993. Proc. Natl. Acad. Sci. 90:1657-1661); progesterone-based inducible systems using a chimeric regulator, GLVP, which is a hybrid protein consisting of the GAL4 binding domain and the herpes simplex virus transcriptional activation domain, VP16, and a truncated form of the human progesterone receptor that retains the ability to bind ligand and can be turned on by RU486 (Wang, et al. 1994. Proc. Natl. Acad. Sci. 91:8180-8184); CID-based inducible systems using chemical inducers of dimerization (CIDs) to regulate gene expression, such as a system wherein rapamycin induces dimerization of the cellular proteins FKBP12 and FRAP (Belshaw, P. J. et al. 1996. J. Chem. Biol. 3:731-738; Fan, L. et al. 1999. Hum. Gene Ther. 10:2273-2285; Shariat, S. F. et al. 2001. Cancer Res. 61:2562-2571; Spencer, D. M. 1996. Curr. Biol. 6:839-847). Chemical substances that activate the chemically inducible promoters can be administered to the animal containing the transgene of interest via any method known to those of skill in the art.

Other examples of cell-specific and constitutive promoters include but are not limited to smooth-muscle SM22 promoter, including chimeric SM22alpha/telokin promoters (Hoggatt A. M. et al., 2002. Circ Res. 91(12):1151-9); ubiquitin C promoter (Biochim Biophys Acta, 2003. Jan. 3; 1625(1):52-63); Hsf2 promoter; murine COMP (cartilage oligomeric matrix protein) promoter; early B cell-specific mb-1 promoter (Sigvardsson M., et al., 2002. Mol. Cell. Biol. 22(24): 8539-51); prostate specific antigen (PSA) promoter (Yoshimura I. et al., 2002, J. Urol. 168(6):2659-64); exorh promoter and pineal expression-promoting element (Asaoka Y., et al., 2002. Proc. Natl. Acad. Sci. 99(24):15456-61); neural and liver ceramidase gene promoters (Okino N. et al., 2002. Biochem. Biophys. Res. Commun. 299(1):160-6); PSP94 gene promoter/enhancer (Gabril M. Y. et al., 2002. Gene Ther. 9(23):1589-99); promoter of the human FAT/CD36 gene (Kuriki C., et al., 2002. Biol. Pharm. Bull. 25(11): 1476-8); VL30 promoter (Staplin W. R. et al., 2002. Blood Oct. 24, 2002); and, IL-10 promoter (Brenner S., et al., 2002. J. Biol. Chem. Dec. 18, 2002). Additional promoters are shown in Table 1.

Examples of avian promoters include, but are not limited to, promoters controlling expression of egg white proteins, such as ovalbumin, ovotransferrin (conalbumin), ovomucoid, lysozyme, ovomucin, g2 ovoglobulin, g3 ovoglobulin, ovoflavoprotein, ovostatin (ovomacroglobin), cystatin, avidin, thiamine-binding protein, glutamyl aminopeptidase minor glycoprotein 1, minor glycoprotein 2; and promoters controlling expression of egg-yolk proteins, such as vitellogenin, very low-density lipoproteins, low density lipoprotein, cobalamin-binding protein, riboflavin-binding protein, biotin-binding protein (Awade, 1996. Z. Lebensm. Unters. Forsch. 202:1-14). An advantage of using the vitellogenin promoter is that it is active during the egg-laying stage of an animal's life-cycle, which allows for the production of the protein of interest to be temporally connected to the import of the protein of interest into the egg yolk when the protein of interest is equipped with an appropriate targeting sequence. As used herein, the "protein of interest" is an antibody. In some embodiments, the avian promoter is an oviduct-specific promoter. As used herein, the term "oviduct-specific promoter" includes, but is not limited to, ovalbumin; ovotransferrin (conalbumin); ovomucoid; 01, 02, 03, 04 or 05 avidin; ovomucin; g2 ovoglobulin; g3 ovoglobulin; ovoflavoprotein; and ovostatin (ovomacroglobin) promoters.

When germline transformation occurs via cardiovascular, intraovarian or intratesticular administration, or when hepatocytes are targeted for incorporation of components of a vector through non-germ line administration, liver-specific promoters may be operably-linked to the gene of interest to achieve liver-specific expression of the transgene. Liver-specific promoters of the present invention include, but are not limited to, the following promoters, vitellogenin promoter, G6P promoter, cholesterol-7-alpha-hydroxylase (CYP7A) promoter, phenylalanine hydroxylase (PAH) promoter, protein C gene promoter, insulin-like growth factor I (IGF-I) promoter, bilirubin UDP-glucuronosyltransferase promoter, aldolase B promoter, furin promoter, metallothionine promoter, albumin promoter, and insulin promoter.

Also included in this invention are modified promoters/enhancers wherein elements of a single promoter are duplicated, modified, or otherwise changed. In one embodiment, steroid hormone-binding domains of the ovalbumin promoter are moved from about −3.5 kb to within approximately the first 1000 base pairs of the gene of interest. Modifying an existing promoter with promoter/enhancer elements not found naturally in the promoter, as well as building an entirely synthetic promoter, or drawing promoter/enhancer elements from various genes together on a non-natural backbone, are all encompassed by the current invention.

Accordingly, it is to be understood that the promoters contained within the transposon-based vectors of the present invention may be entire promoter sequences or fragments of promoter sequences. The constitutive and inducible promoters contained within the transposon-based vectors may also be modified by the addition of one or more modified Kozak sequences comprising any one of SEQ ID NOs:28 to 37.

As indicated above, the present invention includes transposon-based vectors containing one or more enhancers. These enhancers may or may not be operably-linked to their native promoter and may be located at any distance from their operably-linked promoter. A promoter operably-linked to an enhancer and a promoter modified to eliminate repressive regulatory effects are referred to herein as an "enhanced promoter." The enhancers contained within the transposon-based vectors may be enhancers found in birds, such as an ovalbumin enhancer, but are not limited to these types of enhancers. In one embodiment, an approximately 675 base pair enhancer element of an ovalbumin promoter is cloned upstream of an ovalbumin promoter with 300 base pairs of spacer DNA separating the enhancer and promoter. In one embodiment, the enhancer used as a part of the present invention comprises base pairs 1-675 of a chicken ovalbumin enhancer from GenBank accession #S82527.1. The polynucleotide sequence of this enhancer is provided in SEQ ID NO:38.

Also included in some of the transposon-based vectors of the present invention are cap sites and fragments of cap sites. In one embodiment, approximately 50 base pairs of a 5' untranslated region wherein the cap site resides are added on the 3' end of an enhanced promoter or promoter. An exemplary 5' untranslated region is provided in SEQ ID NO:39. A putative cap-site residing in this 5' untranslated region preferably comprises the polynucleotide sequence provided in SEQ ID NO:40.

In one embodiment of the present invention, the first promoter operably-linked to the transposase gene is a constitutive promoter and the second promoter operably-linked to the gene of interest is a cell specific promoter. In the second embodiment, use of the first constitutive promoter allows for constitutive activation of the transposase gene and incorporation of the gene of interest into virtually all cell types, including the germline of the recipient animal. Although the gene of interest is incorporated into the germline generally, the gene of interest may only be expressed in a tissue-specific manner to achieve gene therapy. A transposon-based vector having a constitutive promoter operably-linked to the transposase gene can be administered by any route, and in several embodiments, the vector is administered to the cardiovascular system, directly to an ovary, to an artery leading to the ovary or to a lymphatic system or fluid proximal to the ovary. In another embodiment, the transposon-based vector having a constitutive promoter operably-linked to the transposase gene can be administered to vessels supplying the liver, muscle, brain, lung, kidney, heart or any other desired organ, tissue or cellular target. In another embodiment, the transposon-based vector having a constitutive promoter operably-linked to the transposase gene can be administered to cells for culture in vitro.

It should be noted that cell- or tissue-specific expression as described herein does not require a complete absence of expression in cells or tissues other than the preferred cell or tissue. Instead, "cell-specific" or "tissue-specific" expression refers to a majority of the expression of a particular gene of interest in the preferred cell or tissue, respectively.

When incorporation of the gene of interest into the germline is not preferred, the first promoter operably-linked to the transposase gene can be a tissue-specific or cell-specific promoter. For example, transfection of a transposon-based vector containing a transposase gene operably-linked to a liver specific promoter such as the G6P promoter or vitellogenin promoter provides for activation of the transposase gene and incorporation of the gene of interest in the cells of the liver in vivo, or in vitro, but not into the germline and other cells generally. In another example, transfection of a transposon-based vector containing a transposase gene operably-linked to an oviduct specific promoter such as the ovalbumin promoter provides for activation of the transposase gene and incorporation of the gene of interest in the cells of the oviduct in vivo or into oviduct cells in vitro, but not into the germline and other cells generally. In this embodiment, the second promoter operably-linked to the gene of interest can be a constitutive promoter or an inducible promoter. In one embodiment, both the first promoter and the second promoter are an ovalbumin promoter. In embodiments wherein tissue-specific expression or incorporation is desired, it is preferred that the transposon-based vector is administered directly to the tissue of interest, to the cardiovascular system which provides blood supply to the tissue of interest, to an artery leading to the organ or tissue of interest or to fluids surrounding the organ or tissue of interest. In one embodiment, the tissue of interest is the oviduct and administration is achieved by direct injection into the oviduct, into the cardiovascular system, or an artery leading to the oviduct. In another embodiment, the tissue of interest is the liver and administration is achieved by direct injection into the cardiovascular system, the portal vein or hepatic artery. In another embodiment, the tissue of interest is cardiac muscle tissue in the heart and administration is achieved by direct injection into the coronary arteries or left cardiac ventricle. In another embodiment, the tissue of interest is neural tissue and administration is achieved by direct injection into the cardiovascular system, the left cardiac ventricle, a cerebrovascular or spinovascular artery. In yet another embodiment, the target is a solid tumor and the administration is achieved by injection into a vessel supplying the tumor or by injection into the tumor.

Accordingly, cell specific promoters may be used to enhance transcription in selected tissues. In birds, for example, promoters that are found in cells of the fallopian tube, such as ovalbumin, conalbumin, ovomucoid and/or lysozyme, are used in the vectors to ensure transcription of the gene of interest in the epithelial cells and tubular gland cells of the fallopian tube, leading to synthesis of the desired protein encoded by the gene and deposition into the egg white. In liver cells, the G6P promoter may be employed to drive transcription of the gene of interest for protein production. Proteins made in the liver of birds may be delivered to the egg yolk. Proteins made in transfected cells in vitro may be released into cell culture medium.

In order to achieve higher or more efficient expression of the transposase gene, the promoter and other regulatory sequences operably-linked to the transposase gene may be those derived from the host. These host specific regulatory sequences can be tissue specific as described above or can be of a constitutive nature.

TABLE 1

| Reproductive tissue | Promoter | Ref. | Function/comments |
|---|---|---|---|
| testes, spermatogenesis | SPATA4 | 1 | constitutive 30 d after birth in rat |
| placenta, glycoprotein | ERVWE1 | 2 | URE, Upstream Regulatory Element is tissue spec. enhancer |
| breast epithelium and breast cancer | mammaglobin | 6 | specific to breast epithelium and cancer |
| prostate | EPSA | 17 | enhanced prostate-specific antigen promoter |
| testes | ATC | 25 | AlphaT-catenin specific for testes, skeletal, brain cardiomyocytes |
| prostate | PB | 67 | probasin promoter |
| Vision | | | |
| rod/cone | mCAR | 3 | cone photoreceptors and pinealocytes |
| retina | ATH5 | 15 | functions in retinal ganglia and precursors |
| eye, brain | rhodopsin | 27 | |
| kertocytes | keratocan | 42 | specific to the corneal stroma |
| retina | RPE65 | 59 | |
| Muscle | | | |
| vascular smooth muscle | TFPI | 13 | Tissue Factor Pathway Inhibitor - low level expression in endothelial and smooth muscle cells of vascular system |
| cardiac specific | MLC2v | 14, 26 | ventricular myosin light chain |
| cardiac | CAR3 | 18 | BMP response element that directs cardiac specific expression |
| skeletal | C5-12 | 22 | high level, muscle spec expression to drive target gene |
| skeletal | AdmDys, AdmCTLA4Ig | 32 | muscle creatine kinase promoter |
| smooth muscle | PDE5A | 41 | chromosome 4q26, phosphodiesterase |
| smooth muscle | AlphaTM | 45 | use intronic splicing elements to restrict expression to smooth muscle vs skeletal |
| skeletal | myostatin | 48 | fiber type-specific expression of myostatin |
| Endocrine/nervous | | | |
| glucocorticoid | GR 1B-1E | 4, 12 | glucocorticoid receptor promoter/all cells |
| neuroblastoma | M2-2 | 8, 36 | M2 muscarinic receptor |
| brain | Abeta | 16 | amyloid beta-protein; 30 bp fragment needed for PC12 and glial cell expression |
| brain | enolase | 21 | neuron-specific; high in hippocampus, intermediate in cortex, low in cerebellum |
| synapses | rapsyn | 29 | clusters acetylcholine receptors at neuromuscular junction |
| neuropeptide precursor | VGF | 39 | express limited to neurons in central and peripheral nervous system and specific endocrine cells in adenohypophysis, adrenal medulla, GI tract and pancreas |
| mammalian nervous system | BMP/RA | 46 | use of methylation to control tissue specificity in neural cells. |
| central and peripheral noradrenergic neurons | Phox2a/Phox2b | 47 | regulation of neuron differentiation |
| brain | BAI1-AP4 | 55 | spec to cerebral cortex and hippocampus |
| Gastrointestinal | | | |
| UDP glucoronsyltransferase | UGT1A7 | 11 | gastric mucosa |
| | UGT1A8 | 11 | small intestine and colon |
| | UGT1A10 | 11 | small intestine and colon |
| colon cancer | PKCbetaII | 20 | Protein kinase C betaII (PKCbetaII); express in colon cancer to selectively kill it. |
| Cancer | | | |
| tumor suppressor 4.1B | 4.1B | 5 | 2 isoforms, 1 spec to brain, 1 in kidney |
| nestin | nestin | 63 | second intron regulates tissue specificity |
| cancer spec promoter | hTRT/hSPA1 | 68 | dual promoter system for cancer specificity |
| Blood/lymph system | | | |
| Thyroid | thyroglobulin | 10 | Thyroid spec. - express to kill thyroid tumors |
| Thyroid | calcitonin | 10 | medullary thyroid tumors |
| Thyroid | GR 1A | 12 | |

TABLE 1-continued

| Reproductive tissue | Promoter | Ref. | Function/comments |
|---|---|---|---|
| thyroid | thyroglobulin | 50 | regulation controlled by DREAM transcriptional repressor |
| arterial endothelial cells | ALK1 | 60 | activin receptor-like kinase |
| Nonspecific | | | |
| RNA polymerase II | | 7 | |
| gene silencing | Gnasx1, Nespas | 31 | |
| beta-globin | beta globin | 53 | |
| Cardiac | M2-1 | 8 | M2 muscarinic receptor |
| Lung | hBD-2 | 19 | IL-17 induced transcription in airway epithelium |
| pulmonary surfactant protein | SP-C | 62 | Alveolar type II cells |
| ciliated cell-specific prom | FOZJ1 | 70 | use in ciliated epithelial cells for CF treatment |
| surfactant protein expression | SPA-D | 73 | Possible treatment in premature babies |
| Clara cell secretory protein | CCSP | 75 | |
| Dental | | | |
| teeth/bone | DSPP | 28 | extracellular matrix protein dentin sialophosphoprotein |
| Adipose | | | |
| adipogenesis | EPAS1 | 33 | endothelial PAS domain - role in adipocyte differentiation |
| Epidermal | | | |
| differentiated epidermis | involucrin | 38 | stratum granulosum and stratum |
| desmosomal protein | CDSN | 58 | corneum of epidermis |
| Liver | | | |
| liver spec albumin | Albumin | 49 | |
| serum alpha-fetoprotein | AFP | 56 | liver spec regulation |

REFERENCES

1. Biol Pharm Bull. 2004 November; 27(11):1867-70
2. J Virol. 2004 November; 78(22):12157-68
3. Invest Opthalmol Vis Sci. 2004 November; 45(11):3877-84
4. Biochim Biophys Acta. 2004 Oct. 21; 1680(2):114-28
5. Biochim Biophys Acta. 2004 Oct. 21; 1680(2):71-82
6. Curr Cancer Drug Targets. 2004 September; 4(6):531-42
7. Biotechnol Bioeng. 2004 Nov. 20; 88(4):417-25
8. J Neurochem. 2004 October; 91(1):88-98
10. Curr Drug Targets Immune Endocr Metabol Disord. 2004 September; 4(3):235-44
11. Toxicol Appl Pharmacol. 2004 Sep. 15; 199(3):354-63
12. J Immunol. 2004 Sep. 15; 173(6):3816-24
13. Thromb Haemost. 2004 September; 92(3):495-502
14. Acad Radiol. 2004 September; 11(9):1022-8
15. Development. 2004 September; 131(18):4447-54
16. J Neurochem. 2004 September; 90(6):1432-44
17. Mol Ther. 2004 September; 10(3):545-52
18. Development. 2004 October; 131(19):4709-23. Epub 2004 Aug. 25
19. J Immunol. 2004 Sep. 1; 173(5):3482-91
20. J Biol Chem. 2004 Oct. 29; 279(44):45556-63. Epub 2004 Aug. 20
21. J Biol Chem. 2004 Oct. 22; 279(43):44795-801. Epub 2004 Aug. 20
22. Hum Gene Ther. 2004 August; 15(8):783-92
25. Nucleic Acids Res. 2004 Aug. 9; 32(14):4155-65. Print 2004
26. Mol Imaging. 2004 April; 3(2):69-75
27. J Gene Med. 2004 August; 6(8):906-12
28. J Biol Chem. 2004 Oct. 1; 279(40):42182-91. Epub 2004 Jul. 28
29. Mol Cell Biol. 2004 August; 24(16):7188-96
31. Nat Genet. 2004 August; 36(8):894-9. Epub 2004 Jul. 25
32. Gene Ther. 2004 October; 11(19):1453-61
33. J Biol Chem. 2004 Sep. 24; 279(39):40946-53. Epub 2004 Jul. 15
36. Brain Res Mol Brain Res. 2004 Jul. 26; 126(2):173-80
38. J Invest Dermatol. 2004 August; 123(2):313-8
39. Cell Mol Neurobiol. 2004 August; 24(4):517-33
41. Int J Impot Res. 2004 June; 16 Suppl 1:S8-S10
42. Invest Opthalmol Vis Sci. 2004 July; 45(7):2194-200
45. J Biol Chem. 2004 Aug. 27; 279(35):36660-9. Epub 2004 Jun. 11
46. Brain Res Mol Brain Res. 2004 Jun. 18; 125(1-2):47-59
47. Brain Res Mol Brain Res. 2004 Jun. 18; 125(1-2):29-39
48. Am J Physiol Cell Physiol. 2004 October; 287(4):C1031-40. Epub 2004 Jun. 9
49. Xi Bao Yu Fen Zi Mian Yi Xue Za Zhi. 2003 November; 19(6):601-3
50. J Biol Chem. 2004 Aug. 6; 279(32):33114-22. Epub 2004 Jun. 4
53. Brief Funct Genomic Proteomic. 2004 February; 2(4):344-54
55. FEBS Lett. 2004 May 21; 566(1-3):87-94
56. Biochem Biophys Res Commun. 2004 Jun. 4; 318(3):773-85
58. J Invest Dermatol. 2004 March; 122(3):730-8
59. Mol Vis. 2004 Mar. 26; 10:208-14
60. Circ Res. 2004 Apr. 30; 94(8):e72-7. Epub 2004 Apr. 1
62. Am J Physiol Lung Cell Mol Physiol. 2004 Dec. 3; [Epub ahead of print]
63. Lab Invest. 2004 December; 84(12):1581-92
67. Prostate. 2004 Jun. 1; 59(4):370-82
68. Cancer Res. 2004 Jan. 1; 64(1):363-9
70. Mol Ther. 2003 October; 8(4):637-45
73. Front Biosci. 2003 May 1; 8:d751-64
75. Am J Respir Cell Mol Biol. 2002 August; 27(2):186-93

B. Methods of Transfecting Cells

1. Transfection of LMH or LMH2A Cells In Vitro

DNA

Antibody expression vector DNA (e.g., any one of SEQ ID NOs:17-27) DNA was prepared in either methylating or non-methylating bacteria, and was endotoxin-free. Agarose gels showed a single plasmid of the appropriate size. DNA was resuspended in molecular biology grade, sterile water at a concentration of at least 0.5 μg/μl. The concentration was verified by spectrophotometry, and the 260/280 ratio was 1.8 or greater. A stock of each DNA sample, diluted to 0.5 μg/μl in sterile, molecular biology grade water, was prepared in the cell culture lab, and this stock used for all transfections. When not in use, the DNA stocks were kept frozen at −30° C. in small aliquots to avoid repeated freezing and thawing.

Transfection

The transfection reagent used for LMH2A cells was FuGENE 6 (Roche Applied Science). This reagent was used at a 1:6 ratio (μg of DNA: μl of transfection reagent) for all transfections in LMH2A cells. The chart below shows the amount of DNA and FuGENE 6 used for typical cell culture formats (T25 and T75 tissue culture flasks). If it is necessary to perform transfections in other formats, the amounts of serum free medium (SFM), FuGENE 6 and DNA are scaled appropriately based on the surface area of the flask or well used. The diluent (SFM) is any serum-free cell culture media appropriate for the cells, and it did not contain any antibiotics or fungicides.

TABLE 2

DNA:FuGENE = 1:6
[DNA] = 0.5 μg/μl

| | T25 | T75 |
|---|---|---|
| SFM | 250 μl | 800 μl |
| FuGENE 6 | 12 μl | 48 μl |
| DNA | 4 μl | 16 μl |

Protocol

1. Cells used for transfection were split 24-48 hours prior to the experiment, so that they were actively growing and 50-80% confluent at the time of transfection.
2. FuGENE was warmed to room temperature before use. Because FuGENE is sensitive to prolonged exposure to air, the vial was kept tightly closed when not in use. The vial of FuGENE was returned to the refrigerator as soon as possible.
3. The required amount of FuGENE was pipetted into the SFM in a sterile microcentrifuge tube. The fluid was mixed gently but thoroughly, by tapping or flicking the tube, and incubated for 5 minutes at room temperature.
4. The required amount of DNA was added to the diluted FuGENE and mixed by vortexing for one second.
5. The mixture was incubated at room temperature for 1 hour.
6. During the incubation period, media on cells was replaced with fresh growth media. This media optionally contained serum, if needed, but did not contain antibiotics or fungicides unless absolutely required, as this can reduce the transfection efficiency.
7. The entire volume of the transfection complex was added to the cells. The flask was rocked to mix thoroughly.
8. The flasks were incubated at 37° C. and 5% $CO_2$.
9. Cells were fed, and samples obtained as required. After the first 24 hours, cells were optionally fed with media containing antibiotics and/or fungicides, if desired.

2. Transfection of LMH Cells and Tubular Gland Cells

The same methods described above for LMH and LMH2A cells are used for transfection of chicken tubular gland cells or other cell types such as Chinese hamster ovary (CHO) cells, CHO-K1 cells, chicken embryonic fibroblasts, HeLa cells, Vero cells, FAO (liver cells), human 3T3 cells, A20 cells, EL4 cells, HepG2 cells, J744A cells, Jurkat cells, P388D1 cells, RC-4B/c cells, SK-N-SH cells, Sp2/mIL-6 cells, SW480 cells, 3T6 Swiss cells, and human ARPT-19 cells.

C. Purification of Monoclonal Antibodies

Media Preparation

Media containing recombinant monoclonal antibodies produced by transfected cells was harvested and immediately frozen. Later the medium was thawed, filtered through a 0.45 micron cellulose acetate bottle-top filter to ensure that all particulate was removed prior to being loaded on the column.

Purification Procedure

Human monoclonal antibodies (hIgG) were purified using the EGGstract® IgY Purification System (cat.#G2610, Promega, USA) as follows.

1. Stirred the 30 mls cell culture media at room temperature and slowly added 10 mls of Precipitation Solution B (EGGstract® IgY Purification System).
2. Continued stirring the mixture for 5 minutes to precipitate the IgG.
3. Centrifuged the mixture at 10,000×g for 15 minutes at 4° C. (Increased time for lower centrifugal forces.)
4. Poured off the supernatant and discard.
5. Resuspended the IgG pellet in a 1 ml of 1×PBS by capping the 50-ml conical tube and rocking at room temperature for up to 2 hours.

The suspended monoclonal antibodies were concentrated and cleaned using PIERCE PAGEprep® Advance kit (Cat. 89888, Pierce, USA) as follows.

1. Vortexed the PAGE-prep Protein Binding Resin to evenly disperse the resin into a slurry.
2. Used a cut or large-orifice pipette tip to transfer 20 μl of resin slurry into the center of a spin cup. Note: Resin particles may clog ordinary pipette tips.
3. Added 300 μl of suspended IgG in 1×PBS to the resin. Capped tube and briefly vortexed.
4. Added 300 μl of 100% DMSO to the suspended hIgG added in Step 3. Capped tube and briefly vortexed.
5. Incubated sample for 4 minutes at room temperature with occasional mixing to ensure maximum protein adsorption to the resin.
6. Centrifuged sample at 2,000×g for 2 minutes. Discarded flow-through and blotted collection tube on a paper towel.
7. Reinserted spin cup into the same collection tube.
8. Prepared Wash Solution by mixing 3 mls of 100% DMSO with 3 mls of water.
9. Stored Wash Solution at room temperature.
10. Added 300 μl of Wash Solution to the resin. Capped tube and vortexed until a homogeneous suspension was obtained
11. Centrifuged sample at 2,000×g for 2 minutes. Discarded flow-through and blotted collection tube on a paper towel.
12. Reinserted spin cup into the same collection tube.
13. Repeated wash one additional time for a total of two washes.
14. Transferred the spin cup to a new collection tube and add 100 μl of Elution Buffer to the resin. Capped tube and briefly vortexed to obtain a homogeneous suspension.
15. Incubated sample at 60° C. for 5 minutes. After incubation, briefly vortexed the tube.
16. Centrifuged sample at 2,000×g for 2 minutes. Discarded spin cup and resin. Retained the collection tube containing human IgG.

The purification procedure was evaluated at various stages using a sandwich ELISA assay (See section D.1. below). SDS-PAGE analysis with subsequent Coomassie blue staining or Western blotting was done to indicate both molecular weight and purity of the purified monoclonal antibodies (See section D.2. below).

D. Monoclonal Antibody Detection

1. Monoclonal Antibody Measurement with ELISA

Monoclonal antibody was measured using the following sandwich ELISA protocol:

Heavy Chain Detection:

1. Diluted monoclonal anti-human Ig-Fc antibody (Bethyl Laboratories, Inc., A80-104A) 1:100 in carbonate buffer (Bethyl Laboratories, E101) such that the final working dilution concentration was 10 μg/mL.
2. Add 100 μL of the diluted antibody into to the appropriate wells of the ELISA plate.
3. Allowed 96-well plate to coat for 1 hour at 37° C.
4. Washed the ELISA plate five times with wash buffer (1×TBS/0.05% TWEEN).
5. Transferred 200 μL of blocking buffer (Bethyl Laboratories, E101) to the appropriate wells of the ELISA plate and allowed 96-well plate to block for 30 minutes at room temperature.
6. Diluted human reference serum standard (Bethyl Laboratories, RS10-110) in negative control media (5% FCS/Waymouth, Gibco) such that the final working dilution concentration was 50 ng/mL.
7. Diluted test samples in negative control media (5% FCS/Waymouth, Gibco).
8. Removed the blocking buffer by manually "flicking" the ELISA plate into the sink.
9. Added the diluted samples and fusion protein standards into 96-well plate and incubated the ELISA plate at room temperature for 1 hour.
10. Diluted fresh dilute monoclonal anti-IgG-Fc-HRP antibody (Bethyl Laboratories, A80-104P) 1:100,000 such that the final working dilution concentration was 10 ng/mL.
11. Added 100 μL of the diluted antibody into to the appropriate wells of the ELISA plate.
12. Incubated the ELISA plate at room temperature for 1 hour.
13. Mixed equal volumes of TMB peroxidase substrate (KPL, 50-76-01) and peroxidase solution B (KPL, 50-65-00).
14. Washed the ELISA plate five times with wash buffer (1×TBS/0.05% TWEEN).
15. Added 100 μL of the mixed substrate reagents solution to the appropriate wells of the ELISA plate
16. Added 100 μL of 2 M $H_2SO_4$ to the appropriate wells of the ELISA plate to stop the TMB reaction.
17. Using plate reader, took the absorbance readings at 450 nm of the ELISA plate at 20 minutes.

Culture medium was applied to the ELISA either in an undiluted or diluted manner. Monoclonal antibody was detected in this assay. The monoclonal antibody levels were determined by reference to the standard curve and are presented in various figures throughout this application.

SDS-PAGE analysis with subsequent Coomassie blue staining or Western blotting was done to indicate both molecular weight and purity of the purified monoclonal antibody (See section D.2. below).

Light Chain Detection:

1. Diluted monoclonal anti-human lambda light chain antibody (Bethyl Laboratories, Inc., A80-116A) 1:100 in carbonate buffer (Bethyl Laboratories, Inc, E101) such that the final working dilution concentration was 10 μg/mL.
2. Added 100 μL of the diluted antibody into to the appropriate wells of the ELISA plate.
3. Allowed 96-well plate to coat for 1 hour at 37° C.
4. Washed the ELISA plate five times with wash buffer (1×TBS/0.05% TWEEN).
5. Transferred 200 μL of blocking buffer (Bethyl Laboratories, Inc, E101) to the appropriate wells of the ELISA plate and allowed 96-well plate to block for 30 minutes at room temperature.
6. Diluted the human reference serum standard (Bethyl Laboratories, Inc., human reference serum, RS10-110) in negative control media (5% FCS/Waymouth, Gibco) such that the final working dilution concentration was 100 ng/mL.
7. Diluted test samples in negative control media (5% FCS/Waymouth, Gibco).
8. Removed the blocking buffer by manually "flicking" the ELISA plate into the sink.
9. Added the diluted samples and human reference standards into 96-well plate and incubated the ELISA plate at room temperature for 1 hour.
10. Diluted fresh Dilute anti-human lambda light chain-HRP antibody (Bethyl Laboratories, Inc., A80-116P) 1:100,000 such that the final working dilution concentration was 10 ng/mL.
11. Added 100 μL of the diluted antibody into to the appropriate wells of the ELISA plate.
12. Incubated the ELISA plate at room temperature for 1 hour.
13. Mixed equal volumes of TMB peroxidase substrate (KPL, 50-76-01) and peroxidase solution B (KPL, 50-65-00).
14. Washed the ELISA plate five times with wash buffer (1×TBS/0.05% TWEEN).
15. Added 100 μL of the mixed substrate reagents solution to the appropriate wells of the ELISA plate.
16. Added 100 μL of 2 M $H_2SO_4$ to the appropriate wells of the ELISA plate to stop the TMB reaction.
17. Using plate reader, took the absorbance readings at 450 nm of the ELISA plate at 20 minute.

Culture medium was applied to the ELISA either in an undiluted or diluted manner. Monoclonal antibody was detected in this assay. The monoclonal antibody levels were determined by reference to the standard curve and are presented in various figures throughout this application.

SDS-PAGE analysis with subsequent Coomassie blue staining or Western blotting was done to indicate both molecular weight and purity of the purified monoclonal antibody (See section D.2. below).

2. Detection of Monoclonal Antibody Expression with Immunoblotting

SDS-PAGE:

Sample mixtures, including negative control media, were heated under reduced (with DTT) and non-reduced (without DTT) conditions for 8 minutes at 100° C. and loaded onto a 10-20% Tris-HCl gel. The samples were run at 200 V for 1 hour 15 minutes in Tris-Glycine-SDS buffer.

Heavy Chain Antibody Detection:

1. The finished gel was placed into the Western blot transfer buffer for 2 minutes. This equilibrated the gel in the buffer used for the transfer.
2. The gel was rehydrated for 1 minute in Western blot transfer buffer. A sheet of nitrocellulose paper was cut to the exact size of the gel to be transferred.
3. The electrophoretic transfer was occurred for 50 minutes at 100 V.
4. The blot was removed from the transfer apparatus and blocked with 5.0% MILK in TBS/TWEEN 20. Blocking was allowed for 1 hour at 37° C.
5. The blot was washed four times for 5 minutes per wash in TBS/TWEEN 20.

6. The blot was incubated in Dilute monoclonal anti-IgG-Fc-HRP antibody (Bethyl Laboratories, Inc., A80-104P) conjugated with horseradish peroxidase and diluted appropriately 1:5,000 with 1% gelatin in TBS/TWEEN 20 for 1 hour at room temperature.
7. The blot was washed four times for 5 minutes per wash in TBS/TWEEN 20.
8. Antibody bound to antigen was detected by using TMB membrane peroxidase Substrate (KPL, 50-77-00) Liquid Substrate System (KPL). The substrate solution was applied until color was detected (5-10 minutes).
9. Color formation (enzyme reaction) was stopped by rinsing blots with dH2O.
10. The blot was air-dried on paper towel.

Light Chain Antibody Detection:

1. The finished gel was placed into the Western blot transfer buffer for 2 minutes. This equilibrated the gel in the buffer used for the transfer.
2. The gel was rehydrated for 1 minute in Western blot transfer buffer. A sheet of nitrocellulose paper was cut to the exact size of the gel to be transferred.
3. The electrophoretic transfer occurred for 50 minutes at 100 V.
4. The blot was removed from the transfer apparatus and blocked with 5.0% MILK in TBS/TWEEN 20. Blocking was allowed for 1 hour at 37° C.
5. The blot was washed four times for 5 minutes per wash in TBS/TWEEN 20.
6. The blot was incubated in anti-human lambda light chain-HRP antibody (Bethyl Laboratories, Inc., A80-116P) conjugated with horseradish peroxidase and diluted appropriately 1:5,000 with 1% gelatin in TBS/TWEEN 20 for 1 hour at room temperature.
7. The blot was washed four times for 5 minutes per wash in TBS/TWEEN 20.
8. Antibody bound to antigen was detected by using the TMB membrane peroxidase Substrate (KPL, 50-77-00) Liquid Substrate System (KPL). The substrate solution was applied until color was detected (5-10 minutes).
9. Color formation (enzyme reaction) was stopped by rinsing blots with $dH_2O$.
10. The blot was air-dried on paper towel.

3. Vectors for Monoclonal Antibody Production

The expression vectors of the present invention employ some of the vector components (backbone vectors and promoters) described in the previous section and also include the multiple cloning site (MCS) comprising the gene of interest. In one embodiment, the gene of interest encodes for a human monoclonal antibody. In one embodiment, the gene of interest encodes for a human RM2 monoclonal antibody. The following vectors, SEQ ID NOs:17-27, all contain a gene of interest encoding a monoclonal antibody:

(SEQ ID NO:17) #148 HS4 Flanked Backbone Vector (CMVep-Intron A+RM2 mAb)
(SEQ ID NO:18) #210 pTn10, HS4 Flanked Backbone Vector (CMVep-Intron A+RM2 mAb)
(SEQ ID NO:19) #212 pTn10, MAR Flanked Backbone Vector (CMVep-Intron A+RM2 mAb)
(SEQ ID NO:20) #226 pTn10, Puro-MAR Flanked Backbone Vector (CMVep-Intron A+RM2 mAb)
(SEQ ID NO:21) #275 pTn10, Puro-MAR Flanked Backbone Vector (CMV-Ovalp Vs.1–RM2 mAb–OPA in pTn10 PURO-MAR Flanked BV
(SEQ ID NO: 22) #278 pTn10, PURO-MAR Flanked Backbone Vector (CMV-Ovalp Vs.1–ΔCH2 mAb–OPA in pTn10)
(SEQ ID NO: 23) #273 pTn10 PURO-MAR Flanked Backbone Vector (CMV-Ovalp Vs.1–RM2 mAb)
(SEQ ID NO: 24) #146/149 Vitellogenin-Intron A RM2 mAb Flanked with HS4 Backbone Vector in pTnMCS modified
(SEQ ID NO: 25) #267 Codon optimized herceptin (antibody that targets human epidermal growth factor receptor-2) gene, pTn10, Puro-MAR Flanked Backbone Vector (#5021)
(SEQ ID NO: 26) #279 Codon optimized ΔCH2 (antibody with deletion of constant region 2 of the heavy chain) gene, pTn10, Puro-MAR Flanked Backbone Vector (#5021)
(SEQ ID NO: 27) #280 Codon optimized RM2, pTn10, Puro-MAR Flanked Backbone Vector (#5021)

In specific embodiments, the disclosed backbone vectors are defined by the following annotations:

SEQ ID NO:1 (pTnMCS (Base Vector, without MCS Extension) Vector #5001

Bp 1-130 Remainder of F1 (−) ori of pBluescriptII sk(−) (Stratagene) bp1-130
Bp 133-1812 CMV promoter/enhancer taken from vector pGWIZ (Gene Therapy Systems) bp229-1873
Bp 1813-3018 Transposase, modified from Tn10 (GeneBank accession #J01829) Bp 108-1316
Bp 3019-3021 Engineered stop codon
Bp 3022-3374 Non-coding DNA from vector pNK2859
Bp 3375-3417 Lambda DNA from pNK2859
Bp 3418-3487 70 bp of IS10 left from Tn10
Bp 3494-3700 Multiple cloning site from pBluescriptII sk(−), thru the XmaI site Bp 924-718
Bp 3701-3744 Multiple cloning site from pBluescriptII sk(−), from the XmaI site thru the XhoI site. These base pairs are usually lost when cloning into pTnMCS. Bp 717-673
Bp 3745-4184 Multiple cloning site from pBluescriptII sk(−), from the XhoI site bp 672-235
Bp 4190-4259 70 bp of IS10 from Tn10
Bp 4260-4301 Lambda DNA from pNK2859
Bp 4302-5167 Non-coding DNA from pNK2859
Bp 5168-7368 pBluescriptII sk(−) base vector (Stratagene, INC) bp 761-2961

SEQ ID NO: 2 X-MCS (Vector #5005) pTNMCS (Base Vector) with MCS Extension

Bp 1-132 Remainder of F1 (−) ori of pBluescriptII sk(−) (Stratagene) Bp 4-135
Bp 133-1785 CMV Promoter/Enhancer from vector pGWIZ (Gene Therapy Systems)
Bp 1786-3018 Transposase, modified from Tn10 (GeneBank accession #J01829) Bp 81-1313
Bp 3019-3021 Engineered stop codon
Bp 3022-3374 Non-coding DNA from vector pNK2859
Bp 3375-3416 Lambda DNA from pNK2859
Bp 3417-3486 70 bp of IS10 left from Tn10 (GeneBank accession #J01829 Bp 1-70)
Bp 3487-3704 Multiple cloning site from pBluescriptII sk(−), thru XmaI
Bp 3705-3749 Multiple cloning site from pBluescriptII sk(−), from XmaI thru XhoI
Bp 3750-3845 Multiple cloning site extension from XhoI thru PspOMI
BP 3846-4275 Multiple cloning site from pBluescriptII sk(−), from PspOMI
Bp 4276-4345 70 bp of IS10 from Tn10 (GeneBank accession #J01829 Bp 70-1)
Bp 4346-4387 Lambda DNA from pNK2859
Bp 4388-5254 Non-coding DNA from pNK2859
Bp 5255-7455 pBluescriptII sk(−) base vector (Stratagene, INC) Bp 761-2961

SEQ ID NO: 3 HS4 Flanked BV (Vector #5006)

Bp 1-132 Remainder of F1 (−) ori of pBluescriptII sk(−) (Stratagene) Bp 4-135

Bp 133-1785 CMV Promoter/Enhancer from vector pGWIZ (Gene Therapy Systems) Bp 229-1873, including the combination of 2 NruI cut sites Bp 1786-3018 Transposase, modified from Tn10 (GeneBank accession #J01829) Bp 81-1313

Bp 3019-3021 Engineered stop codon

Bp 3022-3374 Non-coding DNA from vector pNK2859

Bp 3375-3416 Lambda DNA from pNK2859

Bp 3417-3490 70 bp of IS10 left from Tn10 (GeneBank accession #J01829 Bp 1-70)

Bp 3491-3680 Multiple cloning site from pBluescriptII sk(−), thru NotI Bp 926-737

Bp 3681-4922 HS4—Beta-globin Insulator Element from Chicken gDNA

Bp 4923-5018 Multiple cloning site extension XhoI thru MluI

Bp 5019-6272 HS4—Beta-globin Insulator Element from Chicken gDNA

Bp 6273-6342 70 bp of IS10 from Tn10 (GeneBank accession #J01829 Bp 70-1)

Bp 6343-6389 Lambda DNA from pNK2859

Bp 6390-8590 pBluescriptII sk(−) base vector (Stratagene, INC) Bp 761-2961

SEQ ID NO: 4 K Tn-10 HS4 Flanked Backbone (Vector #5012)

Bp. 1-132 Remaining of F1 (−) Ori from pBluescript II sk(−) (Stratagene Bp 4-135).

Bp. 133-1806 CMV Promoter/Enhancer from vector pGWIZ (Gene Therapy Systems) Bp. 229-1873.

Bp. 1807-3015 Tn-10 transposase, from pNK2859 (GeneBank accession #J01829 Bp. 81-1313).

Bp. 3016-3367 Non-coding DNA, possible putative poly A, from vector pNK2859.

Bp. 3368-3410 Lambda DNA from pNK2859.

Bp. 3411-3480 70 bp of IS 10 left from Tn10 (GeneBank accession #J01829 bp. 1-70

Bp. 3481-3674 Multiple cloning site from pBluescript II sk(−), thru NotI Bp. 926-737.

Bp. 3675-4916 Chicken Beta Globin HS4 Insulator Element (Genbank Accession #NW_060254.0).

Bp. 4917-5012 Multiple cloning site extension Xho I thru Mlu I.

Bp. 5013-6266 Chicken Beta Globin HS4 Insulator Element (Genbank Accession #NW_060254.0).

Bp. 6267-6337 70 bp of IS 10 left from Tn10 (GeneBank accession #J01829 bp. 1-70

Bp. 6338-6382 Lambda DNA from pNK2859.

Bp. 6383-8584 pBluescript II sk(−) Base Vector (Stratagene, Inc. Bp. 761-2961).

SEQ ID NO: 5 pTn10 MAR Flanked BV (Vector 5018)

Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 1770-1777 CMV Immediate Early Gene, Partial Exon 2 (pGWIZ, Gene Therapy Systems) bp 1866-1873)

Bp 1778-1806 TN10 DNA, 3'end from Genbank Accession #J01829 bp79-107

Bp 1807-3015 Transposon, modified from Tn10 GenBank Accession #J01829 Bp 108-1316

Bp 3016-3367 Putative PolyA from vector pNK2859

Bp 3368-3410 Lambda DNA from pNK2859

Bp 3411-3480 70 bp of IS10 left from Tn10 (GenBank Accession #J01829 Bp 1-70)

Bp 3481-3651 pBluescriptII sk(−) base vector (Stratagene, INC)

Bp 3652-3674 Multiple cloning site from pBluescriptII sk(−) thru NotI, Bp 759-737

Bp 3675-5367 Lysozyme Matrix Attachment Region (MAR)

Bp 5368-5463 Multiple Cloning Site Extension from pTn X-MCS, XhoI thru MluI

Bp 5464-7168 Lysozyme Matrix Attachment Region (MAR)

Bp 7169-7238 70 bp of IS10 from Tn10 (GenBank Accession #J01829 Bp 70-1)

Bp 7239-7281 Lambda DNA from pNK2859

Bp 7282-9486 pBluescriptII sk(−) base vector (Stratagene, INC)

SEQ ID NO:6 (Vector 5020 pTn10 PURO-LysRep2 Flanked BV)

Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 1770-1777 CMV Immediate Early Gene, Partial Exon 2 (pGWIZ, Gene Therapy Systems) bp 1866-1873)

Bp 1778-1806 TN10 DNA, 3'end from Genbank Accession #J01829 bp79-107

Bp 1807-3015 Transposon, modified from Tn10 GenBank Accession #J01829 Bp 108-1316

Bp 3016-3367 Putative PolyA from vector pNK2859

Bp 3368-3410 Lambda DNA from pNK2859

Bp 3411-3480 70 bp of IS10 left from Tn10 (GenBank Accession #J01829 Bp 1-70)

Bp 3481-3484 Synthetic DNA added during construction

Bp 3485-3651 pBluescriptII sk(−) base vector (Stratagene, INC) bp 926-760

Bp 3652-3674 Multiple cloning site from pBluescriptII sk(−) thru NotI, Bp 759-737

Bp 3675-4608 Lysozyme Rep2 from gDNA (corresponds to Genbank Accession #NW_060235)

Bp 4609-4686 Multiple Cloning Site Extension from pTn X-MCS, XhoI thru BsiWI

Bp 4687-4999 HSV-TK polyA from pS65TC1 bp 3873-3561

Bp 5000-5028 Excess DNA from pMOD PURO (invivoGen)

BP 5029-5630 Puromycin resistance gene from pMOD PURO (invivoGen) bp 717-116

Bp 5631-6016 SV40 promoter from pS65TC1, bp 2232-2617

Bp 6017-6022 MluI RE site

Bp 6023-6956 Lysozyme Rep2 from gDNA (corresponds to Genbank Accession #NW_060235)

Bp 6957-6968 Synthetic DNA added during construction including a PspOMI RE site

Bp 6969-7038 70 bp of IS10 from Tn10 (GenBank Accession #J01829 Bp 70-1)

Bp 7039-7081 Lambda DNA from pNK2859

Bp 7082-7085 Synthetic DNA added during construction
Bp 7086-9286 pBluescriptII sk(−) base vector (Stratagene, INC) bp 761-2961
SEQ ID NO: 8 Vector #5021 pTn10 PURO-MAR Flanked BV
Bp 1-132 Remainder of F1 (−) ori of pBluescriptII sk(−) (Stratagene) bp 4-135
Bp 133-148 pGWIZ base vector (Gene Therapy Systems) bp 229-244
Bp 149-747 CMV Enhancer (vector pGWIZ, Gene Therapy Systems bp 245-843)
Bp 748-822 CMV Promoter (vector pGWIZ, Gene Therapy Systems bp 844-918)
Bp 823-943 CMV Immediate Early Gene, Exon 1 (vector pGWIZ, Gene Therapy Systems bp 919-1039)
Bp 944-1769 CMV Intron A (vector pGWIZ, Gene Therapy Systems bp 1040-1865)
Bp 1770-1777 CMV Immediate Early Gene, Partial Exon 2 (pGWIZ, Gene Therapy Systems) bp 1866-1873)
Bp 1778-1806 TN10 DNA, 3'end from Genbank Accession #J01829 bp79-107
Bp 1807-3015 Transposon, modified from Tn10 GenBank Accession #J01829 Bp 108-1316
Bp 3016-3367 Putative PolyA from vector pNK2859
Bp 3368-3410 Lambda DNA from pNK2859
Bp 3411-3480 70 bp of IS10 left from Tn10 (GenBank Accession #J01829 Bp 1-70)
Bp 3481-3651 pBluescriptII sk(−) base vector (Stratagene, INC)
Bp 3652-3674 Multiple cloning site from pBluescriptII sk(−) thru NotI, Bp 759-737
Bp 3675-5367 Lysozyme Matrix Attachment Region (MAR)
Bp 5368-5445 Multiple Cloning Site Extension from pTn X-MCS, XhoI thru BsiWI
Bp 5446-5758 HSV-TK polyA from pS65TC1 bp 3873-3561
BP 5759-6389 Puromycin resistance gene from pMOD PURO (invivoGen)
Bp 6390-6775 SV40 promoter from pS65TC1, bp 2232-2617
Bp 6776-8486 Lysozyme Matrix Attachment Region (MAR)
Bp 8487-8556 70 bp of IS10 from Tn10 (GenBank Accession #J01829 Bp 70-1)
Bp 8557-8599 Lambda DNA from pNK2859
Bp 8600-10804 pBluescriptII sk(−) base vector (Stratagene, INC)
SEQ ID NO:9 (Vector #5022; pTn10 Gen-MAR Flanked BV)
Bp 1-5445 pTn10 MAR Flanked BV, ID #5018
Bp 5446-5900 HSV-TK polyA from Taken from pIRES2-ZsGreen1, bp 4428-3974
Bp 5901-6695 Kanamycin/Neomycin (G418) resistance gene, taken from pIRES2-ZsGreen1, Bp 3973-3179
Bp 6696-7046 SV40 early promoter/enhancer taken from pIRES2-ZsGreen1, bp 3178-2828
Bp 7047-7219 Bacterial promoter for expression of KAN resistance gene, taken from pIRES2-ZsGreen1, bp 2827-2655
Bp 7220-11248 pTn10 MAR Flanked BV, bp 5458-9486
SEQ ID NO: 10 pTn10 MAR Flanked BV Vector #5024
Bp 1-132 Remainder of F1 (−) ori of pBluescriptII sk(−) (Stratagene) bp 4-135
Bp 133-154 pGWIZ base vector (Gene Therapy Systems) bp 229-244
Bp 155-229 CMV promoter (from vector pGWIZ, Gene Therapy Systems bp 844-918
Bp 230-350 CMV Immediate Early Gene, Exon 1 (vector pGWIZ, Gene Therapy Systems bp 919-1039)
Bp 351-1176 CMV Intron A (vector pGWIZ, Gene Therapy Systems bp 1040-1865)
Bp 1177-1184 CMV Immediate Early Gene, Partial Exon 2 (pGWIZ, Gene Therapy Systems) bp 1866-1873)
Bp 1185-1213 TN10 DNA, 3'end from Genbank Accession #J01829 bp79-107
Bp 1214-2422 Transposon, modified from Tn10 GenBank Accession #J01829 bp 108-1316
Bp 2423-2774 Putative PolyA from vector pNK2859
Bp 2775-2817 Lambda DNA from pNK2859
Bp 2818-2887 70 bp of IS10 left from Tn10 (GenBank Accession #J01829 Bp 1-70)
Bp 2888-3058 pBluescriptII sk(−) base vector (Stratagene, INC) Bp 3059-3081 Multiple cloning site from pBluescriptII sk(−) thru NotI,
Bp 3082-4774 Chicken 5' Lysozyme Matrix Attachment Region (MAR) from chicken gDNA corresponding to GenBank Accession #X98408
Bp 4775-4870 Multiple Cloning Site Extension from pTn X-MCS, XhoI thru MluI
Bp 4871-6575 Chicken 3' Lysozyme Matrix Attachment Region (MAR) from chicken gDNA corresponding to GenBank Accession #X98408
Bp 6576-6645 70 bp of IS10 from Tn10 (GenBank Accession #J01829 Bp 70-1)
Bp 6646-6688 Lambda DNA from pNK2859
Bp 6689-8893 pBluescriptII sk(−) base vector (Stratagene, INC)
SEQ ID NO: 11 Vector #5025 pTn10 (-CMV Enh.)PURO-MAR Flanked BV
Bp 1-132 Remainder of F1 (−) ori of pBluescriptII sk(−) (Stratagene) bp 4-135
Bp 133-154 pGWIZ base vector (Gene Therapy Systems) bp 229-244
Bp 155-229 CMV Promoter (vector pGWIZ, Gene Therapy Systems bp 844-918)
Bp 230-350 CMV Immediate Early Gene, Exon 1 (vector pGWIZ, Gene Therapy Systems bp 919-1039)
Bp 351-1176 CMV Intron A (vector pGWIZ, Gene Therapy Systems bp 1040-1865)
Bp 1177-1184 CMV Immediate Early Gene, Partial Exon 2 (pGWIZ, Gene Therapy Systems) bp 1866-1873)
Bp 1185-1213 TN10 DNA, 3'end from Genbank Accession #J01829 bp79-107
Bp 1214-2422 Transposon, modified from Tn10 GenBank Accession #J01829 Bp 108-1316
Bp 2423-2774 Putative PolyA from vector pNK2859
Bp 2775-2817 Lambda DNA from pNK2859
Bp 2818-2887 70 bp of IS10 left from Tn10 (GenBank Accession #J01829 Bp 1-70)
Bp 2888-3058 pBluescriptII sk(−) base vector (Stratagene, INC)
Bp 3059-3081 Multiple cloning site from pBluescriptII sk(−) thru NotI, Bp 759-737
Bp 3082-4774 Lysozyme Matrix Attachment Region (MAR) from chicken gDNA corresponding to GenBank Accession #X98408
Bp 4775-4852 Multiple Cloning Site Extension from pTn X-MCS, XhoI thru BsiWI
Bp 4853-5165 HSV-TK polyA from pS65TC1 bp 3873-3561
BP 5166-5796 Puromycin resistance gene from pMOD PURO (invivoGen)
Bp 5797-6182 SV40 promoter from pS65TC1, bp 2232-2617
Bp 6183-7893 Lysozyme Matrix Attachment Region (MAR)
Bp 7894-7963 70 bp of IS10 from Tn10 (GenBank Accession #J01829 Bp 70-1)
Bp 7964-8010 Lambda DNA from pNK2859
Bp 8011-10211 pBluescriptII sk(−) base vector (Stratagene, INC) bp 761-2961

SEQ ID NO: 12 Vector #5026 pTn10 MAR Flanked BV #5026

Bp 1-132 Remainder of F1 (−) ori of pBluescriptII sk(−) (Stratagene) bp 4-135

Bp 133-154 pGWIZ base vector (Gene Therapy Systems) bp 229-244

Bp 155-540 SV40 promoter from pS65TC1 bp 2232-2617

Bp 541-661 CMV Immediate Early Gene, Exon 1 (vector pGWIZ, Gene Therapy Systems bp 919-1039)

Bp 662-1487 CMV Intron A (vector pGWIZ, Gene Therapy Systems bp 1040-1865)

Bp 1488-1495 CMV Immediate Early Gene, Partial Exon 2 (pGWIZ, Gene Therapy Systems) bp 1866-1873)

Bp 1496-1524 TN10 DNA, 3'end from Genbank Accession #J01829 bp79-107

Bp 1525-2733 Transposon, modified from Tn10 GenBank Accession #J01829 bp 108-1316

Bp 2734-3085 Putative PolyA from vector pNK2859

Bp 3086-3128 Lambda DNA from pNK2859

Bp 3129-3198 70 bp of IS10 left from Tn10 (GenBank Accession #J01829 Bp 1-70)

Bp 3199-3369 pBluescriptII sk(−) base vector (Stratagene, INC)

Bp 3370-3392 Multiple cloning site from pBluescriptII sk(−) thru NotI, Bp 759-737

Bp 3393-5085 Chicken 5' Lysozyme Matrix Attachment Region (MAR) from chicken gDNA corresponding to GenBank Accession #X98408

Bp 5086-5181 Multiple Cloning Site Extension from pTn X-MCS, XhoI thru MluI

Bp 5182-6886 Chicken 3' Lysozyme Matrix Attachment Region (MAR) from chicken gDNA corresponding to GenBank Accession #X98408

Bp 6887-6956 70 bp of IS10 from Tn10 (GenBank Accession #J01829 Bp 70-1)

Bp 6957-6999 Lambda DNA from pNK2859

Bp 7000-9204 pBluescriptII sk(−) base vector (Stratagene, INC)

SEQ ID NO: 13 pTn10 SV 40 Pr.PURO-MAR Flanked BV Vector #5027

Bp 1-132 Remainder of F1 (−) ori of pBluescriptII sk(−) (Stratagene) bp 4-135

Bp 133-154 pGWIZ base vector (Gene Therapy Systems) bp 229-244

Bp 155-540 SV40 Promoter from pS65TC1, Bp 2232-2617

Bp 541-661 CMV Immediate Early Gene, Exon 1 (vector pGWIZ, Gene Therapy Systems bp 919-1039)

Bp 662-1487 CMV Intron A (vector pGWIZ, Gene Therapy Systems bp 1040-1865)

Bp 1488-1495 CMV Immediate Early Gene, Partial Exon 2 (pGWIZ, Gene Therapy Systems) bp 1866-1873)

Bp 1496-1524 TN10 DNA, 3'end from Genbank Accession #J01829 bp79-107

Bp 1525-2733 Transposon, modified from Tn10 GenBank Accession #J01829 Bp 108-1316

Bp 2734-3085 Putative PolyA from vector pNK2859

Bp 3086-3128 Lambda DNA from pNK2859

Bp 3129-3198 70 bp of IS10 left from Tn10 (GenBank Accession #J01829 Bp 1-70)

Bp 3199-3369 pBluescriptII sk(−) base vector (Stratagene, INC)

Bp 3370-3392 Multiple cloning site from pBluescriptII sk(−) thru NotI, Bp 759-737

Bp 3393-5085 Lysozyme Matrix Attachment Region (MAR) from chicken gDNA GenBank Accession #X98408.

Bp 5086-5163 Multiple Cloning Site Extension from pTn X-MCS, XhoI thru BsiWI

Bp 5164-5476 HSV-TK polyA from pS65TC1 bp 3873-3561

BP 5477-6107 Puromycin resistance gene from pMOD PURO (invivoGen)

Bp 6108-6499 SV40 promoter from pS65TC1, bp 2232-2617

Bp 6500-8204 Lysozyme Matrix Attachment Region (MAR)

Bp 8205-8274 70 bp of IS10 from Tn10 (GenBank Accession #J01829 Bp 70-1)

Bp 8275-8317 Lambda DNA from pNK2859

Bp 8318-10522 pBluescriptII sk(−) base vector (Stratagene, INC) bp 761-2961

In specific embodiments, the disclosed hybrid promoters are defined by the following annotations:

SEQ ID NO:14 (CMV/Oval promoter Version 1=ChOvp/CMVenh/CMVp)

Bp 1-840: corresponds to bp 421-1260 from the chicken ovalbumin promoter, GenBank accession number Bp 841-1439: CMV Enhancer bp 245-843 taken from vector pGWhiz CMV promoter and enhancer bp 844-918 taken from vector pGWhiz (includes the CAAT box at 857-861 and the TATA box at 890-896).

Bp 1440-1514 CMV promoter

SEQ ID NO:15 (CMV/Oval promoter Version 2=ChSDRE/CMVenh/ChNRE/CMVp)

Bp 1-180: Chicken steroid dependent response element from ovalbumin promoter

Bp 181-779: CMV Enhancer bp 245-843 taken from vector pGWhiz

Bp 780-1049: Chicken ovalbumin promoter negative response element

Bp 1050-1124: CMV promoter bp 844-918 taken from vector pGWhiz (includes the CAAT box at 857-861 and the TATA box at 890-896. Some references overlap the enhancer to different extents.)

In specific embodiments, the disclosed expression vectors are defined by the following annotations:

SEQ ID NO:17 (ID#148—CMVep-Intron A RM2 mAb in HS4 Flanked BV)

Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 770-1777 CMV Immediate Early Gene, Partial Exon 2 (pGWIZ, Gene Therapy Systems) bp 1866-1873)

Bp 1778-1785 Synthetic DNA added during construction (combination of two NruI RE sites)

Bp 1786-3021 Transposase modified from Tn10 GenBank Accession #J01829 Bp 81-1316

Bp 3022-3373 Non-coding DNA from vector pNK2859

Bp 3374-3416 Lambda DNA from pNK2859

Bp 3417-3486 70 bp of IS10 left from Tn10 (GenBank Accession #J01829 Bp 1-70)

Bp 3487-3490 Synthetic DNA added during construction

Bp 3491-3657 pBluescriptII sk(−) base vector (Stratagene, INC) bp 926-760

Bp 3658-3680 Multiple cloning site from pBluescriptII sk(−) thru NotI, Bp 759-737

Bp 3681-4922 Chicken HS4—Beta Globin enhancer element from gDNA (corresponds to Genbank Accession #NW__060254 bp 215169-216410)

Bp 4923-4936 Multiple Cloning Site Extension from pTn X-MCS, XhoI thru AscI

Bp 4937-5535 CMV Enhancer (vector pGWIZ, Gene Therapy Systems bp 245-843)

Bp 5536-5610 CMV Promoter (vector pGWIZ, Gene Therapy Systems bp 844-918)

Bp 5611-5731 CMV Immediate Early Gene, Exon 1 (vector pGWIZ, Gene Therapy Systems bp 919-1039)

Bp 5732-6557 CMV Intron A (vector pGWIZ, Gene Therapy Systems bp 1040-1865)

Bp 6558-6565 CMV Immediate Early Gene, Partial Exon 2 (pGWIZ, Gene Therapy Systems) bp 1866-1873)

Bp 6566-6574 Synthetic DNA added to form EcoRV RE site and includes Vitellogenin II Kozak sequence (6572-6577)

Bp 6575-6622 Chicken Vitellogenin Signal Sequence (corresponds to GenBank Accession NM_001031276, Bp 1-48)

Bp 6623-7270 Light chain gene construct taken from antibody RM2 provided by Mark Glassy (Shantha West, Inc.) —codon optimized for chicken Bp 7271-7276 Synthetic DNA added to form AatII RE cut site Bp 7277-7745 Chicken Vitellogenin PolyA (corresponds to GenBank Accession#W_060416.1, Bp 5417698-5418166)

BP 7746-8269 Chicken Vitellogenin 3' Flanking region (corresponds to GenBank Accession #Y00324, Bp 2215-2738)

Bp 8270-8277 Synthetic DNA added from combination of two PacI RE cut sites

Bp 8278-8801 Chicken Vitellogenin 3' Flanking region (corresponds to GenBank Accession #Y00324, Bp 2738-2215)

Bp 8802-9270 Chicken Vitellogenin PolyA (corresponds to GenBank Accession#NW_060416.1, Bp 5418166-5417698)

Bp 9271-9273 Synthetic DNA added to form AatII RE cut site

Bp 9274-10644 Heavy chain gene construct taken from antibody RM2 provided by Mark Glassy (Shantha West, Inc.) —codon optimized for chicken, reverse compliment Bp 10645-10692 Chicken Vitellogenin Signal Sequence (corresponds to GenBank Accession #NM_001031276, Bp 48-1)

Bp 10693-10701 Synthetic DNA added to form EcoRV RE site & includes Vitellogenin II Kozak sequence (10690-10695)

Bp 10702-10709 CMV Immediate Early Gene, Partial Exon 2 (pGWIZ, Gene Therapy Systems bp 1873-1866)

Bp 10710-11535 CMV Intron A (vector pGWIZ, Gene Therapy Systems Bp 1865-1040)

Bp 11536-11656 CMV Immediate Early Gene, Exon 1 (vector pGWIZ, Gene Therapy Systems bp 1039-919)

Bp 11657-11731 CMV Promoter (vector pGWIZ, Gene Therapy Systems bp 918-844)

Bp 11732-12330 CMV Enhancer (vector pGWIZ, Gene Therapy Systems bp 843-245)

BP 12331-12354 Multiple Cloning Site Extension from pTn X-MCS, BsiWI thru MluI

Bp 12355-13596 Chicken HS4—Beta Globin enhancer element from gDNA (corresponds to Genbank Accession #NW_060254 bp 215169-216410)

Bp 13597-13608 Synthetic DNA added during construction including a PspOMI RE site Bp 13609-13678 70 bp of IS10 from Tn10 (GenBank Accession #J01829 Bp 70-1)

Bp 13679-13721 Lambda DNA from pNK2859

Bp 13722-13725 Synthetic DNA added during construction

Bp 13726-15926 pBluescriptII sk(−) base vector (Stratagene, INC) bp 761-2961

SEQ ID NO:18 (ID#210—CMVep-Intron A RM2 mAb in pTn10 HS4 Flanked BV)

Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 1770-1777 CMV Immediate Early Gene, Partial Exon 2 (pGWIZ, Gene Therapy Systems) bp 1866-1873)

Bp 1778-1806 TN10 DNA, 3'end from Genbank Accession #J01829 bp79-107

Bp 1807-3015 Transposon, modified from Tn10 GenBank Accession #J01829 Bp 108-1316

Bp 3016-3367 Putative PolyA from vector pNK2859

Bp 3368-3410 Lambda DNA from pNK2859

Bp 3411-3480 70 bp of IS10 left from Tn10 (GenBank Accession #J01829 Bp 1-70)

Bp 3481-3484 Synthetic DNA added during construction

Bp 3485-3651 pBluescriptII sk(−) base vector (Stratagene, INC) bp 926-760

Bp 3652-3674 Multiple cloning site from pBluescriptII sk(−) thru NotI, Bp 759-737

Bp 3675-4916 Chicken HS4—Beta Globin enhancer element from gDNA (corresponds to Genbank Accession #NW_060254 bp 215169-216410)

Bp 4917-4930 Multiple Cloning Site Extension from pTn X-MCS, XhoI thru AscI

Bp 4931-5529 CMV Enhancer (vector pGWIZ, Gene Therapy Systems bp 245-843)

Bp 5530-5604 CMV Promoter (vector pGWIZ, Gene Therapy Systems bp 844-918)

Bp 5605-5725 CMV Immediate Early Gene, Exon 1 (vector pGWIZ, Gene Therapy Systems bp 919-1039)

Bp 5726-6551 CMV Intron A (vector pGWIZ, Gene Therapy Systems bp 1040-1865)

Bp 6552-6559 CMV Immediate Early Gene, Partial Exon 2 (pGWIZ, Gene Therapy Systems) bp 1866-1873)

Bp 6560-6568 Synthetic DNA added to form EcoRV RE site & includes Vitellogenin II Kozak sequence (6566-6571)

Bp 6569-6616 Chicken Vitellogenin Signal Sequence (corresponds to GenBank Accession NM_001031276, Bp 1-48)

Bp 6617-7264 Light chain gene construct taken from antibody RM2 provided by Mark Glassy (Shantha West, Inc.) —codon optimized for chicken Bp 7265-7270 Synthetic DNA added to form AatII RE site Bp 7271-7739 Chicken Vitellogenin PolyA (corresponds to GenBank Accession#NW_060416.1, Bp 5417698-5418166)

BP 7740-8263 Chicken Vitellogenin 3' Flanking region (corresponds to GenBank Accession #Y00324, Bp 2215-2738)

Bp 8264-8271 Synthetic DNA added from combination of two PacI RE sites

Bp 8272-8795 Chicken Vitellogenin 3' Flanking region (corresponds to GenBank Accession #Y00324, Bp 2738-2215)

Bp 8796-9264 Chicken Vitellogenin PolyA (corresponds to GenBank Accession#NW_060416.1, Bp 5418166-5417698)

Bp 9265-9267 Synthetic DNA added to form AatII RE cut site

Bp 9268-10638 Heavy chain gene construct taken from antibody RM2 provided by Mark Glassy (Shantha West, Inc.) —codon optimized for chicken, reverse compliment Bp 10639-10686 Chicken Vitellogenin Signal Sequence (corresponds to GenBank Accession #NM_001031276, Bp 48-1)

Bp 10687-10695 Synthetic DNA added to form EcoRV RE site & includes Vitellogenin II Kozak sequence (10684-10689)

Bp 10696-10703 CMV Immediate Early Gene, Partial Exon 2 (pGWIZ, Gene Therapy Systems bp 1873-1866)

Bp 10704-11529 CMV Intron A (vector pGWIZ, Gene Therapy Systems Bp 1865-1040)

Bp 11530-11650 CMV Immediate Early Gene, Exon 1 (vector pGWIZ, Gene Therapy Systems bp 1039-919)

Bp 11651-11725 CMV Promoter (vector pGWIZ, Gene Therapy Systems bp 918-844)

Bp 11726-12324 CMV Enhancer (vector pGWIZ, Gene Therapy Systems bp 843-245)

BP 12325-12348 Multiple Cloning Site Extension from pTn X-MCS, BsiWI thru MluI

Bp 12349-13590 Chicken HS4—Beta Globin enhancer element from gDNA (corresponds to Genbank Accession #NW_060254 bp 215169-216410)

Bp 13591-13602 Synthetic DNA added during construction including a PspOMI RE site Bp 13603-13672 70 bp of IS10 from Tn10 (GenBank Accession #J01829 Bp 70-1)

Bp 13673-13715 Lambda DNA from pNK2859

Bp 13716-13719 Synthetic DNA added during construction

Bp 13720-15920 pBluescriptII sk(−) base vector (Stratagene, INC) bp 761-2961

SEQ ID NO:20 (ID#226—CMVep-Intron A RM2 mAb in pTn10 PURO-MAR Flanked BV)

Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 1770-1777 CMV Immediate Early Gene, Partial Exon 2 (pGWIZ, Gene Therapy Systems) bp 1866-1873)

Bp 1778-1806 TN10 DNA, 3'end from Genbank Accession #J01829 bp79-107

Bp 1807-3015 Transposon, modified from Tn10 GenBank Accession #J01829 Bp 108-1316

Bp 3016-3367 Putative PolyA from vector pNK2859

Bp 3368-3410 Lambda DNA from pNK2859

Bp 3411-3480 70 bp of IS10 left from Tn10 (GenBank Accession #J01829 Bp 1-70)

Bp 3481-3484 Synthetic DNA added during construction

Bp 3485-3651 pBluescriptII sk(−) base vector (Stratagene, INC) bp 926-760

Bp 3652-3674 Multiple cloning site from pBluescriptII sk(−) thru NotI, Bp 759-737

Bp 3675-5367 Lysozyme Matrix Attachment Region (MAR)

Bp 5368-5381 Multiple Cloning Site Extension from pTn X-MCS, XhoI thru AscI

Bp 5382-5980 CMV Enhancer (vector pGWIZ, Gene Therapy Systems bp 245-843)

Bp 5981-6055 CMV Promoter (vector pGWIZ, Gene Therapy Systems bp 844-918)

Bp 6056-6176 CMV Immediate Early Gene, Exon 1 (vector pGWIZ, Gene Therapy Systems bp 919-1039)

Bp 6177-7002 CMV Intron A (vector pGWIZ, Gene Therapy Systems bp 1040-1865)

Bp 7003-7010 CMV Immediate Early Gene, Partial Exon 2 (pGWIZ, Gene Therapy Systems) bp 1866-1873)

Bp 7011-7019 Synthetic DNA added to form EcoRV RE site & includes Vitellogenin II Kozak sequence (7017-7022)

Bp 7020-7067 Chicken Vitellogenin Signal Sequence (corresponds to GenBank Accession NM_001031276, Bp 1-48)

Bp 7068-7715 Light chain gene construct taken from antibody RM2 provided by Mark Glassy (Shantha West, Inc.) —codon optimized for chicken Bp 7716-7721 Synthetic DNA added to form AatII RE site Bp 7722-8190 Chicken Vitellogenin PolyA (corresponds to GenBank Accession#NW_060416.1, Bp 5417698-5418166)

BP 8191-8714 Chicken Vitellogenin 3' Flanking region (corresponds to GenBank Accession #Y00324, Bp 2215-2738)

Bp 8715-8722 Synthetic DNA added from combination of two PacI RE sites

Bp 8723-9246 Chicken Vitellogenin 3' Flanking region (corresponds to GenBank Accession #Y00324, Bp 2738-2215)

Bp 9247-9715 Chicken Vitellogenin PolyA (corresponds to GenBank Accession#NW_060416.1, Bp 5418166-5417698)

Bp 9716-9718 Synthetic DNA added to form AatII RE site

Bp 9719-11089 Heavy chain gene construct taken from antibody RM2 provided by Mark Glassy (Shantha West, Inc.) — codon optimized for chicken, reverse compliment Bp 11090-11137 Chicken Vitellogenin Signal Sequence (corresponds to GenBank Accession #NM_001031276, Bp 48-1)

Bp 11138-11146 Synthetic DNA added to form EcoRV RE site & includes Vitellogenin II Kozak sequence (11135-11140)

Bp 11147-11154 CMV Immediate Early Gene, Partial Exon 2 (pGWIZ, Gene Therapy Systems bp 1873-1866)

Bp 11155-11980 CMV Intron A (vector pGWIZ, Gene Therapy Systems Bp 1865-1040)

Bp 11981-12101 CMV Immediate Early Gene, Exon 1 (vector pGWIZ, Gene Therapy Systems bp 1039-919)

Bp 12102-12176 CMV Promoter (vector pGWIZ, Gene Therapy Systems bp 918-844)

Bp 12177-12775 CMV Enhancer (vector pGWIZ, Gene Therapy Systems bp 843-245)

Bp 12776-12781 BsiWI RE site

Bp 12782-13094 HSV-TK polyA from pS65TC1 bp 3873-3561

Bp 13095-13123 Excess DNA from pMOD PURO (invivoGen)

BP 13124-13725 Puromyacin resistance gene from pMOD PURO (invivoGen) bp 717-116

Bp 13726-14111 SV40 promoter from pS65TC1, bp 2232-2617

Bp 14112-11417 MluI RE site

BP 11418-15810 Lysozyme Matrix Attachment Region (MAR)

Bp 15811-15822 Synthetic DNA added during construction including a PspOMI RE site Bp 15823-15892 70 bp of IS10 from Tn10 (GenBank Accession #J01829 Bp 70-1)

Bp 15893-15935 Lambda DNA from pNK2859

Bp 15936-15939 Synthetic DNA added during construction

Bp 15940-18140 pBluescriptII sk(−) base vector (Stratagene, INC) bp 761-2961

SEQ ID NO:21 ID#275—CMV-Ovalp Vs.1–RM2 mAb–OPA in pTn10 PURO-MAR Flanked BV

Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 1770-1777 CMV Immediate Early Gene, Partial Exon 2 (pGWIZ, Gene Therapy Systems) bp 1866-1873)

Bp 1778-1806 TN10 DNA, 3'end from Genbank Accession #J01829 bp79-107

Bp 1807-3015 Transposon, modified from Tn10 GenBank Accession #J01829 Bp 108-1316

Bp 3016-3367 Putative PolyA from vector pNK2859

Bp 3368-3410 Lambda DNA from pNK2859

Bp 3411-3480 70 bp of IS10 left from Tn10 (GenBank Accession #J01829 Bp 1-70)

Bp 3481-3484 Synthetic DNA added during construction

Bp 3485-3651 pBluescriptII sk(−) base vector (Stratagene, INC) bp 926-760

Bp 3652-3674 Multiple cloning site from pBluescriptII sk(−) thru NotI, Bp 759-737

Bp 3675-5367 Chicken Lysozyme Matrix Attachment region (MAR) from gDNA

Bp 5368-5381 Multiple Cloning Site Extension from pTn X-MCS, XhoI thru AscI

Bp 5382-6222 Chicken Ovalbumin promoter from gDNA (Genbank Accession #J00895 bp 421-1261)

Bp 6223-6228 EcoRI RE site

BP 6229-6827 CMV Enhancer (vector pGWIZ, Gene Therapy Systems bp 245-843)

Bp 6828-6905 CMV Promoter (vector pGWIZ, Gene Therapy Systems bp 844-899, CTC, 900-918)

Bp 6906-7026 CMV Immediate Early Gene, Exon 1 (vector pGWIZ, Gene Therapy Systems bp 919-1039)

BP 7027-7852 CMV Intron A (vector pGWIZ, Gene Therapy Systems bp 1040-1865)

Bp 7853-7860 CMV Immediate Early Gene, Partial Exon 2 (pGWIZ, Gene Therapy Systems) bp 1866-1873)

Bp 7861-7869 Synthetic DNA added to form EcoRV RE site (includes Vitellogenin II Kozak sequence (7867-7872)

Bp 7870-7917 Chicken Vitellogenin Signal Sequence (GenBank Accession NM_001031276, Bp 1-48)

Bp 7918-8565 Light chain gene construct from antibody RM2 (provided by Shantha West, Inc.)

Bp 8566-8571 Synthetic DNA added to form AatII RE site

Bp 8572-9487 Chicken Ovalbumin polyA from gDNA (corresponds to GenBank Accession #J00895 bp 8260-9175)

Bp 9488-9507 Multiple Cloning Site Extension from pTn X-MCS, PacI thru SbfI

Bp 9508-9820 HSV-TK polyA from pS65TC1 bp 3873-3561

Bp 9821-9849 Excess DNA from pMOD PURO (invivoGen)

BP 9850-10451 Puromycin resistance gene from pMOD PURO (invivoGen) bp 717-116

Bp 10452-10837 SV40 promoter from pS65TC1, bp 2617-2232

BP 10838-10843 BsiWI RE site

Bp 10844-11759 Chicken Ovalbumin polyA from gDNA (corresponds to GenBank Accession #J00895 bp 9175-8260)

Bp 11760-11762 Synthetic DNA added to form AatII RE site

Bp 11763-13133 Heavy chain gene construct from antibody RM2 (provided by Shantha West, Inc.)

Bp 13134-13181 Chicken Vitellogenin Signal Sequence (GenBank Accession #NM_001031276, Bp 48-1)

Bp 13182-13190 Synthetic DNA added to form EcoRV RE site (includes Vitellogenin II Kozak sequence (13179-13184)

Bp 13191-13198 CMV Immediate Early Gene, Partial Exon 2 (pGWIZ, Gene Therapy Systems bp 1873-1866)

Bp 13199-14024 CMV Intron A (vector pGWIZ, Gene Therapy Systems Bp 1865-1040)

Bp 14025-14145 CMV Immediate Early Gene, Exon 1 (vector pGWIZ, Gene Therapy Systems bp 1039-919)

Bp 14146-14223 CMV Promoter (vector pGWIZ, Gene Therapy Systems bp 844-899, CTC, 900-918)

BP 14224-14822 CMV Enhancer (vector pGWIZ, Gene Therapy Systems bp 245-843)

Bp 14823-14828 EcoRI RE site

Bp 14829-15669 Chicken Ovalbumin promoter from gDNA (Genbank Accession #J00895 bp 421-1261)

Bp 15670-15675 MluI RE site

Bp 15676-17368 Chicken Lysozyme Matrix Attachment region (MAR) from gDNA

Bp 17369-17380 Synthetic DNA added during construction including a PspOMI RE site Bp 17381-17450 70 bp of IS10 from Tn10 (GenBank Accession #J01829 Bp 70-1)

Bp 17451-17493 Lambda DNA from pNK2859

Bp 17494-17497 Synthetic DNA added during construction

Bp 17498-19698 pBluescriptII sk(−) base vector (Stratagene, INC) bp 761-2961

SEQ ID NO:22 ID#278—CMV-Ovalp Vs.1−ΔCH2 mAb−OPA in pTn10 PURO-MAR Flanked BV

Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 1770-1777 CMV Immediate Early Gene, Partial Exon 2 (pGWIZ, Gene Therapy Systems) bp 1866-1873)

Bp 1778-1806 TN10 DNA, 3'end from Genbank Accession #J01829 bp79-107

Bp 1807-3015 Transposon, modified from Tn10 GenBank Accession #J01829 Bp 108-1316

Bp 3016-3367 Putative PolyA from vector pNK2859

Bp 3368-3410 Lambda DNA from pNK2859

Bp 3411-3480 70 bp of IS10 left from Tn10 (GenBank Accession #J01829 Bp 1-70)

Bp 3481-3484 Synthetic DNA added during construction

Bp 3485-3651 pBluescriptII sk(−) base vector (Stratagene, INC) bp 926-760

Bp 3652-3674 Multiple cloning site from pBluescriptII sk(−) thru NotI, Bp 759-737

Bp 3675-5367 Chicken Lysozyme Matrix Attachment region (MAR) from gDNA

Bp 5368-5381 Multiple Cloning Site Extension from pTn X-MCS, XhoI thru AscI

Bp 5382-6222 Chicken Ovalbumin promoter from gDNA (Genbank Accession #J00895 bp 421-1261)

Bp 6223-6228 EcoRI RE site

BP 6229-6827 CMV Enhancer (vector pGWIZ, Gene Therapy Systems bp 245-843)

Bp 6828-6905 CMV Promoter (vector pGWIZ, Gene Therapy Systems bp 844-899, CTC, 900-918)

Bp 6906-7026 CMV Immediate Early Gene, Exon 1 (vector pGWIZ, Gene Therapy Systems bp 919-1039)

BP 7027-7852 CMV Intron A (vector pGWIZ, Gene Therapy Systems bp 1040-1865)

Bp 7853-7860 CMV Immediate Early Gene, Partial Exon 2 (pGWIZ, Gene Therapy Systems) bp 1866-1873)

Bp 7861-7869 Synthetic DNA added to form EcoRV RE site (includes Vitellogenin II Kozak sequence (7867-7872)

Bp 7870-7917 Chicken Vitellogenin Signal Sequence (GenBank Accession NM_001031276, Bp 1-48)

Bp 7918-8550 Light chain gene construct from antibody CC49ΔCH2V15 (provided by NCI)

Bp 8551-8586 Synthetic DNA added to form AatII RE site

Bp 8587-9502 Chicken Ovalbumin polyA from gDNA (corresponds to GenBank Accession #J00895 bp 8260-9175)

Bp 9503-9522 Multiple Cloning Site Extension from pTn X-MCS, PacI thru SbfI

Bp 9523-9835 HSV-TK polyA from pS65TC1 bp 3873-3561

Bp 9836-9864 Excess DNA from pMOD PURO (invivoGen)

BP 9865-10466 Puromyacin resistance gene from pMOD PURO (invivoGen) bp 717-116

Bp 10467-10852 SV40 promoter from pS65TC1, bp 2617-2232

BP 10853-10858 BsiWI RE site

Bp 10859-11774 Chicken Ovalbumin polyA from gDNA (corresponds to GenBank Accession #J00895 bp 9175-8260)

Bp 11775-11780 Synthetic DNA added to form AatII RE site

Bp 11781-12815 Heavy chain gene construct from antibody CC49ΔCH2V15 (provided by NCI)

Bp 12816-12863 Chicken Vitellogenin Signal Sequence (GenBank Accession #NM_001031276, Bp 48-1)

Bp 12864-12872 Synthetic DNA added to form EcoRV RE site (includes Vitellogenin II Kozak sequence (12861-12866)

Bp 12873-12880 CMV Immediate Early Gene, Partial Exon 2 (pGWIZ, Gene Therapy Systems bp 1873-1866)

Bp 12881-13706 CMV Intron A (vector pGWIZ, Gene Therapy Systems Bp 1865-1040)

Bp 13707-13827 CMV Immediate Early Gene, Exon 1 (vector pGWIZ, Gene Therapy Systems bp 1039-919)

Bp 13828-13905 CMV Promoter (vector pGWIZ, Gene Therapy Systems bp 844-899, CTC, 900-918)

BP 13906-14504 CMV Enhancer (vector pGWIZ, Gene Therapy Systems bp 245-843)

Bp 14505-14510 EcoRI RE site

Bp 14511-15351 Chicken Ovalbumin promoter from gDNA (Genbank Accession #J00895 bp 421-1261)

Bp 15352-15357 MluI RE site

Bp 15358-17050 Chicken Lysozyme Matrix Attachment region (MAR) from gDNA

Bp 17051-17062 Synthetic DNA added during construction including a PspOMI RE site Bp 17063-17132 70 bp of IS10 from Tn10 (GenBank Accession #J01829 Bp 70-1)

Bp 17133-17175 Lambda DNA from pNK2859

Bp 17176-17179 Synthetic DNA added during construction

Bp 17180-19380 pBluescriptII sk(−) base vector (Stratagene, INC) bp 761-2961

SEQ ID NO:23 ID#273—CMV-Ovalp Vs.1−RM2 mAb in pTn10 PURO-MAR Flanked BV

Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 1770-1777 CMV Immediate Early Gene, Partial Exon 2 (pGWIZ, Gene Therapy Systems) bp 1866-1873)

Bp 1778-1806 TN10 DNA, 3'end from Genbank Accession #J01829 bp79-107

Bp 1807-3015 Transposon, modified from Tn10 GenBank Accession #J01829 Bp 108-1316

Bp 3016-3367 Putative PolyA from vector pNK2859

Bp 3368-3410 Lambda DNA from pNK2859

Bp 3411-3480 70 bp of IS10 left from Tn10 (GenBank Accession #J01829 Bp 1-70)

Bp 3481-3484 Synthetic DNA added during construction

Bp 3485-3651 pBluescriptII sk(−) base vector (Stratagene, INC) bp 926-760

Bp 3652-3674 Multiple cloning site from pBluescriptII sk(−) thru NotI, Bp 759-737

Bp 3675-5367 Chicken Lysozyme Matrix Attachment region (MAR) from gDNA

Bp 5368-5381 Multiple Cloning Site Extension from pTn X-MCS, XhoI thru AscI

Bp 5382-6222 Chicken Ovalbumin promoter from gDNA (Genbank Accession #J00895 bp 421-1261)

Bp 6223-6228 EcoRI RE site

BP 6229-6827 CMV Enhancer (vector pGWIZ, Gene Therapy Systems bp 245-843)

Bp 6828-6905 CMV Promoter (vector pGWIZ, Gene Therapy Systems bp 844-899, CTC, 900-918)

Bp 6906-7026 CMV Immediate Early Gene, Exon 1 (vector pGWIZ, Gene Therapy Systems bp 919-1039)

BP 7027-7852 CMV Intron A (vector pGWIZ, Gene Therapy Systems bp 1040-1865)

Bp 7853-7860 CMV Immediate Early Gene, Partial Exon 2 (pGWIZ, Gene Therapy Systems) bp 1866-1873)

Bp 7861-7869 Synthetic DNA added to form EcoRV RE site (includes Vitellogenin II Kozak sequence (7867-7872)

Bp 7870-7917 Chicken Vitellogenin Signal Sequence (GenBank Accession NM_001031276, Bp 1-48)

Bp 7918-8565 Light chain gene construct from antibody RM2 (provided by Shantha West, Inc.)

Bp 8566-8571 Synthetic DNA added to form AatII RE site

Bp 8572-9040 Chicken Vitellogenin PolyA (corresponds to GenBank Accession#NW_060416.1, Bp 5417698-5418166)

BP 9041-9564 Chicken Vitellogenin 3' Flanking region (corresponds to GenBank Accession #Y00324, Bp 2215-2738)

Bp 9565-9584 Multiple Cloning Site Extension from pTn X-MCS, PacI thru SbfI

Bp 9585-9897 HSV-TK polyA from pS65TC1 bp 3873-3561

Bp 9898-9926 Excess DNA from pMOD PURO (invivoGen)

BP 9927-10528 Puromycin resistance gene from pMOD PURO (invivoGen) bp 717-116

Bp 10529-10914 SV40 promoter from pS65TC1, bp 2617-2232

BP 10915-10920 BsiWI RE site

Bp 10921-11444 Chicken Vitellogenin 3' Flanking region (GenBank Accession #Y00324, Bp 2738-2215)

Bp 11445-11913 Chicken Vitellogenin PolyA (GenBank Accession#NW_060416.1, Bp 5418166-5417698)

Bp 11914-11916 Synthetic DNA added to form AatII RE site
Bp 11917-13287 Heavy chain gene construct from antibody RM2 (provided by Shantha West, Inc.)
Bp 13288-13335 Chicken Vitellogenin Signal Sequence (GenBank Accession #NM_001031276, Bp 48-1)
Bp 13336-13344 Synthetic DNA added to form EcoRV RE site (includes Vitellogenin II Kozak sequence (13333-13338)
Bp 13345-13352 CMV Immediate Early Gene, Partial Exon 2 (pGWIZ, Gene Therapy Systems bp 1873-1866)
Bp 13353-14178 CMV Intron A (vector pGWIZ, Gene Therapy Systems Bp 1865-1040)
Bp 14179-14299 CMV Immediate Early Gene, Exon 1 (vector pGWIZ, Gene Therapy Systems bp 1039-919)
Bp 14300-14377 CMV Promoter (vector pGWIZ, Gene Therapy Systems bp 844-899, CTC, 900-918)
BP 14378-14976 CMV Enhancer (vector pGWIZ, Gene Therapy Systems bp 245-843)
Bp 14977-14981 EcoRI RE site
Bp 14982-15822 Chicken Ovalbumin promoter from gDNA (Genbank Accession #J00895 bp 421-1261)
Bp 15823-15829 MluI RE site
Bp 15830-17522 Chicken Lysozyme Matrix Attachment region (MAR) from gDNA
Bp 17523-17534 Synthetic DNA added during construction including a PspOMI RE site
Bp 17535-17604 70 bp of IS10 from Tn10 (GenBank Accession #J01829 Bp 70-1)
Bp 17605-17647 Lambda DNA from pNK2859
Bp 17648-17651 Synthetic DNA added during construction
Bp 17652-19852 pBluescriptII sk(−) base vector (Stratagene, INC) bp 761-2961

SEQ ID NO:24 Vitellogenin-Intron A RM2 mAb Flanked with HS4 in pTnMCS Modified BV Bp 1-132 Remainder of F1 (−) ori of pBluescriptII sk(−) (Stratagene) bp 4-135
Bp 133-148 pGWIZ base vector (Gene Therapy Systems) bp 229-244
Bp 149-747 CMV Enhancer (vector pGWIZ, Gene Therapy Systems bp 245-843)
Bp 748-822 CMV Promoter (vector pGWIZ, Gene Therapy Systems bp 844-918)
Bp 823-943 CMV Immediate Early Gene, Exon 1 (vector pGWIZ, Gene Therapy Systems bp 919-1039)
Bp 944-1769 CMV Intron A (vector pGWIZ, Gene Therapy Systems bp 1040-1865)
Bp 1770-1777 CMV Immediate Early Gene, Partial Exon 2 (pGWIZ, Gene Therapy Systems bp 1866-1873)
Bp 1778-1785 Synthetic DNA added during construction (combination of 2 NruI sites)
Bp 1786-3018 Transposase, modified from Tn10 (GenBank accession #J01829 Bp 81-1313)
Bp 3019-3021 Engineered stop codon
Bp 3022-3373 Non-coding DNA from vector pNK2859
Bp 3374-3416 Lambda DNA from pNK2859
Bp 3417-3486 70 bp of IS10 left from Tn10 (GenBank Accession #J01829 Bp 1-70)
Bp 3487-3490 Synthetic DNA added during construction
Bp 3491-3657 pBluescriptII sk(−) base vector (Stratagene, INC) bp 926-760
Bp 3658-3680 Multiple cloning site from pBluescriptII sk(−) thru NotI, Bp 759-737
Bp 3681-4922 Chicken Beta globin enhancer element (corresponds to GenBank Accession #NW_060254, Bp 215169-216410)
Bp 4923-4935 Multiple Cloning Site Extension from pTn X-MCS, XhoI thru AscI
Bp 4936-6079 Chicken Vitellogenin Promoter (corresponds to GenBank Accession #X00345, Bp 1-1144)
Bp 6080-6095 pGWIZ base vector (Gene Therapy Systems) bp 903-918
Bp 6096-6216 CMV Immediate Early Gene, Exon 1 (vector pGWIZ, Gene Therapy Systems bp 919-1039)
Bp 6217-7042 CMV Intron A (vector pGWIZ, Gene Therapy Systems Bp 1040-1865)
Bp 7043-7050 CMV Immediate Early Gene, Partial Exon 2 (pGWIZ, Gene Therapy Systems bp 1866-1873)
Bp 7051-7059 Synthetic DNA added to form EcoRV RE site & includes Vitellogenin II Kozak sequence (7057-7062)
Bp 7060-7107 Chicken Vitellogenin Signal Sequence (corresponds to GenBank Accession NM_01031276, Bp 1-48)
Bp 7108-7755 Light chain gene construct taken from antibody RM2 provided by Mark Glassy (Shantha West, Inc.) —codon optimized for chicken
Bp 7756-7761 Synthetic DNA added to form AatII RE site
Bp 7762-8230 Chicken Vitellogenin PolyA (corresponds to GenBank Accession#NW_060416.1, Bp 5417698-5418166)
BP 8231-8754 Chicken Vitellogenin 3' Flanking region (corresponds to GenBank Accession #Y00324, Bp 2215-2738)
Bp 8755-8762 Synthetic DNA added from combination of two PacI RE sites
Bp 8763-9286 Chicken Vitellogenin 3' Flanking region (corresponds to GenBank Accession #Y00324, Bp 2738-2215)
Bp 9287-9755 Chicken Vitellogenin PolyA (corresponds to GenBank Accession#NW_060416.1, Bp 5418166-5417698)
Bp 9756-9758 Synthetic DNA added to form AatII RE site
Bp 9759-11129 Heavy chain gene construct taken from antibody RM2 provided by Mark Glassy (Shantha West, Inc.) —codon optimized for chicken, reverse compliment
Bp 11130-11177 Chicken Vitellogenin Signal Sequence (corresponds to GenBank Accession #NM_001031276, Bp 48-1)
Bp 11178-11186 Synthetic DNA added to form EcoRV RE site & includes Vitellogenin II Kozak sequence (11175-11180)
Bp 11187-11194 CMV Immediate Early Gene, Partial Exon 2 (pGWIZ, Gene Therapy Systems bp 1873-1866)
Bp 11195-12020 CMV Intron A (vector pGWIZ, Gene Therapy Systems Bp 1865-1040)
Bp 12021-12141 CMV Immediate Early Gene, Exon 1 (vector pGWIZ, Gene Therapy Systems bp 1039-919)
Bp 12142-12157 pGWIZ base vector (Gene Therapy Systems) bp 918-903
Bp 12158-13301 Chicken Vitellogenin Promoter (corresponds to GenBank Accession #X00345, Bp 1144-1)
BP 13302-13324 Multiple Cloning Site Extension from pTn X-MCS, BsiWI thru MluI
Bp 13325-14566 Chicken Beta globin enhancer element (corresponds to GenBank Accession #NW_060254, Bp 216410-215169)
Bp 14567-14578 Synthetic DNA added during construction including a PspOMI RE site
Bp 14579-14648 70 bp of IS10 from Tn10 (GenBank Accession #J01829 Bp 70-1)
Bp 14649-14691 Lambda DNA from pNK2859
Bp 14692-14695 Synthetic DNA added during construction
Bp 14696-16896 pBluescriptII sk(−) base vector (Stratagene, INC) bp 761-2961

SEQ ID NO:25 267-5021—Puro/Mar (CMV.Ovalp vs.1/Conss(-AA)/Herceptin HC/OvpyA/OvpyA/Herceptin LC/Conss(-AA)/CMV.Ovalp vs. 1)

Bp 1-5381 Puro/Mar backbone (bp 1-5381)
Bp 5382-6228 Chicken Ovalbumin Promoter (bp 1090-1929), including synthetic DNA added during vector construction (EcoRI site used for ligation) on 3' end
Bp 6229-6905 CMV enhancer/promoter, bp 245-899 of gWIZ blank Vector, CTC, bp 900-918 of CMVpromoter from gWIZ blank vector
Bp 6906-7866 CMV intron A (bp 919-1873 of gWIZ; includes CMV immediate-early gene, Exon1; CMV intron A; CMV immediate-early gene, partial Exon 2), including synthetic DNA added during vector construction (SalI site used for ligation) on 3' end
Bp 7867-7926 Chicken Conalbumin Signal Sequence+ Kozak sequence (7867-7872) (from GenBank Accession #X02009)
Bp 7927-8301 Synthetic construct of humAb4D5-8 humanized heavy chain variable region, taken from GenBank Accession #: AY513484 (bp 1-375)
Bp 8302-9285 Human immunoglobulin kappa heavy chain constant region, taken from GenBank Accession #: Y14735 (bp 480-1457), including synthetic DNA added during vector construction (BamHI site used for ligation) on 3' end
Bp 9286-10202 Chicken Ovalbumin PolyA (taken from GenBank Accession #J00895, bp 8260-9176)
Bp 10203-10236 Puro/Mar backbone (bp 5385-5418); part of the multiple cloning site
Bp 10237-11159 Chicken Ovalbumin PolyA taken from GenBank Accession #J00895 (bp 9176-8260), including synthetic DNA added during vector construction (BamHI site for ligation)
Bp 11160-11481 Human immunoglobulin kappa light chain constant region, taken from GenBank Accession #Y14736 (bp 725-410)
Bp 11482-11804 Synthetic construct of humAb4D5-8 humanized antibody light chain variable region, taken from GenBank Accession #AY513485 (bp 323-1)
Bp 11805-11870 Chicken Conalbumin Signal Sequence+ Kozak sequence (11859-11864) (from GenBank Accession #X02009); reverse compliment, including synthetic DNA added during vector construction (SalI site used for ligation) on 3' end
Bp 11871-12825 CMV intron A' (bp 1873-919 of gWiz; includes CMV immediate-early gene, partial Exon2; CMV intron A; CMV immediate-early gene, Exon 1)
Bp 12826-13508 bp 918-900 of CMVpromoter from gWIZ blank vector, GAG, CMV enhancer/promoter (bp 899-245 of gWIZ blank vector), including synthetic DNA added during vector construction (EcoRI site used for ligation) on 3' end
Bp 13509-14349 Chicken Ovalbumin Promoter (bp 1929-1090)
Bp 14350-19714 Puro/Mar backbone (bp 5440-10804)

SEQ ID NO:26 ID#279 HPvs1/CMViA/CAss+koz/coΔCH2 mAb/OPA in pTn10 PURO-MAR Flanked BV Bp 1-132 Remainder of F1 (−) ori of pBluescriptII sk(−) (Stratagene) bp 4-135
Bp 133-148 pGWIZ base vector (Gene Therapy Systems) bp 229-244
Bp 149-747 CMV Enhancer (vector pGWIZ, Gene Therapy Systems bp 245-843)
Bp 748-822 CMV Promoter (vector pGWIZ, Gene Therapy Systems bp 844-918)
Bp 823-943 CMV Immediate Early Gene, Exon 1 (vector pGWIZ, Gene Therapy Systems bp 919-1039)
Bp 944-1769 CMV Intron A (vector pGWIZ, Gene Therapy Systems bp 1040-1865)
Bp 1770-1777 CMV Immediate Early Gene, Partial Exon 2 (pGWIZ, Gene Therapy Systems) bp 1866-1873)
Bp 1778-1806 TN10 DNA, 3'end from Genbank Accession #J01829 bp79-107
Bp 1807-3015 Transposon, modified from Tn10 GenBank Accession #J01829 Bp 108-1316
Bp 3016-3367 Putative PolyA from vector pNK2859
Bp 3368-3410 Lambda DNA from pNK2859
Bp 3411-3480 70 bp of IS10 left from Tn10 (GenBank Accession #J01829 Bp 1-70)
Bp 3481-3651 pBluescriptII sk(−) base vector (Stratagene, INC)
Bp 3652-3674 Multiple cloning site from pBluescriptII sk(−) thru NotI, Bp 759-737
Bp 3675-5367 Chicken Lysozyme Matrix Attachment region (MAR) from gDNA
Bp 5368-5381 Multiple Cloning Site Extension from pTn X-MCS, XhoI thru AscI
Bp 5382-6223 Chicken Ovalbumin promoter from gDNA (Genbank Accession #J00895 bp 421-1261)
BP 6224-6827 CMV Enhancer (vector pGWIZ, Gene Therapy Systems bp 245-843) with 5' EcoRI RE site
Bp 6828-6905 CMV Promoter (vector pGWIZ, Gene Therapy Systems bp 844-899, CTC, 900-918)
Bp 6906-7026 CMV Immediate Early Gene, Exon 1 (vector pGWIZ, Gene Therapy Systems bp 919-1039)
BP 7027-7852 CMV Intron A (vector pGWIZ, Gene Therapy Systems bp 1040-1865)
Bp 7853-7860 CMV Immediate Early Gene, Partial Exon 2 (pGWIZ, Gene Therapy Systems) bp 1866-1873)
Bp 7861-7926 Conalbumin Signal Peptide (Genbank #Y00407 bp 340-385, 1699-1715) with 5'SalI RE site. Kozak sequence (7867-7872)
Bp 7927-8589 Light chain gene construct-codon optimized from antibody CC49ΔCH2V15 (provided by NCI)
Bp 8590-9511 Chicken Ovalbumin polyA from gDNA (GenBank #J00895 bp 8260-9175) with 5'AgeI RE site
Bp 9512-9531 Multiple Cloning Site Extension from pTn X-MCS, PacI thru SbfI
Bp 9532-9844 HSV-TK polyA from pS65TC1 bp 3873-3561
BP 9845-10475 Puromyacin resistance gene from pMOD PURO (invivoGen)
Bp 10476-10867 SV40 promoter from pS65TC1, bp 2617-2232 with 5' BsiWI RE site
Bp 10868-11791 Chicken Ovalbumin polyA from gDNA (GenBank #J00895 bp 9175-8260) with 5'AsiSI RE site
Bp 11792-12826 Heavy chain gene construct-codon optimized from antibody CC49ΔCH2V15 (provided by NCI)
Bp 12827-12892 Conalbumin Signal Peptide (Genbank #Y00407 bp 340-385, 1699-1715) with 5'SalI RE site. Kozak sequence (12881-12886)
Bp 12893-12900 CMV Immediate Early Gene, Partial Exon 2 (pGWIZ, Gene Therapy Systems bp 1873-1866)
Bp 12901-13726 CMV Intron A (vector pGWIZ, Gene Therapy Systems Bp 1865-1040)
Bp 13727-13847 CMV Immediate Early Gene, Exon 1 (vector pGWIZ, Gene Therapy Systems bp 1039-919)
Bp 13848-13925 CMV Promoter (vector pGWIZ, Gene Therapy Systems bp 918-900, CTC, 899-844)
BP 13926-14530 CMV Enhancer (vector pGWIZ, Gene Therapy Systems bp 843-245) with 5' EcoRI RE site
Bp 14531-15377 Chicken Ovalbumin promoter from gDNA (Genbank #J00895 bp 1261-421) with 5'MluI RE site
Bp 15378-17082 Chicken Lysozyme Matrix Attachment region (MAR) from gDNA
Bp 17083-17152 70 bp of IS10 from Tn10 (GenBank Accession #J01829 Bp 70-1)

Bp 17153-17195 Lambda DNA from pNK2859

Bp 17196-19400 pBluescriptII sk(−) base vector (Stratagene, INC)

SEQ ID NO: 27 VID#280 Hybrid Promoter Vs.1–co-RM2 mAb–OPA in pTn10 PURO-MAR Flanked BV Bp 1-132 Remainder of F1 (−) ori of pBluescriptII sk(−) (Stratagene) bp 4-135

Bp 133-148 pGWIZ base vector (Gene Therapy Systems) bp 229-244

Bp 149-747 CMV Enhancer (vector pGWIZ, Gene Therapy Systems bp 245-843)

Bp 748-822 CMV Promoter (vector pGWIZ, Gene Therapy Systems bp 844-918)

Bp 823-943 CMV Immediate Early Gene, Exon 1 (vector pGWIZ, Gene Therapy Systems bp 919-1039)

Bp 944-1769 CMV Intron A (vector pGWIZ, Gene Therapy Systems bp 1040-1865)

Bp 1770-1777 CMV Immediate Early Gene, Partial Exon 2 (pGWIZ, Gene Therapy Systems) bp 1866-1873)

Bp 1778-1806 TN10 DNA, 3'end from Genbank Accession #J01829 bp79-107

Bp 1807-3015 Transposon, modified from Tn10 GenBank Accession #J01829 Bp 108-1316

Bp 3016-3367 Putative PolyA from vector pNK2859

Bp 3368-3410 Lambda DNA from pNK2859

Bp 3411-3480 70 bp of IS10 left from Tn10 (GenBank Accession #J01829 Bp 1-70)

Bp 3481-3651 pBluescriptII sk(−) base vector (Stratagene, INC)

Bp 3652-3674 Multiple cloning site from pBluescriptII sk(−) thru NotI, Bp 759-737

Bp 3675-5367 Chicken Lysozyme Matrix Attachment region (MAR) from gDNA

Bp 5368-5381 Multiple Cloning Site Extension from pTn X-MCS, XhoI thru AscI

Bp 5382-6223 Chicken Ovalbumin promoter from gDNA (Genbank Accession #J00895 bp 421-1261)

BP 6224-6827 CMV Enhancer (vector pGWIZ, Gene Therapy Systems bp 245-843) with 5' EcoRI RE site Bp 6828-6905 CMV Promoter (vector pGWIZ, Gene Therapy Systems bp 844-899, CTC, 900-918)

Bp 6906-7026 CMV Immediate Early Gene, Exon 1 (vector pGWIZ, Gene Therapy Systems bp 919-1039)

BP 7027-7852 CMV Intron A (vector pGWIZ, Gene Therapy Systems bp 1040-1865)

Bp 7853-7860 CMV Immediate Early Gene, Partial Exon 2 (pGWIZ, Gene Therapy Systems) bp 1866-1873)

Bp 7861-7926 Conalbumin Signal Peptide (Genbank #Y00407 bp 340-385, 1699-1715) with 5'SalI RE site. Kozak sequence (7867-7872)

Bp 7927-8574 Light chain gene-codon optimized from antibody RM2 (provided by Shantha West, Inc.)

Bp 8575-9496 Chicken Ovalbumin polyA from gDNA (GenBank #J00895 bp 8260-9175) with 5'AgeI RE site Bp 9497-9516 Multiple Cloning Site Extension from pTn X-MCS, PacI thru SbfI Bp 9517-9829 HSV-TK polyA from pS65TC1 bp 3873-3561

BP 9830-10460 Puromycin resistance gene from pMOD PURO (invivoGen)

Bp 10461-10852 SV40 promoter from pS65TC1, bp 2617-2232 with 5' BsiWI RE site

Bp 10853-11776 Chicken Ovalbumin polyA from gDNA (GenBank #J00895 bp 9175-8260) with 5'AsiSI RE site Bp 11777-13144 Heavy chain gene construct from antibody RM2 (provided by Shantha West, Inc.)

Bp 13145-13210 Conalbumin Signal Peptide (Genbank #Y00407 bp 340-385, 1699-1715) with 5'SalI RE site. Kozak sequence (13199-13204)

Bp 13211-13218 CMV Immediate Early Gene, Partial Exon 2 (pGWIZ, Gene Therapy Systems bp 1873-1866)

Bp 13219-14044 CMV Intron A (vector pGWIZ, Gene Therapy Systems Bp 1865-1040)

Bp 14045-14165 CMV Immediate Early Gene, Exon 1 (vector pGWIZ, Gene Therapy Systems bp 1039-919)

Bp 14166-14243 CMV Promoter (vector pGWIZ, Gene Therapy Systems bp 918-900, CTC, 899-844)

BP 14244-14848 CMV Enhancer (vector pGWIZ, Gene Therapy Systems bp 843-245) with 5' EcoRI RE site Bp 14849-15695 Chicken Ovalbumin promoter from gDNA (Genbank #J00895 bp 1261-421) with 5'MluI RE site Bp 15696-17400 Chicken Lysozyme Matrix Attachment region (MAR) from gDNA Bp 17401-17470 70 bp of IS10 from Tn10 (GenBank Accession #J01829 Bp 70-1)

Bp 17471-17513 Lambda DNA from pNK2859

Bp 17514-19718 pBluescriptII sk(−) base vector (Stratagene, INC)

In one embodiment, the present application provides a novel sequence comprising a promoter, a gene of interest, and a poly A sequence. Each of these novel sequences may be identified from the annotations for each expression vector shown above, and also as sequences within the sequence listing for each expression vector. The specific bases of these novel sequences are provided in Table 3 below for each expression vector SEQ ID NOs: 17 to 27.

TABLE 3

| | mAb's | |
|---|---|---|
| SEQ ID NO | Light Chain | Heavy Chain |
| 17 | 4937-8269 | 8278-12330 |
| 18 | 4931-8263 | 8272-12324 |
| 19 | 5382-8714 | 8723-12775 |
| 20 | 5382-8714 | 8723-12775 |
| 21 | 5382-9487 | 10844-15669 |
| 22 | 5382-9502 | 10859-15351 |
| 23 | 5382-9564 | 10921-15822 |
| 24 | 4936-8754 | 8763-13301 |
| 25 | 5382-10202 | 10237-13508 |
| 26 | 5382-9511 | 10868-15377 |
| 27 | 5382-9496 | 10853-15695 |

E. Methods of In Vivo Administration

The polynucleotide cassettes may be delivered through the vascular system to be distributed to the cells supplied by that vessel. For example, the compositions may be administered through the cardiovascular system to reach target tissues and cells receiving blood supply. In one embodiment, the compositions may be administered through any chamber of the heart, including the right ventricle, the left ventricle, the right atrium or the left atrium. Administration into the right side of the heart may target the pulmonary circulation and tissues supplied by the pulmonary artery. Administration into the left side of the heart may target the systemic circulation through the aorta and any of its branches, including but not limited to the coronary vessels, the ovarian or testicular arteries, the renal arteries, the arteries supplying the gastrointestinal and pelvic tissues, including the celiac, cranial mesenteric and caudal mesenteric vessels and their branches, the common iliac arteries and their branches to the pelvic organs, the gastrointestinal system and the lower extremity, the carotid, brachiocephalic and subclavian arteries. It is to be understood that the specific names of blood vessels change with the species under consideration and are known to one of ordinary skill in the art. Administration into the left ventricle or ascending or descending aorta supplies any of the tissues receiving blood supply from the aorta and its branches, including but not limited to the testes, ovary, oviduct, and liver. Germline cells and other cells may be transfected in this manner. For example, the compositions may be placed in the left ventricle, the aorta or directly into an artery supplying the ovary or supplying the fallopian tube to transfect cells in those tissues. In this manner, follicles could be transfected to create a germline transgenic animal. Alternatively, supplying the compositions through the artery leading to the oviduct would preferably transfect the tubular gland and epithelial cells. Such transfected cells could manufacture a desired protein or peptide for deposition in the egg white. Administration of the compositions through the left cardiac ventricle, the portal vein or hepatic artery would target uptake and transformation of hepatic cells. Administration may occur through any means, for example by injection into the left ventricle, or by administration through a cannula or needle introduced into the left atrium, left ventricle, aorta or a branch thereof.

Intravascular administration further includes administration in to any vein, including but not limited to veins in the systemic circulation and veins in the hepatic portal circulation. Intravascular administration further includes administration into the cerebrovascular system, including the carotid arteries, the vertebral arteries and branches thereof.

Intravascular administration may be coupled with methods known to influence the permeability of vascular barriers such as the blood brain barrier and the blood testes barrier, in order to enhance transfection of cells that are difficult to affect through vascular administration. Such methods are known to one of ordinary skill in the art and include use of hyperosmotic agents, mannitol, hypothermia, nitric oxide, alkylglycerols, lipopolysaccharides (Haluska et al., Clin. J. Oncol. Nursing 8(3): 263-267, 2004; Brown et al., Brain Res., 1014: 221-227, 2004; Ikeda et al., Acta Neurochir. Suppl. 86:559-563, 2004; Weyerbrock et al., J. Neurosurg. 99(4):728-737, 2003; Erdlenbruch et al., Br. J. Pharmacol. 139(4):685-694, 2003; Gaillard et al., Microvasc. Res. 65(1):24-31, 2003; Lee et al., Biol. Reprod. 70(2):267-276, 2004)).

Intravascular administration may also be coupled with methods known to influence vascular diameter, such as use of beta blockers, nitric oxide generators, prostaglandins and other reagents that increase vascular diameter and blood flow.

Administration through the urethra and into the bladder would target the transitional epithelium of the bladder. Administration through the vagina and cervix would target the lining of the uterus and the epithelial cells of the fallopian tube.

The polynucleotide cassettes may be administered in a single administration, multiple administrations, continuously, or intermittently. The polynucleotide cassettes may be administered by injection, via a catheter, an osmotic minipump or any other method. In some embodiments, a polynucleotide cassette is administered to an animal in multiple administrations, each administration containing the polynucleotide cassette and a different transfecting reagent.

In a preferred embodiment, the animal is an egg-laying animal, and more preferably, an avian, and the transposon-based vectors comprising the polynucleotide cassettes are administered into the vascular system, preferably into the heart. The vector may be injected into the venous system in locations such as the jugular vein and the metatarsal vein. In one embodiment, between approximately 1 and 1000 μg, 1 and 200 μg, 5 and 200 μg, or 5 and 150 μg of a transposon-based vector containing the polynucleotide cassette is administered to the vascular system, preferably into the heart. In a chicken, it is preferred that between approximately 1 and 300 μg, or 5 and 200 μg are administered to the vascular system, preferably into the heart, more preferably into the left ventricle. The total injection volume for administration into the left ventricle of a chicken may range from about 10 μl to about 5.0 ml, or from about 100 μl to about 1.5 ml, or from about 200 μl to about 1.0 ml, or from about 200 μl to about 800 μl. It is to be understood that the total injection volume may vary depending on the duration of the injection. Longer injection durations may accommodate higher total volumes. In a quail, it is preferred that between approximately 1 and 200 μg, or between approximately 5 and 200 μg are administered to the vascular system, preferably into the heart, more preferably into the left ventricle. The total injection volume for administration into the left ventricle of a quail may range from about 10 μl to about 1.0 ml, or from about 100 μl to about 800 μl, or from about 200 μl to about 600 μl. It is to be understood that the total injection volume may vary depending on the duration of the injection. Longer injection durations may accommodate higher total volumes. The microgram quantities represent the total amount of the vector with the transfection reagent.

In another embodiment, the animal is an egg-laying animal, and more preferably, an avian. In one embodiment, between approximately 1 and 150 μg, 1 and 100 μg, 1 and 50 μg, preferably between 1 and 20 μg, and more preferably between 5 and 10 μg of a transposon-based vector containing the polynucleotide cassette is administered to the oviduct of a bird. In a chicken, it is preferred that between approximately 1 and 100 μg, or 5 and 50 μg are administered. In a quail, it is preferred that between approximately 5 and 10 μg are administered. Optimal ranges depending upon the type of bird and the bird's stage of sexual maturity. Intraoviduct administration of the transposon-based vectors of the present invention result in a PCR positive signal in the oviduct tissue, whereas intravascular administration results in a PCR positive signal in the liver, ovary and other tissues. In other embodiments, the polynucleotide cassettes is administered to the cardiovascular system, for example the left cardiac ventricle, or directly into an artery that supplies the oviduct or the liver. These methods of administration may also be combined with any methods for facilitating transfection, including without limitation, electroporation, gene guns, injection of naked DNA, and use of dimethyl sulfoxide (DMSO). U.S. Pat. No. 7,527,966, U.S. Publication No. 2008/0235815, and PCT Publication No. WO 2005/062881 are hereby incorporated by reference in their entirety.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Preparation of Vectors for In Vitro Expression of RM2 Monoclonal Antibody

Several expression vectors were constructed to include genes which encode the light and heavy chains of an RM2 monoclonal antibody.

Vector #148 (SEQ ID NO:17) was made by digesting both the pTn10 HS4 flanked backbone (pTn10 HFB #5006) vector (SEQ ID NO:3) and a pTopo vector comprising the RM2 cassette with Asc I and BsiWI. This digestion linearized the pTn10 HFB #5006 vector and released the RM2 cassette from the pTopo vector. The RM2 cassette was purified from restriction enzymes using a Zymo DNA Clean and Concentrator kit (Zymo Research) and ligated into the linearized pTn10 HFB #5006 vector.

Vector #210 (SEQ ID NO:18) was made by digesting both the pTn10 HS4 flanked backbone (pTn10 HFB) vector (SEQ ID NO:4) and a pTopo vector comprising the RM2 cassette with Asc I and BsiWI. This digestion linearized the pTn10 HFB vector and released the RM2 cassette from the pTopo vector. The RM2 cassette was purified from restriction enzymes using a Zymo DNA Clean and Concentrator kit (Zymo Research) and ligated into the linearized pTn10 HFB vector.

Vector #212 (SEQ ID NO:19) was made by digesting both the pTn10 MAR flanked backbone (pTn10 MAR) vector (SEQ ID NO:5) and a pTopo vector comprising the RM2 cassette with Asc I and BsiWI. This digestion linearized the pTn10 MAR vector and released the RM2 cassette from the pTopo vector. The RM2 cassette was purified from restriction enzymes using a Zymo DNA Clean and Concentrator kit (Zymo Research) and ligated into the linearized pTn10 MAR vector.

Vector #226 (SEQ ID NO:20) was made by digesting both the pTn10 PURO-MAR flanked backbone (pTn10 PURO-MAR) vector (SEQ ID NO:8) and a pTopo vector comprising the RM2 cassette with Asc I and BsiWI. This digestion linearized the pTn10 PURO-MAR vector and released the RM2 cassette from the pTopo vector. The RM2 cassette was purified from restriction enzymes using a Zymo DNA Clean and Concentrator kit (Zymo Research) and ligated into the linearized pTn10 PURO-MAR vector.

Vector #275 (SEQ ID NO:21) was made by digesting both the pTn10 PURO-MAR flanked backbone (pTn10 PURO-MAR) vector (SEQ ID NO:8) and a pTopo vector comprising the RM2 LC cassette with Asc I and Pac I. This digestion linearized the pTn10 PURO-MAR vector and released the RM2 LC cassette from the pTopo vector. The RM2 LC cassette was purified from restriction enzymes using a Zymo DNA Clean and Concentrator kit (Zymo Research) and ligated into the linearized pTn10 PURO-MAR vector. The resulting vector and a pTopo vector comprising the RM2 HC cassette was then digested with Mlu I and BsiW I. This digestion linearized the RM2 LC cassette+pTn10 PURO-MAR vector and released the RM2 HC cassette from the pTopo vector. The RM2 HC cassette was purified from restriction enzymes using a Zymo DNA Clean and Concentrator kit (Zymo Research) and ligated into the linearized RM2 LC cassette+pTn10 PURO-MAR vector.

Vector #278 (SEQ ID NO:22) was made by digesting both the pTn10 PURO-MAR flanked backbone (pTn10 PURO-MAR) vector (SEQ ID NO:8) and a pTopo vector comprising the ΔCH2 LC cassette with Asc I and Pac I. This digestion linearized the pTn10 PURO-MAR vector and released the ΔCH2 LC cassette from the pTopo vector. The ΔCH2 LC cassette was purified from restriction enzymes using a Zymo DNA Clean and Concentrator kit (Zymo Research) and ligated into the linearized pTn10 PURO-MAR vector. The resulting vector and a pTopo vector comprising the ΔCH2 HC cassette was then digested with Mlu I and BsiW I. This digestion linearized the ΔCH2 LC cassette+pTn10 PURO-MAR vector and released the ΔCH2 HC cassette from the pTopo vector. The ΔCH2 HC cassette was purified from restriction enzymes using a Zymo DNA Clean and Concentrator kit (Zymo Research) and ligated into the linearized ΔCH2 LC cassette+pTn10 PURO-MAR vector.

Construction of Vectors #273 (SEQ ID NO:23)

The pTopo containing the RM2 monoclonal antibody (mAb) cassettes driven by either the hybrid promoter version 1 (SEQ ID NO:14) or version 2 (SEQ ID NO:15) were digested with restriction enzymes AscI, PacI, BsiWI, and MluI (New England Biolabs, Beverly, Mass.) according to the manufacturer's protocol. Digested DNA was purified from restriction enzymes using a Zymo DNA Clean and Concentrator kit (Zymo Research). To insert the RM2 light chain (LC) cassette into the MCS of the p5021 vector (SEQ ID NO:8), the purified LC DNA and the p5021 vector (SEQ ID NO:8) were digested with AscI and PacI, purified as described above, and ligated using a Quick T4 DNA Ligase Kit (New England Biolabs, Beverly, Mass.) according to the manufacturer's protocol. To insert the RM2 heavy chain (HC) cassette into the MCS of the p5021 vector (SEQ ID NO:8), the purified HC DNA and the p5021 vector (SEQ ID NO:8) were digested with BsiWI and MluI, purified as described above, and ligated using a Quick T4 DNA Ligase Kit (New England Biolabs, Beverly, Mass.) according to the manufacturer's protocol. Ligated product was transformed into *E. coli* XL10-Gold Ultracompetent cells (Stratagene, Inc. La Jolla, Calif.) using chemical transformation according to Stratagene's protocol. Transformed bacteria were incubated in 0.9 ml of NZY Plus (TEKnova, CAT#N1215) broth for 1 hour at 37° C. before being spread to LB (Luria-Bertani media (broth or agar)) plates supplemented with 100 μg/ml ampicillin (LB/amp plates). These plates were incubated overnight at 37° C. and resulting colonies picked to LB/amp broth for overnight growth at 37° C. Plasmid DNA was isolated using a modified alkaline lysis protocol (Sambrook et al., 1989), electrophoresed on a 1% agarose gel, and visualized on a U.V. transilluminator after ethidium bromide staining Colonies producing a plasmid of the expected size were cultured in at least 250 ml of LB/amp broth and plasmid DNA harvested using a Qiagen Maxi-Prep Kit (column purification) according to the manufacturer's protocol (Qiagen, Inc., Chatsworth, Calif.). Column purified DNA was used as template for sequencing to verify the changes made in the vector were the desired changes and no further changes or mutations occurred. All sequencing was done on a Beckman Coulter CEQ 8000 Genetic Analysis System.

Construction of Vectors #146/149 (SEQ ID NO:24)

The pTopo containing the RM2 monoclonal antibody (mAb) cassettes driven by the Vitellogenin II promoter were digested with restriction enzymes AscI, BsiWI, and PacI (New England Biolabs, Beverly, Mass.) according to the manufacturer's protocol. Digested DNA was purified from restriction enzymes using a Zymo DNA Clean and Concentrator kit (Zymo Research). To insert the RM2 light chain (LC) cassette into the MCS of the p5006 vector (SEQ ID NO:3), the purified LC DNA and the p5006 vector (SEQ ID NO:3) were digested with AscI and PacI, purified as described above, and ligated using a Quick T4 DNA Ligase Kit (New England Biolabs, Beverly, Mass.) according to the manufacturer's protocol. To insert the RM2 heavy chain (HC) cassette into the MCS of the p5006 vector (SEQ ID NO:3), the purified HC DNA and the p5006 vector (SEQ ID NO:3) were digested with BsiWI and PacI, purified as described above, and ligated using a Quick T4 DNA Ligase Kit (New England Biolabs, Beverly, Mass.) according to the manufacturer's protocol. Ligated product was transformed into *E. coli* XL10-Gold Ultracompetent cells (Stratagene, Inc. La Jolla, Calif.) using chemical transformation according to Stratagene's protocol. Transformed bacteria were incubated in 0.9 ml of NZY Plus (TEKnova, CAT#N1215) broth for 1 hour at 37° C. before being spread to LB (Luria-Bertani media (broth or agar)) plates supplemented with 100 μg/ml ampicillin (LB/amp plates). These plates were incubated overnight at 37° C. and resulting colonies picked to LB/amp broth for overnight growth at 37° C. Plasmid DNA was isolated using a modified alkaline lysis protocol (Sambrook et al., 1989), electrophoresed on a 1% agarose gel, and visualized on a U.V. transilluminator after ethidium bromide staining. Colonies producing a plasmid of the expected size were cultured in at least 250 ml of LB/amp broth and plasmid DNA harvested using a Qiagen Maxi-Prep Kit (column purification) according to the manufacturer's protocol (Qiagen, Inc., Chatsworth, Calif.). Column purified DNA was used as template for sequencing to verify the changes made in the vector were the desired changes and no further changes or mutations occurred. All sequencing was done on a Beckman Coulter CEQ 8000 Genetic Analysis System.

Once a clone was identified that contained both the Light Chain and Heavy Chain gene, the DNA was isolated by standard procedures. Briefly, *Escherichia coli* containing the plasmid was grown in 500 mL aliquots of LB broth (supplemented with an appropriate antibiotic) at 37° C. overnight with shaking. Plasmid DNA was recovered from the bacteria using a Qiagen EndoFree Plasmid Maxi-Prep kit (Qiagen, Inc., Chatsworth, Calif.) according to the manufacturer's protocol. Plasmid DNA was resuspended in 600 μL of Endotoxin free water and stored at −20° C. until needed.

Construction of Vector #267 (SEQ ID NO:25)

Invitrogen's pTopo plasmid (Carlsbad, Calif.) containing the Herceptin monoclonal antibody (mAb) cassettes driven by the hybrid promoter version 1 (SEQ ID NO:14) are digested with restriction enzymes AscI, AsiSI, SbFI, and BsiWI (New England Biolabs, Beverly, Mass.) according to the manufacturer's protocol. Digested DNA is purified using a Zymo DNA Clean and Concentrator kit (Zymo Research, Orange, Calif.). To insert the Herceptin heavy chain (HHC) cassette into the MCS of vector p5021 (SEQ ID NO:8), HHC and p5021 vector DNA (SEQ ID NO:8) are digested with AscI and AsiSI, purified as described above, and ligated using a Quick T4 DNA Ligase Kit (New England Biolabs, Beverly, Mass.) according to the manufacturer's protocol. To insert the Herceptin light chain (HLC) cassette into the MCS of p5021 (SEQ ID NO:5), HLC DNA and vector p5021 (SEQ ID NO:8) containing the Herceptin HC cassette, are digested with SbFI and BsiWI, purified and ligated as described above. Ligated product is transformed into *E. coli* XL10-Gold Ultracompetent cells (Stratagene, Inc. La Jolla, Calif.) using chemical transformation according to the manufacturer's protocol. Transformed bacterial cells are incubated in 0.9 ml of NZY Plus (TEKnova, CAT#N1215) broth for 1 hour at 37° C. then spread to LB (Luria-Bertani) agar plates supplemented with 100 μg/ml ampicillin (LB/amp plates). All plates are incubated overnight at 37° C. Resulting colonies are picked into LB/amp broth for overnight growth at 37° C. Plasmid DNA is isolated using a modified alkaline lysis protocol (Sambrook et al., 1989), electrophoresed on a 0.8% agarose gel, and visualized on a U.V. transilluminator after ethidium bromide staining. Colonies producing a plasmid of the expected size are cultured in a minimum of 250 ml of LB/amp broth. Plasmid DNA is harvested using a Qiagen Maxi-Prep Kit according to the manufacturer's protocol (Qiagen, Inc., Chatsworth, Calif.). The DNA is then used as a sequencing template to verify that the changes made in the vector are the desired changes and that no further changes or mutations occurred. All sequencing is performed using Beckman Coulter's CEQ 8000 Genetic Analysis System.

Once a clone is identified that contains both the Herceptin Heavy Chain and Herceptin Light Chain gene, the DNA is isolated by standard procedures. Briefly, *E. coli* bacteria containing the plasmid are grown in 250 ml of LB broth (supplemented with an appropriate antibiotic) at 37° C. overnight in a shaking incubator. Plasmid DNA is isolated from the bacterial cells using a Qiagen EndoFree Plasmid Maxi-Prep kit (Qiagen, Inc., Chatsworth, Calif.) according to the manufacturer's protocol. Plasmid DNA is resuspended in 500 μL of endotoxin free water and stored at −20° C. until needed.

Construction of Vector #279 (SEQ ID NO:26)

Invitrogen's pTopo plasmid (Carlsbad, Calif.) containing the codon-optimized ΔCH2 monoclonal antibody (mAb) cassettes driven by the hybrid promoter version 1 (SEQ ID NO:14) were digested with restriction enzymes AscI, PacI, BsiWI, and MluI (New England Biolabs, Beverly, Mass.) according to the manufacturer's protocol. Digested DNA was purified using a Zymo DNA Clean and Concentrator kit (Zymo Research). To insert the codon-optimized ΔCH2 light chain (LC) cassette into the MCS of vector p5021 (SEQ ID NO:8), LC and p5021 DNA (SEQ ID NO:8) were digested with AscI and PacI, purified as described above, and ligated using a Quick T4 DNA Ligase Kit (New England Biolabs, Beverly, Mass.) according to the manufacturer's protocol. To insert the codon-optimized ΔCH2 heavy chain (HC) cassette into the MCS of the p5021 vector (SEQ ID NO:8), HC and the p5021 DNA (SEQ ID NO:8) were digested with BsiWI and MluI, purified and ligated as described above. Ligated product was transformed into *E. coli* XL10-Gold Ultracompetent cells (Stratagene, Inc. La Jolla, Calif.) using chemical transformation according to the manufacturer's protocol. Transformed bacterial cells were incubated in 0.9 ml of NZY Plus (TEKnova, CAT#N1215) broth for 1 hour at 37° C. then spread onto LB (Luria-Bertani) agar plates supplemented with 100 μg/ml ampicillin (LB/amp plates). All plates were incubated overnight at 37° C. Resulting colonies were picked into LB/amp broth for overnight growth at 37° C. Plasmid DNA was isolated using a modified alkaline lysis protocol (Sambrook et al., 1989), electrophoresed on a 0.8% agarose gel, and visualized on a U.V. transilluminator after ethidium bromide staining Colonies producing a plasmid of the expected size were cultured in a minimum of 250 ml of LB/amp broth. Plasmid DNA was harvested using a Qiagen Maxi-Prep Kit according to the manufacturer's protocol (Qiagen, Inc., Chatsworth, Calif.). The DNA was then used as a sequencing template to verify that the changes made in the vector were the desired changes and that no further changes or mutations occurred. All sequencing was performed using Beckman Coulter's CEQ 8000 Genetic Analysis System.

Once a clone was identified that contained both the codon-optimized Light Chain and codon-optimized Heavy Chain cassettes, the DNA was isolated by standard procedures. Briefly, *E. coli* bacteria containing the plasmid of interest were grown in 250 ml of LB broth (supplemented with an appropriate antibiotic) at 37° C. overnight in a shaking incubator. Plasmid DNA was isolated from the bacterial cells using a Qiagen EndoFree Plasmid Maxi-Prep kit (Qiagen, Inc., Chatsworth, Calif.) according to the manufacturer's protocol. Plasmid DNA was resuspended in 500 μL of endotoxin free water and stored at −20° C. until needed.

Construction of Vector #280 (SEQ ID NO:27)

Invitrogen's pTopo plasmid (Carlsbad, Calif.) containing the codon-optimized RM2 monoclonal antibody (mAb) cassettes driven by the hybrid promoter version 1 (SEQ ID NO:14) were digested with restriction enzymes AscI, PacI, BsiWI, and MluI (New England Biolabs, Beverly, Mass.) according to the manufacturer's protocol. Digested DNA was purified using a Zymo DNA Clean and Concentrator kit (Zymo Research). To insert the codon-optimized RM2 light chain (LC) cassette into the MCS of the p5021 vector (SEQ ID NO:8), LC and p5021 DNA (SEQ ID NO:8) were digested with AscI and PacI, purified as described above, and ligated using a Quick T4 DNA Ligase Kit (New England Biolabs, Beverly, Mass.) according to the manufacturer's protocol. To insert the codon-optimized RM2 heavy chain (HC) cassette into the MCS of the p5021 vector (SEQ ID NO:8), the HC DNA and the p5021 (SEQ ID NO:8) were digested with BsiWI and MluI, purified and ligated as described above. Ligated product was transformed into *E. coli* XL10-Gold Ultracompetent cells (Stratagene, Inc. La Jolla, Calif.) using chemical transformation according to the manufacturer's protocol. Transformed bacterial cells were incubated in 0.9 ml of NZY Plus (TEKnova, CAT#N1215) broth for 1 hour at 37° C. then spread to LB (Luria-Bertani) agar plates supplemented with 100 μg/ml ampicillin (LB/amp plates). All plates were incubated overnight at 37° C., and resulting colonies were picked into LB/amp broth for overnight growth at 37° C. Plasmid DNA was isolated using a modified alkaline lysis protocol (Sambrook et al., 1989), electrophoresed on a 1% agarose gel, and visualized on a U.V. transilluminator after ethidium bromide staining Colonies producing a plasmid of the expected size were cultured in at least 250 ml of LB/amp broth. Plasmid DNA was harvested using a Qiagen Maxi-Prep Kit according to the manufacturer's protocol (Qiagen, Inc., Chatsworth, Calif.). The DNA was then used as a sequencing template to verify the changes made in the vector were the desired changes and no further changes or mutations occurred. All sequencing was performed using Beckman Coulter's CEQ 8000 Genetic Analysis System.

Once a clone was identified that contained both the codon-optimized Light Chain and codon-optimized Heavy Chain cassettes, the DNA was isolated by standard procedures. Briefly, *E. coli* bacteria containing the plasmid of interest was grown in 250 ml of LB broth (supplemented with an appropriate antibiotic) at 37° C. overnight in a shaking incubator. Plasmid DNA was isolated from the bacterial cells using a Qiagen EndoFree Plasmid Maxi-Prep kit (Qiagen, Inc., Chatsworth, Calif.) according to the manufacturer's protocol. Plasmid DNA was resuspended in 500 μL of endotoxin free water and stored at −20° C. until needed.

For each of the vectors, the following steps occurred after ligation of the antibody gene cassette into the appropriate vector for expression:

Column purified DNA was used as template for sequencing to verify the changes made in the vector were the desired changes (i.e., that the RM2 cassette was inserted) and that no further changes or mutations occurred. All sequencing was done on a Beckman Coulter CEQ 8000 Genetic Analysis System.

Table 4 shows some details of four of the vectors used for the in vitro production of the RM2 monoclonal antibody, along with the label that corresponds to that vector in the data shown in Example 2 below. All include the same production cassette for the heavy and light chain of the RM2 monoclonal antibody. These vectors differ only in the backbone vector used.

TABLE 4

| Flask | Vector | Backbone Vector | Promoter | SEQ ID NO: |
|---|---|---|---|---|
| C1 | N/A | N/A | N/A | N/A |
| T1 | 148 | Old HFB | CMV | 17 |
| T4 | 210 | K10 HFB | CMV | 18 |
| T6 | 212 | K10 MAR HFB | CMV | 19 |
| — | 226 | K10 PURO MAR HFB | CMV | 20 |

Schematics of these vectors are shown in FIGS. 2-5, respectively. The sequences of the vectors (SEQ ID NO:17, 18, 19, and 20) are shown below in the Appendix.

EXAMPLE 2

In Vitro Expression of Monoclonal Antibody

These experiments were performed to verify that vectors 148 (SEQ ID NO:17), 210 (SEQ ID NO:18), 212 (SEQ ID NO:19), and 226 (SEQ ID NO:20) produced the light and heavy chain polypeptides of RM2 antibody, and to determine whether these antibody products were toxic to the transfected cells.

Figure 6:
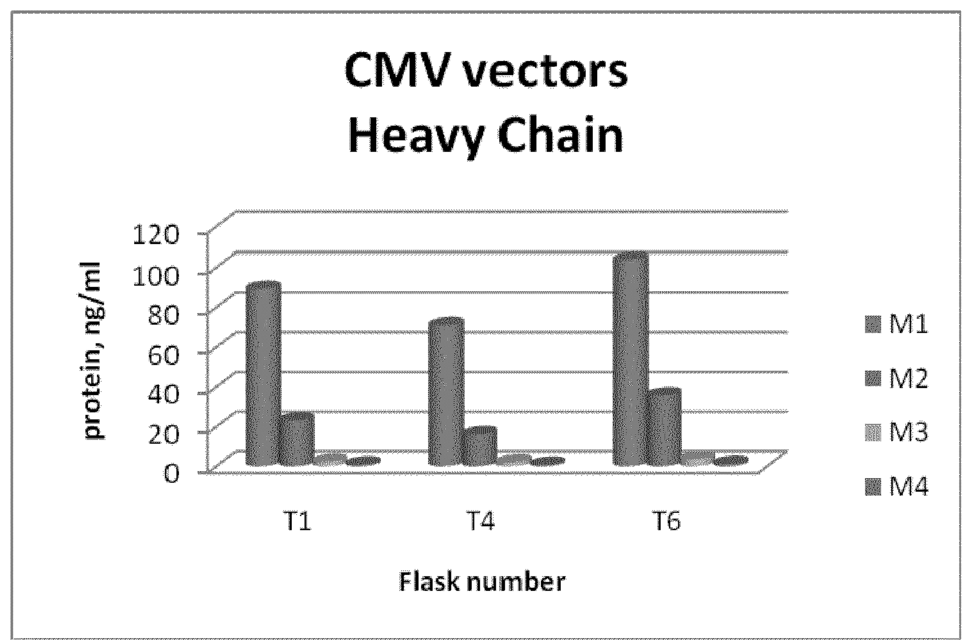
FIG. 6 is a graph showing the results of an enzyme linked immunosorbent assay (ELISA) demonstrating the efficient expression of the RM2 monoclonal antibody light chain (Panel B) and heavy chain (Panel A) in LMH2A cells using the expression vectors described herein. T1, T4, and T6 correspond to cells transfected with SEQ ID NOs:17, 18, and 19, respectively. Control flasks also were run, but exhibited readings that were too low to detect (data not shown). M1, M2, M3, and M4 are samples taken 3 days, 8 days, 11 days, and 14 days post transfection, respectively. The bars from left to right in each group correspond to M1, M2, M3, and M4 samples, respectively.
Figure 6:
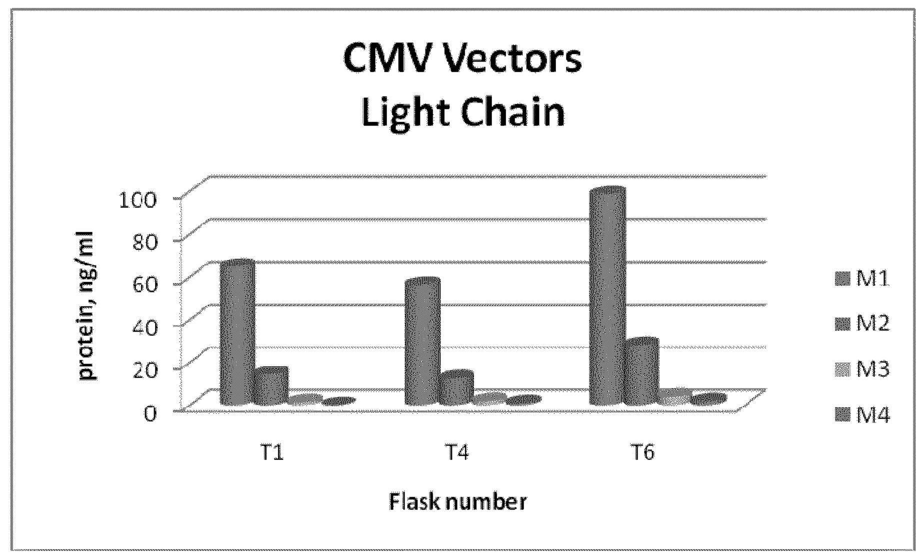

The graphs in FIG. 6 show the ELISA readings for the media samples from one experiment. T1, T4, and T6 represent flasks containing cells transfected with vector #148 (SEQ ID NO:17), 210 (SEQ ID NO:18), and 212 (SEQ ID NO:19), respectively. Vector #212 (SEQ ID NO:19) demonstrated the highest expression of both the heavy and the light chains of the RM2 antibody. Control flasks also were run, but the readings were too low to detect at these dilution levels (data not shown). Vector #226 (SEQ ID NO:20) also demonstrated expression of the RM2 monoclonal antibody light and heavy chains as is shown in Table 5.

TABLE 5

| Sample | Heavy chain ng/ml | Light chain ng/ml |
|---|---|---|
| 1159R M1 | 412.685 | 337.950 |
| 1159 M2 | 173.698 | 143.789 |
| 1159 M3 | 48.504 | 40.781 |
| 1159 M4 | 13.640 | 11.367 |

There was no indication that the products produced were toxic in any way to the cells. The cells remained alive, healthy, and demonstrated typical morphology throughout the experiment.

The remaining expression vectors also have been assayed for their ability to produce heavy chain, light chain, kappa chain, or lambda chain of an antibody as discussed in this example. Typical maximum results for the expression vectors are shown in Table 6.

TABLE 6

| Vector # | SEQ ID NO: | Cell Type | Protein | Max amt of protein (ng/ml) |
|---|---|---|---|---|
| 278 | 22 | LMH | Heavy Chain | 14.54 |
| 278 | 22 | LMH | Kappa Chain | 16.86 |
| 278 | 22 | 2A | Heavy Chain | 6.58 |
| 278 | 22 | 2A | Kappa Chain | 5.02 |
| 275 | 21 | LMH | Heavy Chain | 494.8 |
| 275 | 21 | LMH | Lambda Chain | 417.2 |
| 275 | 21 | LMH-2A | Heavy Chain | 263.9 |
| 275 | 21 | LMH-2A | Lambda Chain | 219.6 |
| 273 | 23 | LMH | Heavy Chain | 428.2 |
| 273 | 23 | LMH | Light Chain | 353.2 |
| 273 | 23 | LMH-2A | Heavy Chain | 144 |
| 273 | 23 | LMH-2A | Light Chain | 136.7 |
| 226 | 20 | LMH | Heavy Chain | 687.5 |
| 226 | 20 | LMH | Light Chain | 597.5 |
| 226 | 20 | LMH-2A | Heavy Chain | 239.4 |

TABLE 6-continued

| Vector # | SEQ ID NO: | Cell Type | Protein | Max amt of protein (ng/ml) |
|---|---|---|---|---|
| 226 | 20 | LMH-2A | Light Chain | 201.4 |
| 148 | 17 | LMH-2A | Heavy Chain | 23.08 |
| 148 | 17 | LMH-2A | Light Chain | 14.519 |
| 149 | 17 | LMH-2A | Heavy Chain | 1.02 |
| 149 | 17 | LMH-2A | Light Chain | 2.204 |
| 210 | 18 | LMH-2A | Heavy Chain | 16.21 |
| 210 | 18 | LMH-2A | Light Chain | 12.568 |
| 212 | 18 | LMH-2A | Heavy Chain | 35.74 |
| 212 | 18 | LMH-2A | Light Chain | 28.114 |

EXAMPLE 3

Purification of Monoclonal Antibody from Culture Media

Monoclonal antibodies were purified from the culture media using the procedure as described above under Section C.

EXAMPLE 4

Transfection Efficiency in LMH Cells and LMH 2A Cells

This experiment compared transfection efficiency and protein production in LMH cells to LMH2A cells. Vectors already proven in cell culture for three of the fusion proteins of interest were used. Transfection was carried out by the standard Fugene 6 protocol using 2 ug DNA/flask and Fugene 6:DNA at 6:1. The cultures were grown on Waymouth's+10% FCS+G418 until confluent, then fed with Waymouth's+5% FCS+G418. Samples were taken for M1, 2 days post transfection; M2, 6 days post transfection; M3, 9 days post transfection; and M4, 12 days post transfection. When referring to the data presented in FIG. 7, mAb is reported in nanograms/ml. Two graphs are used due to the differences in scale.

TABLE 7

| Flask | Cell line | Vector | Protein |
|---|---|---|---|
| C1 control | LMH | N/A | — |
| T5 | LMH | 226 | mAb |
| T6 | LMH 2A | 226 | mAb |
| C2 control | LMH 2A | N/A | — |

Figure 7:
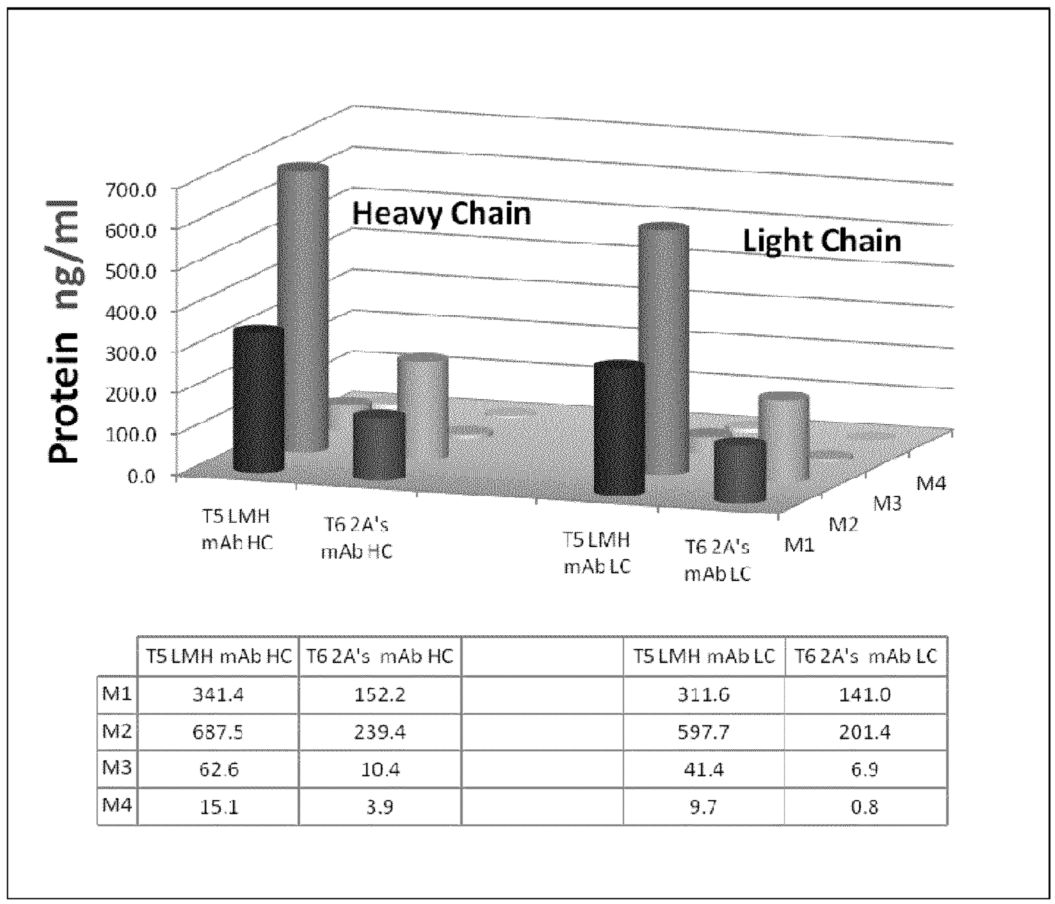
FIG. 7 is a graph showing the results of an enzyme linked immunosorbent assay (ELISA) demonstrating the efficient expression of the RM2 monoclonal antibody light chain (LC) and heavy chain (HC) in LMH and LMH2A (2A's) cells using vector #226 (SEQ ID NO:20) described herein. M1, M2, M3, and M4 represent samples taken at 2, 6, 9 and 12 days later, respectively.

FIG. 7 shows expression levels of mAb in both LMH cells and LMH2A cells. Based on these data, the vectors are capable of efficient mAb expression in both LMH and LMH2A cells.

EXAMPLE 5

Transfection Efficiency in LMH Cells and LMH 2A Cells

The suspensions of both LMH cells and LMH2A cells were adjusted to deliver $8\times10^5$ cells/T25 flask. After overnight growth, the confluence was consistent between the two cell lines at 60%. One T75 flask of each cell line was dissociated and brought up to 10 ml with PBS+20% FCS. 500 ul of each suspension was centrifuged in a Volupac tube to determine packed cell volume (PCV) and number of cells/ml. LMH=$3.25\times10^6$ cells/ml, LMH 2A's=$2.9\times10^6$ cells/ml. Each cell suspension was diluted to equal $8\times10^5$ cells/ml and seeded 1 ml per T25 flask in Waymouth's+10% FCS+HEPES (+/−G418). Thirteen T25 flasks of each cell line were prepared for transfection and control.

TABLE 8

| Flask | Cell line | Vector | Protein |
|---|---|---|---|
| C1 control | LMH | N/A | — |
| T7, 8, 9 | LMH | 226 | MAb |
| T19, 20, 21 | 2A | 226 | MAb |
| C2 control | 2A | N/A | — |

Transfection was carried out by the standard Fugene 6 protocol using 2 ug DNA/flask and Fugene 6:DNA at 6:1. Complex formation was done in Waymouth's (no additives) and the transfection was done in Waymouth's+10% FBS+HEPES (no antibiotics). After 48 hr the cultures were grown on Waymouth's+5% FCS+H (+/−G418). Transfection occurred on Nov. 14, 2008 with samples taken M1, M2 and M3 at 3, 7 and 10 days later, respectively. mAb results are reported in nanograms/ml (ng/ml).

Figure 8:
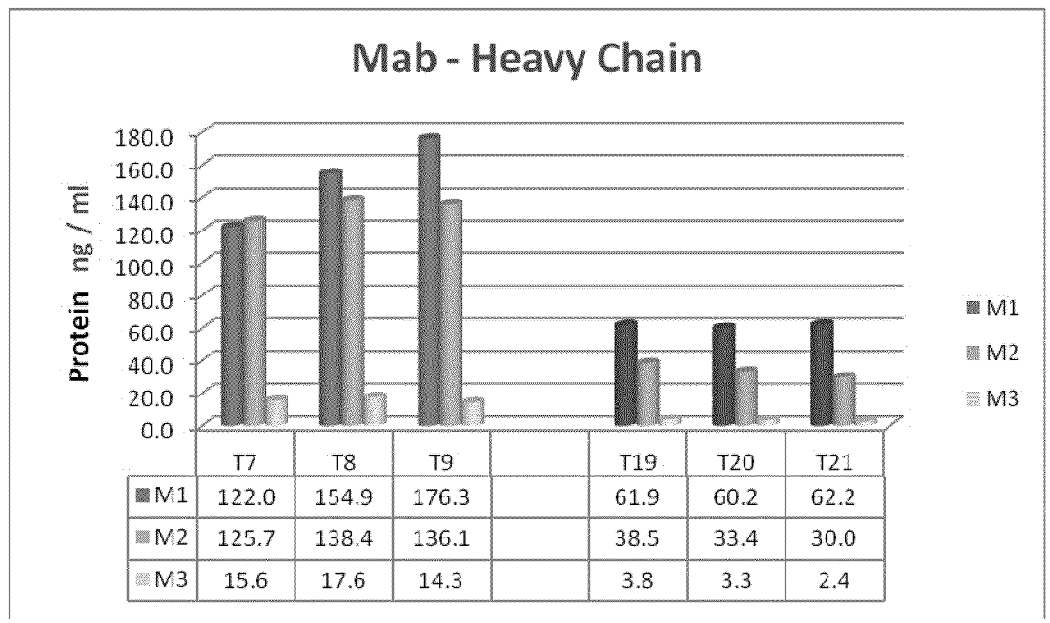
FIG. 8 is a graph showing the results of an ELISA demonstrating the efficient expression of the RM2 monoclonal antibody heavy chain in LMH (left three groups) and LMH2A (right three groups) cells using vector #226 (SEQ ID NO:20) described herein. M1, M2, and M3 represent samples taken at 3, 7, and 10 days later, respectively, and are shown in each group from left (M1) to right (M3).
Figure 9:
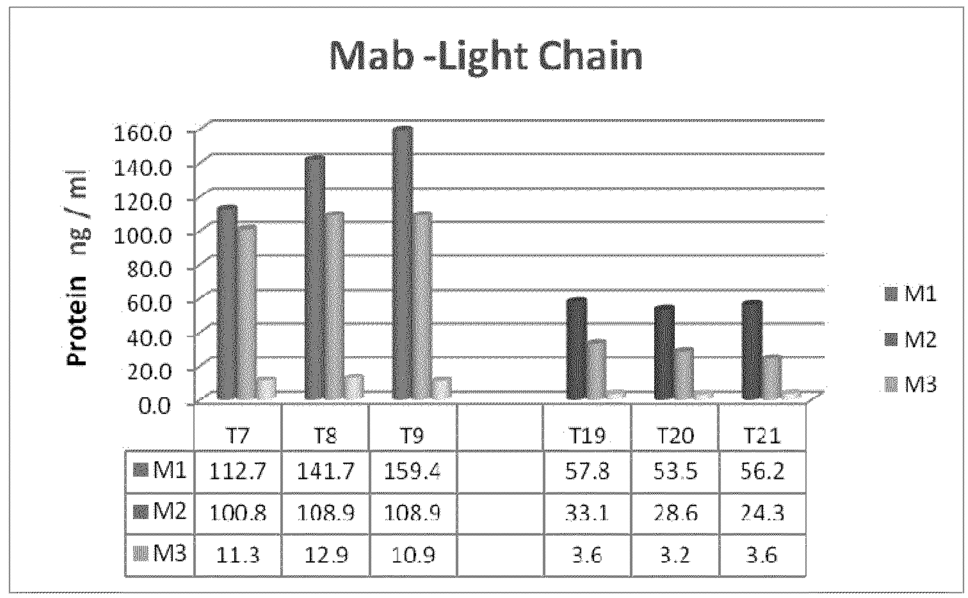
FIG. 9 is a graph showing the results of an ELISA demonstrating the efficient expression of the RM2 monoclonal antibody light chain in LMH (left three groups) and LMH2A (right three groups) cells using vector #226 (SEQ ID NO:20) described herein. M1, M2, and M3 represent samples taken at 3, 7, and 10 days later, respectively, and are shown in each group from left (M1) to right (M3).
Figure 10:
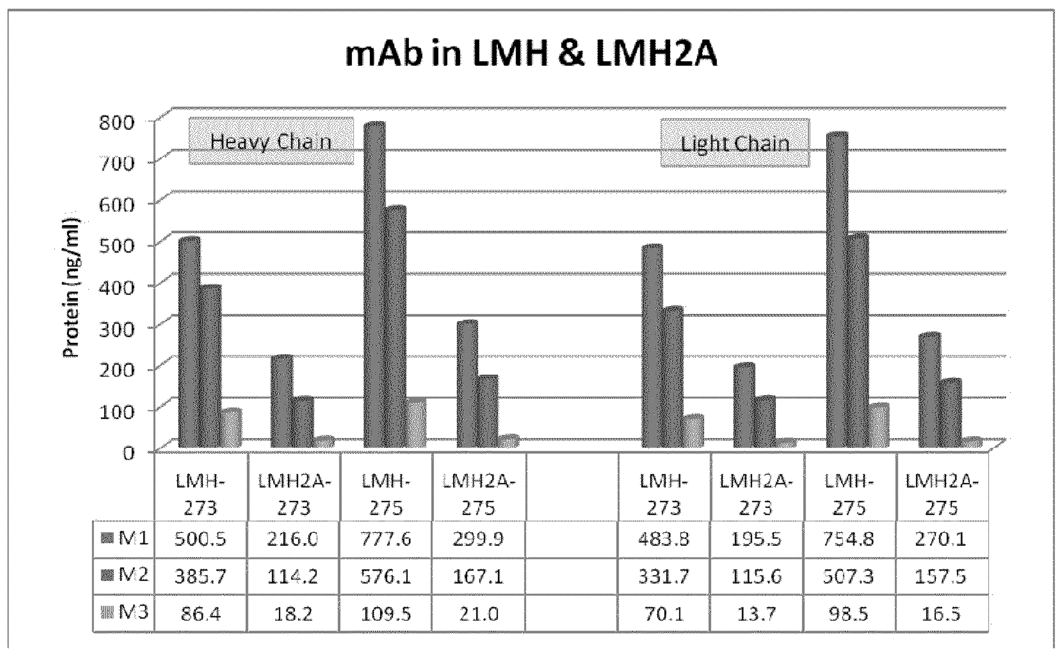
FIG. 10 is a graph showing the results of an ELISA demonstrating the efficient expression of the RM2 monoclonal antibody light chain (ng/ml) in LMH and LMH2A cells using the expression vectors described herein (#275 (SEQ ID NO:21) and (#273 (SEQ ID NO:23)). M1, M2, and M3 represent samples taken at 3, 6, and 9 days post-transfection, respectively, and are shown in each group from left (M1) to right (M3).

The LMH line appeared to grow somewhat faster and more evenly across the surface of the flask when split, whereas the LMH2A cells began to grow on top of each other before they were confluent. After 3-4 days, the media from LMH flasks was more yellow than LMH 2A media suggesting increased number of cells or increased metabolic activity. Once confluence was reached, the LMH cells continued to grow and build layers just as the LMH2A cells. During extended growth in flask culture, both cell lines formed 3-dimensional patterns of growth reminiscent of the physical tissue structure of liver. FIG. 8 shows that LMH cells appeared to produce more mAb heavy chain than LMH2A cells. FIG. 9 shows that LMH cells appear to produce more mAb light chain than LMH2A cells.

EXAMPLE 6

Perfusion of LMH2A Cells in AutoVaxID

The AutoVaxID cultureware (Biovest) is installed, and the Fill-Flush procedure is performed following the procedures in the AutoVaxID Operations Manual. The following day, the Pre-inoculation procedure and the pH calibration are done. The cultureware is seeded with $10^9$ AIA cells that are transfected with an expression vector comprising gene(s) encoding the light and/or heavy chains of an antibody. The cells are propagated in Lonza UltraCULTURE media supplemented with cholesterol (Sigma, 50 μg/ml) in 20 gelatin-coated T150 cell culture flasks, and are dissociated with Accutase (Sigma). They are counted, gently pelleted (600×G for 6 minutes), and resuspended in 50 mls of growth media (Lonza UltraCULTURE containing GlutaMax (Invitrogen) and SyntheChol (1:500), Soy Hydrolysate (1:50), and Fatty Acid Supplement (1:500) (all from Sigma). This is the same media which is included in the "Factor" bags for the AutoVaxID, used for the EC (extra-capillary) media. A 10 L bag of Lonza UltraCULTURE media (with GlutaMax) is used initially for the IC (intra-capillary) media. This is designed to give the cells a richer media for the first 7-10 days, to allow them to become established quickly in the hollow fiber system. After this bag is exhausted, the IC media is switched to DMEM/F12 (also including GlutaMax), also purchased from Lonza. This media is purchased in SOL drums, and is removed from the cold room and allowed to warm to room temperature before being connected to the system. The AutoVaxID system is placed under Lactate Control, and pump rates are modified and daily tasks performed, as specified by the AutoVaxID Operating Procedures Manual, provided by the manufacturer (Biovest).

Six days later, cells can be seen growing on the hollow fibers in the bioreactor. Up until this time, there is ample evidence that the cells are growing and metabolizing in the system; the Lactate Controller is increasing the media pump rate regularly in order to keep the lactate levels below the setpoint, and the pH Controller is continually decreasing the percentage of $CO_2$ in the gas mix, indicating that the cells are producing increasing amounts of acidic metabolic products. After the IC media is changed from the Lonza UltraCULTURE media to the DMEM/F12, however, the metabolic rate of the cells may slow dramatically, to the point where the Lactate Controller slows the media pumps all the way to baseline levels, and the lactate levels may still drop. Samples are taken for protein analysis 4 days later. Samples are taken from the EC (showing current production) from the Harvest Bag (showing accumulated production) and from the IC (showing any protein which crossed the membrane and was lost in the wasted media). By four days later, there may be both visual and metabolic evidence that the cells are growing, so cycling is initiated. For the next week, regular sampling is continued, and cells appear to grow and metabolize normally, although it may become physically difficult to pull samples from the EC sample port. The run is allowed to continue for a couple weeks, although cycling times become greatly extended. Final samples are taken, and the run is ended. All samples are analyzed for proteins to determine if the cells are capable of producing significant amounts of protein in this system.

EXAMPLE 7 mAb Production in LMH and LMH2A Cells

This experiment tested 2 vectors, 273 (SEQ ID NO:23) and 275 (SEQ ID NO:21), containing the gene for RM2 mAb. Both vectors were built with the CMV-Oval hybrid promoter, version 1, in the Puro/Mar backbone. Vector 273 contains the vitellogenin polyA, while vector 275 used the ovalbumin polyA. Both vectors were tested in the LMH and LMH2A cells.

One day prior to transfection the flasks were seeded with equal amounts of cells from each cell type in Waymouth+10% FCS. The transfection was done with Fugene 6 using 2 ug DNA/T25 following our standard protocol. The LMH cells were about 90% confluent and the LMH2A cells were about 60-70% confluent at the time of transfection. Since the LMH seemed to be growing faster, at the time of the final media harvest, 2 random flasks of each type were measured for cell population. The cell count was virtually the same in all flasks. The difference in confluence may be due more to the morphology and growth pattern of the 2 cell types rather that the actual number of cells. The LMH cells seem to spread more while the LMH2A seem to tend to grow in clumps. Media samples were collected and cultures were fed with Waymouth+5% FCS every 3 days. In both cell lines, vector 275 (SEQ ID NO:21), containing the Oval polyA, gave better expression. M1, M2 and M3 are 3, 6, and 9 days, respectively after transfection.

EXAMPLE 8

Production of Transgenic Chicken and Quail that Successfully Passed the hmAb Transgene Through Two Generations Using SEQ ID NO:24

SEQ ID NO:24 (Vector 146/149) has been employed in vivo and in vitro. Separate in vivo experiments in chicken and quail have demonstrated successful passage of the transgene encoding for human monoclonal antibody (hmAb) contained in SEQ ID NO:24 through two generations. Briefly, germ line cells of both chicken and quail were made transgenic following administration of SEQ ID NO:24 containing a gene encoding for hmAb, into the left cardiac ventricle, the source of the aorta which provides an artery leading to the ovary. These birds were mated with naïve males and the resulting eggs hatched. These chicks (G1 birds) contained the transgene encoding hmAb as their blood cells were positive for the transgene encoding hmAb, and 3) These transgenic progeny (G1 birds) were subsequently bred and their progeny (G2 birds) were positive for the transgene encoding hmAb.

Transgenic G1 and G2 quail were generated by injecting females in the left cardiac ventricle. The experiment employed five seven-week old quail hens. The hens were each injected into the left ventricle, allowed to recover, and then mated with naïve males. Isofluorane was used to lightly anesthetize the birds during the injection procedure. Eggs were collected daily for six days and set to hatch on the seventh day. At about 2 weeks of age, the chicks were bled and DNA harvested as described in a kit protocol from Qiagen for isolating genomic DNA from blood and tissue. PCR was conducted using primers specific to the gene of interest. In both experiments, transgene-positive G1 animals were obtained. These transgene-positive G1 animals were raised to sexual maturity and bred. The G2 animals were screened at 2 weeks of age and transgenic animals were identified in each experiment. A transposon-based vector (SEQ ID NO:24) containing a gene for a hmAb was injected. A total of 85 μg complexed with branched polyethylenimine (BPEI) in a 300 μL total volume was used. G1 and G2 quail were positive for the monoclonal antibody transgene following analysis of blood samples.

Transgenic G1 and G2 chickens were generated by injecting females in the left cardiac ventricle. The experiment was conducted in 20 week old chickens. In the second experiment, the same transposon-based vector (SEQ ID NO:24) containing a gene for a hmAb as described above for quail was injected. DNA (complexed to BPEI) was delivered to the birds at a rate of 1 mg/kg body (up to 3 ml total volume) weight by injection into the left cardiac ventricle. Isofluorane was used to lightly anesthetize the birds during the injection procedure. Once the birds recovered from the anesthesia, they were place in pens with mature, naïve males. All eggs were collected for 5 days and then incubated. In the first experiment, the eggs were incubated for about 12 days, candled to check for viable embryos; any egg showing a viable embryo was cracked open and tissue samples (liver) taken from the embryo for PCR. The eggs were allowed to hatch, and a blood sample was taken at two days to test the animals for the presence of the transgene using PCR. Approximately 14% of the chicks were positive for the hmAb transgene.

EXAMPLE 9

Production of Human Monoclonal Antibody In Vitro Using SEQ ID NO:24

LMH2A cells were grown to 50-80% confluency for transfection, the media removed from the cells, and 2 μg of DNA containing SEQ ID NO:24 complexed with Fugene-6 in a final volume of 1 ml media was added to the cells and incubated at 37° C. for 1 to 2 hours. After incubation, the DNA/Fugene complex was removed and fresh media added to the flask. Media was harvested every 48 hours (for a total of three harvests designated M1, M2, and M3) and stored at 4° C. until the experiment was completed. Once all samples were obtained, an ELISA was conducted using anti-Human antibody. Three were conducted. As an example, in Experiment 1105, vector 149 yielded an absorbance of about 0.3 compared to the negative control absorbance of 0.074 and the positive control absorbance of 1.12-0.111 (180 minutes reading at 405 nm) and an average protein concentration of about 4.3 ng/ml. This was the highest absorbance obtained in Experiment 1105. It should be noted that this is a transient transfection, and no selection pressure was applied to these cells.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. A vector comprising:

a modified transposase gene operably linked to a first promoter, wherein the nucleotide sequence 3' to the first promoter comprises a modified Kozak sequence, and wherein a plurality of the first twenty codons of the transposase gene are modified from the wild-type sequence by changing the nucleotide at the third base position of the codon to an adenine or thymine without modifying the amino acid encoded by the codon;

a multiple cloning site capable of receiving a gene of interest;

transposon insertion sequences recognized by a transposase encoded by the modified transposase gene, wherein the transposon insertion sequences flank the multiple cloning site; and, one or more insulator elements located between the transposon insertion sequences and the multiple cloning site, wherein the one or more insulator elements comprise a lysozyme replicator element, a combination of a lysozyme replicator element and an HS4 element, or a matrix attachment region element, wherein when the gene of interest is inserted into the multiple cloning site, the start codon of the gene of interest is located no more than 2502 bp and no less than 1652 bp from the one or more insulator elements located 5' to the start codon of the gene of interest.

2. The vector of claim 1, further comprising a second promoter, wherein the second promoter is SEQ ID NO: 14 or SEQ ID NO: 15.

3. The vector of claim 1, further comprising a gene encoding for an antibody inserted into the multiple cloning site.

4. The vector of claim 3, wherein the vector comprises SEQ ID NO: 25.

5. A transposon-based vector comprising:

a modified transposase gene operably linked to a first promoter, wherein the nucleotide sequence 3' to the first promoter comprises a modified Kozak sequence, and wherein a plurality of the first twenty codons of the transposase gene are modified from the wild-type sequence by changing the nucleotide at the third base position of the codon to an adenine or thymine without modifying the amino acid encoded by the codon;

one or more genes of interest encoding an antibody operably-linked to one or more additional promoters, wherein the one or more genes of interest encoding the antibody and their operably-linked promoters are flanked by transposon insertion sequences recognized by a transposase encoded by the modified transposase gene; and, one or more insulator elements located between the transposon insertion sequences and the one or more genes of interest encoding the antibody, wherein the start codon of the gene of interest is located about 2502 bp to about 1652 bp from the one or more insulator elements located 5' to the start codon of the gene of interest, and wherein the one or more insulator elements comprise a lysozyme replicator element, a combination of a lysozyme replicator element and an HS4 element, or a matrix attachment region element.

6. A method of producing an antibody comprising:

transfecting a cell with a vector comprising a modified transposase gene operably linked to a first promoter, wherein the nucleotide sequence 3' to the first promoter comprises a modified Kozak sequence, and wherein a plurality of the first twenty codons of the transposase gene are modified from the wild-type sequence by changing the nucleotide at the third base position of the codon to an adenine or thymine without modifying the amino acid encoded by the codon;

one or more genes of interest encoding an antibody operably-linked to one or more additional promoters, wherein the one or more genes of interest encoding the antibody and their operably-linked promoters are flanked by transposon insertion sequences recognized by a transposase encoded by the modified transposase gene; and, one or more insulator elements located between the transposon insertion sequences and the one or more genes of interest encoding the antibody, wherein the start codon of the gene of interest is located about 2502 bp to about 1652 bp from the one or more insulator elements located 5' to the start codon of the gene of interest, and wherein the one or more insulator elements comprise a lysozyme replicator element, a combination of a lysozyme replicator element and an HS4 element, or a matrix attachment region element;

culturing the transfected cell in culture medium;

permitting the cell to release the antibody into the culture medium;

collecting the culture medium; and, isolating the antibody.

7. The method of claim 6 wherein the vector comprises SEQ ID NO:25.

8. The method of claim 6 wherein the antibody is a human antibody.

9. The method of claim 6 wherein the antibody is a monoclonal antibody.

* * * * *

SEQUENCE LISTING

<160> NUMBER OF SEQ ID NOS: 40

<210> SEQ ID NO 1
<211> LENGTH: 7368
<212> TYPE: DNA
<213> ORGANISM: Artificial Sequence
<220> FEATURE:
<223> OTHER INFORMATION: Synthetic construct

<400> SEQUENCE: 1
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggcatcaga ttggctattg gccattgcat acgttgtatc catatcataa 180
tatgtacatt tatattggct catgtccaac attaccgcca tgttgacatt gattattgac 240
tagttattaa tagtaatcaa ttacggggtc attagttcat agcccatata tggagttccg 300
cgttacataa cttacggtaa atggcccgcc tggctgaccg cccaacgacc cccgcccatt 360
gacgtcaata atgacgtatg ttcccatagt aacgccaata gggactttcc attgacgtca 420
atgggtggag tatttacggt aaactgccca cttggcagta catcaagtgt atcatatgcc 480
aagtacgccc cctattgacg tcaatgacgg taaatggccc gcctggcatt atgcccagta 540
catgacctta tgggactttc ctacttggca gtacatctac gtattagtca tcgctattac 600
catggtgatg cggttttggc agtacatcaa tgggcgtgga tagcggtttg actcacgggg 660
atttccaagt ctccacccca ttgacgtcaa tgggagtttg ttttggcacc aaaatcaacg 720
ggactttcca aaatgtcgta acaactccgc cccattgacg caaatgggcg gtaggcgtgt 780
acggtgggag gtctatataa gcagagctcg tttagtgaac cgtcagatcg cctggagacg 840
ccatccacgc tgttttgacc tccatagaag acaccgggac cgatccagcc tccgcggccg 900
ggaacggtgc attggaacgc ggattccccg tgccaagagt gacgtaagta ccgcctatag 960
actctatagg cacacccctt tggctcttat gcatgctata ctgtttttgg cttggggcct 1020
atacaccccc gcttccttat gctataggtg atggtatagc ttagcctata ggtgtgggtt 1080
attgaccatt attgaccact cccctattgg tgacgatact ttccattact aatccataac 1140
atggctcttt gccacaacta tctctattgg ctatatgcca atactctgtc cttcagagac 1200
tgacacggac tctgtatttt tacaggatgg ggtcccattt attatttaca aattcacata 1260
tacaacaacg ccgtcccccg tgcccgcagt ttttattaaa catagcgtgg gatctccacg 1320
cgaatctcgg gtacgtgttc cggacatggg ctcttctccg gtagcggcgg agcttccaca 1380
tccgagccct ggtcccatgc ctccagcggc tcatggtcgc tcggcagctc cttgctccta 1440
acagtggagg ccagacttag gcacagcaca atgcccacca ccaccagtgt gccgcacaag 1500
gccgtggcgg tagggtatgt gtctgaaaat gagcgtggag attgggctcg cacggctgac 1560
gcagatggaa gacttaaggc agcggcagaa gaagatgcag gcagctgagt tgttgtattc 1620
tgataagagt cagaggtaac tcccgttgcg gtgctgttaa cggtggaggg cagtgtagtc 1680

```
tgagcagtac tcgttgctgc cgcgcgcgcc accagacata atagctgaca gactaacaga   1740
ctgttccttt ccatgggtct tttctgcagt caccgtctcg cgacagcgaa aaatcaataa   1800
tcagacaaca agatgtgcga actcgatatt ttacacgact ctctttacca attctgcccc   1860
gaattacact taaaacgact caacagctta acgttggctt gccacgcatt acttgactgt   1920
aaaactctca ctcttaccga acttggccgt aacctgccaa ccaaagcgag aacaaaacat   1980
aacatcaaac gaatcgaccg attgttaggt aatcgtcacc tccacaaaga gcgactcgct   2040
gtataccgtt ggcatgctag ctttatctgt tcgggcaata cgatgcccat tgtacttgtt   2100
gactggtctg atattcgtga gcaaaaacga cttatggtat tgcgagcttc agtcgcacta   2160
cacggtcgtt ctgttactct ttatgagaaa gcgttcccgc tttcagagca atgttcaaag   2220
aaagctcatg accaatttct agccgacctt gcgagcattc taccgagtaa caccacaccg   2280
ctcattgtca gtgatgctgg ctttaaagtg ccatggtata aatccgttga gaagctgggt   2340
tggtactggt taagtcgagt aagaggaaaa gtacaatatg cagacctagg agcggaaaac   2400
tggaaaccta tcagcaactt acatgatatg tcatctagtc actcaaagac tttaggctat   2460
aagaggctga ctaaaagcaa tccaatctca tgccaaattc tattgtataa atctcgctct   2520
aaaggccgaa aaaatcagcg ctcgacacgg actcattgtc accacccgtc acctaaaatc   2580
tactcagcgt cggcaaagga gccatgggtt ctagcaacta acttacctgt tgaaattcga   2640
acacccaaac aacttgttaa tatctattcg aagcgaatgc agattgaaga aaccttccga   2700
gacttgaaaa gtcctgccta cggactaggc ctacgccata gccgaacgag cagctcagag   2760
cgttttgata tcatgctgct aatcgccctg atgcttcaac taacatgttg gcttgcgggc   2820
gttcatgctc agaaacaagg ttgggacaag cacttccagg ctaacacagt cagaaatcga   2880
aacgtactct caacagttcg cttaggcatg gaagttttgc ggcattctgg ctacacaata   2940
acaagggaag acttactcgt ggctgcaacc ctactagctc aaaatttatt cacacatggt   3000
tacgctttgg ggaaattatg aggggatcgc tctagagcga tccgggatct cgggaaaagc   3060
gttggtgacc aaaggtgcct tttatcatca ctttaaaaat aaaaaacaat tactcagtgc   3120
ctgttataag cagcaattaa ttatgattga tgcctacatc acaacaaaaa ctgatttaac   3180
aaatggttgg tctgccttag aaagtatatt tgaacattat cttgattata ttattgataa   3240
taataaaaac cttatcccta tccaagaagt gatgcctatc attggttgga atgaacttga   3300
aaaaaattag ccttgaatac attactggta aggtaaacgc cattgtcagc aaattgatcc   3360
aagagaacca acttaaagct ttcctgacgg aatgttaatt ctcgttgacc ctgagcactg   3420
atgaatcccc taatgatttt ggtaaaaatc attaagttaa ggtggataca catcttgtca   3480
tatgatcccg gtaatgtgag ttagctcact cattaggcac cccaggcttt acactttatg   3540
cttccggctc gtatgttgtg tggaattgtg agcggataac aatttcacac aggaaacagc   3600
tatgaccatg attacgccaa gcgcgcaatt aaccctcact aaagggaaca aaagctggag   3660
ctccaccgcg gtggcggccg ctctagaact agtggatccc ccgggctgca ggaattcgat   3720
atcaagctta tcgataccgt cgacctcgag ggggggcccg gtacccaatt cgccctatag   3780
tgagtcgtat tacgcgcgct cactggccgt cgttttacaa cgtcgtgact gggaaaaccc   3840
tggcgttacc caacttaatc gccttgcagc acatccccct ttcgccagct ggcgtaatag   3900
cgaagaggcc cgcaccgatc gcccttccca acagttgcgc agcctgaatg gcgaatggaa   3960
attgtaagcg ttaatatttt gttaaaattc gcgttaaatt tttgttaaat cagctcattt   4020
ttttaaccaa taggccgaaa tcggcaaaat cccttataaa tcaaaagaat agaccgagat   4080
```

```
agggttgagt gttgttccag tttggaacaa gagtccacta ttaaagaacg tggactccaa   4140
cgtcaaaggg cgaaaaaccg tctatcaggg cgatggccca ctactccggg atcatatgac   4200
aagatgtgta tccaccttaa cttaatgatt tttaccaaaa tcattagggg attcatcagt   4260
gctcagggtc aacgagaatt aacattccgt caggaaagct tatgatgatg atgtgcttaa   4320
aaacttactc aatggctggt tatgcatat  cgcaatacat gcgaaaaacc taaaagagct   4380
tgccgataaa aaaggccaat ttattgctat ttaccgcggc tttttattga gcttgaaaga   4440
taaataaaat agataggttt tatttgaagc taaatcttct ttatcgtaaa aaatgccctc   4500
ttgggttatc aagagggtca ttatatttcg cggaataaca tcatttggtg acgaaataac   4560
taagcacttg tctcctgttt actcccctga gcttgagggg ttaacatgaa ggtcatcgat   4620
agcaggataa taatacagta aaacgctaaa ccaataatcc aaatccagcc atcccaaatt   4680
ggtagtgaat gattataaat aacagcaaac agtaatgggc caataacacc ggttgcattg   4740
gtaaggctca ccaataatcc ctgtaaagca ccttgctgat gactctttgt ttggatagac   4800
atcactccct gtaatgcagg taaagcgatc ccaccaccag ccaataaaat taaaacaggg   4860
aaaactaacc aaccttcaga tataaacgct aaaaaggcaa atgcactact atctgcaata   4920
aatccgagca gtactgccgt tttttcgccc catttagtgg ctattcttcc tgccacaaag   4980
gcttggaata ctgagtgtaa aagaccaaga cccgctaatg aaaagccaac catcatgcta   5040
ttccatccaa aacgattttc ggtaaatagc acccacaccg ttgcaggaat ttggcctatc   5100
aatgcgctga aaaataataa atcaacaaaa tgggcatcgt tttaaataaa gtgatgtata   5160
ccgaattcag cttttgttcc ctttagtgag ggttaattgc gcgcttggcg taatcatggt   5220
catagctgtt tcctgtgtga aattgttatc cgctcacaat tccacacaac atacgagccg   5280
gaagcataaa gtgtaaagcc tggggtgcct aatgagtgag ctaactcaca ttaattgcgt   5340
tgcgctcact gcccgctttc cagtcgggaa acctgtcgtg ccagctgcat taatgaatcg   5400
gccaacgcgc ggggagaggc ggtttgcgta ttgggcgctc ttccgcttcc tcgctcactg   5460
actcgctgcg ctcggtcgtt cggctgcggc gagcggtatc agctcactca aaggcggtaa   5520
tacggttatc cacagaatca ggggataacg caggaaagaa catgtgagca aaaggccagc   5580
aaaaggccag gaaccgtaaa aaggccgcgt tgctggcgtt tttccatagg ctccgccccc   5640
ctgacgagca tcacaaaaat cgacgctcaa gtcagaggtg gcgaaacccg acaggactat   5700
aaagatacca ggcgtttccc cctggaagct ccctcgtgcg ctctcctgtt ccgaccctgc   5760
cgcttaccgg atacctgtcc gcctttctcc cttcgggaag cgtggcgctt tctcatagct   5820
cacgctgtag gtatctcagt tcggtgtagg tcgttcgctc caagctgggc tgtgtgcacg   5880
aaccccccgt tcagcccgac cgctgcgcct tatccggtaa ctatcgtctt gagtccaacc   5940
cggtaagaca cgacttatcg ccactggcag cagccactgg taacaggatt agcagagcga   6000
ggtatgtagg cggtgctaca gagttcttga agtggtggcc taactacggc tacactagaa   6060
ggacagtatt tggtatctgc gctctgctga agccagttac cttcggaaaa agagttggta   6120
gctcttgatc cggcaaacaa accaccgctg gtagcggtgg tttttttgtt tgcaagcagc   6180
agattacgcg cagaaaaaaa ggatctcaag aagatccttt gatcttttct acggggtctg   6240
acgctcagtg gaacgaaaac tcacgttaag ggattttggt catgagatta tcaaaaagga   6300
tcttcaccta gatcctttta aattaaaaat gaagttttaa atcaatctaa agtatatatg   6360
agtaaacttg gtctgacagt taccaatgct taatcagtga ggcacctatc tcagcgatct   6420
```

```
gtctatttcg ttcatccata gttgcctgac tccccgtcgt gtagataact acgatacggg   6480

agggcttacc atctggcccc agtgctgcaa tgataccgcg agacccacgc tcaccggctc   6540

cagatttatc agcaataaac cagccagccg gaagggccga gcgcagaagt ggtcctgcaa   6600

ctttatccgc ctccatccag tctattaatt gttgccggga agctagagta agtagttcgc   6660

cagttaatag tttgcgcaac gttgttgcca ttgctacagg catcgtggtg tcacgctcgt   6720

cgtttggtat ggcttcattc agctccggtt cccaacgatc aaggcgagtt acatgatccc   6780

ccatgttgtg caaaaaagcg gttagctcct tcggtcctcc gatcgttgtc agaagtaagt   6840

tggccgcagt gttatcactc atggttatgg cagcactgca taattctctt actgtcatgc   6900

catccgtaag atgcttttct gtgactggtg agtactcaac caagtcattc tgagaatagt   6960

gtatgcggcg accgagttgc tcttgcccgg cgtcaatacg ggataatacc gcgccacata   7020

gcagaacttt aaaagtgctc atcattggaa aacgttcttc ggggcgaaaa ctctcaagga   7080

tcttaccgct gttgagatcc agttcgatgt aacccactcg tgcacccaac tgatcttcag   7140

catcttttac tttcaccagc gtttctgggt gagcaaaaac aggaaggcaa aatgccgcaa   7200

aaaagggaat aagggcgaca cggaaatgtt gaatactcat actcttcctt tttcaatatt   7260

attgaagcat ttatcagggt tattgtctca tgagcggata catatttgaa tgtatttaga   7320

aaaataaaca aataggggtt ccgcgcacat ttccccgaaa agtgccac                7368
```

```
<210> SEQ ID NO 2
<211> LENGTH: 7455
<212> TYPE: DNA
<213> ORGANISM: Artificial Sequence
<220> FEATURE:
<223> OTHER INFORMATION: Synthetic construct

<400> SEQUENCE: 2

ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600

catggtgatg cggttttggc agtacatcaa tgggcgtgga tagcggtttg actcacgggg    660

atttccaagt ctccacccca ttgacgtcaa tgggagtttg ttttggcacc aaaatcaacg    720

ggactttcca aaatgtcgta acaactccgc cccattgacg caaatgggcg gtaggcgtgt    780

acggtgggag gtctatataa gcagagctcg tttagtgaac cgtcagatcg cctggagacg    840

ccatccacgc tgttttgacc tccatagaag acaccgggac cgatccagcc tccgcggccg    900

ggaacggtgc attggaacgc ggattccccg tgccaagagt gacgtaagta ccgcctatag    960

actctatagg cacacccctt tggctcttat gcatgctata ctgtttttgg cttggggcct   1020

atacaccccc gcttccttat gctataggtg atggtatagc ttagcctata ggtgtgggtt   1080

attgaccatt attgaccact cccctattgg tgacgatact ttccattact aatccataac   1140
```

```
atggctcttt gccacaacta tctctattgg ctatatgcca atactctgtc cttcagagac   1200

tgacacggac tctgtatttt tacaggatgg ggtcccattt attatttaca aattcacata   1260

tacaacaacg ccgtcccccg tgcccgcagt ttttattaaa catagcgtgg gatctccacg   1320

cgaatctcgg gtacgtgttc cggacatggg ctcttctccg gtagcggcgg agcttccaca   1380

tccgagccct ggtcccatgc ctccagcggc tcatggtcgc tcggcagctc cttgctccta   1440

acagtggagg ccagacttag gcacagcaca atgcccacca ccaccagtgt gccgcacaag   1500

gccgtggcgg tagggtatgt gtctgaaaat gagcgtggag attgggctcg cacggctgac   1560

gcagatggaa gacttaaggc agcggcagaa gaagatgcag gcagctgagt tgttgtattc   1620

tgataagagt cagaggtaac tcccgttgcg gtgctgttaa cggtggaggg cagtgtagtc   1680

tgagcagtac tcgttgctgc cgcgcgcgcc accagacata atagctgaca gactaacaga   1740

ctgttccttt ccatgggtct tttctgcagt caccgtctcg cgacagcgaa aaatcaataa   1800

tcagacaaca agatgtgcga actcgatatt ttacacgact ctctttacca attctgcccc   1860

gaattacact taaaacgact caacagctta acgttggctt gccacgcatt acttgactgt   1920

aaaactctca ctcttaccga acttggccgt aacctgccaa ccaaagcgag aacaaaacat   1980

aacatcaaac gaatcgagcg attgttaggt aatcgtcacc tccacaaaga gcgactcgct   2040

gtataccgtt ggcatgctag ctttatctgt tcgggcaata cgatgcccat tgtacttgtt   2100

gactggtctg atattcgtga gcaaaaacga cttatggtat tgcgagcttc agtcgcacta   2160

cacggtcgtt ctgttactct ttatgagaaa gcgttcccgc tttcagagca atattcaaag   2220

aaagctcatg accaatttct agccgacctt gcgagcattc taccgagtaa caccacaccg   2280

ctcattgtca gtgatgctgg ctttaaagtg ccatggtata aatccgttga gaagctgggt   2340

tggtactggt taagtcgagt aagaggaaaa gtacaatatg cagacctagg agcggaaaac   2400

tggaaaccta tcagcaactt acatgatatg tcatctagtc actcaaagac tttaggctat   2460

aagaggctga ctaaaagcaa tccaatctca tgccaaattc tattgtataa atctcgctct   2520

aaaggccgaa aaaatcagcg ctcgacacgg actcattatc accacccgtc acctaaaatc   2580

tactcagcgt cggcaaagga gccatgggtt ctagcaacta acttacctgt tgaaattcga   2640

acacccaaac aacttgttaa tatctattcg aagcgaatgc agattgaaga aaccttccga   2700

gacttgaaaa gtcctgccta cggactaggc ctacgccata gccgaacgag cagctcagag   2760

cgttttgata tcatgctgct aatcgccctg atgcttcaac taacatgttg gcttgcgggc   2820

gttcatgctc agaaacaagg ttgggacaag cacttccagg ctaacacagt cagaaatcga   2880

aacgtactct caacagttcg cttaggcatg gaagttttgc ggcattctgg ctacacaata   2940

acaagggaag acttactcgt ggctgcaacc ctactagctc aaaatttatt cacacatggt   3000

tacgctttgg ggaaattatg aggggatcgc tctagagcga tccgggatct cgggaaaagc   3060

gttggtgacc aaaggtgcct tttatcatca ctttaaaaat aaaaaacaat tactcagtgc   3120

ctgttataag cagcaattaa ttatgattga tgcctacatc acaacaaaaa ctgatttaac   3180

aaatggttgg tctgccttag aaagtatatt tgaacattat cttgattata ttattgataa   3240

taataaaaac cttatcccta tccaagaagt gatgcctatc attggttgga atgaacttga   3300

aaaaattagc cttgaataca ttactggtaa ggtaaacgcc attgtcagca aattgatcca   3360

agagaaccaa cttaaagctt tcctgacgga atgttaattc tcgttgaccc tgagcactga   3420

tgaatcccct aatgattttg gtaaaaatca ttaagttaag gtggatacac atcttgtcat   3480
```

```
atgatcccgg taatgtgagt tagctcactc attaggcacc ccaggcttta cactttatgc   3540
ttccggctcg tatgttgtgt ggaattgtga gcggataaca atttcacaca ggaaacagct   3600
atgaccatga ttacgccaag cgcgcaatta accctcacta aagggaacaa aagctggagc   3660
tccaccgcgg tggcggccgc tctagaacta gtggatcccc cgggctgcag gaattcgata   3720
tcaagcttat cgataccgtc gacctcgagg gcgcgcctca gcgatcgcag atctttaatt   3780
aaggcgcctg caggatttaa atcacgtgat cacgtcgtac gcaattggtt taaacgcgtg   3840
ggcccggtac ccaattcgcc ctatagtgag tcgtattacg cgcgctcact ggccgtcgtt   3900
ttacaacgtc gtgactggga aaaccctggc gttacccaac ttaatcgcct tgcagcacat   3960
ccccctttcg ccagctggcg taatagcgaa gaggcccgca ccgatcgccc ttcccaacag   4020
ttgcgcagcc tgaatggcga atggaaattg taagcgttaa tattttgtta aaattcgcgt   4080
taaatttttg ttaaatcagc tcattttttt aaccaatagg ccgaaatcgg caaaatccct   4140
tataaatcaa aagaatagac cgagataggg ttgagtgttg ttccagtttg gaacaagagt   4200
ccactattaa agaacgtgga ctccaacgtc aaagggcgaa aaaccgtcta tcagggcgat   4260
ggcccactac tccgggatca tatgacaaga tgtgtatcca ccttaactta atgattttta   4320
ccaaaatcat taggggattc atcagtgctc agggtcaacg agaattaaca ttccgtcagg   4380
aaagcttatg atgatgatgt gcttaaaaac ttactcaatg gctggtttat gcatatcgca   4440
atacatgcga aaaacctaaa agagcttgcc gataaaaaag gccaatttat tgctatttac   4500
cgcggctttt tattgagctt gaaagataaa taaaatagat aggttttatt tgaagctaaa   4560
tcttctttat cgtaaaaaat gccctcttgg gttatcaaga gggtcattat atttcgcgga   4620
ataacatcat ttggtgacga aataactaag cacttgtctc ctgtttactc ccctgagctt   4680
gaggggttaa catgaaggtc atcgatagca ggataataat acagtaaaac gctaaaccaa   4740
taatccaaat ccagccatcc caaattggta gtgaatgatt ataaataaca gcaaacagta   4800
atgggccaat aacaccggtt gcattggtaa ggctcaccaa taatccctgt aaagcacctt   4860
gctgatgact ctttgtttgg atagacatca ctccctgtaa tgcaggtaaa gcgatcccac   4920
caccagccaa taaaattaaa acagggaaaa ctaaccaacc ttcagatata aacgctaaaa   4980
aggcaaatgc actactatct gcaataaatc cgagcagtac tgccgttttt tcgccccatt   5040
tagtggctat tcttcctgcc acaaaggctt ggaatactga gtgtaaaaga ccaagacccg   5100
ctaatgaaaa gccaaccatc atgctattcc atccaaaacg attttcggta aatagcaccc   5160
acaccgttgc gggaatttgg cctatcaatt gcgctgaaaa ataaataatc aacaaaatgg   5220
gcatcgtttt aaataaagtg atgtataccg aattcagctt ttgttccctt tagtgagggt   5280
taattgcgcg cttggcgtaa tcatggtcat agctgtttcc tgtgtgaaat tgttatccgc   5340
tcacaattcc acacaacata cgagccggaa gcataaagtg taaagcctgg ggtgcctaat   5400
gagtgagcta actcacatta attgcgttgc gctcactgcc cgctttccag tcgggaaacc   5460
tgtcgtgcca gctgcattaa tgaatcggcc aacgcgcggg gagaggcggt ttgcgtattg   5520
ggcgctcttc cgcttcctcg ctcactgact cgctgcgctc ggtcgttcgg ctgcggcgag   5580
cggtatcagc tcactcaaag gcggtaatac ggttatccac agaatcaggg gataacgcag   5640
gaaagaacat gtgagcaaaa ggccagcaaa aggccaggaa ccgtaaaaag gccgcgttgc   5700
tggcgttttt ccataggctc cgcccccctg acgagcatca caaaaatcga cgctcaagtc   5760
agaggtggcg aaacccgaca ggactataaa gataccaggc gtttccccct ggaagctccc   5820
tcgtgcgctc tcctgttccg accctgccgc ttaccggata cctgtccgcc tttctccctt   5880
```

```
cgggaagcgt ggcgctttct catagctcac gctgtaggta tctcagttcg gtgtaggtcg   5940

ttcgctccaa gctgggctgt gtgcacgaac cccccgttca gcccgaccgc tgcgccttat   6000

ccggtaacta tcgtcttgag tccaacccgg taagacacga cttatcgcca ctggcagcag   6060

ccactggtaa caggattagc agagcgaggt atgtaggcgg tgctacagag ttcttgaagt   6120

ggtggcctaa ctacggctac actagaagaa cagtatttgg tatctgcgct ctgctgaagc   6180

cagttacctt cggaaaaaga gttggtagct cttgatccgg caaacaaacc accgctggta   6240

gcggtggttt ttttgtttgc aagcagcaga ttacgcgcag aaaaaaagga tctcaagaag   6300

atcctttgat cttttctacg gggtctgacg ctcagtggaa cgaaaactca cgttaaggga   6360

ttttggtcat gagattatca aaaaggatct tcacctagat ccttttaaat taaaaatgaa   6420

gttttaaatc aatctaaagt atatatgagt aaacttggtc tgacagttac caatgcttaa   6480

tcagtgaggc acctatctca gcgatctgtc tatttcgttc atccatagtt gcctgactcc   6540

ccgtcgtgta gataactacg atacgggagg gcttaccatc tggccccagt gctgcaatga   6600

taccgcgaga cccacgctca ccggctccag atttatcagc aataaaccag ccagccggaa   6660

gggccgagcg cagaagtggt cctgcaactt tatccgcctc catccagtct attaattgtt   6720

gccgggaagc tagagtaagt agttcgccag ttaatagttt gcgcaacgtt gttgccattg   6780

ctacaggcat cgtggtgtca cgctcgtcgt ttggtatggc ttcattcagc tccggttccc   6840

aacgatcaag gcgagttaca tgatccccca tgttgtgcaa aaaagcggtt agctccttcg   6900

gtcctccgat cgttgtcaga agtaagttgg ccgcagtgtt atcactcatg gttatggcag   6960

cactgcataa ttctcttact gtcatgccat ccgtaagatg cttttctgtg actggtgagt   7020

actcaaccaa gtcattctga gaatagtgta tgcggcgacc gagttgctct tgcccggcgt   7080

caatacggga taataccgcg ccacatagca gaactttaaa agtgctcatc attggaaaac   7140

gttcttcggg gcgaaaactc tcaaggatct taccgctgtt gagatccagt tcgatgtaac   7200

ccactcgtgc acccaactga tcttcagcat cttttacttt caccagcgtt tctgggtgag   7260

caaaaacagg aaggcaaaat gccgcaaaaa agggaataag ggcgacacgg aaatgttgaa   7320

tactcatact cttccttttt caatattatt gaagcattta tcagggttat tgtctcatga   7380

gcggatacat atttgaatgt atttagaaaa ataaacaaat aggggttccg cgcacatttc   7440

cccgaaaagt gccac                                                    7455
```

```
<210> SEQ ID NO 3
<211> LENGTH: 8590
<212> TYPE: DNA
<213> ORGANISM: Artificial Sequence
<220> FEATURE:
<223> OTHER INFORMATION: Synthetic construct

<400> SEQUENCE: 3
```

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420
```

```
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgacagcgaa aaatcaataa   1800
tcagacaaca agatgtgcga actcgatatt ttacacgact ctctttacca attctgcccc   1860
gaattacact taaaacgact caacagctta acgttggctt gccacgcatt acttgactgt   1920
aaaactctca ctcttaccga acttggccgt aacctgccaa ccaaagcgag aacaaaacat   1980
aacatcaaac gaatcgagcg attgttaggt aatcgtcacc tccacaaaga gcgactcgct   2040
gtataccgtt ggcatgctag ctttatctgt tcgggcaata cgatgcccat tgtacttgtt   2100
gactggtctg atattcgtga gcaaaaacga cttatggtat tgcgagcttc agtcgcacta   2160
cacggtcgtt ctgttactct ttatgagaaa gcgttcccgc tttcagagca atattcaaag   2220
aaagctcatg accaatttct agccgacctt gcgagcattc taccgagtaa caccacaccg   2280
ctcattgtca gtgatgctgg ctttaaagtg ccatggtata aatccgttga gaagctgggt   2340
tggtactggt taagtcgagt aagaggaaaa gtacaatatg cagacctagg agcggaaaac   2400
tggaaaccta tcagcaactt acatgatatg tcatctagtc actcaaagac tttaggctat   2460
aagaggctga ctaaaagcaa tccaatctca tgccaaattc tattgtataa atctcgctct   2520
aaaggccgaa aaaatcagcg ctcgacacgg actcattatc accacccgtc acctaaaatc   2580
tactcagcgt cggcaaagga gccatgggtt ctagcaacta acttacctgt tgaaattcga   2640
acacccaaac aacttgttaa tatctattcg aagcgaatgc agattgaaga aaccttccga   2700
gacttgaaaa gtcctgccta cggactaggc ctacgccata gccgaacgag cagctcagag   2760
cgttttgata tcatgctgct aatcgccctg atgcttcaac taacatgttg gcttgcgggc   2820
```

```
gttcatgctc agaaacaagg ttgggacaag cacttccagg ctaacacagt cagaaatcga   2880
aacgtactct caacagttcg cttaggcatg gaagttttgc ggcattctgg ctacacaata   2940
acaagggaag acttactcgt ggctgcaacc ctactagctc aaaatttatt cacacatggt   3000
tacgctttgg ggaaattatg aggggatcgc tctagagcga tccgggatct cgggaaaagc   3060
gttggtgacc aaaggtgcct tttatcatca ctttaaaaat aaaaaacaat tactcagtgc   3120
ctgttataag cagcaattaa ttatgattga tgcctacatc acaacaaaaa ctgatttaac   3180
aaatggttgg tctgccttag aaagtatatt tgaacattat cttgattata ttattgataa   3240
taataaaaac cttatcccta tccaagaagt gatgcctatc attggttgga atgaacttga   3300
aaaaattagc cttgaataca ttactggtaa ggtaaacgcc attgtcagca aattgatcca   3360
agagaaccaa cttaaagctt tcctgacgga atgttaattc tcgttgaccc tgagcactga   3420
tgaatcccct aatgattttg gtaaaaatca ttaagttaag gtggatacac atcttgtcat   3480
atgatcccgg taatgtgagt tagctcactc attaggcacc ccaggcttta cactttatgc   3540
ttccggctcg tatgttgtgt ggaattgtga gcggataaca atttcacaca ggaaacagct   3600
atgaccatga ttacgccaag cgcgcaatta accctcacta aagggaacaa aagctggagc   3660
tccaccgcgg tggcggccgc tcctggaagg tcctggaagg gggcgtccgc gggagctcac   3720
ggggagagcc cccccccaaa gcccccaggg atgtaattac gtccctcccc cgctaggggg   3780
cagcagcgag ccgcccgggg ctccgctccg gtccggcgct ccccccgcat ccccgagccg   3840
gcagcgtgcg gggacagccc gggcacgggg aaggtggcac gggatcgctt tcctctgaac   3900
gcttctcgct gctctttgag cctgcagaca cctgggggga tacggggaaa aagctttagg   3960
ctgaaagaga gatttagaat gacagaatca cagaatggcc tgggttggaa aggcccacaa   4020
tgctcatcca gttccaaccc ctgctatgtg cagggtcgcc aaccagcagc ccaggctgcc   4080
cagagacaca tccagcctgg cctggaatgc ctgcagggat ggggcatcca cagcctcctt   4140
gggcaacctg ttcagtgcgt caccaccctc tgggggaaaa actgcctctt catatccaac   4200
ccaaacctcc cctgtctaag tgtaaagcca ttcccccttg tcctatcaag gggggagtttg  4260
ctgtgacatt gttggtctgg ggtgacacat gtttgccaat tcagtgcatc acggagaggc   4320
agatcttggg gataaggaag agcaggacag catggacgtg ggacatgcag gtgttgaggg   4380
ctctgggaca ctctccaagt cacagcgttc agaacagcct taaggatcag aagataggat   4440
agaaggacaa agagcaagtt aaaacccagc atggagagga gcacaaaaag gccacagaca   4500
ctgctggtcc ctgtgtctga gcctgcatgt ttgatggtgt ctggatgcaa gcagaagggg   4560
tggaagagct tgcctggaga gatacagctg ggtcagtagg actgggacag gcagctggag   4620
aattgccatg tagatgttca cacaatcgtc aaatcatgaa ggctggaaaa gccctccaag   4680
atccccaaga ccaaccccaa cccacccacc gtgcccactg gccatgtccc tcagtgccac   4740
atccccacag ttcttcatca cctccaggga cggtgacccc cccacctccg tgggcagctg   4800
tgccactgca gcaccgctct ttggagaagg taaatcttgc taaatccagc ccgaccctcc   4860
cctggcacaa cgtaaggcca ttatctctca tcctactcca ggacggagtc agtgagaata   4920
ttctcgaggg cgcgcctcag cgatcgcaga tctttaatta aggcgcctgc aggatttaaa   4980
tcacgtgatc acgtcgtacg caattggttt aaacgcgtaa tattctcact gactccgtcc   5040
tggagtagga tgagagataa tggccttacg ttgtgccagg ggagggtcgg gctggattta   5100
gcaagattta ccttctccaa agagcggtgc tgcagtggca cagctgccca cggaggtggg   5160
```

-continued

```
ggggtcaccg tccctggagg tgatgaagaa ctgtggggat gtggcactga gggacatggc   5220
cagtgggcac ggtgggtggg ttggggttgg tcttggggat cttggagggc ttttccagcc   5280
ttcatgattt gacgattgtg tgaacatcta catggcaatt ctccagctgc ctgtcccagt   5340
cctactgacc cagctgtatc tctccaggca agctcttcca ccccttctgc ttgcatccag   5400
acaccatcaa acatgcaggc tcagacacag ggaccagcag tgtctgtggc ctttttgtgc   5460
tcctctccat gctgggtttt aacttgctct ttgtccttct atcctatctt ctgatcctta   5520
aggctgttct gaacgctgtg acttggagag tgtcccagag ccctcaacac ctgcatgtcc   5580
cacgtccatg ctgtcctgct cttccttatc cccaagatct gcctctccgt gatgcactga   5640
attggcaaac atgtgtcacc ccagaccaac aatgtcacag caaactcccc cttgatagga   5700
caagggggaa tggctttaca cttagacagg ggaggtttgg gttggatatg aagaggcagt   5760
ttttccccca gagggtggtg acgcactgaa caggttgccc aaggaggctg tggatgcccc   5820
atccctgcag gcattccagg ccaggctgga tgtgtctctg ggcagcctgg gctgctggtt   5880
ggcgaccctg cacatagcag gggttggaac tggatgagca ttgtgggcct ttccaaccca   5940
ggccattctg tgattctgtc attctaaatc tctctttcag cctaaagctt tttccccgta   6000
tccccccagg tgtctgcagg ctcaaagagc agcgagaagc gttcagagga aagcgatccc   6060
gtgccacctt ccccgtgccc gggctgtccc cgcacgctgc cggctcgggg atgcgggggg   6120
agcgccggac cggagcggag ccccgggcgg ctcgctgctg ccccctagcg gggagggac    6180
gtaattacat ccctgggggc tttggggggg ggctctcccc gtgagctccc gcggacgccc   6240
ccttccagga ccttccagga gggcccctcc gggatcatat gacaagatgt gtatccacct   6300
taacttaatg atttttacca aaatcattag gggattcatc agtgctcagg gtcaacgaga   6360
attaacattc cgtcaggaaa gcttgaattc agcttttgtt ccctttagtg agggttaatt   6420
gcgcgcttgg cgtaatcatg gtcatagctg tttcctgtgt gaaattgtta tccgctcaca   6480
attccacaca acatacgagc cggaagcata aagtgtaaag cctggggtgc ctaatgagtg   6540
agctaactca cattaattgc gttgcgctca ctgcccgctt tccagtcggg aaacctgtcg   6600
tgccagctgc attaatgaat cggccaacgc gcggggagag gcggtttgcg tattgggcgc   6660
tcttccgctt cctcgctcac tgactcgctg cgctcggtcg ttcggctgcg gcgagcggta   6720
tcagctcact caaaggcggt aatacggtta tccacagaat caggggataa cgcaggaaag   6780
aacatgtgag caaaaggcca gcaaaaggcc aggaaccgta aaaaggccgc gttgctggcg   6840
tttttccata ggctccgccc ccctgacgag catcacaaaa atcgacgctc aagtcagagg   6900
tggcgaaacc cgacaggact ataaagatac caggcgtttc cccctggaag ctccctcgtg   6960
cgctctcctg ttccgaccct gccgcttacc ggatacctgt ccgcctttct cccttcggga   7020
agcgtggcgc tttctcatag ctcacgctgt aggtatctca gttcggtgta ggtcgttcgc   7080
tccaagctgg gctgtgtgca cgaacccccc gttcagcccg accgctgcgc cttatccggt   7140
aactatcgtc ttgagtccaa cccggtaaga cacgacttat cgccactggc agcagccact   7200
ggtaacagga ttagcagagc gaggtatgta ggcggtgcta cagagttctt gaagtggtgg   7260
cctaactacg gctacactag aagaacagta tttggtatct gcgctctgct gaagccagtt   7320
accttcggaa aaagagttgg tagctcttga tccggcaaac aaaccaccgc tggtagcggt   7380
ggtttttttg tttgcaagca gcagattacg cgcagaaaaa aaggatctca agaagatcct   7440
ttgatctttt ctacggggtc tgacgctcag tggaacgaaa actcacgtta agggattttg   7500
gtcatgagat tatcaaaaag gatcttcacc tagatccttt taaattaaaa atgaagtttt   7560
```

```
aaatcaatct aaagtatata tgagtaaact tggtctgaca gttaccaatg cttaatcagt   7620

gaggcaccta tctcagcgat ctgtctattt cgttcatcca tagttgcctg actccccgtc   7680

gtgtagataa ctacgatacg ggagggctta ccatctggcc ccagtgctgc aatgataccg   7740

cgagacccac gctcaccggc tccagattta tcagcaataa accagccagc cggaagggcc   7800

gagcgcagaa gtggtcctgc aactttatcc gcctccatcc agtctattaa ttgttgccgg   7860

gaagctagag taagtagttc gccagttaat agtttgcgca acgttgttgc cattgctaca   7920

ggcatcgtgg tgtcacgctc gtcgtttggt atggcttcat tcagctccgg ttcccaacga   7980

tcaaggcgag ttacatgatc ccccatgttg tgcaaaaaag cggttagctc cttcggtcct   8040

ccgatcgttg tcagaagtaa gttggccgca gtgttatcac tcatggttat ggcagcactg   8100

cataattctc ttactgtcat gccatccgta agatgctttt ctgtgactgg tgagtactca   8160

accaagtcat tctgagaata gtgtatgcgg cgaccgagtt gctcttgccc ggcgtcaata   8220

cgggataata ccgcgccaca tagcagaact ttaaaagtgc tcatcattgg aaaacgttct   8280

tcggggcgaa aactctcaag gatcttaccg ctgttgagat ccagttcgat gtaacccact   8340

cgtgcaccca actgatcttc agcatctttt actttcacca gcgtttctgg gtgagcaaaa   8400

acaggaaggc aaaatgccgc aaaaaaggga ataagggcga cacggaaatg ttgaatactc   8460

atactcttcc tttttcaata ttattgaagc atttatcagg gttattgtct catgagcgga   8520

tacatatttg aatgtattta gaaaaataaa caaatagggg ttccgcgcac atttccccga   8580

aaagtgccac                                                          8590
```

<210> SEQ ID NO 4
<211> LENGTH: 8584
<212> TYPE: DNA
<213> ORGANISM: Artificial Sequence
<220> FEATURE:
<223> OTHER INFORMATION: Synthetic construct

<400> SEQUENCE: 4

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600

catggtgatg cggttttggc agtacatcaa tgggcgtgga tagcggtttg actcacgggg    660

atttccaagt ctccacccca ttgacgtcaa tgggagtttg ttttggcacc aaaatcaacg    720

ggactttcca aaatgtcgta acaactccgc cccattgacg caaatgggcg gtaggcgtgt    780

acggtgggag gtctatataa gcagagctcg tttagtgaac cgtcagatcg cctggagacg    840

ccatccacgc tgttttgacc tccatagaag acaccgggac cgatccagcc tccgcggccg    900

ggaacggtgc attggaacgc ggattccccg tgccaagagt gacgtaagta ccgcctatag    960
```

```
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
```

```
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgctcctgg aaggtcctgg aagggggcgt ccgcgggagc tcacggggag   3720
agcccccccc caaagccccc aggatgtaa ttacgtccct cccccgctag ggggcagcag   3780
cgagccgccc ggggctccgc tccggtccgg cgctcccccc gcatccccga gccggcagcg   3840
tgcggggaca gcccgggcac ggggaaggtg gcacgggatc gctttcctct gaacgcttct   3900
cgctgctctt tgagcctgca gacacctggg gggatacggg gaaaaagctt taggctgaaa   3960
gagagattta gaatgacaga atcacagaat ggcctgggtt ggaaaggccc acaatgctca   4020
tccagttcca accccctgcta tgtgcagggt cgccaaccag cagcccaggc tgcccagaga   4080
cacatccagc ctggcctgga atgcctgcag ggatggggca tccacagcct ccttgggcaa   4140
cctgttcagt gcgtcaccac cctctggggg aaaaactgcc tcttcatatc caacccaaac   4200
ctcccctgtc taagtgtaaa gccattcccc cttgtcctat caagggggag tttgctgtga   4260
cattgttggt ctggggtgac acatgtttgc caattcagtg catcacggag aggcagatct   4320
tggggataag gaagagcagg acagcatgga cgtgggacat gcaggtgttg agggctctgg   4380
gacactctcc aagtcacagc gttcagaaca gccttaagga tcagaagata ggatagaagg   4440
acaaagagca agttaaaacc cagcatggag aggagcacaa aaaggccaca gacactgctg   4500
gtccctgtgt ctgagcctgc atgtttgatg gtgtctggat gcaagcagaa ggggtggaag   4560
agcttgcctg gagagataca gctgggtcag taggactggg acaggcagct ggagaattgc   4620
catgtagatg ttcacacaat cgtcaaatca tgaaggctgg aaaagccctc caagatcccc   4680
aagaccaacc ccaacccacc caccgtgccc actggccatg tccctcagtg ccacatcccc   4740
acagttcttc atcacctcca gggacggtga ccccccacc tccgtgggca gctgtgccac   4800
tgcagcaccg ctctttggag aaggtaaatc ttgctaaatc cagcccgacc ctcccctggc   4860
acaacgtaag gccattatct ctcatcctac tccaggacgg agtcagtgag aatattctcg   4920
agggcgcgcc tcagcgatcg cagatcttta attaaggcgc ctgcaggatt taaatcacgt   4980
gatcacgtcg tacgcaattg gtttaaacgc gtaatattct cactgactcc gtcctggagt   5040
aggatgagag ataatggcct tacgttgtgc caggggaggg tcgggctgga tttagcaaga   5100
tttaccttct ccaaagagcg gtgctgcagt ggcacagctg cccacggagg tgggggggtc   5160
accgtccctg gaggtgatga agaactgtgg ggatgtggca ctgagggaca tggccagtgg   5220
gcacggtggg tgggttgggg ttggtcttgg ggatcttgga gggcttttcc agccttcatg   5280
atttgacgat tgtgtgaaca tctacatggc aattctccag ctgcctgtcc cagtcctact   5340
gacccagctg tatctctcca ggcaagctct tccacccctt ctgcttgcat ccagacacca   5400
tcaaacatgc aggctcagac acagggacca gcagtgtctg tggccttttt gtgctcctct   5460
ccatgctggg ttttaacttg ctctttgtcc ttctatccta tcttctgatc cttaaggctg   5520
ttctgaacgc tgtgacttgg agagtgtccc agagccctca acacctgcat gtcccacgtc   5580
catgctgtcc tgctcttcct tatccccaag atctgcctct ccgtgatgca ctgaattggc   5640
aaacatgtgt caccccagac caacaatgtc acagcaaact ccccttgat aggacaaggg   5700
```

-continued

```
ggaatggctt tacacttaga caggggaggt ttgggttgga tatgaagagg cagtttttcc   5760
cccagagggt ggtgacgcac tgaacaggtt gcccaaggag gctgtggatg ccccatccct   5820
gcaggcattc caggccaggc tggatgtgtc tctgggcagc ctgggctgct ggttggcgac   5880
cctgcacata gcaggggttg gaactggatg agcattgtgg gcctttccaa cccaggccat   5940
tctgtgattc tgtcattcta aatctctctt tcagcctaaa gctttttccc cgtatccccc   6000
caggtgtctg caggctcaaa gagcagcgag aagcgttcag aggaaagcga tcccgtgcca   6060
ccttccccgt gcccgggctg tccccgcacg ctgccggctc ggggatgcgg ggggagcgcc   6120
ggaccggagc ggagccccgg gcggctcgct gctgccccct agcgggggag ggacgtaatt   6180
acatccctgg gggctttggg ggggggctct ccccgtgagc tcccgcggac gccccccttcc   6240
aggaccttcc aggagggccc ctccgggatc atatgacaag atgtgtatcc accttaactt   6300
aatgattttt accaaaatca ttaggggatt catcagtgct cagggtcaac gagaattaac   6360
attccgtcag gaaagcttga attcagcttt tgttcccttt agtgagggtt aattgcgcgc   6420
ttggcgtaat catggtcata gctgtttcct gtgtgaaatt gttatccgct cacaattcca   6480
cacaacatac gagccggaag cataaagtgt aaagcctggg gtgcctaatg agtgagctaa   6540
ctcacattaa ttgcgttgcg ctcactgccc gctttccagt cgggaaacct gtcgtgccag   6600
ctgcattaat gaatcggcca acgcgcgggg agaggcggtt tgcgtattgg gcgctcttcc   6660
gcttcctcgc tcactgactc gctgcgctcg gtcgttcggc tgcggcgagc ggtatcagct   6720
cactcaaagg cggtaatacg gttatccaca gaatcagggg ataacgcagg aaagaacatg   6780
tgagcaaaag gccagcaaaa ggccaggaac cgtaaaaagg ccgcgttgct ggcgtttttc   6840
cataggctcc gcccccctga cgagcatcac aaaaatcgac gctcaagtca gaggtggcga   6900
aacccgacag gactataaag ataccaggcg tttccccctg gaagctccct cgtgcgctct   6960
cctgttccga ccctgccgct taccggatac ctgtccgcct ttctcccttc gggaagcgtg   7020
gcgctttctc atagctcacg ctgtaggtat ctcagttcgg tgtaggtcgt tcgctccaag   7080
ctgggctgtg tgcacgaacc ccccgttcag cccgaccgct gcgccttatc cggtaactat   7140
cgtcttgagt ccaacccggt aagacacgac ttatcgccac tggcagcagc cactggtaac   7200
aggattagca gagcgaggta tgtaggcggt gctacagagt tcttgaagtg gtggcctaac   7260
tacggctaca ctagaagaac agtatttggt atctgcgctc tgctgaagcc agttaccttc   7320
ggaaaaagag ttggtagctc ttgatccggc aaacaaacca ccgctggtag cggtggtttt   7380
tttgtttgca agcagcagat tacgcgcaga aaaaaaggat ctcaagaaga tcctttgatc   7440
ttttctacgg ggtctgacgc tcagtggaac gaaaactcac gttaagggat tttggtcatg   7500
agattatcaa aaaggatctt cacctagatc cttttaaatt aaaaatgaag ttttaaatca   7560
atctaaagta tatatgagta aacttggtct gacagttacc aatgcttaat cagtgaggca   7620
cctatctcag cgatctgtct atttcgttca tccatagttg cctgactccc cgtcgtgtag   7680
ataactacga tacgggaggg cttaccatct ggccccagtg ctgcaatgat accgcgagac   7740
ccacgctcac cggctccaga tttatcagca ataaaccagc cagccggaag ggccgagcgc   7800
agaagtggtc ctgcaacttt atccgcctcc atccagtcta ttaattgttg ccgggaagct   7860
agagtaagta gttcgccagt taatagtttg cgcaacgttg ttgccattgc tacaggcatc   7920
gtggtgtcac gctcgtcgtt tggtatggct tcattcagct ccggttccca acgatcaagg   7980
cgagttacat gatcccccat gttgtgcaaa aaagcggtta gctccttcgg tcctccgatc   8040
gttgtcagaa gtaagttggc cgcagtgtta tcactcatgg ttatggcagc actgcataat   8100
```

tctcttactg tcatgccatc cgtaagatgc ttttctgtga ctggtgagta ctcaaccaag 8160
tcattctgag aatagtgtat gcggcgaccg agttgctctt gcccggcgtc aatacgggat 8220
aataccgcgc cacatagcag aactttaaaa gtgctcatca ttggaaaacg ttcttcgggg 8280
cgaaaactct caaggatctt accgctgttg agatccagtt cgatgtaacc cactcgtgca 8340
cccaactgat cttcagcatc ttttactttc accagcgttt ctgggtgagc aaaaacagga 8400
aggcaaaatg ccgcaaaaaa gggaataagg gcgacacgga aatgttgaat actcatactc 8460
ttcctttttc aatattattg aagcatttat cagggttatt gtctcatgag cggatacata 8520
tttgaatgta tttagaaaaa taaacaaata ggggttccgc gcacatttcc ccgaaaagtg 8580
ccac 8584

<210> SEQ ID NO 5
<211> LENGTH: 9486
<212> TYPE: DNA
<213> ORGANISM: Artificial Sequence
<220> FEATURE:
<223> OTHER INFORMATION: Synthetic construct

<400> SEQUENCE: 5
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggcatcaga ttggctattg gccattgcat acgttgtatc catatcataa 180
tatgtacatt tatattggct catgtccaac attaccgcca tgttgacatt gattattgac 240
tagttattaa tagtaatcaa ttacggggtc attagttcat agcccatata tggagttccg 300
cgttacataa cttacggtaa atggcccgcc tggctgaccg cccaacgacc cccgcccatt 360
gacgtcaata atgacgtatg ttcccatagt aacgccaata gggactttcc attgacgtca 420
atgggtggag tatttacggt aaactgccca cttggcagta catcaagtgt atcatatgcc 480
aagtacgccc cctattgacg tcaatgacgg taaatggccc gcctggcatt atgcccagta 540
catgacctta tgggactttc ctacttggca gtacatctac gtattagtca tcgctattac 600
catggtgatg cggttttggc agtacatcaa tgggcgtgga tagcggtttg actcacgggg 660
atttccaagt ctccacccca ttgacgtcaa tgggagtttg ttttggcacc aaaatcaacg 720
ggactttcca aaatgtcgta acaactccgc cccattgacg caaatgggcg gtaggcgtgt 780
acggtgggag gtctatataa gcagagctcg tttagtgaac cgtcagatcg cctggagacg 840
ccatccacgc tgttttgacc tccatagaag acaccgggac cgatccagcc tccgcggccg 900
ggaacggtgc attggaacgc ggattccccg tgccaagagt gacgtaagta ccgcctatag 960
actctatagg cacacccctt tggctcttat gcatgctata ctgtttttgg cttggggcct 1020
atacaccccc gcttccttat gctataggtg atggtatagc ttagcctata ggtgtgggtt 1080
attgaccatt attgaccact cccctattgg tgacgatact ttccattact aatccataac 1140
atggctcttt gccacaacta tctctattgg ctatatgcca atactctgtc cttcagagac 1200
tgacacggac tctgtatttt tacaggatgg ggtcccattt attatttaca aattcacata 1260
tacaacaacg ccgtcccccg tgcccgcagt ttttattaaa catagcgtgg gatctccacg 1320
cgaatctcgg gtacgtgttc cggacatggg ctcttctccg gtagcggcgg agcttccaca 1380
tccgagccct ggtcccatgc ctccagcggc tcatggtcgc tcggcagctc cttgctccta 1440
acagtggagg ccagacttag gcacagcaca atgcccacca ccaccagtgt gccgcacaag 1500

```
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
```

```
ctgatcagtg tttttataag taatgttgaa tattggataa ggctgtgtgt cctttgtctt 3960
gggagacaaa gcccacagca ggtggtggtt ggggtggtgg cagctcagtg acaggagagg 4020
ttttttgcc tgttttttt ttttttttt ttttttttaa gtaaggtgtt cttttttctt 4080
agtaaatttt ctactggact gtatgttttg acaggtcaga aacatttctt caaaagaaga 4140
accttttgga aactgtacag ccctttttctt tcattccctt tttgctttct gtgccaatgc 4200
ctttggttct gattgcatta tggaaaacgt tgatcggaac ttgaggtttt tatttatagt 4260
gtggcttgaa agcttggata gctgttgtta cacgagatac cttattaagt ttaggccagc 4320
ttgatgcttt attttttccc tttgaagtag tgagcgttct ctggtttttt tcctttgaaa 4380
ctggtgaggc ttagattttt ctaatgggat tttttacctg atgatctagt tgcataccca 4440
aatgcttgta aatgttttcc tagttaacat gttgataact tcggatttac atgttgtata 4500
tacttgtcat ctgtgtttct agtaaaaata tatggcattt atagaaatac gtaattcctg 4560
atttcctttt ttttttatct ctatgctctg tgtgtacagg tcaaacagac ttcactccta 4620
tttttattta tagaatttta tatgcagtct gtcgttggtt cttgtgttgt aaggatacag 4680
ccttaaattt cctagagcga tgctcagtaa ggcgggttgt cacatgggtt taaatgtaaa 4740
acgggcacgt ttggctgctg ccttcccgag atccaggaca ctaaactgct tctgcactga 4800
ggtataaatc gcttcagatc ccagggaagt gcagatccac gtgcatattc ttaaagaaga 4860
atgaatactt tctaaaatat tttggcatag gaagcaagct gcatggattt gtttgggact 4920
taaattattt tggtaacgga gtgcataggt tttaaacaca gttgcagcat gctaacgagt 4980
cacagcgttt atgcagaagt gatgcctgga tgcctgttgc agctgtttac ggcactgcct 5040
tgcagtgagc attgcagata ggggtggggt gctttgtgtc gtgttcccac acgctgccac 5100
acagccacct cccggaacac atctcacctg ctgggtactt ttcaaaccat cttagcagta 5160
gtagatgagt tactatgaaa cagagaagtt cctcagttgg atattctcat gggatgtctt 5220
ttttcccatg ttgggcaaag tatgataaag catctctatt tgtaaattat gcacttgtta 5280
gttcctgaat cctttctata gcaccactta ttgcagcagg tgtaggctct ggtgtggcct 5340
gtgtctgtgc ttcaatcttt taagcttctc gagggcgcgc ctcagcgatc gcagatcttt 5400
aattaaggcg cctgcaggat ttaaatcacg tgatcacgtc gtacgcaatt ggtttaaacg 5460
cgtaagctta aaagattgaa gcacagacac aggccacacc agagcctaca cctgctgcaa 5520
taagtggtgc tatagaaagg attcaggaac taacaagtgc ataatttaca aatagagatg 5580
ctttatcata ctttgcccaa catgggaaaa aagacatccc atgagaatat ccaactgagg 5640
aacttctctg tttcatagta actcatctac tactgctaag atggtttgaa aagtacccag 5700
caggtgagat gtgttccggg aggtggctgt gtggcagcgt gtgggaacac gacacaaagc 5760
accccacccc tatctgcaat gctcactgca aggcagtgcc gtaaacagct gcaacaggca 5820
tccaggcatc acttctgcat aaacgctgtg actcgttagc atgctgcaac tgtgtttaaa 5880
acctatgcac tccgttacca aaataattta agtcccaaac aaatccatgc agcttgcttc 5940
ctatgccaaa atattttaga aagtattcat tcttctttaa gaatatgcac gtggatctgc 6000
acttccctgg gatctgaagc gatttatacc tcagtgcaga agcagtttag tgtcctggat 6060
ctcgggaagg cagcagccaa acgtgcccgt tttacattta aacccatgtg acaacccgcc 6120
ttactgagca tcgctctagg aaatttaagg ctgtatcctt acaacacaag aaccaacgac 6180
agactgcata taaaattcta taaataaaaa taggagtgaa gtctgtttga cctgtacaca 6240
```

```
cagagcatag agataaaaaa aaaaggaaat caggaattac gtatttctat aaatgccata   6300

tatttttact agaaacacag atgacaagta tatacaacat gtaaatccga agttatcaac   6360

atgttaacta ggaaaacatt tacaagcatt tgggtatgca actagatcat caggtaaaaa   6420

atcccattag aaaaatctaa gcctcaccag tttcaaagga aaaaaaccag agaacgctca   6480

ctacttcaaa gggaaaaaat aaagcatcaa gctggcctaa acttaataag gtatctcgtg   6540

taacaacagc tatccaagct ttcaagccac actataaata aaaacctcaa gttccgatca   6600

acgttttcca taatgcaatc agaaccaaag gcattggcac agaaagcaaa aagggaatga   6660

aagaaaaggg ctgtacagtt tccaaaaggt tcttcttttg aagaaatgtt tctgacctgt   6720

caaaacatac agtccagtag aaaatttact aagaaaaaag aacaccttac ttaaaaaaaa   6780

aaaaaaaaaa aaaaaaaaca ggcaaaaaaa cctctcctgt cactgagctg ccaccacccc   6840

aaccaccacc tgctgtgggc tttgtctccc aagacaaagg acacacagcc ttatccaata   6900

ttcaacatta cttataaaaa cactgatcag aagaaatacc aagtatttcc tcacagactg   6960

ttatacagac tgttatatcc tttcatcggc aagaagagat gaaatacaac agagtgaata   7020

tcaaagaagg cggcaggagc caccgtggca ccatcaccgg gcagtgcagt gcccagctgc   7080

cgtttcctga gcacgcacag gaagccgtca gtcacatgta ataaaccaaa acctggtaca   7140

gttatattat ggatccgggc ccctccggga tcatatgaca agatgtgtat ccaccttaac   7200

ttaatgattt ttaccaaaat cattagggga ttcatcagtg ctcagggtca acgagaatta   7260

acattccgtc aggaaagctt gaattcagct tttgttccct ttagtgaggg ttaattgcgc   7320

gcttggcgta atcatggtca tagctgtttc ctgtgtgaaa ttgttatccg ctcacaattc   7380

cacacaacat acgagccgga agcataaagt gtaaagcctg gggtgcctaa tgagtgagct   7440

aactcacatt aattgcgttg cgctcactgc ccgctttcca gtcgggaaac ctgtcgtgcc   7500

agctgcatta atgaatcggc caacgcgcgg ggagaggcgg tttgcgtatt gggcgctctt   7560

ccgcttcctc gctcactgac tcgctgcgct cggtcgttcg gctgcggcga gcggtatcag   7620

ctcactcaaa ggcggtaata cggttatcca cagaatcagg ggataacgca ggaaagaaca   7680

tgtgagcaaa aggccagcaa aaggccagga accgtaaaaa ggccgcgttg ctggcgtttt   7740

tccataggct ccgcccccct gacgagcatc acaaaaatcg acgctcaagt cagaggtggc   7800

gaaacccgac aggactataa agataccagg cgtttccccc tggaagctcc ctcgtgcgct   7860

ctcctgttcc gaccctgccg cttaccggat acctgtccgc ctttctccct tcgggaagcg   7920

tggcgctttc tcatagctca cgctgtaggt atctcagttc ggtgtaggtc gttcgctcca   7980

agctgggctg tgtgcacgaa ccccccgttc agcccgaccg ctgcgcctta tccggtaact   8040

atcgtcttga gtccaacccg gtaagacacg acttatcgcc actggcagca gccactggta   8100

acaggattag cagagcgagg tatgtaggcg gtgctacaga gttcttgaag tggtggccta   8160

actacggcta cactagaaga acagtatttg gtatctgcgc tctgctgaag ccagttacct   8220

tcggaaaaag agttggtagc tcttgatccg gcaaacaaac caccgctggt agcggtggtt   8280

tttttgtttg caagcagcag attacgcgca gaaaaaaagg atctcaagaa gatcctttga   8340

tcttttctac ggggtctgac gctcagtgga acgaaaactc acgttaaggg attttggtca   8400

tgagattatc aaaaaggatc ttcacctaga tccttttaaa ttaaaaatga agttttaaat   8460

caatctaaag tatatatgag taaacttggt ctgacagtta ccaatgctta atcagtgagg   8520

cacctatctc agcgatctgt ctatttcgtt catccatagt tgcctgactc cccgtcgtgt   8580

agataactac gatacgggag ggcttaccat ctggccccag tgctgcaatg ataccgcgag   8640
```

```
acccacgctc accggctcca gatttatcag caataaacca gccagccgga agggccgagc   8700

gcagaagtgg tcctgcaact ttatccgcct ccatccagtc tattaattgt tgccgggaag   8760

ctagagtaag tagttcgcca gttaatagtt tgcgcaacgt tgttgccatt gctacaggca   8820

tcgtggtgtc acgctcgtcg tttggtatgg cttcattcag ctccggttcc caacgatcaa   8880

ggcgagttac atgatccccc atgttgtgca aaaaagcggt tagctccttc ggtcctccga   8940

tcgttgtcag aagtaagttg gccgcagtgt tatcactcat ggttatggca gcactgcata   9000

attctcttac tgtcatgcca tccgtaagat gcttttctgt gactggtgag tactcaacca   9060

agtcattctg agaatagtgt atgcggcgac cgagttgctc ttgcccggcg tcaatacggg   9120

ataataccgc gccacatagc agaactttaa aagtgctcat cattggaaaa cgttcttcgg   9180

ggcgaaaact ctcaaggatc ttaccgctgt tgagatccag ttcgatgtaa cccactcgtg   9240

cacccaactg atcttcagca tcttttactt tcaccagcgt ttctgggtga gcaaaaacag   9300

gaaggcaaaa tgccgcaaaa aagggaataa gggcgacacg gaaatgttga atactcatac   9360

tcttcctttt tcaatattat tgaagcattt atcagggtta ttgtctcatg agcggataca   9420

tatttgaatg tatttagaaa aataaacaaa taggggttcc gcgcacattt ccccgaaaag   9480

tgccac                                                              9486
```

<210> SEQ ID NO 6
<211> LENGTH: 9286
<212> TYPE: DNA
<213> ORGANISM: Artificial Sequence
<220> FEATURE:
<223> OTHER INFORMATION: Synthetic construct

<400> SEQUENCE: 6

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600

catggtgatg cggttttggc agtacatcaa tgggcgtgga tagcggtttg actcacgggg    660

atttccaagt ctccacccca ttgacgtcaa tgggagtttg ttttggcacc aaaatcaacg    720

ggactttcca aaatgtcgta acaactccgc cccattgacg caaatgggcg gtaggcgtgt    780

acggtgggag gtctatataa gcagagctcg tttagtgaac cgtcagatcg cctggagacg    840

ccatccacgc tgttttgacc tccatagaag acaccgggac cgatccagcc tccgcggccg    900

ggaacggtgc attggaacgc ggattccccg tgccaagagt gacgtaagta ccgcctatag    960

actctatagg cacacccctt tggctcttat gcatgctata ctgtttttgg cttggggcct   1020

atacaccccc gcttccttat gctataggtg atggtatagc ttagcctata ggtgtgggtt   1080

attgaccatt attgaccact cccctattgg tgacgatact ttccattact aatccataac   1140
```

-continued

```
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
```

```
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcgccgtg tattgattgc tcagtgaagt cagacctgct cctctcagca   3720
tccttcacca tcgctcagcc ctggcagagt ttctatcatc ccttgtcatc agctgcatga   3780
gcaacgctca gaagtcagcc ctcttctctc ttttgtagct tatctttaca ttagtatcaa   3840
caaaatgcaa acatagataa aaggaggatt tttatagatg ccttattaac agaagctact   3900
tactcactga gtgcaagctt acttaaaaca agctctgaaa ggatcattct ccccctccca   3960
ctctactgaa gtgctgctag tactactaat tcagactggg tgaatttact cttgcttgaa   4020
tccagcacaa gtcatgtgta ctctggggaa gagggggatt aaacagcttt taaattatgt   4080
ttggaagtcc ttctcacaac tctgttcagg ggagggtttt atccactact acttttattt   4140
tattttattt tattttattt tattttattt tgttttattt tattttattt attttggcat   4200
tgtttatgtg tatattcatg ggtttggatc gtgtcaaggc tgctagatag tctttcatca   4260
ctttgtagca tttaacgttt ttggaaaaca ttatctgggt taatacatat tacaaaaaat   4320
gagcattcag tctttttctc tctgtcttaa tttaaatgca gttttgattg aggctgaact   4380
tatgtatttt taattgcaaa taaatgttct gttccctcct ttgctttttt tctttgtctt   4440
ttctttgaaa ctagatgctt cctttgtttt ctgtttatga aaccttttcc agaaaatgat   4500
tacttcatgt atgggtcttt ggtggcacat agagattctg cagatattat tttaattagg   4560
ttgcttggtt ccatttcatg tctaaatggc tgtggcatgg accttgcgct cgagggcgcg   4620
cctcagcgat cgcagatctt taattaaggc gcctgcagga tttaaatcac gtgatcacgt   4680
cgtacggtaa cctgaggcta tggcagggcc tgccgccccg acgttggctg cgagccctgg   4740
gccttcaccc gaacttgggg ggtggggtgg ggaaaaggaa gaaacgcggg cgtattggcc   4800
ccaatggggt ctcggtgggg tatcgacaga gtgccagccc tgggaccgaa ccccgcgttt   4860
atgaacaaac gacccaacac cgtgcgtttt attctgtctt tttattgccg tcatagcgcg   4920
ggttccttcc ggtattgtct ccttccgtgt ttcagttagc ctccccctag ggtgggcgaa   4980
gaactccagc atgagatccg agctcaggat ccgctagcga attcaggttt aagcacctgg   5040
tttgcgagtc atgcaccaag tgcgtgggcc ttctggcact tccacatcag cagtcacagt   5100
gaagcccagg cgttcataga aaggcaggtt gcgtggagct gaggtctcca ggaaagcagg   5160
cacacctgca cgttcagctg cttccacacc aggcagcacc actgcagagc ccaggccctt   5220
accctggtgg tcagggctca cacccacagt tgccaggaac caagcaggtt cttttgggcg   5280
gtgtggtgcc agcagacctt ccatctgctg ttgtgctgcc aggcggctgc cagacagttc   5340
tgccatgcgt gggccaatct cagcaaacac tgcaccagct tcaacagatt caggggtggt   5400
ccacactgcc acagcagcac catcatctgc cacccacact ttgccaatgt ccaggcccac   5460
acgggtcagg aacagctcct gcagttcagt cacacgttca atgtggcggt ctgggtccac   5520
agtgtgacgg gttgcagggt agtcagcaaa tgcagcagcc agggtgcgaa ctgcacgtgg   5580
aacatcatca cgagttgcca ggcgaacagt tggtttgtat tcagtcatga cgatcctcat   5640
cctgtctctt gatcgatctt tgcaaaagcc taggcctcca aaaaagcctc ctcactactt   5700
ctggaatagc tcagaggccg aggcggcctc ggcctctgca taaataaaaa aaattagtca   5760
gccatggggc ggagaatggg cggaactggg cggagttagg ggcgggatgg gcggagttag   5820
gggcgggact atggttgctg actaattgag atgcatgctt tgcatacttc tgcctgctgg   5880
```

```
ggagcctggg gactttccac acctggttgc tgactaattg agatgcatgc tttgcatact   5940
tctgcctgct ggggagcctg gggactttcc acaccctaac tgacacacat tccacagctg   6000
gttctttccg cctcagacgc gtgccgtgta ttgattgctc agtgaagtca gacctgctcc   6060
tctcagcatc cttcaccatc gctcagccct ggcagagttt ctatcatccc ttgtcatcag   6120
ctgcatgagc aacgctcaga agtcagccct cttctctctt ttgtagctta tctttacatt   6180
agtatcaaca aaatgcaaac atagataaaa ggaggatttt tatagatgcc ttattaacag   6240
aagctactta ctcactgagt gcaagcttac ttaaaacaag ctctgaaagg atcattctcc   6300
ccctccccact ctactgaagt gctgctagta ctactaattc agactgggtg aatttactct  6360
tgcttgaatc cagcacaagt catgtgtact ctggggaaga gggggattaa acagctttta   6420
aattatgttt ggaagtcctt ctcacaactc tgttcagggg agggttttat ccactactac   6480
ttttatttta ttttatttta ttttatttta ttttattttg ttttatttta ttttatttat   6540
tttggcattg tttatgtgta tattcatggg tttggatcgt gtcaaggctg ctagatagtc   6600
tttcatcact ttgtagcatt taacgttttt ggaaaacatt atctgggtta atacatatta   6660
caaaaaatga gcattcagtc tttttctctc tgtcttaatt taaatgcagt tttgattgag   6720
gctgaactta tgtattttta attgcaaata aatgttctgt tccctccttt gctttttttc   6780
tttgtctttt ctttgaaact agatgcttcc tttgttttct gtttatgaaa ccttttccag   6840
aaaatgatta cttcatgtat gggtctttgg tggcacatag agattctgca gatattattt   6900
taattaggtt gcttggttcc atttcatgtc taaatggctg tggcatggac cttgcggggc   6960
ccctccggga tcatatgaca agatgtgtat ccaccttaac ttaatgattt ttaccaaaat   7020
cattagggga ttcatcagtg ctcagggtca acgagaatta acattccgtc aggaaagctt   7080
gaattcagct tttgttccct ttagtgaggg ttaattgcgc gcttggcgta atcatggtca   7140
tagctgtttc ctgtgtgaaa ttgttatccg ctcacaattc cacacaacat acgagccgga   7200
agcataaagt gtaaagcctg gggtgcctaa tgagtgagct aactcacatt aattgcgttg   7260
cgctcactgc ccgctttcca gtcgggaaac ctgtcgtgcc agctgcatta atgaatcggc   7320
caacgcgcgg ggagaggcgg tttgcgtatt gggcgctctt ccgcttcctc gctcactgac   7380
tcgctgcgct cggtcgttcg gctgcggcga gcggtatcag ctcactcaaa ggcggtaata   7440
cggttatcca cagaatcagg ggataacgca ggaaagaaca tgtgagcaaa aggccagcaa   7500
aaggccagga accgtaaaaa ggccgcgttg ctggcgtttt tccataggct ccgcccccct   7560
gacgagcatc acaaaaatcg acgctcaagt cagaggtggc gaaacccgac aggactataa   7620
agataccagg cgtttccccc tggaagctcc ctcgtgcgct ctcctgttcc gaccctgccg   7680
cttaccggat acctgtccgc ctttctccct tcgggaagcg tggcgctttc tcatagctca   7740
cgctgtaggt atctcagttc ggtgtaggtc gttcgctcca agctgggctg tgtgcacgaa   7800
ccccccgttc agcccgaccg ctgcgcctta tccggtaact atcgtcttga gtccaacccg   7860
gtaagacacg acttatcgcc actggcagca gccactggta acaggattag cagagcgagg   7920
tatgtaggcg gtgctacaga gttcttgaag tggtggccta actacggcta cactagaaga   7980
acagtatttg gtatctgcgc tctgctgaag ccagttacct tcggaaaaag agttggtagc   8040
tcttgatccg gcaaacaaac caccgctggt agcggtggtt tttttgtttg caagcagcag   8100
attacgcgca gaaaaaaagg atctcaagaa gatcctttga tcttttctac ggggtctgac   8160
gctcagtgga acgaaaactc acgttaaggg attttggtca tgagattatc aaaaaggatc   8220
ttcacctaga tccttttaaa ttaaaaatga agttttaaat caatctaaag tatatatgag   8280
```

```
taaacttggt ctgacagtta ccaatgctta atcagtgagg cacctatctc agcgatctgt   8340

ctatttcgtt catccatagt tgcctgactc cccgtcgtgt agataactac gatacgggag   8400

ggcttaccat ctggccccag tgctgcaatg ataccgcgag acccacgctc accggctcca   8460

gatttatcag caataaacca gccagccgga agggccgagc gcagaagtgg tcctgcaact   8520

ttatccgcct ccatccagtc tattaattgt tgccgggaag ctagagtaag tagttcgcca   8580

gttaatagtt tgcgcaacgt tgttgccatt gctacaggca tcgtggtgtc acgctcgtcg   8640

tttggtatgg cttcattcag ctccggttcc caacgatcaa ggcgagttac atgatccccc   8700

atgttgtgca aaaaagcggt tagctccttc ggtcctccga tcgttgtcag aagtaagttg   8760

gccgcagtgt tatcactcat ggttatggca gcactgcata attctcttac tgtcatgcca   8820

tccgtaagat gcttttctgt gactggtgag tactcaacca agtcattctg agaatagtgt   8880

atgcggcgac cgagttgctc ttgcccggcg tcaatacggg ataataccgc gccacatagc   8940

agaactttaa aagtgctcat cattggaaaa cgttcttcgg ggcgaaaact ctcaaggatc   9000

ttaccgctgt tgagatccag ttcgatgtaa cccactcgtg cacccaactg atcttcagca   9060

tcttttactt tcaccagcgt ttctgggtga gcaaaaacag gaaggcaaaa tgccgcaaaa   9120

aagggaataa gggcgacacg gaaatgttga atactcatac tcttcctttt tcaatattat   9180

tgaagcattt atcagggtta ttgtctcatg agcggataca tatttgaatg tatttagaaa   9240

aataaacaaa taggggttcc gcgcacattt ccccgaaaag tgccac                  9286
```

<210> SEQ ID NO 7
<211> LENGTH: 9902
<212> TYPE: DNA
<213> ORGANISM: Artificial Sequence
<220> FEATURE:
<223> OTHER INFORMATION: Synthetic construct

<400> SEQUENCE: 7

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600

catggtgatg cggttttggc agtacatcaa tgggcgtgga tagcggtttg actcacgggg    660

atttccaagt ctccacccca ttgacgtcaa tgggagtttg ttttggcacc aaaatcaacg    720

ggactttcca aaatgtcgta acaactccgc cccattgacg caaatgggcg gtaggcgtgt    780

acggtgggag gtctatataa gcagagctcg tttagtgaac cgtcagatcg cctggagacg    840

ccatccacgc tgttttgacc tccatagaag acaccgggac cgatccagcc tccgcggccg    900

ggaacggtgc attggaacgc ggattccccg tgccaagagt gacgtaagta ccgcctatag    960

actctatagg cacacccctt tggctcttat gcatgctata ctgtttttgg cttggggcct   1020
```

-continued

```
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
```

```
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgctcctgg aaggtcctgg aagggggcgt ccgcgggagc tcacggggag   3720
agcccccccc caaagccccc agggatgtaa ttacgtccct cccccgctag ggggcagcag   3780
cgagccgccc ggggctccgc tccggtccgg cgctcccccc gcatccccga gccggcagcg   3840
tgcggggaca gcccgggcac ggggaaggtg gcacgggatc gctttcctct gaacgcttct   3900
cgctgctctt tgagcctgca gacacctggg gggatacggg gaaaaagctt taggctgaaa   3960
gagagattta gaatgacaga atcacagaat ggcctgggtt ggaaaggccc acaatgctca   4020
tccagttcca acccctgcta tgtgcagggt cgccaaccag cagcccaggc tgcccagaga   4080
cacatccagc ctggcctgga atgcctgcag ggatggggca tccacagcct ccttgggcaa   4140
cctgttcagt gcgtcaccac cctctggggg aaaaactgcc tcttcatatc caacccaaac   4200
ctcccctgtc taagtgtaaa gccattcccc cttgtcctat caagggggag tttgctgtga   4260
cattgttggt ctggggtgac acatgtttgc caattcagtg catcacggag aggcagatct   4320
tggggataag gaagagcagg acagcatgga cgtgggacat gcaggtgttg agggctctgg   4380
gacactctcc aagtcacagc gttcagaaca gccttaagga tcagaagata ggatagaagg   4440
acaaagagca agttaaaacc cagcatggag aggagcacaa aaaggccaca gacactgctg   4500
gtccctgtgt ctgagcctgc atgtttgatg gtgtctggat gcaagcagaa ggggtggaag   4560
agcttgcctg gagagataca gctgggtcag taggactggg acaggcagct ggagaattgc   4620
catgtagatg ttcacacaat cgtcaaatca tgaaggctgg aaaagccctc caagatcccc   4680
aagaccaacc ccaacccacc caccgtgccc actggccatg tccctcagtg ccacatcccc   4740
acagttcttc atcacctcca gggacggtga cccccccacc tccgtgggca gctgtgccac   4800
tgcagcaccg ctctttggag aaggtaaatc ttgctaaatc cagcccgacc ctcccctggc   4860
acaacgtaag gccattatct ctcatcctac tccaggacgg agtcagtgag aatattctcg   4920
agggcgcgcc tcagcgatcg cagatcttta attaaggcgc ctgcaggatt taaatcacgt   4980
gatcacgtcg tacggtaacc tgaggctatg gcagggcctg ccgccccgac gttggctgcg   5040
agccctgggc cttcacccga acttgggggg tggggtgggg aaaaggaaga aacgcgggcg   5100
tattggcccc aatggggtct cggtggggta tcgacagagt gccagccctg ggaccgaacc   5160
ccgcgtttat gaacaaacga cccaacaccg tgcgttttat tctgtctttt tattgccgtc   5220
atagcgcggg ttccttccgg tattgtctcc ttccgtgttt cagttagcct ccccctaggg   5280
tgggcgaaga actccagcat gagatccgag ctcaggatcc gctagcgaat tcaggtttaa   5340
gcacctggtt tgcgagtcat gcaccaagtg cgtgggcctt ctggcacttc cacatcagca   5400
gtcacagtga agcccaggcg ttcatagaaa ggcaggttgc gtggagctga ggtctccagg   5460
aaagcaggca cacctgcacg ttcagctgct tccacaccag gcagcaccac tgcagagccc   5520
aggcccttac cctggtggtc agggctcaca cccacagttg ccaggaacca agcaggttct   5580
tttgggcggt gtggtgccag cagaccttcc atctgctgtt gtgctgccag gcggctgcca   5640
gacagttctg ccatgcgtgg gccaatctca gcaaacactg caccagcttc aacagattca   5700
ggggtggtcc acactgccac agcagcacca tcatctgcca cccacacttt gccaatgtcc   5760
```

-continued

```
aggcccacac gggtcaggaa cagctcctgc agttcagtca cacgttcaat gtggcggtct   5820
gggtccacag tgtgacgggt tgcagggtag tcagcaaatg cagcagccag ggtgcgaact   5880
gcacgtggaa catcatcacg agttgccagg cgaacagttg gtttgtattc agtcatgacg   5940
atcctcatcc tgtctcttga tcgatctttg caaaagccta ggcctccaaa aaagcctcct   6000
cactacttct ggaatagctc agaggccgag gcggcctcgg cctctgcata aataaaaaaa   6060
attagtcagc catggggcgg agaatgggcg gaactgggcg gagttagggg cgggatgggc   6120
ggagttaggg gcgggactat ggttgctgac taattgagat gcatgctttg catacttctg   6180
cctgctgggg agcctgggga ctttccacac ctggttgctg actaattgag atgcatgctt   6240
tgcatacttc tgcctgctgg ggagcctggg gactttccac accctaactg acacacattc   6300
cacagctggt tctttccgcc tcagacgcgt aatattctca ctgactccgt cctggagtag   6360
gatgagagat aatggcctta cgttgtgcca ggggagggtc gggctggatt tagcaagatt   6420
taccttctcc aaagagcggt gctgcagtgg cacagctgcc cacggaggtg gggggtcac   6480
cgtccctgga ggtgatgaag aactgtgggg atgtggcact gagggacatg gccagtgggc   6540
acggtgggtg ggttggggtt ggtcttgggg atcttggagg gcttttccag ccttcatgat   6600
ttgacgattg tgtgaacatc tacatggcaa ttctccagct gcctgtccca gtcctactga   6660
cccagctgta tctctccagg caagctcttc cacccccttct gcttgcatcc agacaccatc   6720
aaacatgcag gctcagacac agggaccagc agtgtctgtg gccttttttgt gctcctctcc   6780
atgctgggtt ttaacttgct ctttgtcctt ctatcctatc ttctgatcct taaggctgtt   6840
ctgaacgctg tgacttggag agtgtcccag agccctcaac acctgcatgt cccacgtcca   6900
tgctgtcctg ctcttcctta tccccaagat ctgcctctcc gtgatgcact gaattggcaa   6960
acatgtgtca ccccagacca acaatgtcac agcaaactcc cccttgatag gacaaggggg   7020
aatggcttta cacttagaca ggggaggttt gggttggata tgaagaggca gtttttcccc   7080
cagagggtgg tgacgcactg aacaggttgc ccaaggaggc tgtggatgcc ccatccctgc   7140
aggcattcca ggccaggctg gatgtgtctc tgggcagcct gggctgctgg ttggcgaccc   7200
tgcacatagc aggggttgga actggatgag cattgtgggc ctttccaacc caggccattc   7260
tgtgattctg tcattctaaa tctctctttc agcctaaagc tttttccccg tatcccccca   7320
ggtgtctgca ggctcaaaga gcagcgagaa gcgttcagag gaaagcgatc ccgtgccacc   7380
ttccccgtgc ccgggctgtc cccgcacgct gccggctcgg ggatgcgggg ggagcgccgg   7440
accggagcgg agccccgggc ggctcgctgc tgccccctag cgggggaggg acgtaattac   7500
atccctgggg gctttggggg ggggctctcc ccgtgagctc ccgcggacgc cccccttccag   7560
gaccttccag gagggcccct ccgggatcat atgacaagat gtgtatccac cttaacttaa   7620
tgatttttac caaaatcatt aggggattca tcagtgctca gggtcaacga gaattaacat   7680
tccgtcagga aagcttgaat tcagcttttg ttccctttag tgagggttaa ttgcgcgctt   7740
ggcgtaatca tggtcatagc tgtttcctgt gtgaaattgt tatccgctca caattccaca   7800
caacatacga gccggaagca taaagtgtaa agcctggggt gcctaatgag tgagctaact   7860
cacattaatt gcgttgcgct cactgcccgc tttccagtcg ggaaacctgt cgtgccagct   7920
gcattaatga atcggccaac gcgcggggag aggcggtttg cgtattgggc gctcttccgc   7980
ttcctcgctc actgactcgc tgcgctcggt cgttcggctg cggcgagcgg tatcagctca   8040
ctcaaaggcg gtaatacggt tatccacaga atcaggggat aacgcaggaa agaacatgtg   8100
agcaaaaggc cagcaaaagg ccaggaaccg taaaaaggcc gcgttgctgg cgtttttcca   8160
```

taggctccgc cccccctgacg agcatcacaa aaatcgacgc tcaagtcaga ggtggcgaaa 8220
cccgacagga ctataaagat accaggcgtt tccccctgga agctccctcg tgcgctctcc 8280
tgttccgacc ctgccgctta ccggatacct gtccgccttt ctcccttcgg gaagcgtggc 8340
gctttctcat agctcacgct gtaggtatct cagttcggtg taggtcgttc gctccaagct 8400
gggctgtgtg cacgaacccc ccgttcagcc cgaccgctgc gccttatccg gtaactatcg 8460
tcttgagtcc aacccggtaa gacacgactt atcgccactg gcagcagcca ctggtaacag 8520
gattagcaga gcgaggtatg taggcggtgc tacagagttc ttgaagtggt ggcctaacta 8580
cggctacact agaagaacag tatttggtat ctgcgctctg ctgaagccag ttaccttcgg 8640
aaaaagagtt ggtagctctt gatccggcaa acaaaccacc gctggtagcg gtggtttttt 8700
tgtttgcaag cagcagatta cgcgcagaaa aaaaggatct caagaagatc ctttgatctt 8760
ttctacgggg tctgacgctc agtggaacga aaactcacgt taagggattt tggtcatgag 8820
attatcaaaa aggatcttca cctagatcct tttaaattaa aaatgaagtt ttaaatcaat 8880
ctaaagtata tatgagtaaa cttggtctga cagttaccaa tgcttaatca gtgaggcacc 8940
tatctcagcg atctgtctat ttcgttcatc catagttgcc tgactccccg tcgtgtagat 9000
aactacgata cgggagggct taccatctgg ccccagtgct gcaatgatac cgcgagaccc 9060
acgctcaccg gctccagatt tatcagcaat aaaccagcca gccggaaggg ccgagcgcag 9120
aagtggtcct gcaactttat ccgcctccat ccagtctatt aattgttgcc gggaagctag 9180
agtaagtagt tcgccagtta atagtttgcg caacgttgtt gccattgcta caggcatcgt 9240
ggtgtcacgc tcgtcgtttg gtatggcttc attcagctcc ggttcccaac gatcaaggcg 9300
agttacatga tcccccatgt tgtgcaaaaa agcggttagc tccttcggtc ctccgatcgt 9360
tgtcagaagt aagttggccg cagtgttatc actcatggtt atggcagcac tgcataattc 9420
tcttactgtc atgccatccg taagatgctt ttctgtgact ggtgagtact caaccaagtc 9480
attctgagaa tagtgtatgc ggcgaccgag ttgctcttgc ccggcgtcaa tacgggataa 9540
taccgcgcca catagcagaa ctttaaaagt gctcatcatt ggaaaacgtt cttcggggcg 9600
aaaactctca aggatcttac cgctgttgag atccagttcg atgtaaccca ctcgtgcacc 9660
caactgatct tcagcatctt ttactttcac cagcgtttct gggtgagcaa aaacaggaag 9720
gcaaaatgcc gcaaaaaagg gaataagggc gacacggaaa tgttgaatac tcatactctt 9780
cctttttcaa tattattgaa gcatttatca gggttattgt ctcatgagcg gatacatatt 9840
tgaatgtatt tagaaaaata aacaaatagg ggttccgcgc acatttcccc gaaaagtgcc 9900
ac 9902

<210> SEQ ID NO 8
<211> LENGTH: 10804
<212> TYPE: DNA
<213> ORGANISM: Artificial Sequence
<220> FEATURE:
<223> OTHER INFORMATION: Synthetic construct

<400> SEQUENCE: 8
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggcatcaga ttggctattg gccattgcat acgttgtatc catatcataa 180
tatgtacatt tatattggct catgtccaac attaccgcca tgttgacatt gattattgac 240

```
tagttattaa tagtaatcaa ttacggggtc attagttcat agcccatata tggagttccg     300
cgttacataa cttacggtaa atggcccgcc tggctgaccg cccaacgacc cccgcccatt     360
gacgtcaata atgacgtatg ttcccatagt aacgccaata gggactttcc attgacgtca     420
atgggtggag tatttacggt aaactgccca cttggcagta catcaagtgt atcatatgcc     480
aagtacgccc cctattgacg tcaatgacgg taaatggccc gcctggcatt atgcccagta     540
catgacctta tgggactttc ctacttggca gtacatctac gtattagtca tcgctattac     600
catggtgatg cggttttggc agtacatcaa tgggcgtgga tagcggtttg actcacgggg     660
atttccaagt ctccacccca ttgacgtcaa tgggagtttg ttttggcacc aaaatcaacg     720
ggactttcca aaatgtcgta acaactccgc cccattgacg caaatgggcg gtaggcgtgt     780
acggtgggag gtctatataa gcagagctcg tttagtgaac cgtcagatcg cctggagacg     840
ccatccacgc tgttttgacc tccatagaag acaccgggac cgatccagcc tccgcggccg     900
ggaacggtgc attggaacgc ggattccccg tgccaagagt gacgtaagta ccgcctatag     960
actctatagg cacacccctt tggctcttat gcatgctata ctgtttttgg cttggggcct    1020
atacaccccc gcttccttat gctataggtg atggtatagc ttagcctata ggtgtgggtt    1080
attgaccatt attgaccact cccctattgg tgacgatact ttccattact aatccataac    1140
atggctcttt gccacaacta tctctattgg ctatatgcca atactctgtc cttcagagac    1200
tgacacggac tctgtatttt tacaggatgg ggtcccattt attatttaca aattcacata    1260
tacaacaacg ccgtcccccg tgcccgcagt ttttattaaa catagcgtgg gatctccacg    1320
cgaatctcgg gtacgtgttc cggacatggg ctcttctccg gtagcggcgg agcttccaca    1380
tccgagccct ggtcccatgc ctccagcggc tcatggtcgc tcggcagctc cttgctccta    1440
acagtggagg ccagacttag gcacagcaca atgcccacca ccaccagtgt gccgcacaag    1500
gccgtggcgg tagggtatgt gtctgaaaat gagcgtggag attgggctcg cacggctgac    1560
gcagatggaa gacttaaggc agcggcagaa gaagatgcag gcagctgagt tgttgtattc    1620
tgataagagt cagaggtaac tcccgttgcg gtgctgttaa cggtggaggg cagtgtagtc    1680
tgagcagtac tcgttgctgc cgcgcgcgcc accagacata atagctgaca gactaacaga    1740
ctgttccttt ccatgggtct tttctgcagt caccgtctcg cgaaaaatca ataatcagac    1800
aacaagatgt gcgaactcga tattttacac gactctcttt accaattctg ccccgaatta    1860
cacttaaaac gactcaacag cttaacgttg gcttgccacg cattacttga ctgtaaaact    1920
ctcactctta ccgaacttgg ccgtaacctg ccaaccaaag cgagaacaaa acataacatc    1980
aaacgaatcg accgattgtt aggtaatcgt cacctccaca aagagcgact cgctgtatac    2040
cgttggcatg ctagctttat ctgttcgggc aatacgatgc ccattgtact tgttgactgg    2100
tctgatattc gtgagcaaaa acgacttatg gtattgcgag cttcagtcgc actacacggt    2160
cgttctgtta ctctttatga gaaagcgttc ccgctttcag agcaatattc aaagaaagct    2220
catgaccaat ttctagccga ccttgcgagc attctaccga gtaacaccac accgctcatt    2280
gtcagtgatg ctggctttaa agtgccatgg tataaatccg ttgagaagct gggttggtac    2340
tggttaagtc gagtaagagg aaaagtacaa tatgcagacc taggagcgga aaactggaaa    2400
cctatcagca acttacatga tatgtcatct agtcactcaa agactttagg ctataagagg    2460
ctgactaaaa gcaatccaat ctcatgccaa attctattgt ataaatctcg ctctaaaggc    2520
cgaaaaaatc agcgctcgac acggactcat tatcaccacc cgtcacctaa aatctactca    2580
gcgtcggcaa aggagccatg ggttctagca actaacttac ctgttgaaat tcgaacaccc    2640
```

```
aaacaacttg ttaatatcta ttcgaagcga atgcagattg aagaaacctt ccgagacttg   2700

aaaagtcctg cctacggact aggcctacgc catagccgaa cgagcagctc agagcgtttt   2760

gatatcatgc tgctaatcgc cctgatgctt caactaacat gttggcttgc gggcgttcat   2820

gctcagaaac aaggttggga caagcacttc caggctaaca cagtcagaaa tcgaaacgta   2880

ctctcaacag ttcgcttagg catggaagtt ttgcggcatt ctggctacac aataacaagg   2940

gaagacttac tcgtggctgc aaccctacta gctcaaaatt tattcacaca tggttacgct   3000

ttggggaaat tatgagggga tcgctctaga gcgatccggg atctcgggaa aagcgttggt   3060

gaccaaaggt gccttttatc atcactttaa aaataaaaaa caattactca gtgcctgtta   3120

taagcagcaa ttaattatga ttgatgccta catcacaaca aaaactgatt taacaaatgg   3180

ttggtctgcc ttagaaagta tatttgaaca ttatcttgat tatattattg ataataataa   3240

aaaccttatc cctatccaag aagtgatgcc tatcattggt tggaatgaac ttgaaaaaat   3300

tagccttgaa tacattactg gtaaggtaaa cgccattgtc agcaaattga tccaagagaa   3360

ccaacttaaa gctttcctga cggaatgtta attctcgttg accctgagca ctgatgaatc   3420

ccctaatgat tttggtaaaa atcattaagt taaggtggat acacatcttg tcatatgatc   3480

ccggtaatgt gagttagctc actcattagg caccccaggc tttacacttt atgcttccgg   3540

ctcgtatgtt gtgtggaatt gtgagcggat aacaatttca cacaggaaac agctatgacc   3600

atgattacgc caagcgcgca attaaccctc actaaaggga acaaaagctg gagctccacc   3660

gcggtggcgg ccgcggatcc ataatataac tgtaccaggt tttggtttat tacatgtgac   3720

tgacggcttc ctgtgcgtgc tcaggaaacg gcagctgggc actgcactgc ccggtgatgg   3780

tgccacggtg gctcctgccg ccttctttga tattcactct gttgtatttc atctcttctt   3840

gccgatgaaa ggatataaca gtctgtataa cagtctgtga ggaaatactt ggtatttctt   3900

ctgatcagtg tttttataag taatgttgaa tattggataa ggctgtgtgt cctttgtctt   3960

gggagacaaa gcccacagca ggtggtggtt ggggtggtgg cagctcagtg acaggagagg   4020

tttttttgcc tgtttttttt tttttttttt ttttttttaa gtaaggtgtt cttttttctt   4080

agtaaatttt ctactggact gtatgttttg acaggtcaga aacatttctt caaaagaaga   4140

accttttgga aactgtacag ccctttttctt tcattccctt tttgctttct gtgccaatgc   4200

ctttggttct gattgcatta tggaaaacgt tgatcggaac ttgaggtttt tatttatagt   4260

gtggcttgaa agcttggata gctgttgtta cacgagatac cttattaagt ttaggccagc   4320

ttgatgcttt atttttttccc tttgaagtag tgagcgttct ctggtttttt tcctttgaaa   4380

ctggtgaggc ttagattttt ctaatgggat tttttacctg atgatctagt tgcataccca   4440

aatgcttgta aatgttttcc tagttaacat gttgataact tcggatttac atgttgtata   4500

tacttgtcat ctgtgtttct agtaaaaata tatggcattt atagaaatac gtaattcctg   4560

atttcctttt ttttttatct ctatgctctg tgtgtacagg tcaaacagac ttcactccta   4620

tttttattta tagaatttta tatgcagtct gtcgttggtt cttgtgttgt aaggatacag   4680

ccttaaattt cctagagcga tgctcagtaa ggcgggttgt cacatgggtt taaatgtaaa   4740

acgggcacgt ttggctgctg ccttcccgag atccaggaca ctaaactgct tctgcactga   4800

ggtataaatc gcttcagatc ccagggaagt gcagatccac gtgcatattc ttaaagaaga   4860

atgaatactt tctaaaatat tttggcatag gaagcaagct gcatggattt gtttgggact   4920

taaattattt tggtaacgga gtgcataggt tttaaacaca gttgcagcat gctaacgagt   4980
```

```
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
gttcctgaat cctttctata gcaccactta ttgcagcagg tgtaggctct ggtgtggcct   5340
gtgtctgtgc ttcaatcttt taagcttctc gagggcgcgc ctcagcgatc gcagatcttt   5400
aattaaggcg cctgcaggat ttaaatcacg tgatcacgtc gtacggtaac ctgaggctat   5460
ggcagggcct gccgccccga cgttggctgc gagccctggg ccttcacccg aacttggggg   5520
gtggggtggg gaaaaggaag aaacgcgggc gtattggccc caatggggtc tcggtggggt   5580
atcgacagag tgccagccct gggaccgaac cccgcgttta tgaacaaacg acccaacacc   5640
gtgcgtttta ttctgtcttt ttattgccgt catagcgcgg gttccttccg gtattgtctc   5700
cttccgtgtt tcagttagcc tcccccctagg gtgggcgaag aactccagca tgagatccga   5760
gctcaggatc cgctagcgaa ttcaggttta agcacctggt ttgcgagtca tgcaccaagt   5820
gcgtgggcct tctggcactt ccacatcagc agtcacagtg aagcccaggc gttcatagaa   5880
aggcaggttg cgtggagctg aggtctccag gaaagcaggc acacctgcac gttcagctgc   5940
ttccacacca ggcagcacca ctgcagagcc caggccctta ccctggtggt cagggctcac   6000
acccacagtt gccaggaacc aagcaggttc ttttgggcgg tgtggtgcca gcagaccttc   6060
catctgctgt tgtgctgcca ggcggctgcc agacagttct gccatgcgtg ggccaatctc   6120
agcaaacact gcaccagctt caacagattc aggggtggtc cacactgcca cagcagcacc   6180
atcatctgcc acccacactt tgccaatgtc caggcccaca cgggtcagga acagctcctg   6240
cagttcagtc acacgttcaa tgtggcggtc tgggtccaca gtgtgacggg ttgcagggta   6300
gtcagcaaat gcagcagcca gggtgcgaac tgcacgtgga acatcatcac gagttgccag   6360
gcgaacagtt ggtttgtatt cagtcatgac gatcctcatc ctgtctcttg atcgatcttt   6420
gcaaaagcct aggcctccaa aaaagcctcc tcactacttc tggaatagct cagaggccga   6480
ggcggcctcg gcctctgcat aaataaaaaa aattagtcag ccatggggcg gagaatgggc   6540
ggaactgggc ggagttaggg gcgggatggg cggagttagg ggcgggacta tggttgctga   6600
ctaattgaga tgcatgcttt gcatacttct gcctgctggg gagcctgggg actttccaca   6660
cctggttgct gactaattga gatgcatgct ttgcatactt ctgcctgctg gggagcctgg   6720
ggactttcca caccctaact gacacacatt ccacagctgg ttctttccgc ctcagacgcg   6780
taagcttaaa agattgaagc acagacacag gccacaccag agcctacacc tgctgcaata   6840
agtggtgcta tagaaaggat tcaggaacta acaagtgcat aatttacaaa tagagatgct   6900
ttatcatact ttgcccaaca tgggaaaaaa gacatcccat gagaatatcc aactgaggaa   6960
cttctctgtt tcatagtaac tcatctacta ctgctaagat ggtttgaaaa gtacccagca   7020
ggtgagatgt gttccgggag gtggctgtgt ggcagcgtgt gggaacacga cacaaagcac   7080
cccacccccta tctgcaatgc tcactgcaag gcagtgccgt aaacagctgc aacaggcatc   7140
caggcatcac ttctgcataa acgctgtgac tcgttagcat gctgcaactg tgtttaaaac   7200
ctatgcactc cgttaccaaa ataatttaag tcccaaacaa atccatgcag cttgcttcct   7260
atgccaaaat attttagaaa gtattcattc ttctttaaga atatgcacgt ggatctgcac   7320
ttccctggga tctgaagcga tttatacctc agtgcagaag cagtttagtg tcctggatct   7380
```

```
cgggaaggca gcagccaaac gtgcccgttt tacatttaaa cccatgtgac aacccgcctt   7440
actgagcatc gctctaggaa atttaaggct gtatccttac aacacaagaa ccaacgacag   7500
actgcatata aaattctata aataaaaata ggagtgaagt ctgtttgacc tgtacacaca   7560
gagcatagag ataaaaaaaa aaggaaatca ggaattacgt atttctataa atgccatata   7620
tttttactag aaacacagat gacaagtata tacaacatgt aaatccgaag ttatcaacat   7680
gttaactagg aaaacattta caagcatttg ggtatgcaac tagatcatca ggtaaaaaat   7740
cccattagaa aaatctaagc ctcaccagtt tcaaaggaaa aaaaccagag aacgctcact   7800
acttcaaagg gaaaaaataa agcatcaagc tggcctaaac ttaataaggt atctcgtgta   7860
acaacagcta tccaagcttt caagccacac tataaataaa aacctcaagt tccgatcaac   7920
gttttccata atgcaatcag aaccaaaggc attggcacag aaagcaaaaa gggaatgaaa   7980
gaaaagggct gtacagtttc caaaaggttc ttcttttgaa gaaatgtttc tgacctgtca   8040
aaacatacag tccagtagaa aatttactaa gaaaaaagaa caccttactt aaaaaaaaaa   8100
aaaaaaaaaa aaaaaacagg caaaaaaacc tctcctgtca ctgagctgcc accaccccaa   8160
ccaccacctg ctgtgggctt tgtctcccaa gacaaaggac acacagcctt atccaatatt   8220
caacattact tataaaaaca ctgatcagaa gaaataccaa gtatttcctc acagactgtt   8280
atacagactg ttatatcctt tcatcggcaa gaagagatga aatacaacag agtgaatatc   8340
aaagaaggcg gcaggagcca ccgtggcacc atcaccgggc agtgcagtgc ccagctgccg   8400
tttcctgagc acgcacagga agccgtcagt cacatgtaat aaaccaaaac ctggtacagt   8460
tatattatgg atccgggccc ctccgggatc atatgacaag atgtgtatcc accttaactt   8520
aatgattttt accaaaatca ttaggggatt catcagtgct cagggtcaac gagaattaac   8580
attccgtcag gaaagcttga attcagcttt tgttcccttt agtgagggtt aattgcgcgc   8640
ttggcgtaat catggtcata gctgtttcct gtgtgaaatt gttatccgct cacaattcca   8700
cacaacatac gagccggaag cataaagtgt aaagcctggg gtgcctaatg agtgagctaa   8760
ctcacattaa ttgcgttgcg ctcactgccc gctttccagt cgggaaacct gtcgtgccag   8820
ctgcattaat gaatcggcca acgcgcgggg agaggcggtt tgcgtattgg gcgctcttcc   8880
gcttcctcgc tcactgactc gctgcgctcg gtcgttcggc tgcggcgagc ggtatcagct   8940
cactcaaagg cggtaatacg gttatccaca gaatcagggg ataacgcagg aaagaacatg   9000
tgagcaaaag gccagcaaaa ggccaggaac cgtaaaaagg ccgcgttgct ggcgtttttc   9060
cataggctcc gcccccctga cgagcatcac aaaaatcgac gctcaagtca gaggtggcga   9120
aacccgacag gactataaag ataccaggcg tttccccctg gaagctccct cgtgcgctct   9180
cctgttccga ccctgccgct taccggatac ctgtccgcct ttctcccttc gggaagcgtg   9240
gcgctttctc atagctcacg ctgtaggtat ctcagttcgg tgtaggtcgt tcgctccaag   9300
ctgggctgtg tgcacgaacc ccccgttcag cccgaccgct gcgccttatc cggtaactat   9360
cgtcttgagt ccaacccggt aagacacgac ttatcgccac tggcagcagc cactggtaac   9420
aggattagca gagcgaggta tgtaggcggt gctacagagt tcttgaagtg gtggcctaac   9480
tacggctaca ctagaagaac agtatttggt atctgcgctc tgctgaagcc agttaccttc   9540
ggaaaaagag ttggtagctc ttgatccggc aaacaaacca ccgctggtag cggtggtttt   9600
tttgtttgca agcagcagat tacgcgcaga aaaaaaggat ctcaagaaga tcctttgatc   9660
ttttctacgg ggtctgacgc tcagtggaac gaaaactcac gttaagggat tttggtcatg   9720
```

```
agattatcaa aaaggatctt cacctagatc cttttaaatt aaaaatgaag ttttaaatca   9780
atctaaagta tatatgagta aacttggtct gacagttacc aatgcttaat cagtgaggca   9840
cctatctcag cgatctgtct atttcgttca tccatagttg cctgactccc cgtcgtgtag   9900
ataactacga tacgggaggg cttaccatct ggccccagtg ctgcaatgat accgcgagac   9960
ccacgctcac cggctccaga tttatcagca ataaaccagc cagccggaag ggccgagcgc  10020
agaagtggtc ctgcaacttt atccgcctcc atccagtcta ttaattgttg ccgggaagct  10080
agagtaagta gttcgccagt taatagtttg cgcaacgttg ttgccattgc tacaggcatc  10140
gtggtgtcac gctcgtcgtt tggtatggct tcattcagct ccggttccca acgatcaagg  10200
cgagttacat gatcccccat gttgtgcaaa aaagcggtta gctccttcgg tcctccgatc  10260
gttgtcagaa gtaagttggc cgcagtgtta tcactcatgg ttatggcagc actgcataat  10320
tctcttactg tcatgccatc cgtaagatgc ttttctgtga ctggtgagta ctcaaccaag  10380
tcattctgag aatagtgtat gcggcgaccg agttgctctt gcccggcgtc aatacgggat  10440
aataccgcgc cacatagcag aactttaaaa gtgctcatca ttggaaaacg ttcttcgggg  10500
cgaaaactct caaggatctt accgctgttg agatccagtt cgatgtaacc cactcgtgca  10560
cccaactgat cttcagcatc ttttactttc accagcgttt ctgggtgagc aaaaacagga  10620
aggcaaaatg ccgcaaaaaa gggaataagg gcgacacgga aatgttgaat actcatactc  10680
ttcctttttc aatattattg aagcatttat cagggttatt gtctcatgag cggatacata  10740
tttgaatgta tttagaaaaa taaacaaata ggggttccgc gcacatttcc ccgaaaagtg  10800
ccac                                                               10804
```

<210> SEQ ID NO 9
<211> LENGTH: 11248
<212> TYPE: DNA
<213> ORGANISM: Artificial Sequence
<220> FEATURE:
<223> OTHER INFORMATION: Synthetic construct

<400> SEQUENCE: 9

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
```

```
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
```

```
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
ttttttgcc tgttttttt ttttttttt tttttttaa gtaaggtgtt cttttttctt   4080
agtaaatttt ctactggact gtatgttttg acaggtcaga aacatttctt caaaagaaga   4140
accttttgga aactgtacag cccttttctt tcattccctt tttgctttct gtgccaatgc   4200
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt atttttccc tttgaagtag tgagcgttct ctggtttttt tcctttgaaa   4380
ctggtgaggc ttagattttt ctaatgggat tttttacctg atgatctagt tgcatacccca   4440
aatgcttgta aatgttttcc tagttaacat gttgataact tcggatttac atgttgtata   4500
tacttgtcat ctgtgtttct agtaaaaata tatggcattt atagaaatac gtaattcctg   4560
atttcctttt ttttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
gttcctgaat cctttctata gcaccactta ttgcagcagg tgtaggctct ggtgtggcct   5340
gtgtctgtgc ttcaatcttt taagcttctc gagggcgcgc ctcagcgatc gcagatcttt   5400
aattaaggcg cctgcaggat ttaaatcacg tgatcacgtc gtacggtaac ctgaggctat   5460
ggcagggcct gccgccccga cgttggctgc gagccctggg ccttcacccg aacttggggg   5520
gtggggtggg gaaaaggaag aaacgcgggc gtattggccc caatggggtc tcggtggggt   5580
atcgacagag tgccagccct gggaccgaac cccgcgttta tgaacaaacg acccaacacc   5640
gtgcgtttta ttctgtcttt ttattgccgt catagcgcgg gttccttccg gtattgtctc   5700
```

```
cttccgtgtt tcagttagcc tccccctagg gtgggcgaag aactccagca tgagatcccc   5760
gcgctggagg atcatccagc cggcgtcccg gaaaacgatt ccgaagccca acctttcata   5820
gaaggcggcg gtggaatcga aatctcgtga tggcaggttg ggcgtcgctt ggtcggtcat   5880
ttcgaacccc agagtcccgc tcagaagaac tcgtcaagaa ggcgatagaa ggcgatgcgc   5940
tgcgaatcgg gagcggcgat accgtaaagc acgaggaagc ggtcagccca ttcgccgcca   6000
agctcttcag caatatcacg ggtagccaac gctatgtcct gatagcggtc cgccacaccc   6060
agccggccac agtcgatgaa tccagaaaag cggccatttt ccaccatgat attcggcaag   6120
caggcatcgc catgggtcac gacgagatcc tcgccgtcgg gcatgctcgc cttgagcctg   6180
gcgaacagtt cggctggcgc gagcccctga tgctcttcgt ccagatcatc ctgatcgaca   6240
agaccggctt ccatccgagt acgtgctcgc tcgatgcgat gtttcgcttg gtggtcgaat   6300
gggcaggtag ccggatcaag cgtatgcagc cgccgcattg catcagccat gatggatact   6360
ttctcggcag gagcaaggtg agatgacagg agatcctgcc ccggcacttc gcccaatagc   6420
agccagtccc ttcccgcttc agtgacaacg tcgagcacag ctgcgcaagg aacgcccgtc   6480
gtggccagcc acgatagccg cgctgcctcg tcttgcagtt cattcagggc accggacagg   6540
tcggtcttga caaaaagaac cgggcgcccc tgcgctgaca gccggaacac ggcggcatca   6600
gagcagccga ttgtctgttg tgcccagtca tagccgaata gcctctccac ccaagcggcc   6660
ggagaacctg cgtgcaatcc atcttgttca atcatgcgaa acgatcctca tcctgtctct   6720
tgatcgatct ttgcaaaagc ctaggcctcc aaaaaagcct cctcactact tctggaatag   6780
ctcagaggcc gaggcggcct cggcctctgc ataaataaaa aaaattagtc agccatgggg   6840
cggagaatgg gcggaactgg gcggagttag gggcgggatg ggcggagtta ggggcgggac   6900
tatggttgct gactaattga gatgcatgct ttgcatactt ctgcctgctg gggagcctgg   6960
ggactttcca cacctggttg ctgactaatt gagatgcatg ctttgcatac ttctgcctgc   7020
tggggagcct ggggactttc cacaccctaa ctgacacaca ttccacagct ggttctttcc   7080
gcctcaggac tcttcctttt tcaatattat tgaagcattt atcagggtta ttgtctcatg   7140
agcggataca tatttgaatg tatttagaaa aataaacaaa taggggttcc gcgcacattt   7200
ccccgaaaag tgccacctga cgcgtaagct taaaagattg aagcacagac acaggccaca   7260
ccagagccta cacctgctgc aataagtggt gctatagaaa ggattcagga actaacaagt   7320
gcataattta caaatagaga tgctttatca tactttgccc aacatgggaa aaaagacatc   7380
ccatgagaat atccaactga ggaacttctc tgtttcatag taactcatct actactgcta   7440
agatggtttg aaaagtaccc agcaggtgag atgtgttccg ggaggtggct gtgtggcagc   7500
gtgtgggaac acgacacaaa gcaccccacc cctatctgca atgctcactg caaggcagtg   7560
ccgtaaacag ctgcaacagg catccaggca tcacttctgc ataaacgctg tgactcgtta   7620
gcatgctgca actgtgttta aaacctatgc actccgttac caaaataatt taagtcccaa   7680
acaaatccat gcagcttgct tcctatgcca aaatatttta gaaagtattc attcttcttt   7740
aagaatatgc acgtggatct gcacttccct gggatctgaa gcgatttata cctcagtgca   7800
gaagcagttt agtgtcctgg atctcgggaa ggcagcagcc aaacgtgccc gttttacatt   7860
taaacccatg tgacaacccg ccttactgag catcgctcta ggaaatttaa ggctgtatcc   7920
ttacaacaca agaaccaacg acagactgca tataaaattc tataaataaa aataggagtg   7980
aagtctgttt gacctgtaca cacagagcat agagataaaa aaaaaaggaa atcaggaatt   8040
```

```
acgtatttct ataaatgcca tatattttta ctagaaacac agatgacaag tatatacaac    8100
atgtaaatcc gaagttatca acatgttaac taggaaaaca tttacaagca tttgggtatg    8160
caactagatc atcaggtaaa aaatcccatt agaaaaatct aagcctcacc agtttcaaag    8220
gaaaaaaacc agagaacgct cactacttca aagggaaaaa ataaagcatc aagctggcct    8280
aaacttaata aggtatctcg tgtaacaaca gctatccaag ctttcaagcc acactataaa    8340
taaaaacctc aagttccgat caacgttttc cataatgcaa tcagaaccaa aggcattggc    8400
acagaaagca aaaagggaat gaaagaaaag ggctgtacag tttccaaaag gttcttcttt    8460
tgaagaaatg tttctgacct gtcaaaacat acagtccagt agaaaattta ctaagaaaaa    8520
agaacacctt acttaaaaaa aaaaaaaaaa aaaaaaaaaa caggcaaaaa aacctctcct    8580
gtcactgagc tgccaccacc ccaaccacca cctgctgtgg gctttgtctc ccaagacaaa    8640
ggacacacag ccttatccaa tattcaacat tacttataaa aacactgatc agaagaaata    8700
ccaagtattt cctcacagac tgttatacag actgttatat cctttcatcg gcaagaagag    8760
atgaaataca acagagtgaa tatcaaagaa ggcggcagga gccaccgtgg caccatcacc    8820
gggcagtgca gtgcccagct gccgtttcct gagcacgcac aggaagccgt cagtcacatg    8880
taataaacca aaacctggta cagttatatt atggatccgg gcccctccgg gatcatatga    8940
caagatgtgt atccacctta acttaatgat tttaccaaa atcattaggg gattcatcag    9000
tgctcagggt caacgagaat taacattccg tcaggaaagc ttgaattcag cttttgttcc    9060
ctttagtgag ggttaattgc gcgcttggcg taatcatggt catagctgtt tcctgtgtga    9120
aattgttatc cgctcacaat tccacacaac atacgagccg gaagcataaa gtgtaaagcc    9180
tggggtgcct aatgagtgag ctaactcaca ttaattgcgt tgcgctcact gcccgctttc    9240
cagtcgggaa acctgtcgtg ccagctgcat taatgaatcg gccaacgcgc ggggagaggc    9300
ggtttgcgta ttgggcgctc ttccgcttcc tcgctcactg actcgctgcg ctcggtcgtt    9360
cggctgcggc gagcggtatc agctcactca aaggcggtaa tacggttatc cacagaatca    9420
ggggataacg caggaaagaa catgtgagca aaaggccagc aaaaggccag gaaccgtaaa    9480
aaggccgcgt tgctggcgtt tttccatagg ctccgccccc ctgacgagca tcacaaaaat    9540
cgacgctcaa gtcagaggtg gcgaaacccg acaggactat aaagatacca ggcgtttccc    9600
cctggaagct ccctcgtgcg ctctcctgtt ccgaccctgc cgcttaccgg atacctgtcc    9660
gcctttctcc cttcgggaag cgtggcgctt tctcatagct cacgctgtag gtatctcagt    9720
tcggtgtagg tcgttcgctc caagctgggc tgtgtgcacg aaccccccgt tcagcccgac    9780
cgctgcgcct tatccggtaa ctatcgtctt gagtccaacc cggtaagaca cgacttatcg    9840
ccactggcag cagccactgg taacaggatt agcagagcga ggtatgtagg cggtgctaca    9900
gagttcttga agtggtggcc taactacggc tacactagaa gaacagtatt tggtatctgc    9960
gctctgctga agccagttac cttcggaaaa agagttggta gctcttgatc cggcaaacaa   10020
accaccgctg gtagcggtgg tttttttgtt tgcaagcagc agattacgcg cagaaaaaaa   10080
ggatctcaag aagatccttt gatcttttct acggggtctg acgctcagtg gaacgaaaac   10140
tcacgttaag ggattttggt catgagatta tcaaaaagga tcttcaccta gatcctttta   10200
aattaaaaat gaagttttaa atcaatctaa agtatatatg agtaaacttg gtctgacagt   10260
taccaatgct taatcagtga ggcacctatc tcagcgatct gtctatttcg ttcatccata   10320
gttgcctgac tccccgtcgt gtagataact acgatacggg agggcttacc atctggcccc   10380
agtgctgcaa tgataccgcg agacccacgc tcaccggctc cagatttatc agcaataaac   10440
```

```
cagccagccg gaagggccga gcgcagaagt ggtcctgcaa ctttatccgc ctccatccag  10500

tctattaatt gttgccggga agctagagta agtagttcgc cagttaatag tttgcgcaac  10560

gttgttgcca ttgctacagg catcgtggtg tcacgctcgt cgtttggtat ggcttcattc  10620

agctccggtt cccaacgatc aaggcgagtt acatgatccc ccatgttgtg caaaaaagcg  10680

gttagctcct tcggtcctcc gatcgttgtc agaagtaagt tggccgcagt gttatcactc  10740

atggttatgg cagcactgca taattctctt actgtcatgc catccgtaag atgcttttct  10800

gtgactggtg agtactcaac caagtcattc tgagaatagt gtatgcggcg accgagttgc  10860

tcttgcccgg cgtcaatacg ggataatacc gcgccacata gcagaacttt aaaagtgctc  10920

atcattggaa aacgttcttc ggggcgaaaa ctctcaagga tcttaccgct gttgagatcc  10980

agttcgatgt aacccactcg tgcacccaac tgatcttcag catcttttac tttcaccagc  11040

gtttctgggt gagcaaaaac aggaaggcaa aatgccgcaa aaaagggaat aagggcgaca  11100

cggaaatgtt gaatactcat actcttcctt tttcaatatt attgaagcat ttatcagggt  11160

tattgtctca tgagcggata catatttgaa tgtatttaga aaaataaaca aataggggtt  11220

ccgcgcacat ttccccgaaa agtgccac                                      11248
```

<210> SEQ ID NO 10
<211> LENGTH: 8893
<212> TYPE: DNA
<213> ORGANISM: Artificial Sequence
<220> FEATURE:
<223> OTHER INFORMATION: Synthetic construct

<400> SEQUENCE: 10

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccacgcccc attgacgcaa atgggcggta    180

ggcgtgtacg gtgggaggtc tatataagca gagctcgttt agtgaaccgt cagatcgcct    240

ggagacgcca tccacgctgt tttgacctcc atagaagaca ccgggaccga tccagcctcc    300

gcggccggga acggtgcatt ggaacgcgga ttccccgtgc caagagtgac gtaagtaccg    360

cctatagact ctataggcac acccctttgg ctcttatgca tgctatactg tttttggctt    420

ggggcctata cacccccgct tccttatgct ataggtgatg gtatagctta gcctataggt    480

gtgggttatt gaccattatt gaccactccc ctattggtga cgatactttc cattactaat    540

ccataacatg gctctttgcc acaactatct ctattggcta tatgccaata ctctgtcctt    600

cagagactga cacggactct gtatttttac aggatggggt cccatttatt atttacaaat    660

tcacatatac aacaacgccg tcccccgtgc ccgcagtttt tattaaacat agcgtgggat    720

ctccacgcga atctcgggta cgtgttccgg acatgggctc ttctccggta gcggcggagc    780

ttccacatcc gagccctggt cccatgcctc cagcggctca tggtcgctcg gcagctcctt    840

gctcctaaca gtggaggcca gacttaggca cagcacaatg cccaccacca ccagtgtgcc    900

gcacaaggcc gtggcggtag ggtatgtgtc tgaaaatgag cgtggagatt gggctcgcac    960

ggctgacgca gatggaagac ttaaggcagc ggcagaagaa gatgcaggca gctgagttgt   1020

tgtattctga taagagtcag aggtaactcc cgttgcggtg ctgttaacgg tggagggcag   1080

tgtagtctga gcagtactcg ttgctgccgc gcgcgccacc agacataata gctgacagac   1140

taacagactg ttcctttcca tgggtctttt ctgcagtcac cgtctcgcga aaaatcaata   1200
```

```
atcagacaac aagatgtgcg aactcgatat tttacacgac tctctttacc aattctgccc   1260
cgaattacac ttaaaacgac tcaacagctt aacgttggct tgccacgcat tacttgactg   1320
taaaactctc actcttaccg aacttggccg taacctgcca accaaagcga gaacaaaaca   1380
taacatcaaa cgaatcgacc gattgttagg taatcgtcac ctccacaaag agcgactcgc   1440
tgtataccgt tggcatgcta gctttatctg ttcgggcaat acgatgccca ttgtacttgt   1500
tgactggtct gatattcgtg agcaaaaacg acttatggta ttgcgagctt cagtcgcact   1560
acacggtcgt tctgttactc tttatgagaa agcgttcccg ctttcagagc aatattcaaa   1620
gaaagctcat gaccaatttc tagccgacct tgcgagcatt ctaccgagta acaccacacc   1680
gctcattgtc agtgatgctg gctttaaagt gccatggtat aaatccgttg agaagctggg   1740
ttggtactgg ttaagtcgag taagaggaaa agtacaatat gcagacctag gagcggaaaa   1800
ctggaaacct atcagcaact tacatgatat gtcatctagt cactcaaaga ctttaggcta   1860
taagaggctg actaaaagca atccaatctc atgccaaatt ctattgtata aatctcgctc   1920
taaaggccga aaaaatcagc gctcgacacg gactcattat caccacccgt cacctaaaat   1980
ctactcagcg tcggcaaagg agccatgggt tctagcaact aacttacctg ttgaaattcg   2040
aacacccaaa caacttgtta atatctattc gaagcgaatg cagattgaag aaaccttccg   2100
agacttgaaa agtcctgcct acggactagg cctacgccat agccgaacga gcagctcaga   2160
gcgttttgat atcatgctgc taatcgccct gatgcttcaa ctaacatgtt ggcttgcggg   2220
cgttcatgct cagaaacaag gttgggacaa gcacttccag gctaacacag tcagaaatcg   2280
aaacgtactc tcaacagttc gcttaggcat ggaagttttg cggcattctg gctacacaat   2340
aacaagggaa gacttactcg tggctgcaac cctactagct caaaatttat tcacacatgg   2400
ttacgctttg ggaaattat gaggggatcg ctctagagcg atccgggatc tcgggaaaag   2460
cgttggtgac caaaggtgcc ttttatcatc actttaaaaa taaaaaacaa ttactcagtg   2520
cctgttataa gcagcaatta attatgattg atgcctacat cacaacaaaa actgatttaa   2580
caaatggttg gtctgcctta gaaagtatat ttgaacatta tcttgattat attattgata   2640
ataataaaaa ccttatccct atccaagaag tgatgcctat cattggttgg aatgaacttg   2700
aaaaaattag ccttgaatac attactggta aggtaaacgc cattgtcagc aaattgatcc   2760
aagagaacca acttaaagct ttcctgacgg aatgttaatt ctcgttgacc ctgagcactg   2820
atgaatcccc taatgatttt ggtaaaaatc attaagttaa ggtggataca catcttgtca   2880
tatgatcccg gtaatgtgag ttagctcact cattaggcac cccaggcttt acactttatg   2940
cttccggctc gtatgttgtg tggaattgtg agcggataac aatttcacac aggaaacagc   3000
tatgaccatg attacgccaa gcgcgcaatt aaccctcact aaagggaaca aaagctggag   3060
ctccaccgcg gtggcggccg cggatccata atataactgt accaggtttt ggtttattac   3120
atgtgactga cggcttcctg tgcgtgctca ggaaacggca gctgggcact gcactgcccg   3180
gtgatggtgc cacggtggct cctgccgcct tctttgatat tcactctgtt gtatttcatc   3240
tcttcttgcc gatgaaagga tataacagtc tgtataacag tctgtgagga aatacttggt   3300
atttcttctg atcagtgttt ttataagtaa tgttgaatat tggataaggc tgtgtgtcct   3360
ttgtcttggg agacaaagcc cacagcaggt ggtggttggg gtggtggcag ctcagtgaca   3420
ggagaggttt ttttgcctgt ttttttttt tttttttt tttttaagta aggtgttctt   3480
ttttcttagt aaattttcta ctggactgta tgttttgaca ggtcagaaac atttcttcaa   3540
aagaagaacc ttttggaaac tgtacagccc ttttctttca ttccctttt gctttctgtg   3600
```

```
ccaatgcctt tggttctgat tgcattatgg aaaacgttga tcggaacttg aggtttttat   3660
ttatagtgtg gcttgaaagc ttggatagct gttgttacac gagatacctt attaagttta   3720
ggccagcttg atgctttatt ttttcccttt gaagtagtga gcgttctctg gtttttttcc   3780
tttgaaactg gtgaggctta gatttttcta atgggatttt ttacctgatg atctagttgc   3840
atacccaaat gcttgtaaat gttttcctag ttaacatgtt gataacttcg gatttacatg   3900
ttgtatatac ttgtcatctg tgtttctagt aaaaatatat ggcatttata gaaatacgta   3960
attcctgatt tccttttttt tttatctcta tgctctgtgt gtacaggtca aacagacttc   4020
actcctattt ttatttatag aattttatat gcagtctgtc gttggttctt gtgttgtaag   4080
gatacagcct taaatttcct agagcgatgc tcagtaaggc gggttgtcac atgggtttaa   4140
atgtaaaacg ggcacgtttg gctgctgcct tcccgagatc caggacacta aactgcttct   4200
gcactgaggt ataaatcgct tcagatccca gggaagtgca gatccacgtg catattctta   4260
aagaagaatg aatactttct aaaatatttt ggcataggaa gcaagctgca tggatttgtt   4320
tgggacttaa attattttgg taacggagtg cataggtttt aaacacagtt gcagcatgct   4380
aacgagtcac agcgtttatg cagaagtgat gcctggatgc ctgttgcagc tgtttacggc   4440
actgccttgc agtgagcatt gcagataggg gtggggtgct ttgtgtcgtg ttcccacacg   4500
ctgccacaca gccacctccc ggaacacatc tcacctgctg ggtacttttc aaaccatctt   4560
agcagtagta gatgagttac tatgaaacag agaagttcct cagttggata ttctcatggg   4620
atgtcttttt tcccatgttg ggcaaagtat gataaagcat ctctatttgt aaattatgca   4680
cttgttagtt cctgaatcct ttctatagca ccacttattg cagcaggtgt aggctctggt   4740
gtggcctgtg tctgtgcttc aatcttttaa gcttctcgag ggcgcgcctc agcgatcgca   4800
gatctttaat taaggcgcct gcaggattta aatcacgtga tcacgtcgta cgcaattggt   4860
ttaaacgcgt aagcttaaaa gattgaagca cagacacagg ccacaccaga gcctacacct   4920
gctgcaataa gtggtgctat agaaaggatt caggaactaa caagtgcata atttacaaat   4980
agagatgctt tatcatactt tgcccaacat gggaaaaaag acatcccatg agaatatcca   5040
actgaggaac ttctctgttt catagtaact catctactac tgctaagatg gtttgaaaag   5100
tacccagcag gtgagatgtg ttccgggagg tggctgtgtg gcagcgtgtg ggaacacgac   5160
acaaagcacc ccacccctat ctgcaatgct cactgcaagg cagtgccgta aacagctgca   5220
acaggcatcc aggcatcact tctgcataaa cgctgtgact cgttagcatg ctgcaactgt   5280
gtttaaaacc tatgcactcc gttaccaaaa taatttaagt cccaaacaaa tccatgcagc   5340
ttgcttccta tgccaaaata ttttagaaag tattcattct tctttaagaa tatgcacgtg   5400
gatctgcact tccctgggat ctgaagcgat ttatacctca gtgcagaagc agtttagtgt   5460
cctggatctc gggaaggcag cagccaaacg tgcccgtttt acatttaaac ccatgtgaca   5520
acccgcctta ctgagcatcg ctctaggaaa tttaaggctg tatccttaca acacaagaac   5580
caacgacaga ctgcatataa aattctataa ataaaaatag gagtgaagtc tgtttgacct   5640
gtacacacag agcatagaga taaaaaaaaa aggaaatcag gaattacgta tttctataaa   5700
tgccatatat ttttactaga aacacagatg acaagtatat acaacatgta aatccgaagt   5760
tatcaacatg ttaactagga aaacatttac aagcatttgg gtatgcaact agatcatcag   5820
gtaaaaaatc ccattagaaa aatctaagcc tcaccagttt caaaggaaaa aaaccagaga   5880
acgctcacta cttcaaaggg aaaaaataaa gcatcaagct ggcctaaact taataaggta   5940
```

-continued

```
tctcgtgtaa caacagctat ccaagctttc aagccacact ataaataaaa acctcaagtt   6000
ccgatcaacg ttttccataa tgcaatcaga accaaaggca ttggcacaga aagcaaaaag   6060
ggaatgaaag aaaagggctg tacagtttcc aaaaggttct tcttttgaag aaatgtttct   6120
gacctgtcaa aacatacagt ccagtagaaa atttactaag aaaaaagaac accttactta   6180
aaaaaaaaaa aaaaaaaaaa aaaaacaggc aaaaaaacct ctcctgtcac tgagctgcca   6240
ccaccccaac caccacctgc tgtgggcttt gtctcccaag acaaaggaca cacagcctta   6300
tccaatattc aacattactt ataaaaacac tgatcagaag aaataccaag tatttcctca   6360
cagactgtta tacagactgt tatatccttt catcggcaag aagagatgaa atacaacaga   6420
gtgaatatca aagaaggcgg caggagccac cgtggcacca tcaccgggca gtgcagtgcc   6480
cagctgccgt ttcctgagca cgcacaggaa gccgtcagtc acatgtaata aaccaaaacc   6540
tggtacagtt atattatgga tccgggcccc tccgggatca tatgacaaga tgtgtatcca   6600
ccttaactta atgattttta ccaaaatcat taggggattc atcagtgctc agggtcaacg   6660
agaattaaca ttccgtcagg aaagcttgaa ttcagctttt gttcccttta gtgagggtta   6720
attgcgcgct tggcgtaatc atggtcatag ctgtttcctg tgtgaaattg ttatccgctc   6780
acaattccac acaacatacg agccggaagc ataaagtgta aagcctgggg tgcctaatga   6840
gtgagctaac tcacattaat tgcgttgcgc tcactgcccg ctttccagtc gggaaacctg   6900
tcgtgccagc tgcattaatg aatcggccaa cgcgcgggga gaggcggttt gcgtattggg   6960
cgctcttccg cttcctcgct cactgactcg ctgcgctcgg tcgttcggct gcggcgagcg   7020
gtatcagctc actcaaaggc ggtaatacgg ttatccacag aatcagggga taacgcagga   7080
aagaacatgt gagcaaaagg ccagcaaaag gccaggaacc gtaaaaaggc cgcgttgctg   7140
gcgtttttcc ataggctccg cccccctgac gagcatcaca aaaatcgacg ctcaagtcag   7200
aggtggcgaa acccgacagg actataaaga taccaggcgt ttccccctgg aagctccctc   7260
gtgcgctctc ctgttccgac cctgccgctt accggatacc tgtccgcctt tctcccttcg   7320
ggaagcgtgg cgctttctca tagctcacgc tgtaggtatc tcagttcggt gtaggtcgtt   7380
cgctccaagc tgggctgtgt gcacgaaccc cccgttcagc ccgaccgctg cgccttatcc   7440
ggtaactatc gtcttgagtc caacccggta agacacgact tatcgccact ggcagcagcc   7500
actggtaaca ggattagcag agcgaggtat gtaggcggtg ctacagagtt cttgaagtgg   7560
tggcctaact acggctacac tagaagaaca gtatttggta tctgcgctct gctgaagcca   7620
gttaccttcg gaaaaagagt tggtagctct tgatccggca aacaaaccac cgctggtagc   7680
ggtggttttt ttgtttgcaa gcagcagatt acgcgcagaa aaaaaggatc tcaagaagat   7740
cctttgatct tttctacggg gtctgacgct cagtggaacg aaaactcacg ttaagggatt   7800
ttggtcatga gattatcaaa aaggatcttc acctagatcc ttttaaatta aaaatgaagt   7860
tttaaatcaa tctaaagtat atatgagtaa acttggtctg acagttacca atgcttaatc   7920
agtgaggcac ctatctcagc gatctgtcta tttcgttcat ccatagttgc ctgactcccc   7980
gtcgtgtaga taactacgat acgggagggc ttaccatctg gccccagtgc tgcaatgata   8040
ccgcgagacc cacgctcacc ggctccagat ttatcagcaa taaaccagcc agccggaagg   8100
gccgagcgca gaagtggtcc tgcaacttta tccgcctcca tccagtctat taattgttgc   8160
cgggaagcta gagtaagtag ttcgccagtt aatagtttgc gcaacgttgt tgccattgct   8220
acaggcatcg tggtgtcacg ctcgtcgttt ggtatggctt cattcagctc cggttcccaa   8280
cgatcaaggc gagttacatg atcccccatg ttgtgcaaaa aagcggttag ctccttcggt   8340
```

```
cctccgatcg ttgtcagaag taagttggcc gcagtgttat cactcatggt tatggcagca   8400

ctgcataatt ctcttactgt catgccatcc gtaagatgct tttctgtgac tggtgagtac   8460

tcaaccaagt cattctgaga atagtgtatg cggcgaccga gttgctcttg cccggcgtca   8520

atacgggata ataccgcgcc acatagcaga actttaaaag tgctcatcat tggaaaacgt   8580

tcttcggggc gaaaactctc aaggatctta ccgctgttga gatccagttc gatgtaaccc   8640

actcgtgcac ccaactgatc ttcagcatct tttactttca ccagcgtttc tgggtgagca   8700

aaaacaggaa ggcaaaatgc cgcaaaaaag ggaataaggg cgacacggaa atgttgaata   8760

ctcatactct tcctttttca atattattga agcatttatc agggttattg tctcatgagc   8820

ggatacatat ttgaatgtat ttagaaaaat aaacaaatag gggttccgcg cacatttccc   8880

cgaaaagtgc cac                                                      8893
```

<210> SEQ ID NO 11
<211> LENGTH: 10211
<212> TYPE: DNA
<213> ORGANISM: Artificial Sequence
<220> FEATURE:
<223> OTHER INFORMATION: Synthetic construct

<400> SEQUENCE: 11

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccacgcccc attgacgcaa atgggcggta    180

ggcgtgtacg gtgggaggtc tatataagca gagctcgttt agtgaaccgt cagatcgcct    240

ggagacgcca tccacgctgt tttgacctcc atagaagaca ccgggaccga tccagcctcc    300

gcggccggga acggtgcatt ggaacgcgga ttccccgtgc caagagtgac gtaagtaccg    360

cctatagact ctataggcac acccctttgg ctcttatgca tgctatactg tttttggctt    420

ggggcctata cacccccgct tccttatgct ataggtgatg gtatagctta gcctataggt    480

gtgggttatt gaccattatt gaccactccc ctattggtga cgatactttc cattactaat    540

ccataacatg gctctttgcc acaactatct ctattggcta tatgccaata ctctgtcctt    600

cagagactga cacggactct gtatttttac aggatggggt cccatttatt atttacaaat    660

tcacatatac aacaacgccg tcccccgtgc ccgcagtttt tattaaacat agcgtgggat    720

ctccacgcga atctcgggta cgtgttccgg acatgggctc ttctccggta gcggcggagc    780

ttccacatcc gagccctggt cccatgcctc cagcggctca tggtcgctcg gcagctcctt    840

gctcctaaca gtggaggcca gacttaggca cagcacaatg cccaccacca ccagtgtgcc    900

gcacaaggcc gtggcggtag ggtatgtgtc tgaaaatgag cgtggagatt gggctcgcac    960

ggctgacgca gatggaagac ttaaggcagc ggcagaagaa gatgcaggca gctgagttgt   1020

tgtattctga taagagtcag aggtaactcc cgttgcggtg ctgttaacgg tggagggcag   1080

tgtagtctga gcagtactcg ttgctgccgc gcgcgccacc agacataata gctgacagac   1140

taacagactg ttcctttcca tgggtctttt ctgcagtcac cgtctcgcga aaaatcaata   1200

atcagacaac aagatgtgcg aactcgatat tttacacgac tctctttacc aattctgccc   1260

cgaattacac ttaaaacgac tcaacagctt aacgttggct tgccacgcat tacttgactg   1320

taaaactctc actcttaccg aacttggccg taacctgcca accaaagcga gaacaaaaca   1380

taacatcaaa cgaatcgacc gattgttagg taatcgtcac ctccacaaag agcgactcgc   1440
```

```
tgtataccgt tggcatgcta gctttatctg ttcgggcaat acgatgccca ttgtacttgt   1500
tgactggtct gatattcgtg agcaaaaacg acttatggta ttgcgagctt cagtcgcact   1560
acacggtcgt tctgttactc tttatgagaa agcgttcccg ctttcagagc aatattcaaa   1620
gaaagctcat gaccaatttc tagccgacct tgcgagcatt ctaccgagta acaccacacc   1680
gctcattgtc agtgatgctg gctttaaagt gccatggtat aaatccgttg agaagctggg   1740
ttggtactgg ttaagtcgag taagaggaaa agtacaatat gcagacctag gagcggaaaa   1800
ctggaaacct atcagcaact tacatgatat gtcatctagt cactcaaaga ctttaggcta   1860
taagaggctg actaaaagca atccaatctc atgccaaatt ctattgtata aatctcgctc   1920
taaaggccga aaaaatcagc gctcgacacg gactcattat caccacccgt cacctaaaat   1980
ctactcagcg tcggcaaagg agccatgggt tctagcaact aacttacctg ttgaaattcg   2040
aacacccaaa caacttgtta atatctattc gaagcgaatg cagattgaag aaaccttccg   2100
agacttgaaa agtcctgcct acggactagg cctacgccat agccgaacga gcagctcaga   2160
gcgttttgat atcatgctgc taatcgccct gatgcttcaa ctaacatgtt ggcttgcggg   2220
cgttcatgct cagaaacaag gttgggacaa gcacttccag gctaacacag tcagaaatcg   2280
aaacgtactc tcaacagttc gcttaggcat ggaagttttg cggcattctg gctacacaat   2340
aacaagggaa gacttactcg tggctgcaac cctactagct caaaatttat tcacacatgg   2400
ttacgctttg ggaaattat gaggggatcg ctctagagcg atccgggatc tcgggaaaag   2460
cgttggtgac caaaggtgcc ttttatcatc actttaaaaa taaaaaacaa ttactcagtg   2520
cctgttataa gcagcaatta attatgattg atgcctacat cacaacaaaa actgatttaa   2580
caaatggttg gtctgcctta gaaagtatat ttgaacatta tcttgattat attattgata   2640
ataataaaaa ccttatccct atccaagaag tgatgcctat cattggttgg aatgaacttg   2700
aaaaaattag ccttgaatac attactggta aggtaaacgc cattgtcagc aaattgatcc   2760
aagagaacca acttaaagct ttcctgacgg aatgttaatt ctcgttgacc ctgagcactg   2820
atgaatcccc taatgatttt ggtaaaaatc attaagttaa ggtggataca catcttgtca   2880
tatgatcccg gtaatgtgag ttagctcact cattaggcac cccaggcttt acactttatg   2940
cttccggctc gtatgttgtg tggaattgtg agcggataac aatttcacac aggaaacagc   3000
tatgaccatg attacgccaa gcgcgcaatt aaccctcact aaagggaaca aaagctggag   3060
ctccaccgcg gtggcggccg cggatccata atataactgt accaggtttt ggtttattac   3120
atgtgactga cggcttcctg tgcgtgctca ggaaacggca gctgggcact gcactgcccg   3180
gtgatggtgc cacggtggct cctgccgcct tctttgatat tcactctgtt gtatttcatc   3240
tcttcttgcc gatgaaagga tataacagtc tgtataacag tctgtgagga aatacttggt   3300
atttcttctg atcagtgttt ttataagtaa tgttgaatat tggataaggc tgtgtgtcct   3360
ttgtcttggg agacaaagcc cacagcaggt ggtggttggg gtggtggcag ctcagtgaca   3420
ggagaggttt ttttgcctgt ttttttttt ttttttttt tttttaagta aggtgttctt   3480
ttttcttagt aaattttcta ctggactgta tgttttgaca ggtcagaaac atttcttcaa   3540
aagaagaacc ttttggaaac tgtacagccc ttttctttca ttcccttttt gctttctgtg   3600
ccaatgcctt tggttctgat tgcattatgg aaaacgttga tcggaacttg aggtttttat   3660
ttatagtgtg gcttgaaagc ttggatagct gttgttacac gagatacctt attaagttta   3720
ggccagcttg atgctttatt ttttcccttt gaagtagtga gcgttctctg gttttttttcc   3780
tttgaaactg gtgaggctta gatttttcta atgggatttt ttacctgatg atctagttgc   3840
```

```
atacccaaat gcttgtaaat gttttcctag ttaacatgtt gataacttcg gatttacatg   3900
ttgtatatac ttgtcatctg tgtttctagt aaaaatatat ggcatttata gaaatacgta   3960
attcctgatt tccttttttt tttatctcta tgctctgtgt gtacaggtca aacagacttc   4020
actcctattt ttatttatag aattttatat gcagtctgtc gttggttctt gtgttgtaag   4080
gatacagcct taaatttcct agagcgatgc tcagtaaggc gggttgtcac atgggtttaa   4140
atgtaaaacg ggcacgtttg gctgctgcct tcccgagatc caggacacta aactgcttct   4200
gcactgaggt ataaatcgct tcagatccca gggaagtgca gatccacgtg catattctta   4260
aagaagaatg aatactttct aaaatatttt ggcataggaa gcaagctgca tggatttgtt   4320
tgggacttaa attattttgg taacggagtg cataggtttt aaacacagtt gcagcatgct   4380
aacgagtcac agcgtttatg cagaagtgat gcctggatgc ctgttgcagc tgtttacggc   4440
actgccttgc agtgagcatt gcagataggg gtggggtgct ttgtgtcgtg ttcccacacg   4500
ctgccacaca gccacctccc ggaacacatc tcacctgctg ggtacttttc aaaccatctt   4560
agcagtagta gatgagttac tatgaaacag agaagttcct cagttggata ttctcatggg   4620
atgtcttttt tcccatgttg ggcaaagtat gataaagcat ctctatttgt aaattatgca   4680
cttgttagtt cctgaatcct ttctatagca ccacttattg cagcaggtgt aggctctggt   4740
gtggcctgtg tctgtgcttc aatcttttaa gcttctcgag ggcgcgcctc agcgatcgca   4800
gatctttaat taaggcgcct gcaggattta aatcacgtga tcacgtcgta cggtaacctg   4860
aggctatggc agggcctgcc gccccgacgt tggctgcgag ccctgggcct tcacccgaac   4920
ttgggggggtg gggtggggaa aaggaagaaa cgcgggcgta ttggccccaa tggggtctcg   4980
gtggggtatc gacagagtgc cagccctggg accgaacccc gcgtttatga acaaacgacc   5040
caacaccgtg cgttttattc tgtcttttta ttgccgtcat agcgcgggtt ccttccggta   5100
ttgtctcctt ccgtgtttca gttagcctcc ccctagggtg ggcgaagaac tccagcatga   5160
gatccgagct caggatccgc tagcgaattc aggtttaagc acctggtttg cgagtcatgc   5220
accaagtgcg tgggccttct ggcacttcca catcagcagt cacagtgaag cccaggcgtt   5280
catagaaagg caggttgcgt ggagctgagg tctccaggaa agcaggcaca cctgcacgtt   5340
cagctgcttc cacaccaggc agcaccactg cagagcccag gcccttaccc tggtggtcag   5400
ggctcacacc cacagttgcc aggaaccaag caggttcttt tgggcggtgt ggtgccagca   5460
gaccttccat ctgctgttgt gctgccaggc ggctgccaga cagttctgcc atgcgtgggc   5520
caatctcagc aaacactgca ccagcttcaa cagattcagg ggtggtccac actgccacag   5580
cagcaccatc atctgccacc cacactttgc caatgtccag gcccacacgg gtcaggaaca   5640
gctcctgcag ttcagtcaca cgttcaatgt ggcggtctgg gtccacagtg tgacgggttg   5700
cagggtagtc agcaaatgca gcagccaggg tgcgaactgc acgtggaaca tcatcacgag   5760
ttgccaggcg aacagttggt ttgtattcag tcatgacgat cctcatcctg tctcttgatc   5820
gatctttgca aaagcctagg cctccaaaaa agcctcctca ctacttctgg aatagctcag   5880
aggccgaggc ggcctcggcc tctgcataaa taaaaaaaat tagtcagcca tggggcggag   5940
aatgggcgga actgggcgga gttaggggcg ggatgggcgg agttaggggc gggactatgg   6000
ttgctgacta attgagatgc atgctttgca tacttctgcc tgctggggag cctggggact   6060
ttccacacct ggttgctgac taattgagat gcatgctttg catacttctg cctgctgggg   6120
agcctgggga ctttccacac cctaactgac acacattcca cagctggttc tttccgcctc   6180
```

-continued

```
agacgcgtaa gcttaaaaga ttgaagcaca gacacaggcc acaccagagc ctacacctgc   6240
tgcaataagt ggtgctatag aaaggattca ggaactaaca agtgcataat ttacaaatag   6300
agatgcttta tcatactttg cccaacatgg gaaaaaagac atcccatgag aatatccaac   6360
tgaggaactt ctctgtttca tagtaactca tctactactg ctaagatggt ttgaaaagta   6420
cccagcaggt gagatgtgtt ccgggaggtg gctgtgtggc agcgtgtggg aacacgacac   6480
aaagcacccc accctatct gcaatgctca ctgcaaggca gtgccgtaaa cagctgcaac   6540
aggcatccag gcatcacttc tgcataaacg ctgtgactcg ttagcatgct gcaactgtgt   6600
ttaaaaccta tgcactccgt taccaaaata atttaagtcc caaacaaatc catgcagctt   6660
gcttcctatg ccaaaatatt ttagaaagta ttcattcttc tttaagaata tgcacgtgga   6720
tctgcacttc cctgggatct gaagcgattt atacctcagt gcagaagcag tttagtgtcc   6780
tggatctcgg gaaggcagca gccaaacgtg cccgttttac atttaaaccc atgtgacaac   6840
ccgccttact gagcatcgct ctaggaaatt taaggctgta tccttacaac acaagaacca   6900
acgacagact gcatataaaa ttctataaat aaaaatagga gtgaagtctg tttgacctgt   6960
acacacagag catagagata aaaaaaaaag gaaatcagga attacgtatt tctataaatg   7020
ccatatattt ttactagaaa cacagatgac aagtatatac aacatgtaaa tccgaagtta   7080
tcaacatgtt aactaggaaa acatttacaa gcatttgggt atgcaactag atcatcaggt   7140
aaaaaatccc attagaaaaa tctaagcctc accagtttca aaggaaaaaa accagagaac   7200
gctcactact tcaaagggaa aaaataaagc atcaagctgg cctaaactta ataaggtatc   7260
tcgtgtaaca acagctatcc aagctttcaa gccacactat aaataaaaac ctcaagttcc   7320
gatcaacgtt ttccataatg caatcagaac caaaggcatt ggcacagaaa gcaaaaaggg   7380
aatgaaagaa aagggctgta cagtttccaa aaggttcttc ttttgaagaa atgtttctga   7440
cctgtcaaaa catacagtcc agtagaaaat ttactaagaa aaaagaacac cttacttaaa   7500
aaaaaaaaaa aaaaaaaaaa aaacaggcaa aaaaacctct cctgtcactg agctgccacc   7560
accccaacca ccacctgctg tgggctttgt ctcccaagac aaaggacaca cagccttatc   7620
caatattcaa cattacttat aaaaacactg atcagaagaa ataccaagta tttcctcaca   7680
gactgttata cagactgtta tatcctttca tcggcaagaa gagatgaaat acaacagagt   7740
gaatatcaaa gaaggcggca ggagccaccg tggcaccatc accgggcagt gcagtgccca   7800
gctgccgttt cctgagcacg cacaggaagc cgtcagtcac atgtaataaa ccaaaacctg   7860
gtacagttat attatggatc cgggcccctc cgggatcata tgacaagatg tgtatccacc   7920
ttaacttaat gatttttacc aaaatcatta ggggattcat cagtgctcag ggtcaacgag   7980
aattaacatt ccgtcaggaa agcttgaatt cagcttttgt tccctttagt gagggttaat   8040
tgcgcgcttg gcgtaatcat ggtcatagct gtttcctgtg tgaaattgtt atccgctcac   8100
aattccacac aacatacgag ccggaagcat aaagtgtaaa gcctggggtg cctaatgagt   8160
gagctaactc acattaattg cgttgcgctc actgcccgct ttccagtcgg gaaacctgtc   8220
gtgccagctg cattaatgaa tcggccaacg cgcggggaga ggcggtttgc gtattgggcg   8280
ctcttccgct tcctcgctca ctgactcgct gcgctcggtc gttcggctgc ggcgagcggt   8340
atcagctcac tcaaaggcgg taatacggtt atccacagaa tcaggggata acgcaggaaa   8400
gaacatgtga gcaaaaggcc agcaaaaggc caggaaccgt aaaaaggccg cgttgctggc   8460
gtttttccat aggctccgcc cccctgacga gcatcacaaa aatcgacgct caagtcagag   8520
gtggcgaaac ccgacaggac tataaagata ccaggcgttt ccccctggaa gctccctcgt   8580
```

```
gcgctctcct gttccgaccc tgccgcttac cggatacctg tccgcctttc tcccttcggg   8640
aagcgtggcg ctttctcata gctcacgctg taggtatctc agttcggtgt aggtcgttcg   8700
ctccaagctg ggctgtgtgc acgaaccccc cgttcagccc gaccgctgcg ccttatccgg   8760
taactatcgt cttgagtcca acccggtaag acacgactta tcgccactgg cagcagccac   8820
tggtaacagg attagcagag cgaggtatgt aggcggtgct acagagttct tgaagtggtg   8880
gcctaactac ggctacacta gaagaacagt atttggtatc tgcgctctgc tgaagccagt   8940
taccttcgga aaaagagttg gtagctcttg atccggcaaa caaaccaccg ctggtagcgg   9000
tggttttttt gtttgcaagc agcagattac gcgcagaaaa aaaggatctc aagaagatcc   9060
tttgatcttt tctacggggt ctgacgctca gtggaacgaa aactcacgtt aagggatttt   9120
ggtcatgaga ttatcaaaaa ggatcttcac ctagatcctt ttaaattaaa aatgaagttt   9180
taaatcaatc taaagtatat atgagtaaac ttggtctgac agttaccaat gcttaatcag   9240
tgaggcacct atctcagcga tctgtctatt tcgttcatcc atagttgcct gactccccgt   9300
cgtgtagata actacgatac gggagggctt accatctggc cccagtgctg caatgatacc   9360
gcgagaccca cgctcaccgg ctccagattt atcagcaata aaccagccag ccggaagggc   9420
cgagcgcaga agtggtcctg caactttatc cgcctccatc cagtctatta attgttgccg   9480
ggaagctaga gtaagtagtt cgccagttaa tagtttgcgc aacgttgttg ccattgctac   9540
aggcatcgtg gtgtcacgct cgtcgtttgg tatggcttca ttcagctccg gttcccaacg   9600
atcaaggcga gttacatgat cccccatgtt gtgcaaaaaa gcggttagct ccttcggtcc   9660
tccgatcgtt gtcagaagta agttggccgc agtgttatca ctcatggtta tggcagcact   9720
gcataattct cttactgtca tgccatccgt aagatgcttt tctgtgactg gtgagtactc   9780
aaccaagtca ttctgagaat agtgtatgcg gcgaccgagt tgctcttgcc cggcgtcaat   9840
acgggataat accgcgccac atagcagaac tttaaaagtg ctcatcattg gaaaacgttc   9900
ttcggggcga aaactctcaa ggatcttacc gctgttgaga tccagttcga tgtaacccac   9960
tcgtgcaccc aactgatctt cagcatcttt tactttcacc agcgtttctg ggtgagcaaa  10020
aacaggaagg caaaatgccg caaaaaaggg aataagggcg acacggaaat gttgaatact  10080
catactcttc ctttttcaat attattgaag catttatcag ggttattgtc tcatgagcgg  10140
atacatattt gaatgtattt agaaaaataa acaaataggg gttccgcgca catttccccg  10200
aaaagtgcca c                                                       10211
```

<210> SEQ ID NO 12
<211> LENGTH: 9204
<212> TYPE: DNA
<213> ORGANISM: Artificial Sequence
<220> FEATURE:
<223> OTHER INFORMATION: Synthetic construct

<400> SEQUENCE: 12

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccactgagg cggaaagaac cagctgtgga    180
atgtgtgtca gttagggtgt ggaaagtccc caggctcccc agcaggcaga agtatgcaaa    240
gcatgcatct caattagtca gcaaccaggt gtggaaagtc cccaggctcc ccagcaggca    300
gaagtatgca aagcatgcat ctcaattagt cagcaaccat agtcccgccc ctaactccgc    360
```

```
ccatcccgcc cctaactccg cccagttccg cccattctcc gccccatggc tgactaattt    420
tttttattta tgcagaggcc gaggccgcct cggcctctga gctattccag aagtagtgag    480
gaggcttttt tggaggccta ggcttttgca aagatcgatc aagagacagg atgaggatcc    540
tcagatcgcc tggagacgcc atccacgctg ttttgacctc catagaagac accgggaccg    600
atccagcctc cgcggccggg aacggtgcat tggaacgcgg attccccgtg ccaagagtga    660
cgtaagtacc gcctatagac tctataggca caccccttg gctcttatgc atgctatact     720
gtttttggct tggggcctat acacccccgc ttccttatgc tataggtgat ggtatagctt    780
agcctatagg tgtgggttat tgaccattat tgaccactcc cctattggtg acgatacttt    840
ccattactaa tccataacat ggctctttgc cacaactatc tctattggct atatgccaat    900
actctgtcct tcagagactg acacggactc tgtattttta caggatgggg tcccatttat    960
tatttacaaa ttcacatata caacaacgcc gtcccccgtg cccgcagttt ttattaaaca   1020
tagcgtggga tctccacgcg aatctcgggt acgtgttccg gacatgggct cttctccggt   1080
agcggcggag cttccacatc cgagccctgg tcccatgcct ccagcggctc atggtcgctc   1140
ggcagctcct tgctcctaac agtggaggcc agacttaggc acagcacaat gcccaccacc   1200
accagtgtgc cgcacaaggc cgtggcggta gggtatgtgt ctgaaaatga gcgtggagat   1260
tgggctcgca cggctgacgc agatggaaga cttaaggcag cggcagaaga agatgcaggc   1320
agctgagttg ttgtattctg ataagagtca gaggtaactc ccgttgcggt gctgttaacg   1380
gtggagggca gtgtagtctg agcagtactc gttgctgccg cgcgcgccac cagacataat   1440
agctgacaga ctaacagact gttcctttcc atgggtcttt tctgcagtca ccgtctcgcg   1500
aaaaatcaat aatcagacaa caagatgtgc gaactcgata ttttacacga ctctctttac   1560
caattctgcc ccgaattaca cttaaaacga ctcaacagct taacgttggc ttgccacgca   1620
ttacttgact gtaaaactct cactcttacc gaacttggcc gtaacctgcc aaccaaagcg   1680
agaacaaaac ataacatcaa acgaatcgac cgattgttag gtaatcgtca cctccacaaa   1740
gagcgactcg ctgtataccg ttggcatgct agctttatct gttcgggcaa tacgatgccc   1800
attgtacttg ttgactggtc tgatattcgt gagcaaaaac gacttatggt attgcgagct   1860
tcagtcgcac tacacggtcg ttctgttact ctttatgaga aagcgttccc gctttcagag   1920
caatattcaa agaaagctca tgaccaattt ctagccgacc ttgcgagcat tctaccgagt   1980
aacaccacac cgctcattgt cagtgatgct ggctttaaag tgccatggta taaatccgtt   2040
gagaagctgg gttggtactg gttaagtcga gtaagaggaa aagtacaata tgcagaccta   2100
ggagcggaaa actggaaacc tatcagcaac ttacatgata tgtcatctag tcactcaaag   2160
actttaggct ataagaggct gactaaaagc aatccaatct catgccaaat tctattgtat   2220
aaatctcgct ctaaaggccg aaaaaatcag cgctcgacac ggactcatta tcaccacccg   2280
tcacctaaaa tctactcagc gtcggcaaag gagccatggg ttctagcaac taacttacct   2340
gttgaaattc gaacacccaa acaacttgtt aatatctatt cgaagcgaat gcagattgaa   2400
gaaaccttcc gagacttgaa aagtcctgcc tacggactag gcctacgcca tagccgaacg   2460
agcagctcag agcgttttga tatcatgctg ctaatcgccc tgatgcttca actaacatgt   2520
tggcttgcgg gcgttcatgc tcagaaacaa ggttgggaca agcacttcca ggctaacaca   2580
gtcagaaatc gaaacgtact ctcaacagtt cgcttaggca tggaagtttt gcggcattct   2640
ggctacacaa taacaaggga agacttactc gtggctgcaa ccctactagc tcaaaattta   2700
ttcacacatg gttacgcttt ggggaaatta tgaggggatc gctctagagc gatccgggat   2760
```

```
ctcgggaaaa gcgttggtga ccaaaggtgc cttttatcat cactttaaaa ataaaaaaca   2820
attactcagt gcctgttata agcagcaatt aattatgatt gatgcctaca tcacaacaaa   2880
aactgattta acaaatggtt ggtctgcctt agaaagtata tttgaacatt atcttgatta   2940
tattattgat aataataaaa accttatccc tatccaagaa gtgatgccta tcattggttg   3000
gaatgaactt gaaaaaatta gccttgaata cattactggt aaggtaaacg ccattgtcag   3060
caaattgatc caagagaacc aacttaaagc tttcctgacg gaatgttaat tctcgttgac   3120
cctgagcact gatgaatccc ctaatgattt tggtaaaaat cattaagtta aggtggatac   3180
acatcttgtc atatgatccc ggtaatgtga gttagctcac tcattaggca ccccaggctt   3240
tacactttat gcttccggct cgtatgttgt gtggaattgt gagcggataa caatttcaca   3300
caggaaacag ctatgaccat gattacgcca agcgcgcaat taaccctcac taaagggaac   3360
aaaagctgga gctccaccgc ggtggcggcc gcggatccat aatataactg taccaggttt   3420
tggtttatta catgtgactg acggcttcct gtgcgtgctc aggaaacggc agctgggcac   3480
tgcactgccc ggtgatggtg ccacggtggc tcctgccgcc ttctttgata ttcactctgt   3540
tgtatttcat ctcttcttgc cgatgaaagg atataacagt ctgtataaca gtctgtgagg   3600
aaatacttgg tatttcttct gatcagtgtt tttataagta atgttgaata ttggataagg   3660
ctgtgtgtcc tttgtcttgg gagacaaagc ccacagcagg tggtggttgg ggtggtggca   3720
gctcagtgac aggagaggtt tttttgcctg tttttttttt tttttttttt ttttttaagt   3780
aaggtgttct tttttcttag taaattttct actggactgt atgttttgac aggtcagaaa   3840
catttcttca aaagaagaac cttttggaaa ctgtacagcc cttttctttc attccctttt   3900
tgctttctgt gccaatgcct ttggttctga ttgcattatg gaaaacgttg atcggaactt   3960
gaggttttta tttatagtgt ggcttgaaag cttggatagc tgttgttaca cgagatacct   4020
tattaagttt aggccagctt gatgctttat tttttccctt tgaagtagtg agcgttctct   4080
ggtttttttc ctttgaaact ggtgaggctt agatttttct aatgggattt tttacctgat   4140
gatctagttg catacccaaa tgcttgtaaa tgttttccta gttaacatgt tgataacttc   4200
ggatttacat gttgtatata cttgtcatct gtgtttctag taaaaatata tggcatttat   4260
agaaatacgt aattcctgat ttcctttttt ttttatctct atgctctgtg tgtacaggtc   4320
aaacagactt cactcctatt tttatttata gaattttata tgcagtctgt cgttggttct   4380
tgtgttgtaa ggatacagcc ttaaatttcc tagagcgatg ctcagtaagg cgggttgtca   4440
catgggttta aatgtaaaac gggcacgttt ggctgctgcc ttcccgagat ccaggacact   4500
aaactgcttc tgcactgagg tataaatcgc ttcagatccc agggaagtgc agatccacgt   4560
gcatattctt aaagaagaat gaatactttc taaaatattt tggcatagga agcaagctgc   4620
atggatttgt ttgggactta aattattttg gtaacggagt gcataggttt taaacacagt   4680
tgcagcatgc taacgagtca cagcgtttat gcagaagtga tgcctggatg cctgttgcag   4740
ctgtttacgg cactgccttg cagtgagcat tgcagatagg ggtggggtgc tttgtgtcgt   4800
gttcccacac gctgccacac agccacctcc cggaacacat ctcacctgct gggtactttt   4860
caaaccatct tagcagtagt agatgagtta ctatgaaaca gagaagttcc tcagttggat   4920
attctcatgg gatgtctttt ttcccatgtt gggcaaagta tgataaagca tctctatttg   4980
taaattatgc acttgttagt tcctgaatcc tttctatagc accacttatt gcagcaggtg   5040
taggctctgg tgtggcctgt gtctgtgctt caatctttta agcttctcga gggcgcgcct   5100
```

```
cagcgatcgc agatctttaa ttaaggcgcc tgcaggattt aaatcacgtg atcacgtcgt   5160
acgcaattgg tttaaacgcg taagcttaaa agattgaagc acagacacag gccacaccag   5220
agcctacacc tgctgcaata agtggtgcta tagaaaggat tcaggaacta acaagtgcat   5280
aatttacaaa tagagatgct ttatcatact ttgcccaaca tgggaaaaaa gacatcccat   5340
gagaatatcc aactgaggaa cttctctgtt tcatagtaac tcatctacta ctgctaagat   5400
ggtttgaaaa gtacccagca ggtgagatgt gttccgggag gtggctgtgt ggcagcgtgt   5460
gggaacacga cacaaagcac cccaccccta tctgcaatgc tcactgcaag gcagtgccgt   5520
aaacagctgc aacaggcatc caggcatcac ttctgcataa acgctgtgac tcgttagcat   5580
gctgcaactg tgtttaaaac ctatgcactc cgttaccaaa ataatttaag tcccaaacaa   5640
atccatgcag cttgcttcct atgccaaaat attttagaaa gtattcattc ttctttaaga   5700
atatgcacgt ggatctgcac ttccctggga tctgaagcga tttatacctc agtgcagaag   5760
cagtttagtg tcctggatct cgggaaggca gcagccaaac gtgcccgttt tacatttaaa   5820
cccatgtgac aacccgcctt actgagcatc gctctaggaa atttaaggct gtatccttac   5880
aacacaagaa ccaacgacag actgcatata aaattctata aataaaaata ggagtgaagt   5940
ctgtttgacc tgtacacaca gagcatagag ataaaaaaaa aaggaaatca ggaattacgt   6000
atttctataa atgccatata tttttactag aaacacagat gacaagtata tacaacatgt   6060
aaatccgaag ttatcaacat gttaactagg aaaacattta caagcatttg ggtatgcaac   6120
tagatcatca ggtaaaaaat cccattagaa aaatctaagc ctcaccagtt tcaaaggaaa   6180
aaaaccagag aacgctcact acttcaaagg gaaaaaataa agcatcaagc tggcctaaac   6240
ttaataaggt atctcgtgta acaacagcta tccaagcttt caagccacac tataaataaa   6300
aacctcaagt tccgatcaac gttttccata atgcaatcag aaccaaaggc attggcacag   6360
aaagcaaaaa gggaatgaaa gaaaagggct gtacagtttc caaaaggttc ttcttttgaa   6420
gaaatgtttc tgacctgtca aaacatacag tccagtagaa aatttactaa gaaaaaagaa   6480
caccttactt aaaaaaaaaa aaaaaaaaaa aaaaaacagg caaaaaaacc tctcctgtca   6540
ctgagctgcc accaccccaa ccaccacctg ctgtgggctt tgtctcccaa gacaaaggac   6600
acacagcctt atccaatatt caacattact tataaaaaca ctgatcagaa gaaataccaa   6660
gtatttcctc acagactgtt atacagactg ttatatcctt tcatcggcaa gaagagatga   6720
aatacaacag agtgaatatc aaagaaggcg gcaggagcca ccgtggcacc atcaccgggc   6780
agtgcagtgc ccagctgccg tttcctgagc acgcacagga agccgtcagt cacatgtaat   6840
aaaccaaaac ctggtacagt tatattatgg atccgggccc ctccgggatc atatgacaag   6900
atgtgtatcc accttaactt aatgattttt accaaaatca ttaggggatt catcagtgct   6960
cagggtcaac gagaattaac attccgtcag gaaagcttga attcagcttt tgttcccttt   7020
agtgagggtt aattgcgcgc ttggcgtaat catggtcata gctgtttcct gtgtgaaatt   7080
gttatccgct cacaattcca cacaacatac gagccggaag cataaagtgt aaagcctggg   7140
gtgcctaatg agtgagctaa ctcacattaa ttgcgttgcg ctcactgccc gctttccagt   7200
cgggaaacct gtcgtgccag ctgcattaat gaatcggcca acgcgcgggg agaggcggtt   7260
tgcgtattgg gcgctcttcc gcttcctcgc tcactgactc gctgcgctcg gtcgttcggc   7320
tgcggcgagc ggtatcagct cactcaaagg cggtaatacg gttatccaca gaatcagggg   7380
ataacgcagg aaagaacatg tgagcaaaag gccagcaaaa ggccaggaac cgtaaaaagg   7440
ccgcgttgct ggcgtttttc cataggctcc gcccccctga cgagcatcac aaaaatcgac   7500
```

```
gctcaagtca gaggtggcga aacccgacag gactataaag ataccaggcg tttccccctg   7560

gaagctccct cgtgcgctct cctgttccga ccctgccgct taccggatac ctgtccgcct   7620

ttctcccttc gggaagcgtg gcgctttctc atagctcacg ctgtaggtat ctcagttcgg   7680

tgtaggtcgt tcgctccaag ctgggctgtg tgcacgaacc ccccgttcag cccgaccgct   7740

gcgccttatc cggtaactat cgtcttgagt ccaacccggt aagacacgac ttatcgccac   7800

tggcagcagc cactggtaac aggattagca gagcgaggta tgtaggcggt gctacagagt   7860

tcttgaagtg gtggcctaac tacggctaca ctagaagaac agtatttggt atctgcgctc   7920

tgctgaagcc agttaccttc ggaaaaagag ttggtagctc ttgatccggc aaacaaacca   7980

ccgctggtag cggtggtttt tttgtttgca agcagcagat tacgcgcaga aaaaaaggat   8040

ctcaagaaga tcctttgatc ttttctacgg ggtctgacgc tcagtggaac gaaaactcac   8100

gttaagggat tttggtcatg agattatcaa aaaggatctt cacctagatc cttttaaatt   8160

aaaaatgaag ttttaaatca atctaaagta tatatgagta aacttggtct gacagttacc   8220

aatgcttaat cagtgaggca cctatctcag cgatctgtct atttcgttca tccatagttg   8280

cctgactccc cgtcgtgtag ataactacga tacgggaggg cttaccatct ggccccagtg   8340

ctgcaatgat accgcgagac ccacgctcac cggctccaga tttatcagca ataaaccagc   8400

cagccggaag ggccgagcgc agaagtggtc ctgcaacttt atccgcctcc atccagtcta   8460

ttaattgttg ccgggaagct agagtaagta gttcgccagt taatagtttg cgcaacgttg   8520

ttgccattgc tacaggcatc gtggtgtcac gctcgtcgtt tggtatggct tcattcagct   8580

ccggttccca acgatcaagg cgagttacat gatcccccat gttgtgcaaa aaagcggtta   8640

gctccttcgg tcctccgatc gttgtcagaa gtaagttggc cgcagtgtta tcactcatgg   8700

ttatggcagc actgcataat tctcttactg tcatgccatc cgtaagatgc ttttctgtga   8760

ctggtgagta ctcaaccaag tcattctgag aatagtgtat gcggcgaccg agttgctctt   8820

gcccggcgtc aatacgggat aataccgcgc cacatagcag aactttaaaa gtgctcatca   8880

ttggaaaacg ttcttcgggg cgaaaactct caaggatctt accgctgttg agatccagtt   8940

cgatgtaacc cactcgtgca cccaactgat cttcagcatc ttttactttc accagcgttt   9000

ctgggtgagc aaaaacagga aggcaaaatg ccgcaaaaaa gggaataagg gcgacacgga   9060

aatgttgaat actcatactc ttcctttttc aatattattg aagcatttat cagggttatt   9120

gtctcatgag cggatacata tttgaatgta tttagaaaaa taaacaaata ggggttccgc   9180

gcacatttcc ccgaaaagtg ccac                                          9204
```

<210> SEQ ID NO 13
<211> LENGTH: 10522
<212> TYPE: DNA
<213> ORGANISM: Artificial Sequence
<220> FEATURE:
<223> OTHER INFORMATION: Synthetic construct

<400> SEQUENCE: 13

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccactgagg cggaaagaac cagctgtgga    180

atgtgtgtca gttagggtgt ggaaagtccc caggctcccc agcaggcaga agtatgcaaa    240

gcatgcatct caattagtca gcaaccaggt gtggaaagtc cccaggctcc ccagcaggca    300
```

```
gaagtatgca aagcatgcat ctcaattagt cagcaaccat agtcccgccc ctaactccgc    360
ccatcccgcc cctaactccg cccagttccg cccattctcc gccccatggc tgactaattt    420
tttttattta tgcagaggcc gaggccgcct cggcctctga gctattccag aagtagtgag    480
gaggcttttt tggaggccta ggcttttgca aagatcgatc aagagacagg atgaggatcc    540
tcagatcgcc tggagacgcc atccacgctg ttttgacctc catagaagac accgggaccg    600
atccagcctc cgcggccggg aacggtgcat tggaacgcgg attccccgtg ccaagagtga    660
cgtaagtacc gcctatagac tctataggca cacccctttg gctcttatgc atgctatact    720
gtttttggct tggggcctat acacccccgc ttccttatgc tataggtgat ggtatagctt    780
agcctatagg tgtgggttat tgaccattat tgaccactcc cctattggtg acgatacttt    840
ccattactaa tccataacat ggctctttgc cacaactatc tctattggct atatgccaat    900
actctgtcct tcagagactg acacggactc tgtattttta caggatgggg tcccatttat    960
tatttacaaa ttcacatata caacaacgcc gtcccccgtg cccgcagttt ttattaaaca   1020
tagcgtggga tctccacgcg aatctcgggt acgtgttccg gacatgggct cttctccggt   1080
agcggcggag cttccacatc cgagccctgg tcccatgcct ccagcggctc atggtcgctc   1140
ggcagctcct tgctcctaac agtggaggcc agacttaggc acagcacaat gcccaccacc   1200
accagtgtgc cgcacaaggc cgtggcggta gggtatgtgt ctgaaaatga gcgtggagat   1260
tgggctcgca cggctgacgc agatggaaga cttaaggcag cggcagaaga agatgcaggc   1320
agctgagttg ttgtattctg ataagagtca gaggtaactc ccgttgcggt gctgttaacg   1380
gtggagggca gtgtagtctg agcagtactc gttgctgccg cgcgcgccac cagacataat   1440
agctgacaga ctaacagact gttcctttcc atgggtcttt tctgcagtca ccgtctcgcg   1500
aaaaatcaat aatcagacaa caagatgtgc gaactcgata ttttacacga ctctctttac   1560
caattctgcc ccgaattaca cttaaaacga ctcaacagct taacgttggc ttgccacgca   1620
ttacttgact gtaaaactct cactcttacc gaacttggcc gtaacctgcc aaccaaagcg   1680
agaacaaaac ataacatcaa acgaatcgac cgattgttag gtaatcgtca cctccacaaa   1740
gagcgactcg ctgtataccg ttggcatgct agctttatct gttcgggcaa tacgatgccc   1800
attgtacttg ttgactggtc tgatattcgt gagcaaaaac gacttatggt attgcgagct   1860
tcagtcgcac tacacggtcg ttctgttact ctttatgaga aagcgttccc gctttcagag   1920
caatattcaa agaaagctca tgaccaattt ctagccgacc ttgcgagcat tctaccgagt   1980
aacaccacac cgctcattgt cagtgatgct ggctttaaag tgccatggta taaatccgtt   2040
gagaagctgg gttggtactg gttaagtcga gtaagaggaa aagtacaata tgcagaccta   2100
ggagcggaaa actggaaacc tatcagcaac ttacatgata tgtcatctag tcactcaaag   2160
actttaggct ataagaggct gactaaaagc aatccaatct catgccaaat tctattgtat   2220
aaatctcgct ctaaaggccg aaaaaatcag cgctcgacac ggactcatta tcaccacccg   2280
tcacctaaaa tctactcagc gtcggcaaag gagccatggg ttctagcaac taacttacct   2340
gttgaaattc gaacacccaa acaacttgtt aatatctatt cgaagcgaat gcagattgaa   2400
gaaaccttcc gagacttgaa aagtcctgcc tacggactag gcctacgcca tagccgaacg   2460
agcagctcag agcgttttga tatcatgctg ctaatcgccc tgatgcttca actaacatgt   2520
tggcttgcgg gcgttcatgc tcagaaacaa ggttgggaca agcacttcca ggctaacaca   2580
gtcagaaatc gaaacgtact ctcaacagtt cgcttaggca tggaagtttt gcggcattct   2640
ggctacacaa taacaaggga agacttactc gtggctgcaa ccctactagc tcaaaattta   2700
```

```
ttcacacatg gttacgcttt ggggaaatta tgaggggatc gctctagagc gatccgggat   2760
ctcgggaaaa gcgttggtga ccaaaggtgc cttttatcat cactttaaaa ataaaaaaca   2820
attactcagt gcctgttata agcagcaatt aattatgatt gatgcctaca tcacaacaaa   2880
aactgattta acaaatggtt ggtctgcctt agaaagtata tttgaacatt atcttgatta   2940
tattattgat aataataaaa accttatccc tatccaagaa gtgatgccta tcattggttg   3000
gaatgaactt gaaaaaatta gccttgaata cattactggt aaggtaaacg ccattgtcag   3060
caaattgatc caagagaacc aacttaaagc tttcctgacg gaatgttaat tctcgttgac   3120
cctgagcact gatgaatccc ctaatgattt tggtaaaaat cattaagtta aggtggatac   3180
acatcttgtc atatgatccc ggtaatgtga gttagctcac tcattaggca ccccaggctt   3240
tacactttat gcttccggct cgtatgttgt gtggaattgt gagcggataa caatttcaca   3300
caggaaacag ctatgaccat gattacgcca agcgcgcaat taaccctcac taaagggaac   3360
aaaagctgga gctccaccgc ggtggcggcc gcggatccat aatataactg taccaggttt   3420
tggtttatta catgtgactg acggcttcct gtgcgtgctc aggaaacggc agctgggcac   3480
tgcactgccc ggtgatggtg ccacggtggc tcctgccgcc ttctttgata ttcactctgt   3540
tgtatttcat ctcttcttgc cgatgaaagg atataacagt ctgtataaca gtctgtgagg   3600
aaatacttgg tatttcttct gatcagtgtt tttataagta atgttgaata ttggataagg   3660
ctgtgtgtcc tttgtcttgg gagacaaagc ccacagcagg tggtggttgg ggtggtggca   3720
gctcagtgac aggagaggtt tttttgcctg tttttttttt tttttttttt ttttttaagt   3780
aaggtgttct tttttcttag taaattttct actggactgt atgttttgac aggtcagaaa   3840
catttcttca aaagaagaac cttttggaaa ctgtacagcc cttttctttc attccctttt   3900
tgctttctgt gccaatgcct ttggttctga ttgcattatg gaaaacgttg atcggaactt   3960
gaggttttta tttatagtgt ggcttgaaag cttggatagc tgttgttaca cgagatacct   4020
tattaagttt aggccagctt gatgctttat tttttccctt tgaagtagtg agcgttctct   4080
ggtttttttc ctttgaaact ggtgaggctt agatttttct aatgggattt tttacctgat   4140
gatctagttg catacccaaa tgcttgtaaa tgttttccta gttaacatgt tgataacttc   4200
ggatttacat gttgtatata cttgtcatct gtgtttctag taaaaatata tggcatttat   4260
agaaatacgt aattcctgat ttcctttttt ttttatctct atgctctgtg tgtacaggtc   4320
aaacagactt cactcctatt tttatttata gaattttata tgcagtctgt cgttggttct   4380
tgtgttgtaa ggatacagcc ttaaatttcc tagagcgatg ctcagtaagg cgggttgtca   4440
catgggttta aatgtaaaac gggcacgttt ggctgctgcc ttcccgagat ccaggacact   4500
aaactgcttc tgcactgagg tataaatcgc ttcagatccc agggaagtgc agatccacgt   4560
gcatattctt aaagaagaat gaatactttc taaaatattt tggcatagga agcaagctgc   4620
atggatttgt ttgggactta aattattttg gtaacggagt gcataggttt taaacacagt   4680
tgcagcatgc taacgagtca cagcgtttat gcagaagtga tgcctggatg cctgttgcag   4740
ctgtttacgg cactgccttg cagtgagcat tgcagatagg ggtggggtgc tttgtgtcgt   4800
gttcccacac gctgccacac agccacctcc cggaacacat ctcacctgct gggtactttt   4860
caaaccatct tagcagtagt agatgagtta ctatgaaaca gagaagttcc tcagttggat   4920
attctcatgg gatgtctttt ttcccatgtt gggcaaagta tgataaagca tctctatttg   4980
taaattatgc acttgttagt tcctgaatcc tttctatagc accacttatt gcagcaggtg   5040
```

```
taggctctgg tgtggcctgt gtctgtgctt caatctttta agcttctcga gggcgcgcct   5100
cagcgatcgc agatctttaa ttaaggcgcc tgcaggattt aaatcacgtg atcacgtcgt   5160
acggtaacct gaggctatgg cagggcctgc cgccccgacg ttggctgcga gccctgggcc   5220
ttcacccgaa cttggggggt ggggtgggga aaaggaagaa acgcgggcgt attggcccca   5280
atggggtctc ggtggggtat cgacagagtg ccagccctgg gaccgaaccc cgcgtttatg   5340
aacaaacgac ccaacaccgt gcgttttatt ctgtcttttt attgccgtca tagcgcgggt   5400
tccttccggt attgtctcct tccgtgtttc agttagcctc cccctagggt gggcgaagaa   5460
ctccagcatg agatccgagc tcaggatccg ctagcgaatt caggtttaag cacctggttt   5520
gcgagtcatg caccaagtgc gtgggccttc tggcacttcc acatcagcag tcacagtgaa   5580
gcccaggcgt tcatagaaag gcaggttgcg tggagctgag gtctccagga aagcaggcac   5640
acctgcacgt tcagctgctt ccacaccagg cagcaccact gcagagccca ggcccttacc   5700
ctggtggtca gggctcacac ccacagttgc caggaaccaa gcaggttctt ttgggcggtg   5760
tggtgccagc agaccttcca tctgctgttg tgctgccagg cggctgccag acagttctgc   5820
catgcgtggg ccaatctcag caaacactgc accagcttca acagattcag ggtggtccca   5880
cactgccaca gcagcaccat catctgccac ccacactttg ccaatgtcca ggcccacacg   5940
ggtcaggaac agctcctgca gttcagtcac acgttcaatg tggcggtctg ggtccacagt   6000
gtgacgggtt gcagggtagt cagcaaatgc agcagccagg gtgcgaactg cacgtggaac   6060
atcatcacga gttgccaggc gaacagttgg tttgtattca gtcatgacga tcctcatcct   6120
gtctcttgat cgatctttgc aaaagcctag gcctccaaaa aagcctcctc actacttctg   6180
gaatagctca gaggccgagg cggcctcggc ctctgcataa ataaaaaaaa ttagtcagcc   6240
atggggcgga gaatgggcgg aactgggcgg agttaggggc gggatgggcg gagttagggg   6300
cgggactatg gttgctgact aattgagatg catgctttgc atacttctgc ctgctgggga   6360
gcctggggac tttccacacc tggttgctga ctaattgaga tgcatgcttt gcatacttct   6420
gcctgctggg gagcctgggg actttccaca ccctaactga cacacattcc acagctggtt   6480
ctttccgcct cagacgcgta agcttaaaag attgaagcac agacacaggc cacaccagag   6540
cctacacctg ctgcaataag tggtgctata gaaaggattc aggaactaac aagtgcataa   6600
tttacaaata gagatgcttt atcatacttt gcccaacatg ggaaaaaaga catcccatga   6660
gaatatccaa ctgaggaact tctctgtttc atagtaactc atctactact gctaagatgg   6720
tttgaaaagt acccagcagg tgagatgtgt tccgggaggt ggctgtgtgg cagcgtgtgg   6780
gaacacgaca caaagcaccc caccccctatc tgcaatgctc actgcaaggc agtgccgtaa   6840
acagctgcaa caggcatcca ggcatcactt ctgcataaac gctgtgactc gttagcatgc   6900
tgcaactgtg tttaaaacct atgcactccg ttaccaaaat aatttaagtc ccaaacaaat   6960
ccatgcagct tgcttcctat gccaaaatat tttagaaagt attcattctt ctttaagaat   7020
atgcacgtgg atctgcactt ccctgggatc tgaagcgatt tatacctcag tgcagaagca   7080
gtttagtgtc ctggatctcg ggaaggcagc agccaaacgt gcccgtttta catttaaacc   7140
catgtgacaa cccgccttac tgagcatcgc tctaggaaat ttaaggctgt atccttacaa   7200
cacaagaacc aacgacagac tgcatataaa attctataaa taaaaatagg agtgaagtct   7260
gtttgacctg tacacacaga gcatagagat aaaaaaaaaa ggaaatcagg aattacgtat   7320
ttctataaat gccatatatt tttactagaa acacagatga caagtatata caacatgtaa   7380
atccgaagtt atcaacatgt taactaggaa aacatttaca agcatttggg tatgcaacta   7440
```

```
gatcatcagg taaaaaatcc cattagaaaa atctaagcct caccagtttc aaaggaaaaa   7500
aaccagagaa cgctcactac ttcaaaggga aaaaataaag catcaagctg gcctaaactt   7560
aataaggtat ctcgtgtaac aacagctatc caagctttca agccacacta taaataaaaa   7620
cctcaagttc cgatcaacgt tttccataat gcaatcagaa ccaaaggcat tggcacagaa   7680
agcaaaaagg gaatgaaaga aaagggctgt acagtttcca aaaggttctt cttttgaaga   7740
aatgtttctg acctgtcaaa acatacagtc cagtagaaaa tttactaaga aaaaagaaca   7800
ccttacttaa aaaaaaaaaa aaaaaaaaaa aaaacaggca aaaaaacctc tcctgtcact   7860
gagctgccac caccccaacc accacctgct gtgggctttg tctcccaaga caaaggacac   7920
acagccttat ccaatattca acattactta taaaaacact gatcagaaga aataccaagt   7980
atttcctcac agactgttat acagactgtt atatcctttc atcggcaaga agagatgaaa   8040
tacaacagag tgaatatcaa agaaggcggc aggagccacc gtggcaccat caccgggcag   8100
tgcagtgccc agctgccgtt tcctgagcac gcacaggaag ccgtcagtca catgtaataa   8160
accaaaacct ggtacagtta tattatggat ccgggcccct ccgggatcat atgacaagat   8220
gtgtatccac cttaacttaa tgatttttac caaaatcatt aggggattca tcagtgctca   8280
gggtcaacga gaattaacat tccgtcagga aagcttgaat tcagcttttg ttccctttag   8340
tgagggttaa ttgcgcgctt ggcgtaatca tggtcatagc tgtttcctgt gtgaaattgt   8400
tatccgctca caattccaca caacatacga gccggaagca taaagtgtaa agcctggggt   8460
gcctaatgag tgagctaact cacattaatt gcgttgcgct cactgcccgc tttccagtcg   8520
ggaaacctgt cgtgccagct gcattaatga atcggccaac gcgcggggag aggcggtttg   8580
cgtattgggc gctcttccgc ttcctcgctc actgactcgc tgcgctcggt cgttcggctg   8640
cggcgagcgg tatcagctca ctcaaaggcg gtaatacggt tatccacaga atcaggggat   8700
aacgcaggaa agaacatgtg agcaaaaggc cagcaaaagg ccaggaaccg taaaaaggcc   8760
gcgttgctgg cgtttttcca taggctccgc ccccctgacg agcatcacaa aaatcgacgc   8820
tcaagtcaga ggtggcgaaa cccgacagga ctataaagat accaggcgtt tccccctgga   8880
agctccctcg tgcgctctcc tgttccgacc ctgccgctta ccggatacct gtccgccttt   8940
ctcccttcgg gaagcgtggc gctttctcat agctcacgct gtaggtatct cagttcggtg   9000
taggtcgttc gctccaagct gggctgtgtg cacgaacccc ccgttcagcc cgaccgctgc   9060
gccttatccg gtaactatcg tcttgagtcc aacccggtaa gacacgactt atcgccactg   9120
gcagcagcca ctggtaacag gattagcaga gcgaggtatg taggcggtgc tacagagttc   9180
ttgaagtggt ggcctaacta cggctacact agaagaacag tatttggtat ctgcgctctg   9240
ctgaagccag ttaccttcgg aaaaagagtt ggtagctctt gatccggcaa acaaaccacc   9300
gctggtagcg gtggtttttt tgtttgcaag cagcagatta cgcgcagaaa aaaaggatct   9360
caagaagatc ctttgatctt ttctacgggg tctgacgctc agtggaacga aaactcacgt   9420
taagggattt tggtcatgag attatcaaaa aggatcttca cctagatcct tttaaattaa   9480
aaatgaagtt ttaaatcaat ctaaagtata tatgagtaaa cttggtctga cagttaccaa   9540
tgcttaatca gtgaggcacc tatctcagcg atctgtctat ttcgttcatc catagttgcc   9600
tgactccccg tcgtgtagat aactacgata cgggagggct taccatctgg ccccagtgct   9660
gcaatgatac cgcgagaccc acgctcaccg gctccagatt tatcagcaat aaaccagcca   9720
gccggaaggg ccgagcgcag aagtggtcct gcaactttat ccgcctccat ccagtctatt   9780
```

```
aattgttgcc gggaagctag agtaagtagt tcgccagtta atagtttgcg caacgttgtt   9840

gccattgcta caggcatcgt ggtgtcacgc tcgtcgtttg gtatggcttc attcagctcc   9900

ggttcccaac gatcaaggcg agttacatga tcccccatgt tgtgcaaaaa agcggttagc   9960

tccttcggtc ctccgatcgt tgtcagaagt aagttggccg cagtgttatc actcatggtt  10020

atggcagcac tgcataattc tcttactgtc atgccatccg taagatgctt ttctgtgact  10080

ggtgagtact caaccaagtc attctgagaa tagtgtatgc ggcgaccgag ttgctcttgc  10140

ccggcgtcaa tacgggataa taccgcgcca catagcagaa ctttaaaagt gctcatcatt  10200

ggaaaacgtt cttcggggcg aaaactctca aggatcttac cgctgttgag atccagttcg  10260

atgtaaccca ctcgtgcacc caactgatct tcagcatctt ttactttcac cagcgtttct  10320

gggtgagcaa aaacaggaag gcaaaatgcc gcaaaaaagg gaataagggc gacacggaaa  10380

tgttgaatac tcatactctt cctttttcaa tattattgaa gcatttatca gggttattgt  10440

ctcatgagcg gatacatatt tgaatgtatt tagaaaaata aacaaatagg ggttccgcgc  10500

acatttcccc gaaaagtgcc ac                                           10522
```

<210> SEQ ID NO 14
<211> LENGTH: 1514
<212> TYPE: DNA
<213> ORGANISM: Artificial Sequence
<220> FEATURE:
<223> OTHER INFORMATION: Synthetic construct

<400> SEQUENCE: 14

```
gtgctttaca gaggtcagaa tggtttcttt actgtttgtc aattctatta tttcaataca     60

gaacaatagc ttctataact gaaatatatt tgctattgta tattatgatt gtccctcgaa    120

ccatgaacac tcctccagct gaatttcaca attcctctgt catctgccag gccattaagt    180

tattcatgga agatctttga ggaacactgc aagttcatat cataaacaca tttgaaattg    240

agtattgttt tgcattgtat ggagctatgt tttgctgtat cctcagaaaa aaagtttgtt    300

ataaagcatt cacacccata aaaagataga tttaaatatt ccagctatag gaaagaaagt    360

gcgtctgctc ttcactctag tctcagttgg ctccttcaca tgcatgcttc tttatttctc    420

ctattttgtc aagaaaataa taggtcacgt cttgttctca cttatgtcct gcctagcatg    480

gctcagatgc acgttgtaga tacaagaagg atcaaatgaa acagacttct ggtctgttac    540

tacaaccata gtaataagca cactaactaa taattgctaa ttatgttttc catctctaag    600

gttcccacat ttttctgttt tcttaaagat cccattatct ggttgtaact gaagctcaat    660

ggaacatgag caatatttcc cagtcttctc tcccatccaa cagtcctgat ggattagcag    720

aacaggcaga aaacacattg ttacccagaa ttaaaaacta atatttgctc tccattcaat    780

ccaaaatgga cctattgaaa ctaaaatcta acccaatccc attaaatgat ttctatggcg    840

tggccattgc atacgttgta tccatatcat aatatgtaca tttatattgg ctcatgtcca    900

acattaccgc catgttgaca ttgattattg actagttatt aatagtaatc aattacgggg    960

tcattagttc atagcccata tatggagttc cgcgttacat aacttacggt aaatggcccg   1020

cctggctgac cgcccaacga cccccgccca ttgacgtcaa taatgacgta tgttcccata   1080

gtaacgccaa tagggacttt ccattgacgt caatgggtgg agtatttacg gtaaactgcc   1140

cacttggcag tacatcaagt gtatcatatg ccaagtacgc cccctattga cgtcaatgac   1200

ggtaaatggc ccgcctggca ttatgcccag tacatgacct tatgggactt tcctacttgg   1260

cagtacatct acgtattagt catcgctatt accatggtga tgcggttttg gcagtacatc   1320
```

```
aatgggcgtg gatagcggtt tgactcacgg ggatttccaa gtctccaccc cattgacgtc   1380

aatgggagtt tgttttggca ccaaaatcaa cgggactttc caaaatgtcg taacaactcc   1440

gccccattga cgcaaatggg cggtaggcgt gtacggtggg aggtctatat aagcagagct   1500

cgtttagtga accg                                                      1514
```

<210> SEQ ID NO 15
<211> LENGTH: 1124
<212> TYPE: DNA
<213> ORGANISM: Artificial Sequence
<220> FEATURE:
<223> OTHER INFORMATION: Synthetic construct

<400> SEQUENCE: 15

```
tggtttcttt actgtttgtc aattctatta tttcaataca gaacaatagc ttctataact     60

gaaatatatt tgctattgta tattatgatt gtccctcgaa ccatgaacac tcctccagct    120

gaatttcaca attcctctgt catctgccag gccattaagt tattcatgga agatctttga    180

tggccattgc atacgttgta tccatatcat aatatgtaca tttatattgg ctcatgtcca    240

acattaccgc catgttgaca ttgattattg actagttatt aatagtaatc aattacgggg    300

tcattagttc atagcccata tatggagttc cgcgttacat aacttacggt aaatggcccg    360

cctggctgac cgcccaacga cccccgccca ttgacgtcaa taatgacgta tgttcccata    420

gtaacgccaa tagggacttt ccattgacgt caatgggtgg agtatttacg gtaaactgcc    480

cacttggcag tacatcaagt gtatcatatg ccaagtacgc cccctattga cgtcaatgac    540

ggtaaatggc ccgcctggca ttatgcccag tacatgacct tatgggactt tcctacttgg    600

cagtacatct acgtattagt catcgctatt accatggtga tgcggttttg gcagtacatc    660

aatgggcgtg gatagcggtt tgactcacgg ggatttccaa gtctccaccc cattgacgtc    720

aatgggagtt tgttttggca ccaaaatcaa cgggactttc caaaatgtcg taacaactcg    780

taataagcac actaactaat aattgctaat tatgttttcc atctctaagg ttcccacatt    840

tttctgtttt cttaaagatc ccattatctg gttgtaactg aagctcaatg gaacatgagc    900

aatatttccc agtcttctct cccatccaac agtcctgatg gattagcaga acaggcagaa    960

aacacattgt tacccagaat taaaaactaa tatttgctct ccattcaatc caaaatggac   1020

ctattgaaac taaaatctaa cccaatcccc gccccattga cgcaaatggg cggtaggcgt   1080

gtacggtggg aggtctatat aagcagagct cgtttagtga accg                    1124
```

<210> SEQ ID NO 16
<211> LENGTH: 108
<212> TYPE: DNA
<213> ORGANISM: Artificial Sequence
<220> FEATURE:
<223> OTHER INFORMATION: Synthetic construct

<400> SEQUENCE: 16

```
tatctcgagg gcgcgcctca gcgatcgcag atctttaatt aaggcgcctg caggatttaa     60

atcacgtgat cacgtcgtac gcaattggtt taaacgcgtg ggccctttt               108
```

<210> SEQ ID NO 17
<211> LENGTH: 15926
<212> TYPE: DNA
<213> ORGANISM: Artificial Sequence
<220> FEATURE:
<223> OTHER INFORMATION: Synthetic construct

<400> SEQUENCE: 17

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgacagcgaa aaatcaataa   1800
tcagacaaca agatgtgcga actcgatatt ttacacgact ctctttacca attctgcccc   1860
gaattacact taaaacgact caacagctta acgttggctt gccacgcatt acttgactgt   1920
aaaactctca ctcttaccga acttggccgt aacctgccaa ccaaagcgag aacaaaacat   1980
aacatcaaac gaatcgagcg attgttaggt aatcgtcacc tccacaaaga gcgactcgct   2040
gtataccgtt ggcatgctag ctttatctgt tcgggcaata cgatgcccat tgtacttgtt   2100
gactggtctg atattcgtga gcaaaaacga cttatggtat tgcgagcttc agtcgcacta   2160
cacggtcgtt ctgttactct ttatgagaaa gcgttcccgc tttcagagca atattcaaag   2220
aaagctcatg accaatttct agccgacctt gcgagcattc taccgagtaa caccacaccg   2280
ctcattgtca gtgatgctgg ctttaaagtg ccatggtata aatccgttga gaagctgggt   2340
```

```
tggtactggt taagtcgagt aagaggaaaa gtacaatatg cagacctagg agcggaaaac   2400
tggaaaccta tcagcaactt acatgatatg tcatctagtc actcaaagac tttaggctat   2460
aagaggctga ctaaaagcaa tccaatctca tgccaaattc tattgtataa atctcgctct   2520
aaaggccgaa aaaatcagcg ctcgacacgg actcattatc accacccgtc acctaaaatc   2580
tactcagcgt cggcaaagga gccatgggtt ctagcaacta acttacctgt tgaaattcga   2640
acacccaaac aacttgttaa tatctattcg aagcgaatgc agattgaaga aaccttccga   2700
gacttgaaaa gtcctgccta cggactaggc ctacgccata gccgaacgag cagctcagag   2760
cgttttgata tcatgctgct aatcgccctg atgcttcaac taacatgttg gcttgcgggc   2820
gttcatgctc agaaacaagg ttgggacaag cacttccagg ctaacacagt cagaaatcga   2880
aacgtactct caacagttcg cttaggcatg gaagttttgc ggcattctgg ctacacaata   2940
acaagggaag acttactcgt ggctgcaacc ctactagctc aaaatttatt cacacatggt   3000
tacgctttgg ggaaattatg aggggatcgc tctagagcga tccgggatct cgggaaaagc   3060
gttggtgacc aaaggtgcct tttatcatca ctttaaaaat aaaaaacaat tactcagtgc   3120
ctgttataag cagcaattaa ttatgattga tgcctacatc acaacaaaaa ctgatttaac   3180
aaatggttgg tctgccttag aaagtatatt tgaacattat cttgattata ttattgataa   3240
taataaaaac cttatcccta tccaagaagt gatgcctatc attggttgga atgaacttga   3300
aaaaattagc cttgaataca ttactggtaa ggtaaacgcc attgtcagca aattgatcca   3360
agagaaccaa cttaaagctt tcctgacgga atgttaattc tcgttgaccc tgagcactga   3420
tgaatcccct aatgattttg gtaaaaatca ttaagttaag gtggatacac atcttgtcat   3480
atgatcccgg taatgtgagt tagctcactc attaggcacc ccaggcttta cactttatgc   3540
ttccggctcg tatgttgtgt ggaattgtga gcggataaca atttcacaca ggaaacagct   3600
atgaccatga ttacgccaag cgcgcaatta accctcacta aagggaacaa aagctggagc   3660
tccaccgcgg tggcggccgc tcctggaagg tcctggaagg gggcgtccgc gggagctcac   3720
ggggagagcc cccccccaaa gcccccaggg atgtaattac gtccctcccc cgctaggggg   3780
cagcagcgag ccgcccgggg ctccgctccg gtccggcgct ccccccgcat ccccgagccg   3840
gcagcgtgcg gggacagccc gggcacgggg aaggtggcac gggatcgctt tcctctgaac   3900
gcttctcgct gctctttgag cctgcagaca cctgggggga tacggggaaa aagctttagg   3960
ctgaaagaga gatttagaat gacagaatca cagaatggcc tgggttggaa aggcccacaa   4020
tgctcatcca gttccaaccc ctgctatgtg cagggtcgcc aaccagcagc ccaggctgcc   4080
cagagacaca tccagcctgg cctggaatgc ctgcagggat ggggcatcca cagcctcctt   4140
gggcaacctg ttcagtgcgt caccaccctc tgggggaaaa actgcctctt catatccaac   4200
ccaaacctcc cctgtctaag tgtaaagcca ttccccttg tcctatcaag gggagtttg   4260
ctgtgacatt gttggtctgg ggtgacacat gtttgccaat tcagtgcatc acggagaggc   4320
agatcttggg gataaggaag agcaggacag catggacgtg ggacatgcag gtgttgaggg   4380
ctctgggaca ctctccaagt cacagcgttc agaacagcct taaggatcag aagataggat   4440
agaaggacaa agagcaagtt aaaacccagc atggagagga gcacaaaaag gccacagaca   4500
ctgctggtcc ctgtgtctga gcctgcatgt ttgatggtgt ctggatgcaa gcagaagggg   4560
tggaagagct tgcctggaga gatacagctg ggtcagtagg actgggacag gcagctggag   4620
aattgccatg tagatgttca cacaatcgtc aaatcatgaa ggctggaaaa gccctccaag   4680
```

```
atccccaaga ccaaccccaa cccacccacc gtgcccactg gccatgtccc tcagtgccac   4740
atccccacag ttcttcatca cctccaggga cggtgacccc cccacctccg tgggcagctg   4800
tgccactgca gcaccgctct ttggagaagg taaatcttgc taaatccagc ccgaccctcc   4860
cctggcacaa cgtaaggcca ttatctctca tcctactcca ggacggagtc agtgagaata   4920
ttctcgaggg cgcgcctggc cattgcatac gttgtatcca tatcataata tgtacattta   4980
tattggctca tgtccaacat taccgccatg ttgacattga ttattgacta gttattaata   5040
gtaatcaatt acggggtcat tagttcatag cccatatatg gagttccgcg ttacataact   5100
tacggtaaat ggcccgcctg gctgaccgcc caacgacccc cgcccattga cgtcaataat   5160
gacgtatgtt cccatagtaa cgccaatagg gactttccat tgacgtcaat gggtggagta   5220
tttacggtaa actgcccact tggcagtaca tcaagtgtat catatgccaa gtacgccccc   5280
tattgacgtc aatgacggta aatggcccgc ctggcattat gcccagtaca tgaccttatg   5340
ggactttcct acttggcagt acatctacgt attagtcatc gctattacca tggtgatgcg   5400
gttttggcag tacatcaatg ggcgtggata gcggtttgac tcacggggat ttccaagtct   5460
ccaccccatt gacgtcaatg ggagtttgtt ttggcaccaa aatcaacggg actttccaaa   5520
atgtcgtaac aactccgccc cattgacgca aatgggcggt aggcgtgtac ggtgggaggt   5580
ctatataagc agagctcgtt tagtgaaccg tcagatcgcc tggagacgcc atccacgctg   5640
ttttgacctc catagaagac accgggaccg atccagcctc cgcggccggg aacggtgcat   5700
tggaacgcgg attccccgtg ccaagagtga cgtaagtacc gcctatagac tctataggca   5760
cacccctttg gctcttatgc atgctatact gtttttggct tggggcctat acacccccgc   5820
ttccttatgc tataggtgat ggtatagctt agcctatagg tgtgggttat tgaccattat   5880
tgaccactcc cctattggtg acgatacttt ccattactaa tccataacat ggctctttgc   5940
cacaactatc tctattggct atatgccaat actctgtcct tcagagactg acacggactc   6000
tgtattttta caggatgggg tcccatttat tatttacaaa ttcacatata caacaacgcc   6060
gtcccccgtg cccgcagttt ttattaaaca tagcgtggga tctccacgcg aatctcgggt   6120
acgtgttccg gacatgggct cttctccggt agcggcggag cttccacatc cgagccctgg   6180
tcccatgcct ccagcggctc atggtcgctc ggcagctcct tgctcctaac agtggaggcc   6240
agacttaggc acagcacaat gcccaccacc accagtgtgc cgcacaaggc cgtggcggta   6300
gggtatgtgt ctgaaaatga gcgtggagat tgggctcgca cggctgacgc agatggaaga   6360
cttaaggcag cggcagaaga agatgcaggc agctgagttg ttgtattctg ataagagtca   6420
gaggtaactc ccgttgcggt gctgttaacg gtggagggca gtgtagtctg agcagtactc   6480
gttgctgccg cgcgcgccac cagacataat agctgacaga ctaacagact gttcctttcc   6540
atgggtcttt tctgcagtca ccgtcgatat cgctatgagg gggatcatac tggcattagt   6600
gctcaccctt gtaggcagcc agtcctatga gctcacacag ccaccctcgg tgtcagtgtc   6660
cccaggacaa acggccagga tcacctgctc tggagatgca ttgccagaaa aatatgttta   6720
ttggtaccag cagaagtcag gccaggcccc tgtggtggtc atctatgagg acagcaaacg   6780
accctccggg atccctgaga gattctctgg ctccagctca gggacaatgg ccaccttgac   6840
tatcagtggg gcccaggtgg aagatgaagg tgactactac tgttactcaa ctgacagcag   6900
tggttatcat agggaggtgt tcggcggagg gaccaagctg accgtcctag gtcagcccaa   6960
ggctgccccc tcggtcactc tgttcccacc ctcctctgag gagcttcaag ccaacaaggc   7020
cacactggtg tgtctcataa gtgactccta cccgggagcc gtgacagtgg cctggaaggc   7080
```

```
agatagcagc cccgtcaagg cgggagtgga gaccaccaca ccctccaaac aaagcaacaa   7140
caagtacgcg gccagcagct acctgagcct gacgcctgag cagtggaagt cccacaaaag   7200
ctacagctgc caggtcacgc atgaagggag caccgtggag aagacagtgg cccctgcaga   7260
atgttcatga gacgtcagcg gtacgttgca gcactggaga agacagaaac attttcattt   7320
ttattgtgtg gtgtaagaag actcatctta agaagcaata gaaatgttaa attaaacact   7380
taaagatgcg tggaattttc ccaagtaatt taaagtatta aactttatta ttatagaaac   7440
tattctaatt gcctataatt atctgatttc ctaataaata cgtgcatgga aaaaccgatg   7500
aaggcttcct tctttctctg actgtggcaa gaggatgtct gcattgcttc tcttcacccc   7560
acgttttgta gactcgaggc tgtggcagcc tgcggtgtag atgtacacca ggcaagaatc   7620
tgtgtcaggc cccacctgcg atatgggttg tgtggattgg cagaagctgc ctaccaggct   7680
ccagcttgtt tcccctgtgc ttccttccct gctgctgaga tcctgggcac cacagtagga   7740
gttggagcgc tgaccacaga gatgatcaag gggctggagc acttccccta tgaggacagg   7800
ctgagggagc tgggcttatt cagcctggag aagagaaggc tgcgcggtga tcccattgca   7860
gcctttcagt ccctgaaggg agcctataaa caggaaggga gtaaactctt tgaaagggta   7920
gataacagca ggacaagggg caacggtttt aagttgaaag agggaagatt taggttggat   7980
gttaggggaa agttctttac caggagagtg gtgaggtgct ggaacaggct gcccagagag   8040
gttgtggatg ctccgtccct ggaggtgttc aaggccaggt tggatggggc cctgggcaac   8100
ctggtctagt aaatggggat gttggtggcc ctgcccagca ggggggttgg agattcgtga   8160
tcctcgaggt cccttccaac ccaggccatt ctgtgattct gtcatttctg tcatttattt   8220
ttcaatagag cctgtttttt gtactggcaa gacctacctg tatgactact taattaagta   8280
gtcatacagg taggtcttgc cagtacaaaa aacaggctct attgaaaaat aaatgacaga   8340
aatgacagaa tcacagaatg gcctgggttg gaagggacct cgaggatcac gaatctccaa   8400
ccccccctgct gggcagggcc accaacatcc ccatttacta gaccaggttg cccagggccc   8460
catccaacct ggccttgaac acctccaggg acggagcatc cacaacctct ctgggcagcc   8520
tgttccagca cctcaccact ctcctggtaa agaactttcc cctaacatcc aacctaaatc   8580
ttccctcttt caacttaaaa ccgttgcccc ttgtcctgct gttatctacc ctttcaaaga   8640
gtttactccc ttcctgttta taggctycct tcagggactg aaaggctgca atgggatcac   8700
cgcgcagcct tctcttctcc aggctgaata agcccagctc cctcagcctg tcctcatagg   8760
ggaagtgctc cagccccttg atcatctctg tggtcagcgc tccaactcct actgtggtgc   8820
ccaggatctc agcagcaggg aaggaagcac aggggaaaca agctggagcc tggtaggcag   8880
cttctgccaa tccacacaac ccatatcgca ggtggggcct gacacagatt cttgcctggt   8940
gtacatctac accgcaggct gccacagcct cgagtctaca aaacgtgggg tgaagagaag   9000
caatgcagac atcctcttgc cacagtcaga gaaagaagga agccttcatc ggtttttcca   9060
tgcacgtatt tattaggaaa tcagataatt ataggcaatt agaatagttt ctataataat   9120
aaagtttaat actttaaatt acttgggaaa attccacgca tctttaagtg tttaatttaa   9180
catttctatt gcttcttaag atgagtcttc ttacaccaca caataaaaat gaaaatgttt   9240
ctgtcttctc cagtgctgca acgtaccgct gacgtctcat ttacccggag acagggagag   9300
gctcttctgc gtgtagtggt tgtgcagagc ctcatgcatc acggagcatg agaagacgtt   9360
cccctgctgc cacctgctct tgtccacggt gagcttgctg tagaggaaga aggagccgtc   9420
```

```
ggagtccagc acgggaggcg tggtcttgta gttgttctcc ggctgcccat tgctctccca   9480
ctccacggcg atgtcgctgg gatagaagcc tttgaccagg caggtcaggc tgacctggtt   9540
cttggtcagc tcatcccggg atgggggcag ggtgtacacc tgtggttctc ggggctgccc   9600
tttggctttg gagatggttt tctcgatggg ggctgggagg gctttgttgg agaccttgca   9660
cttgtactcc ttgccattca gccagtcctg gtgcaggacg gtgaggacgc tgaccacacg   9720
gtacgtgctg ttgtactgct cctcccgcgg ctttgtcttg gcattatgca cctccacgcc   9780
gtccacgtac cagttgaact tgacctcagg gtcttcgtgg ctcacgtcca ccaccacgca   9840
tgtgacctca ggggtccggg agatcatgag ggtgtccttg ggttttgggg ggaagaggaa   9900
gactgacggt ccccccagga gttcaggtgc tgggcacggt gggcatgtgt gagttttgtc   9960
acaagatttg ggctcaactt tcttgtccac cttggtgttg ctgggcttgt gattcacgtt  10020
gcagatgtag gtctgggtgc ccaagctgct ggagggcacg gtcaccacgc tgctgaggga  10080
gtagagtcct gaggactgta ggacagccgg gaaggtgtgc acgccgctgg tcagggcgcc  10140
tgagttccac gacaccgtca ccggttcggg gaagtagtcc ttgaccaggc agcccagggc  10200
cgctgtgccc ccagaggtgc tcttggagga gggtgccagg gggaagaccg atgggccctt  10260
ggtggaggct gaggagacgg tgaccagggt tccctggccc caattcgggg gagggataac  10320
tcccccaaat gttatcataa tccccgtggt acagtaatat acggctgtgt cctcggcttt  10380
caggctattc atttgcagat ataacgtgtt ttttgaatca tctcttgaga tggtgaatct  10440
gcctttcacg ggtgcagcat agtctgttgt cccaccatca attttgcttt taatacggcc  10500
gacccactcc agccccttcc ctggagcctg gcggacccag ctcatccagg cgtttctgaa  10560
agtgaatcca gaggctgcac aggagactct aagggacccc cccggcttta ccaagcctcc  10620
ccccgactcc tgcagctgca cctgctggct gcctacaagg gtgagcacta atgccagtat  10680
gatccccctc atagcgatat cgacggtgac tgcagaaaag acccatggaa aggaacagtc  10740
tgttagtctg tcagctatta tgtctggtgg cgcgcgcggc agcaacgagt actgctcaga  10800
ctacactgcc ctccaccgtt aacagcaccg caacgggagt tacctctgac tcttatcaga  10860
atacaacaac tcagctgcct gcatcttctt ctgccgctgc cttaagtctt ccatctgcgt  10920
cagccgtgcg agcccaatct ccacgctcat tttcagacac ataccctacc gccacggcct  10980
tgtgcggcac actggtggtg gtgggcattg tgctgtgcct aagtctggcc tccactgtta  11040
ggagcaagga gctgccgagc gaccatgagc cgctggaggc atgggaccag ggctcggatg  11100
tggaagctcc gccgctaccg gagaagagcc catgtccgga acacgtaccc gagattcgcg  11160
tggagatccc acgctatgtt taataaaaac tgcgggcacg ggggacggcg ttgttgtata  11220
tgtgaatttg taaataataa atgggacccc atcctgtaaa aatacagagt ccgtgtcagt  11280
ctctgaagga cagagtattg gcatatagcc aatagagata gttgtggcaa agagccatgt  11340
tatggattag taatggaaag tatcgtcacc aataggggag tggtcaataa tggtcaataa  11400
cccacaccta taggctaagc tataccatca cctatagcat aaggaagcgg gggtgtatag  11460
gccccaagcc aaaaacagta tagcatgcat aagagccaaa ggggtgtgcc tatagagtct  11520
ataggcggta cttacgtcac tcttggcacg gggaatccgc gttccaatgc accgttcccg  11580
gccgcggagg ctggatcggt cccggtgtct tctatggagg tcaaaacagc gtggatggcg  11640
tctccaggcg atctgacggt tcactaaacg agctctgctt atatagacct cccaccgtac  11700
acgcctaccg cccatttgcg tcaatggggc ggagttgtta cgacattttg gaaagtcccg  11760
ttgattttgg tgccaaaaca aactcccatt gacgtcaatg gggtggagac ttggaaatcc  11820
```

```
ccgtgagtca aaccgctatc cacgcccatt gatgtactgc caaaaccgca tcaccatggt  11880
aatagcgatg actaatacgt agatgtactg ccaagtagga aagtcccata aggtcatgta  11940
ctgggcataa tgccaggcgg gccatttacc gtcattgacg tcaatagggg gcgtacttgg  12000
catatgatac acttgatgta ctgccaagtg ggcagtttac cgtaaatact ccacccattg  12060
acgtcaatgg aaagtcccta ttggcgttac tatgggaaca tacgtcatta ttgacgtcaa  12120
tgggcggggg tcgttgggcg gtcagccagg cgggccattt accgtaagtt atgtaacgcg  12180
gaactccata tatgggctat gaactaatga ccccgtaatt gattactatt aataactagt  12240
caataatcaa tgtcaacatg gcggtaatgt tggacatgag ccaatataaa tgtacatatt  12300
atgatatgga tacaacgtat gcaatggcca cgtacgcaat tggtttaaac gcgtaatatt  12360
ctcactgact ccgtcctgga gtaggatgag agataatggc cttacgttgt gccaggggag  12420
ggtcgggctg gatttagcaa gatttacctt ctccaaagag cggtgctgca gtggcacagc  12480
tgcccacgga ggtggggggg tcaccgtccc tggaggtgat gaagaactgt ggggatgtgg  12540
cactgaggga catggccagt gggcacggtg ggtgggttgg ggttggtctt ggggatcttg  12600
gagggctttt ccagccttca tgatttgacg attgtgtgaa catctacatg gcaattctcc  12660
agctgcctgt cccagtccta ctgacccagc tgtatctctc caggcaagct cttccacccc  12720
ttctgcttgc atccagacac catcaaacat gcaggctcag acacagggac cagcagtgtc  12780
tgtggccttt ttgtgctcct ctccatgctg ggttttaact tgctctttgt ccttctatcc  12840
tatcttctga tccttaaggc tgttctgaac gctgtgactt ggagagtgtc ccagagccct  12900
caacacctgc atgtcccacg tccatgctgt cctgctcttc cttatcccca agatctgcct  12960
ctccgtgatg cactgaattg gcaaacatgt gtcaccccag accaacaatg tcacagcaaa  13020
ctccccccttg ataggacaag gggaatggc tttacactta gacaggggag gtttgggttg  13080
gatatgaaga ggcagttttt cccccagagg gtggtgacgc actgaacagg ttgcccaagg  13140
aggctgtgga tgccccatcc ctgcaggcat tccaggccag gctggatgtg tctctgggca  13200
gcctgggctg ctggttggcg accctgcaca tagcaggggt tggaactgga tgagcattgt  13260
gggcctttcc aacccaggcc attctgtgat tctgtcattc taaatctctc tttcagccta  13320
aagcttttttc cccgtatccc cccaggtgtc tgcaggctca aagagcagcg agaagcgttc  13380
agaggaaagc gatcccgtgc caccttcccc gtgcccgggc tgtccccgca cgctgccggc  13440
tcggggatgc ggggggagcg ccggaccgga gcggagcccc gggcggctcg ctgctgcccc  13500
ctagcggggg agggacgtaa ttacatccct gggggctttg gggggggggct ctccccgtga  13560
gctcccgcgg acgccccctt ccaggacctt ccaggagggc ccctccggga tcatatgaca  13620
agatgtgtat ccaccttaac ttaatgattt ttaccaaaat cattagggga ttcatcagtg  13680
ctcagggtca acgagaatta acattccgtc aggaaagctt gaattcagct tttgttccct  13740
ttagtgaggg ttaattgcgc gcttggcgta atcatggtca tagctgtttc ctgtgtgaaa  13800
ttgttatccg ctcacaattc cacacaacat acgagccgga agcataaagt gtaaagcctg  13860
gggtgcctaa tgagtgagct aactcacatt aattgcgttg cgctcactgc ccgctttcca  13920
gtcgggaaac ctgtcgtgcc agctgcatta atgaatcggc caacgcgcgg ggagaggcgg  13980
tttgcgtatt gggcgctctt ccgcttcctc gctcactgac tcgctgcgct cggtcgttcg  14040
gctgcggcga gcggtatcag ctcactcaaa ggcggtaata cggttatcca cagaatcagg  14100
ggataacgca ggaaagaaca tgtgagcaaa aggccagcaa aaggccagga accgtaaaaa  14160
```

```
ggccgcgttg ctggcgtttt tccataggct ccgcccccct gacgagcatc acaaaaatcg  14220
acgctcaagt cagaggtggc gaaacccgac aggactataa agataccagg cgtttccccc  14280
tggaagctcc ctcgtgcgct ctcctgttcc gaccctgccg cttaccggat acctgtccgc  14340
ctttctccct tcgggaagcg tggcgctttc tcatagctca cgctgtaggt atctcagttc  14400
ggtgtaggtc gttcgctcca agctgggctg tgtgcacgaa ccccccgttc agcccgaccg  14460
ctgcgcctta tccggtaact atcgtcttga gtccaacccg gtaagacacg acttatcgcc  14520
actggcagca gccactggta acaggattag cagagcgagg tatgtaggcg gtgctacaga  14580
gttcttgaag tggtggccta actacggcta cactagaaga acagtatttg gtatctgcgc  14640
tctgctgaag ccagttacct tcggaaaaag agttggtagc tcttgatccg gcaaacaaac  14700
caccgctggt agcggtggtt tttttgtttg caagcagcag attacgcgca gaaaaaaagg  14760
atctcaagaa gatcctttga tcttttctac ggggtctgac gctcagtgga acgaaaactc  14820
acgttaaggg attttggtca tgagattatc aaaaaggatc ttcacctaga tccttttaaa  14880
ttaaaaatga agttttaaat caatctaaag tatatatgag taaacttggt ctgacagtta  14940
ccaatgctta atcagtgagg cacctatctc agcgatctgt ctatttcgtt catccatagt  15000
tgcctgactc cccgtcgtgt agataactac gatacgggag ggcttaccat ctggccccag  15060
tgctgcaatg ataccgcgag acccacgctc accggctcca gatttatcag caataaacca  15120
gccagccgga agggccgagc gcagaagtgg tcctgcaact ttatccgcct ccatccagtc  15180
tattaattgt tgccgggaag ctagagtaag tagttcgcca gttaatagtt tgcgcaacgt  15240
tgttgccatt gctacaggca tcgtggtgtc acgctcgtcg tttggtatgg cttcattcag  15300
ctccggttcc caacgatcaa ggcgagttac atgatccccc atgttgtgca aaaaagcggt  15360
tagctccttc ggtcctccga tcgttgtcag aagtaagttg gccgcagtgt tatcactcat  15420
ggttatggca gcactgcata attctcttac tgtcatgcca tccgtaagat gcttttctgt  15480
gactggtgag tactcaacca agtcattctg agaatagtgt atgcggcgac cgagttgctc  15540
ttgcccggcg tcaatacggg ataataccgc gccacatagc agaactttaa aagtgctcat  15600
cattggaaaa cgttcttcgg ggcgaaaact ctcaaggatc ttaccgctgt tgagatccag  15660
ttcgatgtaa cccactcgtg cacccaactg atcttcagca tcttttactt tcaccagcgt  15720
ttctgggtga gcaaaaacag gaaggcaaaa tgccgcaaaa aagggaataa gggcgacacg  15780
gaaatgttga atactcatac tcttcctttt tcaatattat tgaagcattt atcagggtta  15840
ttgtctcatg agcggataca tatttgaatg tatttagaaa aataaacaaa taggggttcc  15900
gcgcacattt ccccgaaaag tgccac                                       15926
```

<210> SEQ ID NO 18
<211> LENGTH: 15920
<212> TYPE: DNA
<213> ORGANISM: Artificial Sequence
<220> FEATURE:
<223> OTHER INFORMATION: Synthetic construct

<400> SEQUENCE: 18

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
```

```
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
```

-continued

```
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgctcctgg aaggtcctgg aagggggcgt ccgcgggagc tcacggggag   3720
agcccccccc caaagccccc agggatgtaa ttacgtccct cccccgctag ggggcagcag   3780
cgagccgccc ggggctccgc tccggtccgg cgctcccccc gcatccccga gccggcagcg   3840
tgcggggaca gcccgggcac ggggaaggtg gcacgggatc gctttcctct gaacgcttct   3900
cgctgctctt tgagcctgca gacacctggg gggatacggg gaaaaagctt taggctgaaa   3960
gagagattta gaatgacaga atcacagaat ggcctgggtt ggaaaggccc acaatgctca   4020
tccagttcca accccctgcta tgtgcagggt cgccaaccag cagcccaggc tgcccagaga   4080
cacatccagc ctggcctgga atgcctgcag ggatggggca tccacagcct ccttgggcaa   4140
cctgttcagt gcgtcaccac cctctggggg aaaaactgcc tcttcatatc caacccaaac   4200
ctcccctgtc taagtgtaaa gccattcccc cttgtcctat caagggggag tttgctgtga   4260
cattgttggt ctggggtgac acatgtttgc caattcagtg catcacggag aggcagatct   4320
tggggataag gaagagcagg acagcatgga cgtgggacat gcaggtgttg agggctctgg   4380
gacactctcc aagtcacagc gttcagaaca gccttaagga tcagaagata ggatagaagg   4440
acaaagagca agttaaaacc cagcatggag aggagcacaa aaaggccaca gacactgctg   4500
gtccctgtgt ctgagcctgc atgtttgatg gtgtctggat gcaagcagaa ggggtggaag   4560
agcttgcctg gagagataca gctgggtcag taggactggg acaggcagct ggagaattgc   4620
catgtagatg ttcacacaat cgtcaaatca tgaaggctgg aaaagccctc caagatcccc   4680
aagaccaacc ccaacccacc caccgtgccc actggccatg tccctcagtg ccacatcccc   4740
acagttcttc atcacctcca gggacggtga cccccccacc tccgtgggca gctgtgccac   4800
tgcagcaccg ctctttggag aaggtaaatc ttgctaaatc cagcccgacc ctcccctggc   4860
acaacgtaag gccattatct ctcatcctac tccaggacgg agtcagtgag aatattctcg   4920
agggcgcgcc tggccattgc atacgttgta tccatatcat aatatgtaca tttatattgg   4980
ctcatgtcca acattaccgc catgttgaca ttgattattg actagttatt aatagtaatc   5040
```

```
aattacgggg tcattagttc atagcccata tatggagttc cgcgttacat aacttacggt   5100
aaatggcccg cctggctgac cgcccaacga cccccgccca ttgacgtcaa taatgacgta   5160
tgttcccata gtaacgccaa tagggacttt ccattgacgt caatgggtgg agtatttacg   5220
gtaaactgcc cacttggcag tacatcaagt gtatcatatg ccaagtacgc cccctattga   5280
cgtcaatgac ggtaaatggc ccgcctggca ttatgcccag tacatgacct tatgggactt   5340
tcctacttgg cagtacatct acgtattagt catcgctatt accatggtga tgcggttttg   5400
gcagtacatc aatgggcgtg gatagcggtt tgactcacgg ggatttccaa gtctccaccc   5460
cattgacgtc aatgggagtt tgttttggca ccaaaatcaa cgggactttc caaaatgtcg   5520
taacaactcc gccccattga cgcaaatggg cggtaggcgt gtacggtggg aggtctatat   5580
aagcagagct cgtttagtga accgtcagat cgcctggaga cgccatccac gctgttttga   5640
cctccataga agacaccggg accgatccag cctccgcggc cgggaacggt gcattggaac   5700
gcggattccc cgtgccaaga gtgacgtaag taccgcctat agactctata ggcacacccc   5760
tttggctctt atgcatgcta tactgttttt ggcttggggc ctatacaccc ccgcttcctt   5820
atgctatagg tgatggtata gcttagccta taggtgtggg ttattgacca ttattgacca   5880
ctcccctatt ggtgacgata ctttccatta ctaatccata acatggctct ttgccacaac   5940
tatctctatt ggctatatgc caatactctg tccttcagag actgacacgg actctgtatt   6000
tttacaggat ggggtcccat ttattattta caaattcaca tatacaacaa cgccgtcccc   6060
cgtgcccgca gtttttatta aacatagcgt gggatctcca cgcgaatctc gggtacgtgt   6120
tccggacatg ggctcttctc cggtagcggc ggagcttcca catccgagcc ctggtcccat   6180
gcctccagcg gctcatggtc gctcggcagc tccttgctcc taacagtgga ggccagactt   6240
aggcacagca caatgcccac caccaccagt gtgccgcaca aggccgtggc ggtagggtat   6300
gtgtctgaaa atgagcgtgg agattgggct cgcacggctg acgcagatgg aagacttaag   6360
gcagcggcag aagaagatgc aggcagctga gttgttgtat tctgataaga gtcagaggta   6420
actcccgttg cggtgctgtt aacggtggag ggcagtgtag tctgagcagt actcgttgct   6480
gccgcgcgcg ccaccagaca taatagctga cagactaaca gactgttcct ttccatgggt   6540
cttttctgca gtcaccgtcg atatcgctat gagggggatc atactggcat tagtgctcac   6600
ccttgtaggc agccagtcct atgagctcac acagccaccc tcggtgtcag tgtccccagg   6660
acaaacggcc aggatcacct gctctggaga tgcattgcca gaaaaatatg tttattggta   6720
ccagcagaag tcaggccagg cccctgtggt ggtcatctat gaggacagca aacgaccctc   6780
cgggatccct gagagattct ctggctccag ctcagggaca atggccacct tgactatcag   6840
tggggcccag gtggaagatg aaggtgacta ctactgttac tcaactgaca gcagtggtta   6900
tcatagggag gtgttcggcg gagggaccaa gctgaccgtc ctaggtcagc ccaaggctgc   6960
cccctcggtc actctgttcc caccctcctc tgaggagctt caagccaaca aggccacact   7020
ggtgtgtctc ataagtgact cctacccggg agccgtgaca gtggcctgga aggcagatag   7080
cagccccgtc aaggcgggag tggagaccac cacaccctcc aaacaaagca acaacaagta   7140
cgcggccagc agctacctga gcctgacgcc tgagcagtgg aagtcccaca aaagctacag   7200
ctgccaggtc acgcatgaag ggagcaccgt ggagaagaca gtggcccctg cagaatgttc   7260
atgagacgtc agcggtacgt tgcagcactg gagaagacag aaacattttc atttttattg   7320
tgtggtgtaa gaagactcat cttaagaagc aatagaaatg ttaaattaaa cacttaaaga   7380
```

```
tgcgtggaat tttcccaagt aatttaaagt attaaacttt attattatag aaactattct   7440
aattgcctat aattatctga tttcctaata aatacgtgca tggaaaaacc gatgaaggct   7500
tccttctttc tctgactgtg gcaagaggat gtctgcattg cttctcttca ccccacgttt   7560
tgtagactcg aggctgtggc agcctgcggt gtagatgtac accaggcaag aatctgtgtc   7620
aggccccacc tgcgatatgg gttgtgtgga ttggcagaag ctgcctacca ggctccagct   7680
tgtttcccct gtgcttcctt ccctgctgct gagatcctgg gcaccacagt aggagttgga   7740
gcgctgacca cagagatgat caaggggctg gagcacttcc cctatgagga caggctgagg   7800
gagctgggct tattcagcct ggagaagaga aggctgcgcg gtgatcccat tgcagccttt   7860
cagtccctga agggagccta taaacaggaa gggagtaaac tctttgaaag ggtagataac   7920
agcaggacaa ggggcaacgg ttttaagttg aaagagggaa gatttaggtt ggatgttagg   7980
ggaaagttct ttaccaggag agtggtgagg tgctggaaca ggctgcccag agaggttgtg   8040
gatgctccgt ccctggaggt gttcaaggcc aggttggatg gggccctggg caacctggtc   8100
tagtaaatgg ggatgttggt ggccctgccc agcagggggg ttggagattc gtgatcctcg   8160
aggtcccttc caacccaggc cattctgtga ttctgtcatt tctgtcattt atttttcaat   8220
agagcctgtt ttttgtactg gcaagaccta cctgtatgac tacttaatta agtagtcata   8280
caggtaggtc ttgccagtac aaaaaacagg ctctattgaa aaataaatga cagaaatgac   8340
agaatcacag aatggcctgg gttggaaggg acctcgagga tcacgaatct ccaacccccc   8400
tgctgggcag ggccaccaac atccccattt actagaccag gttgcccagg gccccatcca   8460
acctggcctt gaacacctcc agggacggag catccacaac ctctctgggc agcctgttcc   8520
agcacctcac cactctcctg gtaaagaact ttcccctaac atccaaccta aatcttccct   8580
ctttcaactt aaaaccgttg ccccttgtcc tgctgttatc taccctttca aagagtttac   8640
tcccttcctg tttataggct yccttcaggg actgaaaggc tgcaatggga tcaccgcgca   8700
gccttctctt ctccaggctg aataagccca gctccctcag cctgtcctca taggggaagt   8760
gctccagccc cttgatcatc tctgtggtca gcgctccaac tcctactgtg gtgcccagga   8820
tctcagcagc agggaaggaa gcacagggga aacaagctgg agcctggtag gcagcttctg   8880
ccaatccaca caacccatat cgcaggtggg gcctgacaca gattcttgcc tggtgtacat   8940
ctacaccgca ggctgccaca gcctcgagtc tacaaaacgt ggggtgaaga gaagcaatgc   9000
agacatcctc ttgccacagt cagagaaaga aggaagcctt catcggtttt tccatgcacg   9060
tatttattag gaaatcagat aattataggc aattagaata gtttctataa taataaagtt   9120
taatacttta aattacttgg gaaaattcca cgcatcttta agtgtttaat ttaacatttc   9180
tattgcttct taagatgagt cttcttacac cacacaataa aaatgaaaat gtttctgtct   9240
tctccagtgc tgcaacgtac cgctgacgtc tcatttaccc ggagacaggg agaggctctt   9300
ctgcgtgtag tggttgtgca gagcctcatg catcacggag catgagaaga cgttcccctg   9360
ctgccacctg ctcttgtcca cggtgagctt gctgtagagg aagaaggagc cgtcggagtc   9420
cagcacggga ggcgtggtct tgtagttgtt ctccggctgc ccattgctct cccactccac   9480
ggcgatgtcg ctgggataga agcctttgac caggcaggtc aggctgacct ggttcttggt   9540
cagctcatcc cgggatgggg gcagggtgta cacctgtggt tctcggggct gccctttggc   9600
tttggagatg gttttctcga tgggggctgg gagggctttg ttggagacct tgcacttgta   9660
ctccttgcca ttcagccagt cctggtgcag gacggtgagg acgctgacca cacggtacgt   9720
gctgttgtac tgctcctccc gcggctttgt cttggcatta tgcacctcca cgccgtccac   9780
```

```
gtaccagttg aacttgacct cagggtcttc gtggctcacg tccaccacca cgcatgtgac   9840
ctcaggggtc cgggagatca tgagggtgtc cttgggtttt ggggggaaga ggaagactga   9900
cggtcccccc aggagttcag gtgctgggca cggtgggcat gtgtgagttt tgtcacaaga   9960
tttgggctca actttcttgt ccaccttggt gttgctgggc ttgtgattca cgttgcagat  10020
gtaggtctgg gtgcccaagc tgctggaggg cacggtcacc acgctgctga gggagtagag  10080
tcctgaggac tgtaggacag ccgggaaggt gtgcacgccg ctggtcaggg cgcctgagtt  10140
ccacgacacc gtcaccggtt cggggaagta gtccttgacc aggcagccca gggccgctgt  10200
gcccccagag gtgctcttgg aggagggtgc caggggggaag accgatgggc ccttggtgga  10260
ggctgaggag acggtgacca gggttccctg gccccaattc gggggaggga taactccccc  10320
aaatgttatc ataatccccg tggtacagta atatacggct gtgtcctcgg ctttcaggct  10380
attcatttgc agatataacg tgtttttga atcatctctt gagatggtga atctgccttt  10440
cacgggtgca gcatagtctg ttgtcccacc atcaattttg cttttaatac ggccgaccca  10500
ctccagcccc ttccctggag cctggcggac ccagctcatc caggcgtttc tgaaagtgaa  10560
tccagaggct gcacaggaga ctctaaggga cccccccggc tttaccaagc ctcccccga  10620
ctcctgcagc tgcacctgct ggctgcctac aagggtgagc actaatgcca gtatgatccc  10680
cctcatagcg atatcgacgg tgactgcaga aaagacccat ggaaaggaac agtctgttag  10740
tctgtcagct attatgtctg gtggcgcgcg cggcagcaac gagtactgct cagactacac  10800
tgccctccac cgttaacagc accgcaacgg gagttacctc tgactcttat cagaatacaa  10860
caactcagct gcctgcatct tcttctgccg ctgccttaag tcttccatct gcgtcagccg  10920
tgcgagccca atctccacgc tcattttcag acacataccc taccgccacg gccttgtgcg  10980
gcacactggt ggtggtgggc attgtgctgt gcctaagtct ggcctccact gttaggagca  11040
aggagctgcc gagcgaccat gagccgctgg aggcatggga ccagggctcg gatgtggaag  11100
ctccgccgct accggagaag agcccatgtc cggaacacgt acccgagatt cgcgtggaga  11160
tcccacgcta tgtttaataa aaactgcggg cacgggggac ggcgttgttg tatatgtgaa  11220
tttgtaaata ataaatggga ccccatcctg taaaaataca gagtccgtgt cagtctctga  11280
aggacagagt attggcatat agccaataga gatagttgtg gcaaagagcc atgttatgga  11340
ttagtaatgg aaagtatcgt caccaatagg ggagtggtca ataatggtca ataacccaca  11400
cctataggct aagctatacc atcacctata gcataaggaa gcgggggtgt ataggcccca  11460
agccaaaaac agtatagcat gcataagagc caaaggggtg tgcctataga gtctataggc  11520
ggtacttacg tcactcttgg cacggggaat ccgcgttcca atgcaccgtt cccggccgcg  11580
gaggctggat cggtcccggt gtcttctatg gaggtcaaaa cagcgtggat ggcgtctcca  11640
ggcgatctga cggttcacta aacgagctct gcttatatag acctcccacc gtacacgcct  11700
accgcccatt tgcgtcaatg gggcggagtt gttacgacat tttggaaagt cccgttgatt  11760
ttggtgccaa aacaaactcc cattgacgtc aatggggtgg agacttggaa atccccgtga  11820
gtcaaaccgc tatccacgcc cattgatgta ctgccaaaac cgcatcacca tggtaatagc  11880
gatgactaat acgtagatgt actgccaagt aggaaagtcc cataaggtca tgtactgggc  11940
ataatgccag gcgggccatt taccgtcatt gacgtcaata gggggcgtac ttggcatatg  12000
atacacttga tgtactgcca agtgggcagt ttaccgtaaa tactccaccc attgacgtca  12060
atggaaagtc cctattggcg ttactatggg aacatacgtc attattgacg tcaatgggcg  12120
```

-continued

```
ggggtcgttg ggcggtcagc caggcgggcc atttaccgta agttatgtaa cgcggaactc  12180
catatatggg ctatgaacta atgaccccgt aattgattac tattaataac tagtcaataa  12240
tcaatgtcaa catggcggta atgttggaca tgagccaata taaatgtaca tattatgata  12300
tggatacaac gtatgcaatg gccacgtacg caattggttt aaacgcgtaa tattctcact  12360
gactccgtcc tggagtagga tgagagataa tggccttacg ttgtgccagg ggagggtcgg  12420
gctggattta gcaagattta ccttctccaa agagcggtgc tgcagtggca cagctgccca  12480
cggaggtggg ggggtcaccg tccctggagg tgatgaagaa ctgtggggat gtggcactga  12540
gggacatggc cagtgggcac ggtgggtggg ttggggttgg tcttggggat cttggagggc  12600
ttttccagcc ttcatgattt gacgattgtg tgaacatcta catggcaatt ctccagctgc  12660
ctgtcccagt cctactgacc cagctgtatc tctccaggca agctcttcca ccccttctgc  12720
ttgcatccag acaccatcaa acatgcaggc tcagacacag ggaccagcag tgtctgtggc  12780
ctttttgtgc tcctctccat gctgggtttt aacttgctct ttgtccttct atcctatctt  12840
ctgatcctta aggctgttct gaacgctgtg acttggagag tgtcccagag ccctcaacac  12900
ctgcatgtcc cacgtccatg ctgtcctgct cttccttatc cccaagatct gcctctccgt  12960
gatgcactga attggcaaac atgtgtcacc ccagaccaac aatgtcacag caaactcccc  13020
cttgatagga caagggggaa tggctttaca cttagacagg ggaggtttgg gttggatatg  13080
aagaggcagt ttttccccca gagggtggtg acgcactgaa caggttgccc aaggaggctg  13140
tggatgcccc atccctgcag gcattccagg ccaggctgga tgtgtctctg ggcagcctgg  13200
gctgctggtt ggcgaccctg cacatagcag ggttggaac tggatgagca ttgtgggcct  13260
ttccaaccca ggccattctg tgattctgtc attctaaatc tctctttcag cctaaagctt  13320
tttccccgta tccccccagg tgtctgcagg ctcaaagagc agcgagaagc gttcagagga  13380
aagcgatccc gtgccacctt ccccgtgccc gggctgtccc cgcacgctgc cggctcgggg  13440
atgcgggggg agcgccggac cggagcggag ccccgggcgg ctcgctgctg ccccctagcg  13500
ggggagggac gtaattacat ccctgggggc tttggggggg ggctctcccc gtgagctccc  13560
gcggacgccc ccttccagga ccttccagga gggcccctcc gggatcatat gacaagatgt  13620
gtatccacct taacttaatg atttttacca aaatcattag gggattcatc agtgctcagg  13680
gtcaacgaga attaacattc cgtcaggaaa gcttgaattc agcttttgtt ccctttagtg  13740
agggttaatt gcgcgcttgg cgtaatcatg gtcatagctg tttcctgtgt gaaattgtta  13800
tccgctcaca attccacaca acatacgagc cggaagcata aagtgtaaag cctggggtgc  13860
ctaatgagtg agctaactca cattaattgc gttgcgctca ctgcccgctt tccagtcggg  13920
aaacctgtcg tgccagctgc attaatgaat cggccaacgc gcggggagag gcggtttgcg  13980
tattgggcgc tcttccgctt cctcgctcac tgactcgctg cgctcggtcg ttcggctgcg  14040
gcgagcggta tcagctcact caaaggcggt aatacggtta tccacagaat caggggataa  14100
cgcaggaaag aacatgtgag caaaaggcca gcaaaaggcc aggaaccgta aaaaggccgc  14160
gttgctggcg tttttccata ggctccgccc ccctgacgag catcacaaaa atcgacgctc  14220
aagtcagagg tggcgaaacc cgacaggact ataaagatac caggcgtttc cccctggaag  14280
ctccctcgtg cgctctcctg ttccgaccct gccgcttacc ggatacctgt ccgcctttct  14340
cccttcggga agcgtggcgc tttctcatag ctcacgctgt aggtatctca gttcggtgta  14400
ggtcgttcgc tccaagctgg gctgtgtgca cgaacccccc gttcagcccg accgctgcgc  14460
cttatccggt aactatcgtc ttgagtccaa cccggtaaga cacgacttat cgccactggc  14520
```

```
agcagccact ggtaacagga ttagcagagc gaggtatgta ggcggtgcta cagagttctt  14580

gaagtggtgg cctaactacg gctacactag aagaacagta tttggtatct gcgctctgct  14640

gaagccagtt accttcggaa aaagagttgg tagctcttga tccggcaaac aaaccaccgc  14700

tggtagcggt ggtttttttg tttgcaagca gcagattacg cgcagaaaaa aaggatctca  14760

agaagatcct ttgatctttt ctacggggtc tgacgctcag tggaacgaaa actcacgtta  14820

agggattttg gtcatgagat tatcaaaaag gatcttcacc tagatccttt taaattaaaa  14880

atgaagtttt aaatcaatct aaagtatata tgagtaaact tggtctgaca gttaccaatg  14940

cttaatcagt gaggcaccta tctcagcgat ctgtctattt cgttcatcca tagttgcctg  15000

actccccgtc gtgtagataa ctacgatacg ggagggctta ccatctggcc ccagtgctgc  15060

aatgataccg cgagacccac gctcaccggc tccagattta tcagcaataa accagccagc  15120

cggaagggcc gagcgcagaa gtggtcctgc aactttatcc gcctccatcc agtctattaa  15180

ttgttgccgg gaagctagag taagtagttc gccagttaat agtttgcgca acgttgttgc  15240

cattgctaca ggcatcgtgg tgtcacgctc gtcgtttggt atggcttcat tcagctccgg  15300

ttcccaacga tcaaggcgag ttacatgatc ccccatgttg tgcaaaaaag cggttagctc  15360

cttcggtcct ccgatcgttg tcagaagtaa gttggccgca gtgttatcac tcatggttat  15420

ggcagcactg cataattctc ttactgtcat gccatccgta agatgctttt ctgtgactgg  15480

tgagtactca accaagtcat tctgagaata gtgtatgcgg cgaccgagtt gctcttgccc  15540

ggcgtcaata cgggataata ccgcgccaca tagcagaact ttaaaagtgc tcatcattgg  15600

aaaacgttct tcggggcgaa aactctcaag gatcttaccg ctgttgagat ccagttcgat  15660

gtaacccact cgtgcaccca actgatcttc agcatctttt actttcacca gcgtttctgg  15720

gtgagcaaaa acaggaaggc aaaatgccgc aaaaaaggga ataagggcga cacggaaatg  15780

ttgaatactc atactcttcc tttttcaata ttattgaagc atttatcagg gttattgtct  15840

catgagcgga tacatatttg aatgtattta gaaaaataaa caaatagggg ttccgcgcac  15900

atttccccga aaagtgccac                                              15920
```

<210> SEQ ID NO 19
<211> LENGTH: 16822
<212> TYPE: DNA
<213> ORGANISM: Artificial Sequence
<220> FEATURE:
<223> OTHER INFORMATION: Synthetic construct

<400> SEQUENCE: 19

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600
```

```
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
```

```
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
tttttttgcc tgtttttttt tttttttttt ttttttttaa gtaaggtgtt ctttttttctt   4080
agtaaatttt ctactggact gtatgttttg acaggtcaga aacatttctt caaaagaaga   4140
accttttgga aactgtacag cccttttctt tcattccctt tttgctttct gtgccaatgc   4200
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt atttttttccc tttgaagtag tgagcgttct ctggtttttt tcctttgaaa   4380
ctggtgaggc ttagattttt ctaatgggat tttttacctg atgatctagt tgcataccca   4440
aatgcttgta aatgttttcc tagttaacat gttgataact tcggatttac atgttgtata   4500
tacttgtcat ctgtgtttct agtaaaaata tatggcattt atagaaatac gtaattcctg   4560
atttcctttt ttttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
gttcctgaat cctttctata gcaccactta ttgcagcagg tgtaggctct ggtgtggcct   5340
```

```
gtgtctgtgc ttcaatcttt taagcttctc gagggcgcgc ctggccattg catacgttgt   5400
atccatatca taatatgtac atttatattg gctcatgtcc aacattaccg ccatgttgac   5460
attgattatt gactagttat taatagtaat caattacggg gtcattagtt catagcccat   5520
atatggagtt ccgcgttaca taacttacgg taaatggccc gcctggctga ccgcccaacg   5580
acccccgccc attgacgtca ataatgacgt atgttcccat agtaacgcca atagggactt   5640
tccattgacg tcaatgggtg gagtatttac ggtaaactgc ccacttggca gtacatcaag   5700
tgtatcatat gccaagtacg ccccctattg acgtcaatga cggtaaatgg cccgcctggc   5760
attatgccca gtacatgacc ttatgggact ttcctacttg gcagtacatc tacgtattag   5820
tcatcgctat taccatggtg atgcggtttt ggcagtacat caatgggcgt ggatagcggt   5880
ttgactcacg gggatttcca agtctccacc ccattgacgt caatgggagt ttgttttggc   5940
accaaaatca acgggacttt ccaaaatgtc gtaacaactc cgccccattg acgcaaatgg   6000
gcggtaggcg tgtacggtgg gaggtctata taagcagagc tcgtttagtg aaccgtcaga   6060
tcgcctggag acgccatcca cgctgttttg acctccatag aagacaccgg gaccgatcca   6120
gcctccgcgg ccgggaacgg tgcattggaa cgcggattcc ccgtgccaag agtgacgtaa   6180
gtaccgccta tagactctat aggcacaccc ctttggctct tatgcatgct atactgtttt   6240
tggcttgggg cctatacacc cccgcttcct tatgctatag gtgatggtat agcttagcct   6300
ataggtgtgg gttattgacc attattgacc actcccctat tggtgacgat actttccatt   6360
actaatccat aacatggctc tttgccacaa ctatctctat tggctatatg ccaatactct   6420
gtccttcaga gactgacacg gactctgtat ttttacagga tggggtccca tttattattt   6480
acaaattcac atatacaaca acgccgtccc ccgtgcccgc agtttttatt aaacatagcg   6540
tgggatctcc acgcgaatct cgggtacgtg ttccggacat gggctcttct ccggtagcgg   6600
cggagcttcc acatccgagc cctggtccca tgcctccagc ggctcatggt cgctcggcag   6660
ctccttgctc ctaacagtgg aggccagact taggcacagc acaatgccca ccaccaccag   6720
tgtgccgcac aaggccgtgg cggtagggta tgtgtctgaa aatgagcgtg gagattgggc   6780
tcgcacggct gacgcagatg gaagacttaa ggcagcggca gaagaagatg caggcagctg   6840
agttgttgta ttctgataag agtcagaggt aactcccgtt gcggtgctgt taacggtgga   6900
gggcagtgta gtctgagcag tactcgttgc tgccgcgcgc gccaccagac ataatagctg   6960
acagactaac agactgttcc tttccatggg tcttttctgc agtcaccgtc gatatcgcta   7020
tgagggggat catactggca ttagtgctca cccttgtagg cagccagtcc tatgagctca   7080
cacagccacc ctcggtgtca gtgtccccag gacaaacggc caggatcacc tgctctggag   7140
atgcattgcc agaaaaatat gtttattggt accagcagaa gtcaggccag gcccctgtgg   7200
tggtcatcta tgaggacagc aaacgaccct ccgggatccc tgagagattc tctggctcca   7260
gctcagggac aatggccacc ttgactatca gtggggccca ggtggaagat gaaggtgact   7320
actactgtta ctcaactgac agcagtggtt atcataggga ggtgttcggc ggagggacca   7380
agctgaccgt cctaggtcag cccaaggctg ccccctcggt cactctgttc ccaccctcct   7440
ctgaggagct tcaagccaac aaggccacac tggtgtgtct cataagtgac tcctacccgg   7500
gagccgtgac agtggcctgg aaggcagata gcagccccgt caaggcggga gtggagacca   7560
ccacaccctc caaacaaagc aacaacaagt acgcggccag cagctacctg agcctgacgc   7620
ctgagcagtg gaagtcccac aaaagctaca gctgccaggt cacgcatgaa gggagcaccg   7680
tggagaagac agtggcccct gcagaatgtt catgagacgt cagcggtacg ttgcagcact   7740
```

```
ggagaagaca gaaacatttt catttttatt gtgtggtgta agaagactca tcttaagaag   7800
caatagaaat gttaaattaa acacttaaag atgcgtggaa ttttcccaag taatttaaag   7860
tattaaactt tattattata gaaactattc taattgccta taattatctg atttcctaat   7920
aaatacgtgc atggaaaaac cgatgaaggc ttccttcttt ctctgactgt ggcaagagga   7980
tgtctgcatt gcttctcttc accccacgtt ttgtagactc gaggctgtgg cagcctgcgg   8040
tgtagatgta caccaggcaa gaatctgtgt caggccccac ctgcgatatg ggttgtgtgg   8100
attggcagaa gctgcctacc aggctccagc ttgtttcccc tgtgcttcct tccctgctgc   8160
tgagatcctg ggcaccacag taggagttgg agcgctgacc acagagatga tcaaggggct   8220
ggagcacttc ccctatgagg acaggctgag ggagctgggc ttattcagcc tggagaagag   8280
aaggctgcgc ggtgatccca ttgcagcctt tcagtccctg aagggagcct ataaacagga   8340
agggagtaaa ctctttgaaa gggtagataa cagcaggaca aggggcaacg gttttaagtt   8400
gaaagaggga agatttaggt tggatgttag gggaaagttc tttaccagga gagtggtgag   8460
gtgctggaac aggctgccca gagaggttgt ggatgctccg tccctggagg tgttcaaggc   8520
caggttggat ggggccctgg gcaacctggt ctagtaaatg gggatgttgg tggccctgcc   8580
cagcaggggg gttggagatt cgtgatcctc gaggtccctt ccaacccagg ccattctgtg   8640
attctgtcat ttctgtcatt tatttttcaa tagagcctgt tttttgtact ggcaagacct   8700
acctgtatga ctacttaatt aagtagtcat acaggtaggt cttgccagta caaaaaaacag   8760
gctctattga aaaataaatg acagaaatga cagaatcaca gaatggcctg ggttggaagg   8820
gacctcgagg atcacgaatc tccaaccccc ctgctgggca gggccaccaa catccccatt   8880
tactagacca ggttgcccag ggccccatcc aacctggcct tgaacacctc cagggacgga   8940
gcatccacaa cctctctggg cagcctgttc cagcacctca ccactctcct ggtaaagaac   9000
tttcccctaa catccaacct aaatcttccc tctttcaact taaaaccgtt gccccttgtc   9060
ctgctgttat ctaccctttc aaagagttta ctcccttcct gtttataggc tyccttcagg   9120
gactgaaagg ctgcaatggg atcaccgcgc agccttctct tctccaggct gaataagccc   9180
agctccctca gcctgtcctc ataggggaag tgctccagcc ccttgatcat ctctgtggtc   9240
agcgctccaa ctcctactgt ggtgcccagg atctcagcag cagggaagga agcacagggg   9300
aaacaagctg gagcctggta ggcagcttct gccaatccac acaacccata tcgcaggtgg   9360
ggcctgacac agattcttgc ctggtgtaca tctacaccgc aggctgccac agcctcgagt   9420
ctacaaaacg tggggtgaag agaagcaatg cagacatcct cttgccacag tcagagaaag   9480
aaggaagcct tcatcggttt ttccatgcac gtatttatta ggaaatcaga taattatagg   9540
caattagaat agtttctata ataataaagt ttaatacttt aaattacttg ggaaaattcc   9600
acgcatcttt aagtgtttaa tttaacattt ctattgcttc ttaagatgag tcttcttaca   9660
ccacacaata aaaatgaaaa tgtttctgtc ttctccagtg ctgcaacgta ccgctgacgt   9720
ctcatttacc cggagacagg gagaggctct tctgcgtgta gtggttgtgc agagcctcat   9780
gcatcacgga gcatgagaag acgttcccct gctgccacct gctcttgtcc acggtgagct   9840
tgctgtagag gaagaaggag ccgtcggagt ccagcacggg aggcgtggtc ttgtagttgt   9900
tctccggctg cccattgctc tcccactcca cggcgatgtc gctgggatag aagcctttga   9960
ccaggcaggt caggctgacc tggttcttgg tcagctcatc ccgggatggg ggcagggtgt  10020
acacctgtgg ttctcggggc tgccctttgg ctttggagat ggttttctcg atgggggctg  10080
```

```
ggagggcttt gttggagacc ttgcacttgt actccttgcc attcagccag tcctggtgca  10140
ggacggtgag gacgctgacc acacggtacg tgctgttgta ctgctcctcc cgcggctttg  10200
tcttggcatt atgcacctcc acgccgtcca cgtaccagtt gaacttgacc tcagggtctt  10260
cgtggctcac gtccaccacc acgcatgtga cctcaggggt ccgggagatc atgagggtgt  10320
ccttgggttt tgggggggaag aggaagactg acggtccccc caggagttca ggtgctgggc  10380
acggtgggca tgtgtgagtt ttgtcacaag atttgggctc aactttcttg tccaccttgg  10440
tgttgctggg cttgtgattc acgttgcaga tgtaggtctg ggtgcccaag ctgctggagg  10500
gcacggtcac cacgctgctg agggagtaga gtcctgagga ctgtaggaca gccgggaagg  10560
tgtgcacgcc gctggtcagg gcgcctgagt tccacgacac cgtcaccggt tcggggaagt  10620
agtccttgac caggcagccc agggccgctg tgcccccaga ggtgctcttg gaggagggtg  10680
ccagggggaa gaccgatggg cccttggtgg aggctgagga gacggtgacc agggttccct  10740
ggccccaatt cgggggaggg ataactcccc caaatgttat cataatcccc gtggtacagt  10800
aatatacggc tgtgtcctcg gctttcaggc tattcatttg cagatataac gtgtttttg  10860
aatcatctct tgagatggtg aatctgcctt tcacgggtgc agcatagtct gttgtcccac  10920
catcaatttt gcttttaata cggccgaccc actccagccc cttccctgga gcctggcgga  10980
cccagctcat ccaggcgttt ctgaaagtga atccagaggc tgcacaggag actctaaggg  11040
acccccccgg ctttaccaag cctccccccg actcctgcag ctgcacctgc tggctgccta  11100
caagggtgag cactaatgcc agtatgatcc ccctcatagc gatatcgacg gtgactgcag  11160
aaaagaccca tggaaaggaa cagtctgtta gtctgtcagc tattatgtct ggtggcgcgc  11220
gcggcagcaa cgagtactgc tcagactaca ctgccctcca ccgttaacag caccgcaacg  11280
ggagttacct ctgactctta tcagaataca acaactcagc tgcctgcatc ttcttctgcc  11340
gctgccttaa gtcttccatc tgcgtcagcc gtgcgagccc aatctccacg ctcattttca  11400
gacacatacc ctaccgccac ggccttgtgc ggcacactgg tggtggtggg cattgtgctg  11460
tgcctaagtc tggcctccac tgttaggagc aaggagctgc cgagcgacca tgagccgctg  11520
gaggcatggg accagggctc ggatgtggaa gctccgccgc taccggagaa gagcccatgt  11580
ccggaacacg tacccgagat tcgcgtggag atcccacgct atgtttaata aaaactgcgg  11640
gcacggggga cggcgttgtt gtatatgtga atttgtaaat aataaatggg accccatcct  11700
gtaaaaatac agagtccgtg tcagtctctg aaggacagag tattggcata tagccaatag  11760
agatagttgt ggcaaagagc catgttatgg attagtaatg gaaagtatcg tcaccaatag  11820
gggagtggtc aataatggtc aataacccac acctataggc taagctatac catcacctat  11880
agcataagga agcgggggtg tataggcccc aagccaaaaa cagtatagca tgcataagag  11940
ccaaaggggt gtgcctatag agtctatagg cggtacttac gtcactcttg gcacggggaa  12000
tccgcgttcc aatgcaccgt tcccggccgc ggaggctgga tcggtcccgg tgtcttctat  12060
ggaggtcaaa acagcgtgga tggcgtctcc aggcgatctg acggttcact aaacgagctc  12120
tgcttatata gacctcccac cgtacacgcc taccgcccat ttgcgtcaat ggggcggagt  12180
tgttacgaca ttttggaaag tcccgttgat tttggtgcca aaacaaactc ccattgacgt  12240
caatggggtg gagacttgga aatccccgtg agtcaaaccg ctatccacgc ccattgatgt  12300
actgccaaaa ccgcatcacc atggtaatag cgatgactaa tacgtagatg tactgccaag  12360
taggaaagtc ccataaggtc atgtactggg cataatgcca ggcgggccat ttaccgtcat  12420
tgacgtcaat agggggcgta cttggcatat gatacacttg atgtactgcc aagtgggcag  12480
```

```
tttaccgtaa atactccacc cattgacgtc aatggaaagt ccctattggc gttactatgg  12540
gaacatacgt cattattgac gtcaatgggc gggggtcgtt gggcggtcag ccaggcgggc  12600
catttaccgt aagttatgta acgcggaact ccatatatgg gctatgaact aatgaccccg  12660
taattgatta ctattaataa ctagtcaata atcaatgtca acatggcggt aatgttggac  12720
atgagccaat ataaatgtac atattatgat atggatacaa cgtatgcaat ggccacgtac  12780
gcaattggtt taaacgcgta agcttaaaag attgaagcac agacacaggc cacaccagag  12840
cctacacctg ctgcaataag tggtgctata gaaaggattc aggaactaac aagtgcataa  12900
tttacaaata gagatgcttt atcatacttt gcccaacatg ggaaaaaaga catcccatga  12960
gaatatccaa ctgaggaact tctctgtttc atagtaactc atctactact gctaagatgg  13020
tttgaaaagt acccagcagg tgagatgtgt tccgggaggt ggctgtgtgg cagcgtgtgg  13080
gaacacgaca caaagcaccc cacccctatc tgcaatgctc actgcaaggc agtgccgtaa  13140
acagctgcaa caggcatcca ggcatcactt ctgcataaac gctgtgactc gttagcatgc  13200
tgcaactgtg tttaaaacct atgcactccg ttaccaaaat aatttaagtc ccaaacaaat  13260
ccatgcagct tgcttcctat gccaaaatat tttagaaagt attcattctt ctttaagaat  13320
atgcacgtgg atctgcactt ccctgggatc tgaagcgatt tatacctcag tgcagaagca  13380
gtttagtgtc ctggatctcg ggaaggcagc agccaaacgt gcccgtttta catttaaacc  13440
catgtgacaa cccgccttac tgagcatcgc tctaggaaat ttaaggctgt atccttacaa  13500
cacaagaacc aacgacagac tgcatataaa attctataaa taaaaatagg agtgaagtct  13560
gtttgacctg tacacacaga gcatagagat aaaaaaaaaa ggaaatcagg aattacgtat  13620
ttctataaat gccatatatt tttactagaa acacagatga caagtatata caacatgtaa  13680
atccgaagtt atcaacatgt taactaggaa aacatttaca agcatttggg tatgcaacta  13740
gatcatcagg taaaaaatcc cattagaaaa atctaagcct caccagtttc aaaggaaaaa  13800
aaccagagaa cgctcactac ttcaaaggga aaaaataaag catcaagctg gcctaaactt  13860
aataaggtat ctcgtgtaac aacagctatc caagctttca agccacacta taaataaaaa  13920
cctcaagttc cgatcaacgt tttccataat gcaatcagaa ccaaaggcat tggcacagaa  13980
agcaaaaagg gaatgaaaga aaagggctgt acagtttcca aaaggttctt cttttgaaga  14040
aatgtttctg acctgtcaaa acatacagtc cagtagaaaa tttactaaga aaaaagaaca  14100
ccttacttaa aaaaaaaaaa aaaaaaaaaa aaaacaggca aaaaaacctc tcctgtcact  14160
gagctgccac caccccaacc accacctgct gtgggctttg tctcccaaga caaaggacac  14220
acagccttat ccaatattca acattactta taaaaacact gatcagaaga aataccaagt  14280
atttcctcac agactgttat acagactgtt atatcctttc atcggcaaga agagatgaaa  14340
tacaacagag tgaatatcaa agaaggcggc aggagccacc gtggcaccat caccgggcag  14400
tgcagtgccc agctgccgtt tcctgagcac gcacaggaag ccgtcagtca catgtaataa  14460
accaaaacct ggtacagtta tattatggat ccgggcccct ccgggatcat atgacaagat  14520
gtgtatccac cttaacttaa tgatttttac caaaatcatt aggggattca tcagtgctca  14580
gggtcaacga gaattaacat tccgtcagga aagcttgaat tcagcttttg ttccctttag  14640
tgagggttaa ttgcgcgctt ggcgtaatca tggtcatagc tgtttcctgt gtgaaattgt  14700
tatccgctca caattccaca caacatacga gccggaagca taaagtgtaa agcctggggt  14760
gcctaatgag tgagctaact cacattaatt gcgttgcgct cactgcccgc tttccagtcg  14820
```

```
ggaaacctgt cgtgccagct gcattaatga atcggccaac gcgcggggag aggcggtttg  14880
cgtattgggc gctcttccgc ttcctcgctc actgactcgc tgcgctcggt cgttcggctg  14940
cggcgagcgg tatcagctca ctcaaaggcg gtaatacggt tatccacaga atcaggggat  15000
aacgcaggaa agaacatgtg agcaaaaggc cagcaaaagg ccaggaaccg taaaaaggcc  15060
gcgttgctgg cgtttttcca taggctccgc ccccctgacg agcatcacaa aaatcgacgc  15120
tcaagtcaga ggtggcgaaa cccgacagga ctataaagat accaggcgtt tccccctgga  15180
agctccctcg tgcgctctcc tgttccgacc ctgccgctta ccggatacct gtccgccttt  15240
ctcccttcgg gaagcgtggc gctttctcat agctcacgct gtaggtatct cagttcggtg  15300
taggtcgttc gctccaagct gggctgtgtg cacgaacccc ccgttcagcc cgaccgctgc  15360
gccttatccg gtaactatcg tcttgagtcc aacccggtaa gacacgactt atcgccactg  15420
gcagcagcca ctggtaacag gattagcaga gcgaggtatg taggcggtgc tacagagttc  15480
ttgaagtggt ggcctaacta cggctacact agaagaacag tatttggtat ctgcgctctg  15540
ctgaagccag ttaccttcgg aaaaagagtt ggtagctctt gatccggcaa acaaaccacc  15600
gctggtagcg gtggtttttt tgtttgcaag cagcagatta cgcgcagaaa aaaaggatct  15660
caagaagatc ctttgatctt ttctacgggg tctgacgctc agtggaacga aaactcacgt  15720
taagggattt tggtcatgag attatcaaaa aggatcttca cctagatcct tttaaattaa  15780
aaatgaagtt ttaaatcaat ctaaagtata tatgagtaaa cttggtctga cagttaccaa  15840
tgcttaatca gtgaggcacc tatctcagcg atctgtctat ttcgttcatc catagttgcc  15900
tgactccccg tcgtgtagat aactacgata cgggagggct taccatctgg ccccagtgct  15960
gcaatgatac cgcgagaccc acgctcaccg gctccagatt tatcagcaat aaaccagcca  16020
gccggaaggg ccgagcgcag aagtggtcct gcaactttat ccgcctccat ccagtctatt  16080
aattgttgcc gggaagctag agtaagtagt tcgccagtta atagtttgcg caacgttgtt  16140
gccattgcta caggcatcgt ggtgtcacgc tcgtcgtttg gtatggcttc attcagctcc  16200
ggttcccaac gatcaaggcg agttacatga tcccccatgt tgtgcaaaaa agcggttagc  16260
tccttcggtc ctccgatcgt tgtcagaagt aagttggccg cagtgttatc actcatggtt  16320
atggcagcac tgcataattc tcttactgtc atgccatccg taagatgctt ttctgtgact  16380
ggtgagtact caaccaagtc attctgagaa tagtgtatgc ggcgaccgag ttgctcttgc  16440
ccggcgtcaa tacgggataa taccgcgcca catagcagaa ctttaaaagt gctcatcatt  16500
ggaaaacgtt cttcggggcg aaaactctca aggatcttac cgctgttgag atccagttcg  16560
atgtaaccca ctcgtgcacc caactgatct tcagcatctt ttactttcac cagcgtttct  16620
gggtgagcaa aaacaggaag gcaaaatgcc gcaaaaaagg gaataagggc gacacggaaa  16680
tgttgaatac tcatactctt cctttttcaa tattattgaa gcatttatca gggttattgt  16740
ctcatgagcg gatacatatt tgaatgtatt tagaaaaata aacaaatagg ggttccgcgc  16800
acatttcccc gaaaagtgcc ac                                            16822
```

<210> SEQ ID NO 20
<211> LENGTH: 18140
<212> TYPE: DNA
<213> ORGANISM: Artificial Sequence
<220> FEATURE:
<223> OTHER INFORMATION: Synthetic construct

<400> SEQUENCE: 20

```
ctgacgcgcc ctgtagcggc gcattaagcg cggcgggtgt ggtggttacg cgcagcgtga     60
```

```
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
```

```
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
tttttttgcc tgtttttttt tttttttttt ttttttttaa gtaaggtgtt ctttttttctt   4080
agtaaatttt ctactggact gtatgttttg acaggtcaga aacatttctt caaaagaaga   4140
accttttgga aactgtacag cccttttctt tcattccctt tttgctttct gtgccaatgc   4200
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt attttttccc tttgaagtag tgagcgttct ctggtttttt tcctttgaaa   4380
ctggtgaggc ttagattttt ctaatgggat tttttacctg atgatctagt tgcataccca   4440
aatgcttgta aatgttttcc tagttaacat gttgataact tcggatttac atgttgtata   4500
tacttgtcat ctgtgtttct agtaaaaata tatggcattt atagaaatac gtaattcctg   4560
atttcctttt ttttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
```

```
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
gttcctgaat cctttctata gcaccactta ttgcagcagg tgtaggctct ggtgtggcct   5340
gtgtctgtgc ttcaatcttt taagcttctc gagggcgcgc ctggccattg catacgttgt   5400
atccatatca taatatgtac atttatattg gctcatgtcc aacattaccg ccatgttgac   5460
attgattatt gactagttat taatagtaat caattacggg gtcattagtt catagcccat   5520
atatggagtt ccgcgttaca taacttacgg taaatggccc gcctggctga ccgcccaacg   5580
acccccgccc attgacgtca ataatgacgt atgttcccat agtaacgcca atagggactt   5640
tccattgacg tcaatgggtg gagtatttac ggtaaactgc ccacttggca gtacatcaag   5700
tgtatcatat gccaagtacg ccccctattg acgtcaatga cggtaaatgg cccgcctggc   5760
attatgccca gtacatgacc ttatgggact ttcctacttg gcagtacatc tacgtattag   5820
tcatcgctat taccatggtg atgcggtttt ggcagtacat caatgggcgt ggatagcggt   5880
ttgactcacg gggatttcca agtctccacc ccattgacgt caatgggagt ttgttttggc   5940
accaaaatca acgggacttt ccaaaatgtc gtaacaactc cgccccattg acgcaaatgg   6000
gcggtaggcg tgtacggtgg gaggtctata taagcagagc tcgtttagtg aaccgtcaga   6060
tcgcctggag acgccatcca cgctgttttg acctccatag aagacaccgg gaccgatcca   6120
gcctccgcgg ccgggaacgg tgcattggaa cgcggattcc ccgtgccaag agtgacgtaa   6180
gtaccgccta tagactctat aggcacaccc ctttggctct tatgcatgct atactgtttt   6240
tggcttgggg cctatacacc cccgcttcct tatgctatag gtgatggtat agcttagcct   6300
ataggtgtgg gttattgacc attattgacc actcccctat tggtgacgat actttccatt   6360
actaatccat aacatggctc tttgccacaa ctatctctat tggctatatg ccaatactct   6420
gtccttcaga gactgacacg gactctgtat ttttacagga tggggtccca tttattattt   6480
acaaattcac atatacaaca acgccgtccc ccgtgcccgc agtttttatt aaacatagcg   6540
tgggatctcc acgcgaatct cgggtacgtg ttccggacat gggctcttct ccggtagcgg   6600
cggagcttcc acatccgagc cctggtccca tgcctccagc ggctcatggt cgctcggcag   6660
ctccttgctc ctaacagtgg aggccagact taggcacagc acaatgccca ccaccaccag   6720
tgtgccgcac aaggccgtgg cggtagggta tgtgtctgaa aatgagcgtg gagattgggc   6780
tcgcacggct gacgcagatg gaagacttaa ggcagcggca gaagaagatg caggcagctg   6840
agttgttgta ttctgataag agtcagaggt aactcccgtt gcggtgctgt taacggtgga   6900
gggcagtgta gtctgagcag tactcgttgc tgccgcgcgc gccaccagac ataatagctg   6960
acagactaac agactgttcc tttccatggg tcttttctgc agtcaccgtc gatatcgcta   7020
tgagggggat catactggca ttagtgctca cccttgtagg cagccagtcc tatgagctca   7080
cacagccacc ctcggtgtca gtgtccccag gacaaacggc caggatcacc tgctctggag   7140
```

```
atgcattgcc agaaaaatat gtttattggt accagcagaa gtcaggccag gcccctgtgg   7200
tggtcatcta tgaggacagc aaacgaccct ccgggatccc tgagagattc tctggctcca   7260
gctcagggac aatggccacc ttgactatca gtggggccca ggtggaagat gaaggtgact   7320
actactgtta ctcaactgac agcagtggtt atcataggga ggtgttcggc ggagggacca   7380
agctgaccgt cctaggtcag cccaaggctg ccccctcggt cactctgttc ccaccctcct   7440
ctgaggagct tcaagccaac aaggccacac tggtgtgtct cataagtgac tcctacccgg   7500
gagccgtgac agtggcctgg aaggcagata gcagccccgt caaggcggga gtggagacca   7560
ccacaccctc caaacaaagc aacaacaagt acgcggccag cagctacctg agcctgacgc   7620
ctgagcagtg gaagtcccac aaaagctaca gctgccaggt cacgcatgaa gggagcaccg   7680
tggagaagac agtggcccct gcagaatgtt catgagacgt cagcggtacg ttgcagcact   7740
ggagaagaca gaaacatttt catttttatt gtgtggtgta agaagactca tcttaagaag   7800
caatagaaat gttaaattaa acacttaaag atgcgtggaa ttttcccaag taatttaaag   7860
tattaaactt tattattata gaaactattc taattgccta taattatctg atttcctaat   7920
aaatacgtgc atggaaaaac cgatgaaggc ttccttcttt ctctgactgt ggcaagagga   7980
tgtctgcatt gcttctcttc accccacgtt ttgtagactc gaggctgtgg cagcctgcgg   8040
tgtagatgta caccaggcaa gaatctgtgt caggccccac ctgcgatatg ggttgtgtgg   8100
attggcagaa gctgcctacc aggctccagc ttgtttcccc tgtgcttcct tccctgctgc   8160
tgagatcctg ggcaccacag taggagttgg agcgctgacc acagagatga tcaaggggct   8220
ggagcacttc ccctatgagg acaggctgag ggagctgggc ttattcagcc tggagaagag   8280
aaggctgcgc ggtgatccca ttgcagcctt tcagtccctg aagggagcct ataaacagga   8340
agggagtaaa ctctttgaaa gggtagataa cagcaggaca aggggcaacg gttttaagtt   8400
gaaagaggga agatttaggt tggatgttag gggaaagttc tttaccagga gagtggtgag   8460
gtgctggaac aggctgccca gagaggttgt ggatgctccg tccctggagg tgttcaaggc   8520
caggttggat ggggccctgg gcaacctggt ctagtaaatg ggatgttggt ggccctgcc    8580
cagcaggggg gttggagatt cgtgatcctc gaggtccctt ccaacccagg ccattctgtg   8640
attctgtcat ttctgtcatt tatttttcaa tagagcctgt tttttgtact ggcaagacct   8700
acctgtatga ctacttaatt aagtagtcat acaggtaggt cttgccagta caaaaaacag   8760
gctctattga aaaataaatg acagaaatga cagaatcaca gaatggcctg ggttggaagg   8820
gacctcgagg atcacgaatc tccaaccccc ctgctgggca gggccaccaa catccccatt   8880
tactagacca ggttgcccag ggccccatcc aacctggcct tgaacacctc cagggacgga   8940
gcatccacaa cctctctggg cagcctgttc cagcacctca ccactctcct ggtaaagaac   9000
tttcccctaa catccaacct aaatcttccc tctttcaact taaaaccgtt gccccttgtc   9060
ctgctgttat ctaccctttc aaagagttta ctcccttcct gtttataggc tyccttcagg   9120
gactgaaagg ctgcaatggg atcaccgcgc agccttctct tctccaggct gaataagccc   9180
agctccctca gcctgtcctc ataggggaag tgctccagcc ccttgatcat ctctgtggtc   9240
agcgctccaa ctcctactgt ggtgcccagg atctcagcag cagggaagga agcacagggg   9300
aaacaagctg gagcctggta ggcagcttct gccaatccac acaacccata tcgcaggtgg   9360
ggcctgacac agattcttgc ctggtgtaca tctacaccgc aggctgccac agcctcgagt   9420
ctacaaaacg tggggtgaag agaagcaatg cagacatcct cttgccacag tcagagaaag   9480
aaggaagcct tcatcggttt ttccatgcac gtatttatta ggaaatcaga taattatagg   9540
```

```
caattagaat agtttctata ataataaagt ttaatacttt aaattacttg ggaaaattcc   9600
acgcatcttt aagtgtttaa tttaacattt ctattgcttc ttaagatgag tcttcttaca   9660
ccacacaata aaaatgaaaa tgtttctgtc ttctccagtg ctgcaacgta ccgctgacgt   9720
ctcatttacc cggagacagg gagaggctct tctgcgtgta gtggttgtgc agagcctcat   9780
gcatcacgga gcatgagaag acgttcccct gctgccacct gctcttgtcc acggtgagct   9840
tgctgtagag gaagaaggag ccgtcggagt ccagcacggg aggcgtggtc ttgtagttgt   9900
tctccggctg cccattgctc tcccactcca cggcgatgtc gctgggatag aagcctttga   9960
ccaggcaggt caggctgacc tggttcttgg tcagctcatc ccgggatggg ggcagggtgt  10020
acacctgtgg ttctcggggc tgccctttgg ctttggagat ggttttctcg atgggggctg  10080
ggagggcttt gttggagacc ttgcacttgt actccttgcc attcagccag tcctggtgca  10140
ggacggtgag gacgctgacc acacggtacg tgctgttgta ctgctcctcc cgcggctttg  10200
tcttggcatt atgcacctcc acgccgtcca cgtaccagtt gaacttgacc tcagggtctt  10260
cgtggctcac gtccaccacc acgcatgtga cctcaggggt ccgggagatc atgagggtgt  10320
ccttgggttt tggggggaag aggaagactg acggtccccc caggagttca ggtgctgggc  10380
acggtgggca tgtgtgagtt ttgtcacaag atttgggctc aactttcttg tccaccttgg  10440
tgttgctggg cttgtgattc acgttgcaga tgtaggtctg ggtgcccaag ctgctggagg  10500
gcacggtcac cacgctgctg agggagtaga gtcctgagga ctgtaggaca gccgggaagg  10560
tgtgcacgcc gctggtcagg gcgcctgagt tccacgacac cgtcaccggt tcggggaagt  10620
agtccttgac caggcagccc agggccgctg tgcccccaga ggtgctcttg gaggagggtg  10680
ccagggggaa gaccgatggg cccttggtgg aggctgagga gacggtgacc agggttccct  10740
ggccccaatt cgggggaggg ataactcccc caaatgttat cataatcccc gtggtacagt  10800
aatatacggc tgtgtcctcg gctttcaggc tattcatttg cagatataac gtgtttttg  10860
aatcatctct tgagatggtg aatctgcctt tcacgggtgc agcatagtct gttgtcccac  10920
catcaatttt gcttttaata cggccgaccc actccagccc cttccctgga gcctggcgga  10980
cccagctcat ccaggcgttt ctgaaagtga atccagaggc tgcacaggag actctaaggg  11040
acccccccgg ctttaccaag cctccccccg actcctgcag ctgcacctgc tggctgccta  11100
caagggtgag cactaatgcc agtatgatcc ccctcatagc gatatcgacg gtgactgcag  11160
aaaagaccca tggaaaggaa cagtctgtta gtctgtcagc tattatgtct ggtggcgcgc  11220
gcggcagcaa cgagtactgc tcagactaca ctgccctcca ccgttaacag caccgcaacg  11280
ggagttacct ctgactctta tcagaataca acaactcagc tgcctgcatc ttcttctgcc  11340
gctgccttaa gtcttccatc tgcgtcagcc gtgcgagccc aatctccacg ctcattttca  11400
gacacatacc ctaccgccac ggccttgtgc ggcacactgg tggtggtggg cattgtgctg  11460
tgcctaagtc tggcctccac tgttaggagc aaggagctgc cgagcgacca tgagccgctg  11520
gaggcatggg accagggctc ggatgtggaa gctccgccgc taccggagaa gagcccatgt  11580
ccggaacacg tacccgagat tcgcgtggag atcccacgct atgtttaata aaaactgcgg  11640
gcacggggga cggcgttgtt gtatatgtga atttgtaaat aataaatggg accccatcct  11700
gtaaaaatac agagtccgtg tcagtctctg aaggacagag tattggcata tagccaatag  11760
agatagttgt ggcaaagagc catgttatgg attagtaatg gaaagtatcg tcaccaatag  11820
gggagtggtc aataatggtc aataacccac acctataggc taagctatac catcacctat  11880
```

```
agcataagga agcgggggtg tataggcccc aagccaaaaa cagtatagca tgcataagag  11940
ccaaaggggt gtgcctatag agtctatagg cggtacttac gtcactcttg gcacggggaa  12000
tccgcgttcc aatgcaccgt tcccggccgc ggaggctgga tcggtcccgg tgtcttctat  12060
ggaggtcaaa acagcgtgga tggcgtctcc aggcgatctg acggttcact aaacgagctc  12120
tgcttatata gacctcccac cgtacacgcc taccgcccat ttgcgtcaat ggggcggagt  12180
tgttacgaca ttttggaaag tcccgttgat tttggtgcca aaacaaactc ccattgacgt  12240
caatggggtg gagacttgga aatccccgtg agtcaaaccg ctatccacgc ccattgatgt  12300
actgccaaaa ccgcatcacc atggtaatag cgatgactaa tacgtagatg tactgccaag  12360
taggaaagtc ccataaggtc atgtactggg cataatgcca ggcgggccat ttaccgtcat  12420
tgacgtcaat agggggcgta cttggcatat gatacacttg atgtactgcc aagtgggcag  12480
tttaccgtaa atactccacc cattgacgtc aatggaaagt ccctattggc gttactatgg  12540
gaacatacgt cattattgac gtcaatgggc gggggtcgtt gggcggtcag ccaggcgggc  12600
catttaccgt aagttatgta acgcggaact ccatatatgg gctatgaact aatgaccccg  12660
taattgatta ctattaataa ctagtcaata atcaatgtca acatggcggt aatgttggac  12720
atgagccaat ataaatgtac atattatgat atggatacaa cgtatgcaat ggccacgtac  12780
ggtaacctga ggctatggca gggcctgccg ccccgacgtt ggctgcgagc cctgggcctt  12840
cacccgaact tgggggtgg ggtggggaaa aggaagaaac gcgggcgtat tggccccaat  12900
ggggtctcgg tggggtatcg acagagtgcc agccctggga ccgaaccccg cgtttatgaa  12960
caaacgaccc aacaccgtgc gttttattct gtctttttat tgccgtcata gcgcgggttc  13020
cttccggtat tgtctccttc cgtgtttcag ttagcctccc cctagggtgg gcgaagaact  13080
ccagcatgag atccgagctc aggatccgct agcgaattca ggtttaagca cctggtttgc  13140
gagtcatgca ccaagtgcgt gggccttctg gcacttccac atcagcagtc acagtgaagc  13200
ccaggcgttc atagaaaggc aggttgcgtg gagctgaggt ctccaggaaa gcaggcacac  13260
ctgcacgttc agctgcttcc acaccaggca gcaccactgc agagcccagg cccttaccct  13320
ggtggtcagg gctcacaccc acagttgcca ggaaccaagc aggttctttt gggcggtgtg  13380
gtgccagcag accttccatc tgctgttgtg ctgccaggcg gctgccagac agttctgcca  13440
tgcgtgggcc aatctcagca aacactgcac cagcttcaac agattcaggg gtggtccaca  13500
ctgccacagc agcaccatca tctgccaccc acactttgcc aatgtccagg cccacacggg  13560
tcaggaacag ctcctgcagt tcagtcacac gttcaatgtg gcggtctggg tccacagtgt  13620
gacgggttgc agggtagtca gcaaatgcag cagccagggt gcgaactgca cgtggaacat  13680
catcacgagt tgccaggcga acagttggtt tgtattcagt catgacgatc ctcatcctgt  13740
ctcttgatcg atctttgcaa aagcctaggc ctccaaaaaa gcctcctcac tacttctgga  13800
atagctcaga ggccgaggcg gcctcggcct ctgcataaat aaaaaaaatt agtcagccat  13860
ggggcggaga atgggcggaa ctgggcggag ttaggggcgg gatgggcgga gttaggggcg  13920
ggactatggt tgctgactaa ttgagatgca tgctttgcat acttctgcct gctggggagc  13980
ctggggactt tccacacctg gttgctgact aattgagatg catgctttgc atacttctgc  14040
ctgctgggga gcctggggac tttccacacc ctaactgaca cacattccac agctggttct  14100
ttccgcctca gacgcgtaag cttaaaagat tgaagcacag acacaggcca caccagagcc  14160
tacacctgct gcaataagtg gtgctataga aaggattcag gaactaacaa gtgcataatt  14220
tacaaataga gatgctttat catactttgc ccaacatggg aaaaaagaca tcccatgaga  14280
```

```
atatccaact gaggaacttc tctgtttcat agtaactcat ctactactgc taagatggtt  14340
tgaaaagtac ccagcaggtg agatgtgttc cgggaggtgg ctgtgtggca gcgtgtggga  14400
acacgacaca aagcacccca cccctatctg caatgctcac tgcaaggcag tgccgtaaac  14460
agctgcaaca ggcatccagg catcacttct gcataaacgc tgtgactcgt tagcatgctg  14520
caactgtgtt taaaacctat gcactccgtt accaaaataa tttaagtccc aaacaaatcc  14580
atgcagcttg cttcctatgc caaaatattt tagaaagtat tcattcttct ttaagaatat  14640
gcacgtggat ctgcacttcc ctgggatctg aagcgattta tacctcagtg cagaagcagt  14700
ttagtgtcct ggatctcggg aaggcagcag ccaaacgtgc ccgttttaca tttaaaccca  14760
tgtgacaacc cgccttactg agcatcgctc taggaaattt aaggctgtat ccttacaaca  14820
caagaaccaa cgacagactg catataaaat tctataaata aaaataggag tgaagtctgt  14880
ttgacctgta cacacagagc atagagataa aaaaaaaagg aaatcaggaa ttacgtattt  14940
ctataaatgc catatatttt tactagaaac acagatgaca agtatataca acatgtaaat  15000
ccgaagttat caacatgtta actaggaaaa catttacaag catttgggta tgcaactaga  15060
tcatcaggta aaaaatccca ttagaaaaat ctaagcctca ccagtttcaa aggaaaaaaa  15120
ccagagaacg ctcactactt caaagggaaa aaataaagca tcaagctggc ctaaacttaa  15180
taaggtatct cgtgtaacaa cagctatcca agctttcaag ccacactata aataaaaacc  15240
tcaagttccg atcaacgttt tccataatgc aatcagaacc aaaggcattg gcacagaaag  15300
caaaaaggga atgaaagaaa agggctgtac agtttccaaa aggttcttct tttgaagaaa  15360
tgtttctgac ctgtcaaaac atacagtcca gtagaaaatt tactaagaaa aaagaacacc  15420
ttacttaaaa aaaaaaaaaa aaaaaaaaaa aacaggcaaa aaaacctctc ctgtcactga  15480
gctgccacca ccccaaccac cacctgctgt gggctttgtc tcccaagaca aaggacacac  15540
agccttatcc aatattcaac attacttata aaaacactga tcagaagaaa taccaagtat  15600
ttcctcacag actgttatac agactgttat atcctttcat cggcaagaag agatgaaata  15660
caacagagtg aatatcaaag aaggcggcag gagccaccgt ggcaccatca ccgggcagtg  15720
cagtgcccag ctgccgtttc ctgagcacgc acaggaagcc gtcagtcaca tgtaataaac  15780
caaaacctgg tacagttata ttatggatcc gggcccctcc gggatcatat gacaagatgt  15840
gtatccacct taacttaatg atttttacca aaatcattag gggattcatc agtgctcagg  15900
gtcaacgaga attaacattc cgtcaggaaa gcttgaattc agcttttgtt ccctttagtg  15960
agggttaatt gcgcgcttgg cgtaatcatg gtcatagctg tttcctgtgt gaaattgtta  16020
tccgctcaca attccacaca acatacgagc cggaagcata aagtgtaaag cctggggtgc  16080
ctaatgagtg agctaactca cattaattgc gttgcgctca ctgcccgctt tccagtcggg  16140
aaacctgtcg tgccagctgc attaatgaat cggccaacgc gcggggagag gcggtttgcg  16200
tattgggcgc tcttccgctt cctcgctcac tgactcgctg cgctcggtcg ttcggctgcg  16260
gcgagcggta tcagctcact caaaggcggt aatacggtta tccacagaat caggggataa  16320
cgcaggaaag aacatgtgag caaaaggcca gcaaaaggcc aggaaccgta aaaaggccgc  16380
gttgctggcg tttttccata ggctccgccc ccctgacgag catcacaaaa atcgacgctc  16440
aagtcagagg tggcgaaacc cgacaggact ataaagatac caggcgtttc cccctggaag  16500
ctccctcgtg cgctctcctg ttccgaccct gccgcttacc ggatacctgt ccgcctttct  16560
cccttcggga agcgtggcgc tttctcatag ctcacgctgt aggtatctca gttcggtgta  16620
```

```
ggtcgttcgc tccaagctgg gctgtgtgca cgaacccccc gttcagcccg accgctgcgc  16680

cttatccggt aactatcgtc ttgagtccaa cccggtaaga cacgacttat cgccactggc  16740

agcagccact ggtaacagga ttagcagagc gaggtatgta ggcggtgcta cagagttctt  16800

gaagtggtgg cctaactacg gctacactag aagaacagta tttggtatct gcgctctgct  16860

gaagccagtt accttcggaa aaagagttgg tagctcttga tccggcaaac aaaccaccgc  16920

tggtagcggt ggtttttttg tttgcaagca gcagattacg cgcagaaaaa aaggatctca  16980

agaagatcct ttgatctttt ctacggggtc tgacgctcag tggaacgaaa actcacgtta  17040

agggattttg gtcatgagat tatcaaaaag gatcttcacc tagatccttt taaattaaaa  17100

atgaagtttt aaatcaatct aaagtatata tgagtaaact tggtctgaca gttaccaatg  17160

cttaatcagt gaggcaccta tctcagcgat ctgtctattt cgttcatcca tagttgcctg  17220

actccccgtc gtgtagataa ctacgatacg ggagggctta ccatctggcc ccagtgctgc  17280

aatgataccg cgagacccac gctcaccggc tccagattta tcagcaataa accagccagc  17340

cggaagggcc gagcgcagaa gtggtcctgc aactttatcc gcctccatcc agtctattaa  17400

ttgttgccgg gaagctagag taagtagttc gccagttaat agtttgcgca acgttgttgc  17460

cattgctaca ggcatcgtgg tgtcacgctc gtcgtttggt atggcttcat tcagctccgg  17520

ttcccaacga tcaaggcgag ttacatgatc ccccatgttg tgcaaaaaag cggttagctc  17580

cttcggtcct ccgatcgttg tcagaagtaa gttggccgca gtgttatcac tcatggttat  17640

ggcagcactg cataattctc ttactgtcat gccatccgta agatgctttt ctgtgactgg  17700

tgagtactca accaagtcat tctgagaata gtgtatgcgg cgaccgagtt gctcttgccc  17760

ggcgtcaata cgggataata ccgcgccaca tagcagaact ttaaaagtgc tcatcattgg  17820

aaaacgttct tcggggcgaa aactctcaag gatcttaccg ctgttgagat ccagttcgat  17880

gtaacccact cgtgcaccca actgatcttc agcatctttt actttcacca gcgtttctgg  17940

gtgagcaaaa acaggaaggc aaaatgccgc aaaaaaggga ataagggcga cacggaaatg  18000

ttgaatactc atactcttcc tttttcaata ttattgaagc atttatcagg gttattgtct  18060

catgagcgga tacatatttg aatgtattta gaaaaataaa caaatagggg ttccgcgcac  18120

atttccccga aaagtgccac                                               18140
```

```
<210> SEQ ID NO 21
<211> LENGTH: 19698
<212> TYPE: DNA
<213> ORGANISM: Artificial Sequence
<220> FEATURE:
<223> OTHER INFORMATION: Synthetic construct

<400> SEQUENCE: 21
```

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540
```

```
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
```

```
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
tttttttgcc tgtttttttt tttttttttt tttttttaa gtaaggtgtt ctttttttctt   4080
agtaaatttt ctactggact gtatgttttg acaggtcaga aacatttctt caaaagaaga   4140
acctttttgga aactgtacag cccttttctt tcattccctt tttgctttct gtgccaatgc   4200
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt attttttccc tttgaagtag tgagcgttct ctggtttttt tcctttgaaa   4380
ctggtgaggc ttagattttt ctaatgggat tttttacctg atgatctagt tgcatacca    4440
aatgcttgta aatgttttcc tagttaacat gttgataact tcggatttac atgttgtata   4500
tacttgtcat ctgtgtttct agtaaaaata tatggcattt atagaaatac gtaattcctg   4560
atttcctttt ttttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
```

```
gttcctgaat cctttctata gcaccactta ttgcagcagg tgtaggctct ggtgtggcct   5340
gtgtctgtgc ttcaatcttt taagcttctc gagggcgcgc cgtgctttac agaggtcaga   5400
atggtttctt tactgtttgt caattctatt atttcaatac agaacaatag cttctataac   5460
tgaaatatat ttgctattgt atattatgat tgtccctcga accatgaaca ctcctccagc   5520
tgaatttcac aattcctctg tcatctgcca ggccattaag ttattcatgg aagatctttg   5580
aggaacactg caagttcata tcataaacac atttgaaatt gagtattgtt ttgcattgta   5640
tggagctatg ttttgctgta tcctcagaaa aaaaagtttg ttataaagca ttcacaccca   5700
taaaaagata gatttaaata ttccaactat aggaaagaaa gtgcgtctgc tcttcactct   5760
agtctcagtt ggctccttca catgcatgct tctttatttc tcctattttg tcaagaaaat   5820
aataggtcac gtcttgttct cacttatgtc ctgcctagca tggctcagat gcacgttgta   5880
catacaagaa ggatcaaatg aaacagactt ctggtctgtt actacaacca tagtaataag   5940
cacactaact aataattgct aattatgttt tccatctcta aggttcccat atttttctgt   6000
tttcttaaag atcccattat ctggttgtaa ctgaagctca atggaacatg agcaatattt   6060
cccagtcttc tctcccatcc aacagtcctg atggattagc agaacaggca gaaaacacat   6120
tgttacccag aattaaaaac taatatttgc tctccattca atccaaaatg gacctattga   6180
aactaaaatc taacccaatc ccattaaatg atttctatgg cggaattctg gccattgcat   6240
acgttgtatc catatcataa tatgtacatt tatattggct catgtccaac attaccgcca   6300
tgttgacatt gattattgac tagttattaa tagtaatcaa ttacggggtc attagttcat   6360
agcccatata tggagttccg cgttacataa cttacggtaa atggcccgcc tggctgaccg   6420
cccaacgacc cccgcccatt gacgtcaata atgacgtatg ttcccatagt aacgccaata   6480
gggactttcc attgacgtca atgggtggag tatttacggt aaactgccca cttggcagta   6540
catcaagtgt atcatatgcc aagtacgccc cctattgacg tcaatgacgg taaatggccc   6600
gcctggcatt atgcccagta catgacctta tgggactttc ctacttggca gtacatctac   6660
gtattagtca tcgctattac catggtgatg cggttttggc agtacatcaa tgggcgtgga   6720
tagcggtttg actcacgggg atttccaagt ctccacccca ttgacgtcaa tgggagtttg   6780
ttttggcacc aaaatcaacg ggactttcca aaatgtcgta acaactccgc cccattgacg   6840
caaatgggcg gtaggcgtgt acggtgggag gtctatataa gcactcgagc tcgtttagtg   6900
aaccgtcaga tcgcctggag acgccatcca cgctgttttg acctccatag aagacaccgg   6960
gaccgatcca gcctccgcgg ccgggaacgg tgcattggaa cgcggattcc ccgtgccaag   7020
agtgacgtaa gtaccgccta tagactctat aggcacaccc ctttggctct tatgcatgct   7080
atactgtttt tggcttgggg cctatacacc cccgcttcct tatgctatag gtgatggtat   7140
agcttagcct ataggtgtgg gttattgacc attattgacc actcccctat tggtgacgat   7200
actttccatt actaatccat aacatggctc tttgccacaa ctatctctat tggctatatg   7260
ccaatactct gtccttcaga gactgacacg gactctgtat ttttacagga tggggtccca   7320
tttattattt acaaattcac atatacaaca acgccgtccc ccgtgcccgc agtttttatt   7380
aaacatagcg tgggatctcc acgcgaatct cgggtacgtg ttccggacat gggctcttct   7440
ccggtagcgg cggagcttcc acatccgagc cctggtccca tgcctccagc ggctcatggt   7500
cgctcggcag ctccttgctc ctaacagtgg aggccagact taggcacagc acaatgccca   7560
ccaccaccag tgtgccgcac aaggccgtgg cggtagggta tgtgtctgaa aatgagcgtg   7620
```

```
gagattgggc tcgcacggct gacgcagatg gaagacttaa ggcagcggca gaagaagatg   7680
caggcagctg agttgttgta ttctgataag agtcagaggt aactcccgtt gcggtgctgt   7740
taacggtgga gggcagtgta gtctgagcag tactcgttgc tgccgcgcgc gccaccagac   7800
ataatagctg acagactaac agactgttcc tttccatggg tcttttctgc agtcaccgtc   7860
gatatcgcta tgagggggat catactggca ttagtgctca cccttgtagg cagccagtcc   7920
tatgagctca cacagccacc ctcggtgtca gtgtccccag gacaaacggc caggatcacc   7980
tgctctggag atgcattgcc agaaaaatat gtttattggt accagcagaa gtcaggccag   8040
gcccctgtgg tggtcatcta tgaggacagc aaacgaccct ccgggatccc tgagagattc   8100
tctggctcca gctcagggac aatggccacc ttgactatca gtggggccca ggtggaagat   8160
gaaggtgact actactgtta ctcaactgac agcagtggtt atcataggga ggtgttcggc   8220
ggagggacca agctgaccgt cctaggtcag cccaaggctg ccccctcggt cactctgttc   8280
ccaccctcct ctgaggagct tcaagccaac aaggccacac tggtgtgtct cataagtgac   8340
tcctacccgg gagccgtgac agtggcctgg aaggcagata gcagccccgt caaggcggga   8400
gtggagacca ccacaccctc caaacaaagc aacaacaagt acgcggccag cagctacctg   8460
agcctgacgc ctgagcagtg gaagtcccac aaaagctaca gctgccaggt cacgcatgaa   8520
gggagcaccg tggagaagac agtggcccct gcagaatgtt catgagacgt caaagaagaa   8580
agctgaaaaa ctctgtccct tccaacaaga cccagagcac tgtagtatca ggggtaaaat   8640
gaaaagtatg ttatctgctg catccagact tcataaaagc tggagcttaa tctagaaaaa   8700
aaatcagaaa gaaattacac tgtgagaaca ggtgcaattc acttttcctt tacacagagt   8760
aatactggta actcatggat gaaggcttaa gggaatgaaa ttggactcac agtactgagt   8820
catcacactg aaaaatgcaa cctgatacat cagcagaagg tttatggggg aaaaatgcag   8880
ccttccaatt aagccagata tctgtatgac caagctgctc cagaattagt cactcaaaat   8940
ctctcagatt aaattatcaa ctgtcaccaa ccattcctat gctgacaagg caattgcttg   9000
ttctctgtgt tcctgatact acaaggctct tcctgacttc ctaaagatgc attataaaaa   9060
tcttataatt cacatttctc cctaaacttt gactcaatca tggtatgttg gcaaatatgg   9120
tatattacta ttcaaattgt tttccttgta cccatatgta atgggtcttg tgaatgtgct   9180
cttttgttcc tttaatcata ataaaaacat gtttaagcaa acacttttca cttgtagtat   9240
ttgaagtaca gcaaggttgt gtagcaggga aagaatgaca tgcagaggaa taagtatgga   9300
cacacaggct agcagcgact gtagaacaag tactaatggg tgagaagttg aacaagagtc   9360
ccctacagca acttaatcta ataagctagt ggtctacatc agctaaaaga gcatagtgag   9420
ggatgaaatt ggttctcctt tctaagcatc acctgggaca actcatctgg agcagtgtgt   9480
ccaatcttta attaaggcgc ctgcagggta acctgaggct atggcagggc ctgccgcccc   9540
gacgttggct gcgagccctg ggccttcacc cgaacttggg gggtggggtg gggaaaagga   9600
agaaacgcgg gcgtattggc cccaatgggg tctcggtggg gtatcgacag agtgccagcc   9660
ctgggaccga accccgcgtt tatgaacaaa cgacccaaca ccgtgcgttt tattctgtct   9720
ttttattgcc gtcatagcgc gggttccttc cggtattgtc tccttccgtg tttcagttag   9780
cctcccccta gggtgggcga agaactccag catgagatcc gagctcagga tccgctagcg   9840
aattcaggtt taagcacctg gtttgcgagt catgcaccaa gtgcgtgggc cttctggcac   9900
ttccacatca gcagtcacag tgaagcccag gcgttcatag aaaggcaggt tgcgtggagc   9960
tgaggtctcc aggaaagcag gcacacctgc acgttcagct gcttccacac caggcagcac  10020
```

```
cactgcagag cccaggccct taccctggtg gtcagggctc acacccacag ttgccaggaa  10080
ccaagcaggt tcttttgggc ggtgtggtgc cagcagacct tccatctgct gttgtgctgc  10140
caggcggctg ccagacagtt ctgccatgcg tgggccaatc tcagcaaaca ctgcaccagc  10200
ttcaacagat tcaggggtgg tccacactgc cacagcagca ccatcatctg ccacccacac  10260
tttgccaatg tccaggccca cacgggtcag gaacagctcc tgcagttcag tcacacgttc  10320
aatgtggcgg tctgggtcca cagtgtgacg ggttgcaggg tagtcagcaa atgcagcagc  10380
cagggtgcga actgcacgtg gaacatcatc acgagttgcc aggcgaacag ttggtttgta  10440
ttcagtcatg acgatcctca tcctgtctct tgatcgatct ttgcaaaagc ctaggcctcc  10500
aaaaaagcct cctcactact tctggaatag ctcagaggcc gaggcggcct cggcctctgc  10560
ataaataaaa aaaattagtc agccatgggg cggagaatgg gcggaactgg gcggagttag  10620
gggcgggatg ggcggagtta ggggcgggac tatggttgct gactaattga gatgcatgct  10680
ttgcatactt ctgcctgctg gggagcctgg ggactttcca cacctggttg ctgactaatt  10740
gagatgcatg ctttgcatac ttctgcctgc tggggagcct ggggactttc cacaccctaa  10800
ctgacacaca ttccacagct ggttctttcc gcctcagcgt acgagattgg acacactgct  10860
ccagatgagt tgtcccaggt gatgcttaga aaggagaacc aatttcatcc ctcactatgc  10920
tcttttagct gatgtagacc actagcttat tagattaagt tgctgtaggg gactcttgtt  10980
caacttctca cccattagta cttgttctac agtcgctgct agcctgtgtg tccatactta  11040
ttcctctgca tgtcattctt tccctgctac acaaccttgc tgtacttcaa atactacaag  11100
tgaaaagtgt ttgcttaaac atgtttttat tatgattaaa ggaacaaaag agcacattca  11160
caagacccat tacatatggg tacaaggaaa acaatttgaa tagtaatata ccatatttgc  11220
caacatacca tgattgagtc aaagtttagg gagaaatgtg aattataaga tttttataat  11280
gcatctttag gaagtcagga agagccttgt agtatcagga acacagagaa caagcaattg  11340
ccttgtcagc ataggaatgg ttggtgacag ttgataattt aatctgagag attttgagtg  11400
actaattctg gagcagcttg gtcatacaga tatctggctt aattggaagg ctgcattttt  11460
cccccataaa ccttctgctg atgtatcagg ttgcattttt cagtgtgatg actcagtact  11520
gtgagtccaa tttcattccc ttaagccttc atccatgagt taccagtatt actctgtgta  11580
aaggaaaagt gaattgcacc tgttctcaca gtgtaatttc tttctgattt tttttctaga  11640
ttaagctcca gcttttatga agtctggatg cagcagataa catacttttc attttacccc  11700
tgatactaca gtgctctggg tcttgttgga agggacagag tttttcagct ttcttctttg  11760
acgtctcatt tacccggaga cagggagagg ctcttctgcg tgtagtggtt gtgcagagcc  11820
tcatgcatca cggagcatga gaagacgttc ccctgctgcc acctgctctt gtccacggtg  11880
agcttgctgt agaggaagaa ggagccgtcg gagtccagca cgggaggcgt ggtcttgtag  11940
ttgttctccg gctgcccatt gctctcccac tccacggcga tgtcgctggg atagaagcct  12000
ttgaccaggc aggtcaggct gacctggttc ttggtcagct catcccggga tgggggcagg  12060
gtgtacacct gtggttctcg gggctgccct ttggctttgg agatggtttt ctcgatgggg  12120
gctgggaggg ctttgttgga gaccttgcac ttgtactcct tgccattcag ccagtcctgg  12180
tgcaggacgg tgaggacgct gaccacacgg tacgtgctgt tgtactgctc ctcccgcggc  12240
tttgtcttgg cattatgcac ctccacgccg tccacgtacc agttgaactt gacctcaggg  12300
tcttcgtggc tcacgtccac caccacgcat gtgacctcag ggtccgggga gatcatgagg  12360
```

```
gtgtccttgg gttttggggg gaagaggaag actgacggtc cccccaggag ttcaggtgct  12420
gggcacggtg ggcatgtgtg agttttgtca caagatttgg gctcaacttt cttgtccacc  12480
ttggtgttgc tgggcttgtg attcacgttg cagatgtagg tctgggtgcc caagctgctg  12540
gagggcacgg tcaccacgct gctgagggag tagagtcctg aggactgtag gacagccggg  12600
aaggtgtgca cgccgctggt cagggcgcct gagttccacg acaccgtcac cggttcgggg  12660
aagtagtcct tgaccaggca gcccagggcc gctgtgcccc cagaggtgct cttggaggag  12720
ggtgccaggg ggaagaccga tgggcccttg gtggaggctg aggagacggt gaccagggtt  12780
ccctggcccc aattcggggg agggataact cccccaaatg ttatcataat ccccgtggta  12840
cagtaatata cggctgtgtc ctcggctttc aggctattca tttgcagata taacgtgttt  12900
tttgaatcat ctcttgagat ggtgaatctg cctttcacgg gtgcagcata gtctgttgtc  12960
ccaccatcaa ttttgctttt aatacggccg acccactcca gccccttccc tggagcctgg  13020
cggacccagc tcatccaggc gtttctgaaa gtgaatccag aggctgcaca ggagactcta  13080
agggaccccc ccggctttac caagcctccc cccgactcct gcagctgcac ctgctggctg  13140
cctacaaggg tgagcactaa tgccagtatg atccccctca tagcgatatc gacggtgact  13200
gcagaaaaga cccatggaaa ggaacagtct gttagtctgt cagctattat gtctggtggc  13260
gcgcgcggca gcaacgagta ctgctcagac tacactgccc tccaccgtta acagcaccgc  13320
aacgggagtt acctctgact cttatcagaa tacaacaact cagctgcctg catcttcttc  13380
tgccgctgcc ttaagtcttc catctgcgtc agccgtgcga gcccaatctc cacgctcatt  13440
ttcagacaca taccctaccg ccacggcctt gtgcggcaca ctggtggtgg tgggcattgt  13500
gctgtgccta agtctggcct ccactgttag gagcaaggag ctgccgagcg accatgagcc  13560
gctggaggca tgggaccagg gctcggatgt ggaagctccg ccgctaccgg agaagagccc  13620
atgtccggaa cacgtacccg agattcgcgt ggagatccca cgctatgttt aataaaaact  13680
gcgggcacgg gggacggcgt tgttgtatat gtgaatttgt aaataataaa tgggacccca  13740
tcctgtaaaa atacagagtc cgtgtcagtc tctgaaggac agagtattgg catatagcca  13800
atagagatag ttgtggcaaa gagccatgtt atggattagt aatggaaagt atcgtcacca  13860
ataggggagt ggtcaataat ggtcaataac ccacacctat aggctaagct ataccatcac  13920
ctatagcata aggaagcggg ggtgtatagg ccccaagcca aaaacagtat agcatgcata  13980
agagccaaag ggtgtgcct atagagtcta taggcggtac ttacgtcact cttggcacgg  14040
ggaatccgcg ttccaatgca ccgttcccgg ccgcggaggc tggatcggtc ccggtgtctt  14100
ctatggaggt caaaacagcg tggatggcgt ctccaggcga tctgacggtt cactaaacga  14160
gctcgagtgc ttatatagac ctcccaccgt acacgcctac cgcccatttg cgtcaatggg  14220
gcggagttgt tacgacattt tggaaagtcc cgttgatttt ggtgccaaaa caaactccca  14280
ttgacgtcaa tggggtggag acttggaaat ccccgtgagt caaaccgcta tccacgccca  14340
ttgatgtact gccaaaaccg catcaccatg gtaatagcga tgactaatac gtagatgtac  14400
tgccaagtag gaaagtccca taaggtcatg tactgggcat aatgccaggc gggccattta  14460
ccgtcattga cgtcaatagg gggcgtactt ggcatatgat acacttgatg tactgccaag  14520
tgggcagttt accgtaaata ctccacccat tgacgtcaat ggaaagtccc tattggcgtt  14580
actatgggaa catacgtcat tattgacgtc aatgggcggg ggtcgttggg cggtcagcca  14640
ggcgggccat ttaccgtaag ttatgtaacg cggaactcca tatatgggct atgaactaat  14700
gaccccgtaa ttgattacta ttaataacta gtcaataatc aatgtcaaca tggcggtaat  14760
```

gttggacatg agccaatata aatgtacata ttatgatatg gatacaacgt atgcaatggc 14820
cagaattccg ccatagaaat catttaatgg gattgggtta gattttagtt tcaataggtc 14880
cattttggat tgaatggaga gcaaatatta gtttttaatt ctgggtaaca atgtgttttc 14940
tgcctgttct gctaatccat caggactgtt ggatgggaga gaagactggg aaatattgct 15000
catgttccat tgagcttcag ttacaaccag ataatgggat ctttaagaaa acagaaaaat 15060
atgggaacct tagagatgga aaacataatt agcaattatt agttagtgtg cttattacta 15120
tggttgtagt aacagaccag aagtctgttt catttgatcc ttcttgtatg tacaacgtgc 15180
atctgagcca tgctaggcag gacataagtg agaacaagac gtgacctatt attttcttga 15240
caaaatagga gaaataaaga agcatgcatg tgaaggagcc aactgagact agagtgaaga 15300
gcagacgcac tttctttcct atagttggaa tatttaaatc tatcttttta tgggtgtgaa 15360
tgctttataa caaacttttt tttctgagga tacagcaaaa catagctcca tacaatgcaa 15420
aacaatactc aatttcaaat gtgtttatga tatgaacttg cagtgttcct caaagatctt 15480
ccatgaataa cttaatggcc tggcagatga cagaggaatt gtgaaattca gctggaggag 15540
tgttcatggt tcgagggaca atcataatat acaatagcaa atatatttca gttatagaag 15600
ctattgttct gtattgaaat aatagaattg acaaacagta aagaaaccat tctgacctct 15660
gtaaagcaca cgcgtaagct taaaagattg aagcacagac acaggccaca ccagagccta 15720
cacctgctgc aataagtggt gctatagaaa ggattcagga actaacaagt gcataattta 15780
caaatagaga tgctttatca tactttgccc aacatgggaa aaaagacatc ccatgagaat 15840
atccaactga ggaacttctc tgtttcatag taactcatct actactgcta agatggtttg 15900
aaaagtaccc agcaggtgag atgtgttccg ggaggtggct gtgtggcagc gtgtgggaac 15960
acgacacaaa gcaccccacc cctatctgca atgctcactg caaggcagtg ccgtaaacag 16020
ctgcaacagg catccaggca tcacttctgc ataaacgctg tgactcgtta gcatgctgca 16080
actgtgttta aaacctatgc actccgttac caaaataatt taagtcccaa acaaatccat 16140
gcagcttgct tcctatgcca aaatatttta gaaagtattc attcttcttt aagaatatgc 16200
acgtggatct gcacttccct gggatctgaa gcgatttata cctcagtgca gaagcagttt 16260
agtgtcctgg atctcgggaa ggcagcagcc aaacgtgccc gttttacatt taaacccatg 16320
tgacaacccg ccttactgag catcgctcta ggaaatttaa ggctgtatcc ttacaacaca 16380
agaaccaacg acagactgca tataaaattc tataaataaa aataggagtg aagtctgttt 16440
gacctgtaca cacagagcat agagataaaa aaaaaaggaa atcaggaatt acgtatttct 16500
ataaatgcca tatattttta ctagaaacac agatgacaag tatatacaac atgtaaatcc 16560
gaagttatca acatgttaac taggaaaaca tttacaagca tttgggtatg caactagatc 16620
atcaggtaaa aaatcccatt agaaaaatct aagcctcacc agtttcaaag gaaaaaaacc 16680
agagaacgct cactacttca aagggaaaaa ataaagcatc aagctggcct aaacttaata 16740
aggtatctcg tgtaacaaca gctatccaag ctttcaagcc acactataaa taaaaacctc 16800
aagttccgat caacgttttc cataatgcaa tcagaaccaa aggcattggc acagaaagca 16860
aaaagggaat gaaagaaaag ggctgtacag tttccaaaag gttcttcttt tgaagaaatg 16920
tttctgacct gtcaaaacat acagtccagt agaaaattta ctaagaaaaa agaacacctt 16980
acttaaaaaa aaaaaaaaaa aaaaaaaaaa caggcaaaaa aacctctcct gtcactgagc 17040
tgccaccacc ccaaccacca cctgctgtgg gctttgtctc ccaagacaaa ggacacacag 17100

```
ccttatccaa tattcaacat tacttataaa aacactgatc agaagaaata ccaagtattt  17160
cctcacagac tgttatacag actgttatat cctttcatcg gcaagaagag atgaaataca  17220
acagagtgaa tatcaaagaa ggcggcagga gccaccgtgg caccatcacc gggcagtgca  17280
gtgcccagct gccgtttcct gagcacgcac aggaagccgt cagtcacatg taataaacca  17340
aaacctggta cagttatatt atggatccgg gcccctccgg gatcatatga caagatgtgt  17400
atccacctta acttaatgat ttttaccaaa atcattaggg gattcatcag tgctcagggt  17460
caacgagaat taacattccg tcaggaaagc ttgaattcag cttttgttcc ctttagtgag  17520
ggttaattgc gcgcttggcg taatcatggt catagctgtt tcctgtgtga aattgttatc  17580
cgctcacaat tccacacaac atacgagccg gaagcataaa gtgtaaagcc tggggtgcct  17640
aatgagtgag ctaactcaca ttaattgcgt tgcgctcact gcccgctttc cagtcgggaa  17700
acctgtcgtg ccagctgcat taatgaatcg gccaacgcgc ggggagaggc ggtttgcgta  17760
ttgggcgctc ttccgcttcc tcgctcactg actcgctgcg ctcggtcgtt cggctgcggc  17820
gagcggtatc agctcactca aaggcggtaa tacggttatc cacagaatca ggggataacg  17880
caggaaagaa catgtgagca aaaggccagc aaaaggccag gaaccgtaaa aaggccgcgt  17940
tgctggcgtt tttccatagg ctccgccccc ctgacgagca tcacaaaaat cgacgctcaa  18000
gtcagaggtg gcgaaacccg acaggactat aaagatacca ggcgtttccc cctggaagct  18060
ccctcgtgcg ctctcctgtt ccgaccctgc cgcttaccgg atacctgtcc gcctttctcc  18120
cttcgggaag cgtggcgctt tctcatagct cacgctgtag gtatctcagt tcggtgtagg  18180
tcgttcgctc caagctgggc tgtgtgcacg aaccccccgt tcagcccgac cgctgcgcct  18240
tatccggtaa ctatcgtctt gagtccaacc cggtaagaca cgacttatcg ccactggcag  18300
cagccactgg taacaggatt agcagagcga ggtatgtagg cggtgctaca gagttcttga  18360
agtggtggcc taactacggc tacactagaa gaacagtatt tggtatctgc gctctgctga  18420
agccagttac cttcggaaaa agagttggta gctcttgatc cggcaaacaa accaccgctg  18480
gtagcggtgg tttttttgtt tgcaagcagc agattacgcg cagaaaaaaa ggatctcaag  18540
aagatccttt gatcttttct acggggtctg acgctcagtg gaacgaaaac tcacgttaag  18600
ggattttggt catgagatta tcaaaaagga tcttcaccta gatcctttta aattaaaaat  18660
gaagttttaa atcaatctaa agtatatatg agtaaacttg gtctgacagt taccaatgct  18720
taatcagtga ggcacctatc tcagcgatct gtctatttcg ttcatccata gttgcctgac  18780
tccccgtcgt gtagataact acgatacggg agggcttacc atctggcccc agtgctgcaa  18840
tgataccgcg agacccacgc tcaccggctc cagatttatc agcaataaac cagccagccg  18900
gaagggccga gcgcagaagt ggtcctgcaa ctttatccgc ctccatccag tctattaatt  18960
gttgccggga agctagagta agtagttcgc cagttaatag tttgcgcaac gttgttgcca  19020
ttgctacagg catcgtggtg tcacgctcgt cgtttggtat ggcttcattc agctccggtt  19080
cccaacgatc aaggcgagtt acatgatccc ccatgttgtg caaaaaagcg gttagctcct  19140
tcggtcctcc gatcgttgtc agaagtaagt tggccgcagt gttatcactc atggttatgg  19200
cagcactgca taattctctt actgtcatgc catccgtaag atgcttttct gtgactggtg  19260
agtactcaac caagtcattc tgagaatagt gtatgcggcg accgagttgc tcttgcccgg  19320
cgtcaatacg ggataatacc gcgccacata gcagaacttt aaaagtgctc atcattggaa  19380
aacgttcttc ggggcgaaaa ctctcaagga tcttaccgct gttgagatcc agttcgatgt  19440
aacccactcg tgcacccaac tgatcttcag catcttttac tttcaccagc gtttctgggt  19500
```

gagcaaaaac aggaaggcaa aatgccgcaa aaaagggaat aagggcgaca cggaaatgtt 19560
gaatactcat actcttcctt tttcaatatt attgaagcat ttatcagggt tattgtctca 19620
tgagcggata catatttgaa tgtatttaga aaaataaaca aataggggtt ccgcgcacat 19680
ttccccgaaa agtgccac 19698

<210> SEQ ID NO 22
<211> LENGTH: 19380
<212> TYPE: DNA
<213> ORGANISM: Artificial Sequence
<220> FEATURE:
<223> OTHER INFORMATION: Synthetic construct

<400> SEQUENCE: 22
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggcatcaga ttggctattg gccattgcat acgttgtatc catatcataa 180
tatgtacatt tatattggct catgtccaac attaccgcca tgttgacatt gattattgac 240
tagttattaa tagtaatcaa ttacggggtc attagttcat agcccatata tggagttccg 300
cgttacataa cttacggtaa atggcccgcc tggctgaccg cccaacgacc cccgcccatt 360
gacgtcaata atgacgtatg ttcccatagt aacgccaata gggactttcc attgacgtca 420
atgggtggag tatttacggt aaactgccca cttggcagta catcaagtgt atcatatgcc 480
aagtacgccc cctattgacg tcaatgacgg taaatggccc gcctggcatt atgcccagta 540
catgacctta tgggactttc ctacttggca gtacatctac gtattagtca tcgctattac 600
catggtgatg cggttttggc agtacatcaa tgggcgtgga tagcggtttg actcacgggg 660
atttccaagt ctccacccca ttgacgtcaa tgggagtttg ttttggcacc aaaatcaacg 720
ggactttcca aaatgtcgta acaactccgc cccattgacg caaatgggcg gtaggcgtgt 780
acggtgggag gtctatataa gcagagctcg tttagtgaac cgtcagatcg cctggagacg 840
ccatccacgc tgttttgacc tccatagaag acaccgggac cgatccagcc tccgcggccg 900
ggaacggtgc attggaacgc ggattccccg tgccaagagt gacgtaagta ccgcctatag 960
actctatagg cacacccctt tggctcttat gcatgctata ctgtttttgg cttggggcct 1020
atacaccccc gcttccttat gctataggtg atggtatagc ttagcctata ggtgtgggtt 1080
attgaccatt attgaccact cccctattgg tgacgatact ttccattact aatccataac 1140
atggctcttt gccacaacta tctctattgg ctatatgcca atactctgtc cttcagagac 1200
tgacacggac tctgtatttt tacaggatgg ggtcccattt attatttaca aattcacata 1260
tacaacaacg ccgtcccccg tgcccgcagt ttttattaaa catagcgtgg gatctccacg 1320
cgaatctcgg gtacgtgttc cggacatggg ctcttctccg gtagcggcgg agcttccaca 1380
tccgagccct ggtcccatgc ctccagcggc tcatggtcgc tcggcagctc cttgctccta 1440
acagtggagg ccagacttag gcacagcaca atgcccacca ccaccagtgt gccgcacaag 1500
gccgtggcgg tagggtatgt gtctgaaaat gagcgtggag attgggctcg cacggctgac 1560
gcagatggaa gacttaaggc agcggcagaa gaagatgcag gcagctgagt tgttgtattc 1620
tgataagagt cagaggtaac tcccgttgcg gtgctgttaa cggtggaggg cagtgtagtc 1680
tgagcagtac tcgttgctgc cgcgcgcgcc accagacata atagctgaca gactaacaga 1740
ctgttccttt ccatgggtct tttctgcagt caccgtctcg cgaaaaatca ataatcagac 1800

```
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
ttttttttgcc tgtttttttt tttttttttt tttttttaa gtaaggtgtt ctttttttctt   4080
agtaaatttt ctactggact gtatgttttg acaggtcaga aacatttctt caaaagaaga   4140
accttttgga aactgtacag ccctttttctt tcattccctt tttgctttct gtgccaatgc   4200
```

```
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt atttttttccc tttgaagtag tgagcgttct ctggtttttt tcctttgaaa   4380
ctggtgaggc ttagattttt ctaatgggat tttttacctg atgatctagt tgcataccca   4440
aatgcttgta aatgttttcc tagttaacat gttgataact tcggatttac atgttgtata   4500
tacttgtcat ctgtgtttct agtaaaaata tatggcattt atagaaatac gtaattcctg   4560
atttcctttt tttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
gttcctgaat cctttctata gcaccactta ttgcagcagg tgtaggctct ggtgtggcct   5340
gtgtctgtgc ttcaatcttt taagcttctc gagggcgcgc cgtgctttac agaggtcaga   5400
atggtttctt tactgtttgt caattctatt atttcaatac agaacaatag cttctataac   5460
tgaaatatat ttgctattgt atattatgat tgtccctcga accatgaaca ctcctccagc   5520
tgaatttcac aattcctctg tcatctgcca ggccattaag ttattcatgg aagatctttg   5580
aggaacactg caagttcata tcataaacac atttgaaatt gagtattgtt ttgcattgta   5640
tggagctatg ttttgctgta tcctcagaaa aaaaagtttg ttataaagca ttcacaccca   5700
taaaaagata gatttaaata ttccaactat aggaaagaaa gtgcgtctgc tcttcactct   5760
agtctcagtt ggctccttca catgcatgct tctttatttc tcctattttg tcaagaaaat   5820
aataggtcac gtcttgttct cacttatgtc ctgcctagca tggctcagat gcacgttgta   5880
catacaagaa ggatcaaatg aaacagactt ctggtctgtt actacaacca tagtaataag   5940
cacactaact aataattgct aattatgttt tccatctcta aggttcccat atttttctgt   6000
tttcttaaag atcccattat ctggttgtaa ctgaagctca atggaacatg agcaatattt   6060
cccagtcttc tctcccatcc aacagtcctg atggattagc agaacaggca gaaaacacat   6120
tgttacccag aattaaaaac taatatttgc tctccattca atccaaaatg gacctattga   6180
aactaaaatc taacccaatc ccattaaatg atttctatgg cggaattctg gccattgcat   6240
acgttgtatc catatcataa tatgtacatt tatattggct catgtccaac attaccgcca   6300
tgttgacatt gattattgac tagttattaa tagtaatcaa ttacggggtc attagttcat   6360
agcccatata tggagttccg cgttacataa cttacggtaa atggcccgcc tggctgaccg   6420
cccaacgacc cccgcccatt gacgtcaata atgacgtatg ttcccatagt aacgccaata   6480
gggactttcc attgacgtca atgggtggag tatttacggt aaactgccca cttggcagta   6540
```

```
catcaagtgt atcatatgcc aagtacgccc cctattgacg tcaatgacgg taaatggccc   6600
gcctggcatt atgcccagta catgacctta tgggactttc ctacttggca gtacatctac   6660
gtattagtca tcgctattac catggtgatg cggttttggc agtacatcaa tgggcgtgga   6720
tagcggtttg actcacgggg atttccaagt ctccacccca ttgacgtcaa tgggagtttg   6780
ttttggcacc aaaatcaacg ggactttcca aaatgtcgta acaactccgc cccattgacg   6840
caaatgggcg gtaggcgtgt acggtgggag gtctatataa gcactcgagc tcgtttagtg   6900
aaccgtcaga tcgcctggag acgccatcca cgctgttttg acctccatag aagacaccgg   6960
gaccgatcca gcctccgcgg ccgggaacgg tgcattggaa cgcggattcc ccgtgccaag   7020
agtgacgtaa gtaccgccta tagactctat aggcacaccc ctttggctct tatgcatgct   7080
atactgtttt tggcttgggg cctatacacc cccgcttcct tatgctatag gtgatggtat   7140
agcttagcct ataggtgtgg gttattgacc attattgacc actcccctat tggtgacgat   7200
actttccatt actaatccat aacatggctc tttgccacaa ctatctctat tggctatatg   7260
ccaatactct gtccttcaga gactgacacg gactctgtat ttttacagga tggggtccca   7320
tttattattt acaaattcac atatacaaca acgccgtccc ccgtgcccgc agtttttatt   7380
aaacatagcg tgggatctcc acgcgaatct cgggtacgtg ttccggacat gggctcttct   7440
ccggtagcgg cggagcttcc acatccgagc cctggtccca tgcctccagc ggctcatggt   7500
cgctcggcag ctccttgctc ctaacagtgg aggccagact taggcacagc acaatgccca   7560
ccaccaccag tgtgccgcac aaggccgtgg cggtagggta tgtgtctgaa aatgagcgtg   7620
gagattgggc tcgcacggct gacgcagatg gaagacttaa ggcagcggca gaagaagatg   7680
caggcagctg agttgttgta ttctgataag agtcagaggt aactcccgtt gcggtgctgt   7740
taacggtgga gggcagtgta gtctgagcag tactcgttgc tgccgcgcgc gccaccagac   7800
ataatagctg acagactaac agactgttcc tttccatggg tcttttctgc agtcaccgtc   7860
gtcgacgcta tgagggggat catactggca ttagtgctca cccttgtagg cagccaggat   7920
atcgtgatga gccagtctcc agactccctg gccgtgtccc tgggcgagag ggtgactctg   7980
aattgcaagt ccagccagtc cctgctctat agcagcaata gcaagaacta tctcgcctgg   8040
tatcagcaga aaccagggca gagccctaaa ctgctgattt actgggcatc caccagggaa   8100
tccggcgtac ctgatcgctt cagcggcagc ggatctggga cagacttcac tctgacaatc   8160
agcagcgtgc aggcagaaga cgtggcagtc tattattgtc agcagcccta tagctatccc   8220
ctcagcttcg gcgctggcac caagctggaa ctgaaacggg ccgcggctgc accatctgtc   8280
ttcatcttcc cgccatctga tgagcagttg aaatctggaa ctgcctctgt tgtgtgcctg   8340
ctgaataact tctatcccag agaggccaaa gtacagtgga aggtggataa cgccctccaa   8400
tcgggtaact cccaggagag tgtcacagag caggacagca aggacagcac ctacagcctc   8460
agcagcaccc tgacgctgag caaagcagac tacgagaaac acaaagtcta cgcctgcgaa   8520
gtcacccatc agggcctgag ttcgcccgtc acaaagagct tcaacagggg agagtgttag   8580
gacgtcaaag aagaaagctg aaaaactctg tcccttccaa caagacccag agcactgtag   8640
tatcaggggt aaaatgaaaa gtatgttatc tgctgcatcc agacttcata aaagctggag   8700
cttaatctag aaaaaaaatc agaaagaaat tacactgtga gaacaggtgc aattcacttt   8760
tcctttacac agagtaatac tggtaactca tggatgaagg cttaagggaa tgaaattgga   8820
ctcacagtac tgagtcatca cactgaaaaa tgcaacctga tacatcagca gaaggtttat   8880
gggggaaaaa tgcagccttc caattaagcc agatatctgt atgaccaagc tgctccagaa   8940
```

```
ttagtcactc aaaatctctc agattaaatt atcaactgtc accaaccatt cctatgctga   9000
caaggcaatt gcttgttctc tgtgttcctg atactacaag gctcttcctg acttcctaaa   9060
gatgcattat aaaaatctta taattcacat ttctccctaa actttgactc aatcatggta   9120
tgttggcaaa tatggtatat tactattcaa attgttttcc ttgtacccat atgtaatggg   9180
tcttgtgaat gtgctctttt gttcctttaa tcataataaa aacatgttta agcaaacact   9240
tttcacttgt agtatttgaa gtacagcaag gttgtgtagc agggaaagaa tgacatgcag   9300
aggaataagt atggacacac aggctagcag cgactgtaga acaagtacta atgggtgaga   9360
agttgaacaa gagtccccta cagcaactta atctaataag ctagtggtct acatcagcta   9420
aaagagcata gtgagggatg aaattggttc tcctttctaa gcatcacctg ggacaactca   9480
tctggagcag tgtgtccaat ctttaattaa ggcgcctgca gggtaacctg aggctatggc   9540
agggcctgcc gccccgacgt tggctgcgag ccctgggcct tcacccgaac ttgggggtg   9600
gggtggggaa aaggaagaaa cgcgggcgta ttggccccaa tggggtctcg gtggggtatc   9660
gacagagtgc cagccctggg accgaacccc gcgtttatga acaaacgacc caacaccgtg   9720
cgttttattc tgtcttttta ttgccgtcat agcgcgggtt ccttccggta ttgtctcctt   9780
ccgtgtttca gttagcctcc ccctagggtg ggcgaagaac tccagcatga gatccgagct   9840
caggatccgc tagcgaattc aggtttaagc acctggtttg cgagtcatgc accaagtgcg   9900
tgggccttct ggcacttcca catcagcagt cacagtgaag cccaggcgtt catagaaagg   9960
caggttgcgt ggagctgagg tctccaggaa agcaggcaca cctgcacgtt cagctgcttc  10020
cacaccaggc agcaccactg cagagcccag gcccttaccc tggtggtcag ggctcacacc  10080
cacagttgcc aggaaccaag caggttcttt tgggcggtgt ggtgccagca gaccttccat  10140
ctgctgttgt gctgccaggc ggctgccaga cagttctgcc atgcgtgggc caatctcagc  10200
aaacactgca ccagcttcaa cagattcagg ggtggtccac actgccacag cagcaccatc  10260
atctgccacc cacactttgc caatgtccag gcccacacgg gtcaggaaca gctcctgcag  10320
ttcagtcaca cgttcaatgt ggcggtctgg gtccacagtg tgacgggttg cagggtagtc  10380
agcaaatgca gcagccaggg tgcgaactgc acgtggaaca tcatcacgag ttgccaggcg  10440
aacagttggt ttgtattcag tcatgacgat cctcatcctg tctcttgatc gatctttgca  10500
aaagcctagg cctccaaaaa agcctcctca ctacttctgg aatagctcag aggccgaggc  10560
ggcctcggcc tctgcataaa taaaaaaaat tagtcagcca tggggcggag aatgggcgga  10620
actgggcgga gttaggggcg ggatgggcgg agttaggggc gggactatgg ttgctgacta  10680
attgagatgc atgctttgca tacttctgcc tgctggggag cctggggact ttccacacct  10740
ggttgctgac taattgagat gcatgctttg catacttctg cctgctgggg agcctgggga  10800
ctttccacac cctaactgac acacattcca cagctggttc tttccgcctc agcgtacgag  10860
attggacaca ctgctccaga tgagttgtcc caggtgatgc ttagaaagga gaaccaattt  10920
catccctcac tatgctcttt tagctgatgt agaccactag cttattagat taagttgctg  10980
taggggactc ttgttcaact tctcacccat tagtacttgt tctacagtcg ctgctagcct  11040
gtgtgtccat acttattcct ctgcatgtca ttctttccct gctacacaac cttgctgtac  11100
ttcaaatact acaagtgaaa agtgtttgct taaacatgtt tttattatga ttaaaggaac  11160
aaaagagcac attcacaaga cccattacat atgggtacaa ggaaaacaat ttgaatagta  11220
atataccata tttgccaaca taccatgatt gagtcaaagt ttagggagaa atgtgaatta  11280
```

```
taagattttt ataatgcatc tttaggaagt caggaagagc cttgtagtat caggaacaca  11340
gagaacaagc aattgccttg tcagcatagg aatggttggt gacagttgat aatttaatct  11400
gagagatttt gagtgactaa ttctggagca gcttggtcat acagatatct ggcttaattg  11460
gaaggctgca tttttccccc ataaaccttc tgctgatgta tcaggttgca tttttcagtg  11520
tgatgactca gtactgtgag tccaatttca ttcccttaag ccttcatcca tgagttacca  11580
gtattactct gtgtaaagga aaagtgaatt gcacctgttc tcacagtgta atttctttct  11640
gattttttt ctagattaag ctccagcttt tatgaagtct ggatgcagca gataacatac  11700
ttttcatttt accccctgata ctacagtgct ctgggtcttg ttggaaggga cagagttttt  11760
cagctttctt ctttgacgtc tcatttaccc ggagacaggg agaggctctt ctgcgtgtag  11820
tggttgtgca gagcctcatg catcacggag catgagaaga cgttcccctg ctgccacctg  11880
ctcttgtcca cggtgagctt gctgtagagg aagaaggagc cgtcggagtc cagcacggga  11940
ggcgtggtct tgtagttgtt ctccggctgc ccattgctct cccactccac ggcgatgtcg  12000
ctgggataga agcctttgac caggcaggtc aggctgacct ggttcttggt cagctcatcc  12060
cgggatgggg gcagggtgta cacctgtggt tctcggggct gccctccgga tccgcctcca  12120
ctcgagccac ctccgcacgg tggcatgtg tgagttttgt cacaagattc gggctcaact  12180
ttcttgtcca ccttggtgtt gctgggcttg tgattcacgt tgcagatgta ggtctgggtg  12240
cccaagctgc tggagggcac ggtcaccacg ctgctgaggg agtagagtcc tgaggactgt  12300
aggacagccg ggaaggtgtg cacgccgctg gtcagggcgc ctgagttcca cgacaccgtc  12360
accggttcgg ggaagtagtc cttgaccagg cagcccaggg ccgctgtgcc cccagaggtg  12420
ctcttggagg agggtgccag ggggaagacc gatgggcccg tagttttggc gctggagacg  12480
gtgaccaggg ttccctgtcc ccagtaggcc atattcaggg atcttgtgca gaagtacact  12540
gcagtatcct cggatctcag gctggagagc tccacgtagg cagtgctggc agatgtgtct  12600
gcagtcaggg tggccttgcc ctggaacttc tgtgagtact taaaatcatc gtttccggga  12660
gagaaatatc caatccactc caggcgctgt ccaggattct gtttcaccca gtggattgcg  12720
tgatcagtga aggtgtagcc gcttgccttg caggaaatct tcacggaagc cccaggtttc  12780
accacctcag cgccggactg caccagctgg acctgctggc tgcctacaag ggtgagcact  12840
aatgccagta tgatccccct catagcgata tcgacggtga ctgcagaaaa gacccatgga  12900
aaggaacagt ctgttagtct gtcagctatt atgtctggtg gcgcgcgcgg cagcaacgag  12960
tactgctcag actacactgc cctccaccgt taacagcacc gcaacgggag ttacctctga  13020
ctcttatcag aatacaacaa ctcagctgcc tgcatcttct tctgccgctg ccttaagtct  13080
tccatctgcg tcagccgtgc gagcccaatc tccacgctca ttttcagaca cataccctac  13140
cgccacggcc ttgtgcggca cactggtggt ggtgggcatt gtgctgtgcc taagtctggc  13200
ctccactgtt aggagcaagg agctgccgag cgaccatgag ccgctggagg catgggacca  13260
gggctcggat gtggaagctc cgccgctacc ggagaagagc ccatgtccgg aacacgtacc  13320
cgagattcgc gtggagatcc cacgctatgt ttaataaaaa ctgcgggcac gggggacggc  13380
gttgttgtat atgtgaattt gtaaataata aatgggaccc catcctgtaa aaatacagag  13440
tccgtgtcag tctctgaagg acagagtatt ggcatatagc caatagagat agttgtggca  13500
aagagccatg ttatggatta gtaatggaaa gtatcgtcac caatagggga gtggtcaata  13560
atggtcaata acccacacct ataggctaag ctataccatc acctatagca taaggaagcg  13620
ggggtgtata ggccccaagc caaaaacagt atagcatgca taagagccaa aggggtgtgc  13680
```

```
ctatagagtc tataggcggt acttacgtca ctcttggcac ggggaatccg cgttccaatg  13740
caccgttccc ggccgcggag gctggatcgg tcccggtgtc ttctatggag gtcaaaacag  13800
cgtggatggc gtctccaggc gatctgacgg ttcactaaac gagctcgagt gcttatatag  13860
acctcccacc gtacacgcct accgcccatt tgcgtcaatg gggcggagtt gttacgacat  13920
tttggaaagt cccgttgatt ttggtgccaa aacaaactcc cattgacgtc aatggggtgg  13980
agacttggaa atccccgtga gtcaaaccgc tatccacgcc cattgatgta ctgccaaaac  14040
cgcatcacca tggtaatagc gatgactaat acgtagatgt actgccaagt aggaaagtcc  14100
cataaggtca tgtactgggc ataatgccag gcgggccatt taccgtcatt gacgtcaata  14160
gggggcgtac ttggcatatg atacacttga tgtactgcca agtgggcagt ttaccgtaaa  14220
tactccaccc attgacgtca atggaaagtc cctattggcg ttactatggg aacatacgtc  14280
attattgacg tcaatgggcg ggggtcgttg ggcggtcagc caggcgggcc atttaccgta  14340
agttatgtaa cgcggaactc catatatggg ctatgaacta atgaccccgt aattgattac  14400
tattaataac tagtcaataa tcaatgtcaa catggcggta atgttggaca tgagccaata  14460
taaatgtaca tattatgata tggatacaac gtatgcaatg gccagaattc cgccatagaa  14520
atcatttaat gggattgggt tagattttag tttcaatagg tccattttgg attgaatgga  14580
gagcaaatat tagtttttaa ttctgggtaa caatgtgttt tctgcctgtt ctgctaatcc  14640
atcaggactg ttggatggga gagaagactg ggaaatattg ctcatgttcc attgagcttc  14700
agttacaacc agataatggg atctttaaga aaacagaaaa atatgggaac cttagagatg  14760
gaaaacataa ttagcaatta ttagttagtg tgcttattac tatggttgta gtaacagacc  14820
agaagtctgt ttcatttgat ccttcttgta tgtacaacgt gcatctgagc catgctaggc  14880
aggacataag tgagaacaag acgtgaccta ttattttctt gacaaaatag gagaaataaa  14940
gaagcatgca tgtgaaggag ccaactgaga ctagagtgaa gagcagacgc actttctttc  15000
ctatagttgg aatatttaaa tctatctttt tatgggtgtg aatgctttat aacaaacttt  15060
tttttctgag gatacagcaa aacatagctc catacaatgc aaaacaatac tcaatttcaa  15120
atgtgtttat gatatgaact tgcagtgttc ctcaaagatc ttccatgaat aacttaatgg  15180
cctggcagat gacagaggaa ttgtgaaatt cagctggagg agtgttcatg gttcgaggga  15240
caatcataat atacaatagc aaatatattt cagttataga agctattgtt ctgtattgaa  15300
ataatagaat tgacaaacag taaagaaacc attctgacct ctgtaaagca cacgcgtaag  15360
cttaaaagat tgaagcacag acacaggcca caccagagcc tacacctgct gcaataagtg  15420
gtgctataga aaggattcag gaactaacaa gtgcataatt tacaaataga gatgctttat  15480
catactttgc ccaacatggg aaaaaagaca tcccatgaga atatccaact gaggaacttc  15540
tctgtttcat agtaactcat ctactactgc taagatggtt tgaaaagtac ccagcaggtg  15600
agatgtgttc cgggaggtgg ctgtgtggca gcgtgtggga acacgacaca aagcacccca  15660
cccctatctg caatgctcac tgcaaggcag tgccgtaaac agctgcaaca ggcatccagg  15720
catcacttct gcataaacgc tgtgactcgt tagcatgctg caactgtgtt taaaacctat  15780
gcactccgtt accaaaataa tttaagtccc aaacaaatcc atgcagcttg cttcctatgc  15840
caaaatattt tagaaagtat tcattcttct ttaagaatat gcacgtggat ctgcacttcc  15900
ctgggatctg aagcgattta tacctcagtg cagaagcagt ttagtgtcct ggatctcggg  15960
aaggcagcag ccaaacgtgc ccgttttaca tttaaaccca tgtgacaacc cgccttactg  16020
```

```
agcatcgctc taggaaattt aaggctgtat ccttacaaca caagaaccaa cgacagactg  16080
catataaaat tctataaata aaaataggag tgaagtctgt ttgacctgta cacacagagc  16140
atagagataa aaaaaaaagg aaatcaggaa ttacgtattt ctataaatgc catatatttt  16200
tactagaaac acagatgaca agtatataca acatgtaaat ccgaagttat caacatgtta  16260
actaggaaaa catttacaag catttgggta tgcaactaga tcatcaggta aaaaatccca  16320
ttagaaaaat ctaagcctca ccagtttcaa aggaaaaaaa ccagagaacg ctcactactt  16380
caaagggaaa aaataaagca tcaagctggc ctaaacttaa taaggtatct cgtgtaacaa  16440
cagctatcca agctttcaag ccacactata aataaaaacc tcaagttccg atcaacgttt  16500
tccataatgc aatcagaacc aaaggcattg gcacagaaag caaaaaggga atgaaagaaa  16560
agggctgtac agtttccaaa aggttcttct tttgaagaaa tgtttctgac ctgtcaaaac  16620
atacagtcca gtagaaaatt tactaagaaa aaagaacacc ttacttaaaa aaaaaaaaaa  16680
aaaaaaaaaa aacaggcaaa aaaacctctc ctgtcactga gctgccacca ccccaaccac  16740
cacctgctgt gggctttgtc tcccaagaca aaggacacac agccttatcc aatattcaac  16800
attacttata aaaacactga tcagaagaaa taccaagtat ttcctcacag actgttatac  16860
agactgttat atcctttcat cggcaagaag agatgaaata caacagagtg aatatcaaag  16920
aaggcggcag gagccaccgt ggcaccatca ccgggcagtg cagtgcccag ctgccgtttc  16980
ctgagcacgc acaggaagcc gtcagtcaca tgtaataaac caaaacctgg tacagttata  17040
ttatggatcc gggcccctcc gggatcatat gacaagatgt gtatccacct taacttaatg  17100
atttttacca aaatcattag gggattcatc agtgctcagg gtcaacgaga attaacattc  17160
cgtcaggaaa gcttgaattc agcttttgtt ccctttagtg agggttaatt gcgcgcttgg  17220
cgtaatcatg gtcatagctg tttcctgtgt gaaattgtta tccgctcaca attccacaca  17280
acatacgagc cggaagcata aagtgtaaag cctggggtgc ctaatgagtg agctaactca  17340
cattaattgc gttgcgctca ctgcccgctt tccagtcggg aaacctgtcg tgccagctgc  17400
attaatgaat cggccaacgc gcggggagag gcggtttgcg tattgggcgc tcttccgctt  17460
cctcgctcac tgactcgctg cgctcggtcg ttcggctgcg gcgagcggta tcagctcact  17520
caaaggcggt aatacggtta tccacagaat caggggataa cgcaggaaag aacatgtgag  17580
caaaaggcca gcaaaaggcc aggaaccgta aaaaggccgc gttgctggcg tttttccata  17640
ggctccgccc ccctgacgag catcacaaaa atcgacgctc aagtcagagg tggcgaaacc  17700
cgacaggact ataaagatac caggcgtttc cccctggaag ctccctcgtg cgctctcctg  17760
ttccgaccct gccgcttacc ggatacctgt ccgcctttct cccttcggga agcgtggcgc  17820
tttctcatag ctcacgctgt aggtatctca gttcggtgta ggtcgttcgc tccaagctgg  17880
gctgtgtgca cgaacccccc gttcagcccg accgctgcgc cttatccggt aactatcgtc  17940
ttgagtccaa cccggtaaga cacgacttat cgccactggc agcagccact ggtaacagga  18000
ttagcagagc gaggtatgta ggcggtgcta cagagttctt gaagtggtgg cctaactacg  18060
gctacactag aagaacagta tttggtatct gcgctctgct gaagccagtt accttcggaa  18120
aaagagttgg tagctcttga tccggcaaac aaaccaccgc tggtagcggt ggtttttttg  18180
tttgcaagca gcagattacg cgcagaaaaa aaggatctca agaagatcct ttgatctttt  18240
ctacggggtc tgacgctcag tggaacgaaa actcacgtta agggattttg gtcatgagat  18300
tatcaaaaag gatcttcacc tagatccttt taaattaaaa atgaagtttt aaatcaatct  18360
aaagtatata tgagtaaact tggtctgaca gttaccaatg cttaatcagt gaggcaccta  18420
```

```
tctcagcgat ctgtctattt cgttcatcca tagttgcctg actccccgtc gtgtagataa  18480
ctacgatacg ggagggctta ccatctggcc ccagtgctgc aatgataccg cgagacccac  18540
gctcaccggc tccagattta tcagcaataa accagccagc cggaagggcc gagcgcagaa  18600
gtggtcctgc aactttatcc gcctccatcc agtctattaa ttgttgccgg gaagctagag  18660
taagtagttc gccagttaat agtttgcgca acgttgttgc cattgctaca ggcatcgtgg  18720
tgtcacgctc gtcgtttggt atggcttcat tcagctccgg ttcccaacga tcaaggcgag  18780
ttacatgatc ccccatgttg tgcaaaaaag cggttagctc cttcggtcct ccgatcgttg  18840
tcagaagtaa gttggccgca gtgttatcac tcatggttat ggcagcactg cataattctc  18900
ttactgtcat gccatccgta agatgctttt ctgtgactgg tgagtactca accaagtcat  18960
tctgagaata gtgtatgcgg cgaccgagtt gctcttgccc ggcgtcaata cgggataata  19020
ccgcgccaca tagcagaact ttaaaagtgc tcatcattgg aaaacgttct tcggggcgaa  19080
aactctcaag gatcttaccg ctgttgagat ccagttcgat gtaacccact cgtgcaccca  19140
actgatcttc agcatctttt actttcacca gcgtttctgg gtgagcaaaa acaggaaggc  19200
aaaatgccgc aaaaaaggga ataagggcga cacggaaatg ttgaatactc atactcttcc  19260
tttttcaata ttattgaagc atttatcagg gttattgtct catgagcgga tacatatttg  19320
aatgtattta gaaaaataaa caaatagggg ttccgcgcac atttccccga aaagtgccac  19380
```

<210> SEQ ID NO 23
<211> LENGTH: 19852
<212> TYPE: DNA
<213> ORGANISM: Artificial Sequence
<220> FEATURE:
<223> OTHER INFORMATION: Synthetic construct

<400> SEQUENCE: 23

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
```

```
attgaccatt attgaccact ccccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
```

```
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
tttttttgcc tgtttttttt tttttttttt ttttttttaa gtaaggtgtt ctttttttctt   4080
agtaaatttt ctactggact gtatgttttg acaggtcaga aacatttctt caaaagaaga   4140
accttttgga aactgtacag ccctttttctt tcattccctt tttgctttct gtgccaatgc   4200
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt atttttttccc tttgaagtag tgagcgttct ctggtttttt tcctttgaaa   4380
ctggtgaggc ttagattttt ctaatgggat tttttacctg atgatctagt tgcataccca   4440
aatgcttgta aatgttttcc tagttaacat gttgataact tcggatttac atgttgtata   4500
tacttgtcat ctgtgtttct agtaaaaata tatggcattt atagaaatac gtaattcctg   4560
atttcctttt ttttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
gttcctgaat cctttctata gcaccactta ttgcagcagg tgtaggctct ggtgtggcct   5340
gtgtctgtgc ttcaatcttt taagcttctc gagggcgcgc cgtgctttac agaggtcaga   5400
atggtttctt tactgtttgt caattctatt atttcaatac agaacaatag cttctataac   5460
tgaaatatat ttgctattgt atattatgat tgtccctcga accatgaaca ctcctccagc   5520
tgaatttcac aattcctctg tcatctgcca ggccattaag ttattcatgg aagatctttg   5580
aggaacactg caagttcata tcataaacac atttgaaatt gagtattgtt ttgcattgta   5640
tggagctatg ttttgctgta tcctcagaaa aaaaagtttg ttataaagca ttcacaccca   5700
taaaaagata gatttaaata ttccaactat aggaaagaaa gtgcgtctgc tcttcactct   5760
agtctcagtt ggctccttca catgcatgct tctttatttc tcctattttg tcaagaaaat   5820
```

-continued

```
aataggtcac gtcttgttct cacttatgtc ctgcctagca tggctcagat gcacgttgta   5880
catacaagaa ggatcaaatg aaacagactt ctggtctgtt actacaacca tagtaataag   5940
cacactaact aataattgct aattatgttt tccatctcta aggttcccat atttttctgt   6000
tttcttaaag atcccattat ctggttgtaa ctgaagctca atggaacatg agcaatattt   6060
cccagtcttc tctcccatcc aacagtcctg atggattagc agaacaggca gaaaacacat   6120
tgttacccag aattaaaaac taatatttgc tctccattca atccaaaatg gacctattga   6180
aactaaaatc taacccaatc ccattaaatg atttctatgg cggaattctg gccattgcat   6240
acgttgtatc catatcataa tatgtacatt tatattggct catgtccaac attaccgcca   6300
tgttgacatt gattattgac tagttattaa tagtaatcaa ttacggggtc attagttcat   6360
agcccatata tggagttccg cgttacataa cttacggtaa atggcccgcc tggctgaccg   6420
cccaacgacc cccgcccatt gacgtcaata atgacgtatg ttcccatagt aacgccaata   6480
gggactttcc attgacgtca atgggtggag tatttacggt aaactgccca cttggcagta   6540
catcaagtgt atcatatgcc aagtacgccc cctattgacg tcaatgacgg taaatggccc   6600
gcctggcatt atgcccagta catgacctta tgggactttc ctacttggca gtacatctac   6660
gtattagtca tcgctattac catggtgatg cggttttggc agtacatcaa tgggcgtgga   6720
tagcggtttg actcacgggg atttccaagt ctccacccca ttgacgtcaa tgggagtttg   6780
ttttggcacc aaaatcaacg ggactttcca aaatgtcgta acaactccgc cccattgacg   6840
caaatgggcg gtaggcgtgt acggtgggag gtctatataa gcactcgagc tcgtttagtg   6900
aaccgtcaga tcgcctggag acgccatcca cgctgttttg acctccatag aagacaccgg   6960
gaccgatcca gcctccgcgg ccgggaacgg tgcattggaa cgcggattcc ccgtgccaag   7020
agtgacgtaa gtaccgccta tagactctat aggcacaccc ctttggctct tatgcatgct   7080
atactgtttt tggcttgggg cctatacacc cccgcttcct tatgctatag gtgatggtat   7140
agcttagcct ataggtgtgg gttattgacc attattgacc actcccctat tggtgacgat   7200
actttccatt actaatccat aacatggctc tttgccacaa ctatctctat tggctatatg   7260
ccaatactct gtccttcaga gactgacacg gactctgtat ttttacagga tggggtccca   7320
tttattattt acaaattcac atatacaaca acgccgtccc ccgtgcccgc agtttttatt   7380
aaacatagcg tgggatctcc acgcgaatct cgggtacgtg ttccggacat gggctcttct   7440
ccggtagcgg cggagcttcc acatccgagc cctggtccca tgcctccagc ggctcatggt   7500
cgctcggcag ctccttgctc ctaacagtgg aggccagact taggcacagc acaatgccca   7560
ccaccaccag tgtgccgcac aaggccgtgg cggtagggta tgtgtctgaa aatgagcgtg   7620
gagattgggc tcgcacggct gacgcagatg gaagacttaa ggcagcggca gaagaagatg   7680
caggcagctg agttgttgta ttctgataag agtcagaggt aactcccgtt gcggtgctgt   7740
taacggtgga gggcagtgta gtctgagcag tactcgttgc tgccgcgcgc gccaccagac   7800
ataatagctg acagactaac agactgttcc tttccatggg tcttttctgc agtcaccgtc   7860
gatatcgcta tgagggggat catactggca ttagtgctca cccttgtagg cagccagtcc   7920
tatgagctca cacagccacc ctcggtgtca gtgtccccag gacaaacggc caggatcacc   7980
tgctctggag atgcattgcc agaaaaatat gtttattggt accagcagaa gtcaggccag   8040
gcccctgtgg tggtcatcta tgaggacagc aaacgaccct ccgggatccc tgagagattc   8100
tctggctcca gctcagggac aatggccacc ttgactatca gtggggccca ggtggaagat   8160
gaaggtgact actactgtta ctcaactgac agcagtggtt atcataggga ggtgttcggc   8220
```

```
ggagggacca agctgaccgt cctaggtcag cccaaggctg ccccctcggt cactctgttc   8280
ccaccctcct ctgaggagct tcaagccaac aaggccacac tggtgtgtct cataagtgac   8340
tcctacccgg gagccgtgac agtggcctgg aaggcagata gcagccccgt caaggcggga   8400
gtggagacca ccacaccctc caaacaaagc aacaacaagt acgcggccag cagctacctg   8460
agcctgacgc ctgagcagtg gaagtcccac aaaagctaca gctgccaggt cacgcatgaa   8520
gggagcaccg tggagaagac agtggcccct gcagaatgtt catgagacgt cagcggtacg   8580
ttgcagcact ggagaagaca gaaacatttt catttttatt gtgtggtgta agaagactca   8640
tcttaagaag caatagaaat gttaaattaa acacttaaag atgcgtggaa ttttcccaag   8700
taatttaaag tattaaactt tattattata gaaactattc taattgccta taattatctg   8760
atttcctaat aaatacgtgc atggaaaaac cgatgaaggc ttccttcttt ctctgactgt   8820
ggcaagagga tgtctgcatt gcttctcttc accccacgtt ttgtagactc gaggctgtgg   8880
cagcctgcgg tgtagatgta caccaggcaa gaatctgtgt caggccccac ctgcgatatg   8940
ggttgtgtgg attggcagaa gctgcctacc aggctccagc ttgtttcccc tgtgcttcct   9000
tccctgctgc tgagatcctg ggcaccacag taggagttgg agcgctgacc acagagatga   9060
tcaaggggct ggagcacttc ccctatgagg acaggctgag ggagctgggc ttattcagcc   9120
tggagaagag aaggctgcgc ggtgatccca ttgcagcctt tcagtccctg aagggagcct   9180
ataaacagga agggagtaaa ctctttgaaa gggtagataa cagcaggaca aggggcaacg   9240
gttttaagtt gaaagaggga agatttaggt tggatgttag gggaaagttc tttaccagga   9300
gagtggtgag gtgctggaac aggctgccca gagaggttgt ggatgctccg tccctggagg   9360
tgttcaaggc caggttggat ggggccctgg gcaacctggt ctagtaaatg gggatgttgg   9420
tggccctgcc cagcaggggg gttggagatt cgtgatcctc gaggtccctt ccaacccagg   9480
ccattctgtg attctgtcat ttctgtcatt tatttttcaa tagagcctgt tttttgtact   9540
ggcaagacct acctgtatga ctacttaatt aaggcgcctg cagggtaacc tgaggctatg   9600
gcagggcctg ccgccccgac gttggctgcg agccctgggc cttcacccga acttgggggg   9660
tggggtgggg aaaaggaaga aacgcgggcg tattggcccc aatggggtct cggtggggta   9720
tcgacagagt gccagccctg ggaccgaacc ccgcgtttat gaacaaacga cccaacaccg   9780
tgcgttttat tctgtctttt tattgccgtc atagcgcggg ttccttccgg tattgtctcc   9840
ttccgtgttt cagttagcct cccccctaggg tgggcgaaga actccagcat gagatccgag   9900
ctcaggatcc gctagcgaat tcaggtttaa gcacctggtt tgcgagtcat gcaccaagtg   9960
cgtgggcctt ctggcacttc cacatcagca gtcacagtga agcccaggcg ttcatagaaa  10020
ggcaggttgc gtggagctga ggtctccagg aaagcaggca cacctgcacg ttcagctgct  10080
tccacaccag gcagcaccac tgcagagccc aggcccttac cctggtggtc agggctcaca  10140
cccacagttg ccaggaacca agcaggttct tttgggcggt gtggtgccag cagaccttcc  10200
atctgctgtt gtgctgccag gcggctgcca gacagttctg ccatgcgtgg gccaatctca  10260
gcaaacactg caccagcttc aacagattca ggggtggtcc acactgccac agcagcacca  10320
tcatctgcca cccacacttt gccaatgtcc aggcccacac gggtcaggaa cagctcctgc  10380
agttcagtca cacgttcaat gtggcggtct gggtccacag tgtgacgggt tgcagggtag  10440
tcagcaaatg cagcagccag ggtgcgaact gcacgtggaa catcatcacg agttgccagg  10500
cgaacagttg gtttgtattc agtcatgacg atcctcatcc tgtctcttga tcgatctttg  10560
```

```
caaaagccta ggcctccaaa aaagcctcct cactacttct ggaatagctc agaggccgag  10620
gcggcctcgg cctctgcata aataaaaaaa attagtcagc catggggcgg agaatgggcg  10680
gaactgggcg gagttagggg cgggatgggc ggagttaggg gcgggactat ggttgctgac  10740
taattgagat gcatgctttg catacttctg cctgctgggg agcctgggga ctttccacac  10800
ctggttgctg actaattgag atgcatgctt tgcatacttc tgcctgctgg ggagcctggg  10860
gactttccac accctaactg acacacattc cacagctggt tctttccgcc tcagcgtacg  10920
gtagtcatac aggtaggtct tgccagtaca aaaaacaggc tctattgaaa aataaatgac  10980
agaaatgaca gaatcacaga atggcctggg ttggaaggga cctcgaggat cacgaatctc  11040
caacccccct gctgggcagg gccaccaaca tccccattta ctagaccagg ttgcccaggg  11100
ccccatccaa cctggccttg aacacctcca gggacggagc atccacaacc tctctgggca  11160
gcctgttcca gcacctcacc actctcctgg taaagaactt tcccctaaca tccaacctaa  11220
atcttccctc tttcaactta aaaccgttgc cccttgtcct gctgttatct accctttcaa  11280
agagtttact cccttcctgt ttataggcty ccttcaggga ctgaaaggct gcaatgggat  11340
caccgcgcag ccttctcttc tccaggctga ataagcccag ctccctcagc ctgtcctcat  11400
aggggaagtg ctccagcccc ttgatcatct ctgtggtcag cgctccaact cctactgtgg  11460
tgcccaggat ctcagcagca gggaaggaag cacaggggaa acaagctgga gcctggtagg  11520
cagcttctgc caatccacac aacccatatc gcaggtgggg cctgacacag attcttgcct  11580
ggtgtacatc tacaccgcag gctgccacag cctcgagtct acaaaacgtg gggtgaagag  11640
aagcaatgca gacatcctct tgccacagtc agagaaagaa ggaagccttc atcggttttt  11700
ccatgcacgt atttattagg aaatcagata attataggca attagaatag tttctataat  11760
aataaagttt aatactttaa attacttggg aaaattccac gcatctttaa gtgtttaatt  11820
taacatttct attgcttctt aagatgagtc ttcttacacc acacaataaa aatgaaaatg  11880
tttctgtctt ctccagtgct gcaacgtacc gctgacgtct catttacccg gagacaggga  11940
gaggctcttc tgcgtgtagt ggttgtgcag agcctcatgc atcacggagc atgagaagac  12000
gttcccctgc tgccacctgc tcttgtccac ggtgagcttg ctgtagagga agaaggagcc  12060
gtcggagtcc agcacgggag gcgtggtctt gtagttgttc tccggctgcc cattgctctc  12120
ccactccacg gcgatgtcgc tgggatagaa gcctttgacc aggcaggtca ggctgacctg  12180
gttcttggtc agctcatccc gggatggggg cagggtgtac acctgtggtt ctcggggctg  12240
ccctttggct ttggagatgg ttttctcgat gggggctggg agggctttgt tggagacctt  12300
gcacttgtac tccttgccat tcagccagtc ctggtgcagg acggtgagga cgctgaccac  12360
acggtacgtg ctgttgtact gctcctcccg cggctttgtc ttggcattat gcacctccac  12420
gccgtccacg taccagttga acttgacctc agggtcttcg tggctcacgt ccaccaccac  12480
gcatgtgacc tcaggggtcc gggagatcat gagggtgtcc ttgggttttg gggggaagag  12540
gaagactgac ggtcccccca ggagttcagg tgctgggcac ggtgggcatg tgtgagtttt  12600
gtcacaagat ttgggctcaa ctttcttgtc caccttggtg ttgctgggct tgtgattcac  12660
gttgcagatg taggtctggg tgcccaagct gctggagggc acggtcacca cgctgctgag  12720
ggagtagagt cctgaggact gtaggacagc cgggaaggtg tgcacgccgc tggtcagggc  12780
gcctgagttc cacgacaccg tcaccggttc ggggaagtag tccttgacca ggcagcccag  12840
ggccgctgtg cccccagagg tgctcttgga ggagggtgcc agggggaaga ccgatgggcc  12900
cttggtggag gctgaggaga cggtgaccag ggttccctgg ccccaattcg gggagggat  12960
```

```
aactccccca aatgttatca taatccccgt ggtacagtaa tatacggctg tgtcctcggc  13020
tttcaggcta ttcatttgca gatataacgt gttttttgaa tcatctcttg agatggtgaa  13080
tctgcctttc acgggtgcag catagtctgt tgtcccacca tcaattttgc ttttaatacg  13140
gccgacccac tccagcccct tccctggagc ctggcggacc cagctcatcc aggcgtttct  13200
gaaagtgaat ccagaggctg cacaggagac tctaagggac ccccccggct ttaccaagcc  13260
tccccccgac tcctgcagct gcacctgctg gctgcctaca agggtgagca ctaatgccag  13320
tatgatcccc ctcatagcga tatcgacggt gactgcagaa aagacccatg gaaaggaaca  13380
gtctgttagt ctgtcagcta ttatgtctgg tggcgcgcgc ggcagcaacg agtactgctc  13440
agactacact gccctccacc gttaacagca ccgcaacggg agttacctct gactcttatc  13500
agaatacaac aactcagctg cctgcatctt cttctgccgc tgccttaagt cttccatctg  13560
cgtcagccgt gcgagcccaa tctccacgct cattttcaga cacataccct accgccacgg  13620
ccttgtgcgg cacactggtg gtggtgggca ttgtgctgtg cctaagtctg gcctccactg  13680
ttaggagcaa ggagctgccg agcgaccatg agccgctgga ggcatgggac cagggctcgg  13740
atgtggaagc tccgccgcta ccggagaaga gcccatgtcc ggaacacgta cccgagattc  13800
gcgtggagat cccacgctat gtttaataaa aactgcgggc acgggggacg gcgttgttgt  13860
atatgtgaat ttgtaaataa taaatgggac cccatcctgt aaaaatacag agtccgtgtc  13920
agtctctgaa ggacagagta ttggcatata gccaatagag atagttgtgg caaagagcca  13980
tgttatggat tagtaatgga aagtatcgtc accaataggg gagtggtcaa taatggtcaa  14040
taacccacac ctataggcta agctatacca tcacctatag cataaggaag cgggggtgta  14100
taggccccaa gccaaaaaca gtatagcatg cataagagcc aaaggggtgt gcctatagag  14160
tctataggcg gtacttacgt cactcttggc acggggaatc cgcgttccaa tgcaccgttc  14220
ccggccgcgg aggctggatc ggtcccggtg tcttctatgg aggtcaaaac agcgtggatg  14280
gcgtctccag gcgatctgac ggttcactaa acgagctcga gtgcttatat agacctccca  14340
ccgtacacgc ctaccgccca tttgcgtcaa tggggcggag ttgttacgac attttggaaa  14400
gtcccgttga ttttggtgcc aaaacaaact cccattgacg tcaatggggt ggagacttgg  14460
aaatccccgt gagtcaaacc gctatccacg cccattgatg tactgccaaa accgcatcac  14520
catggtaata gcgatgacta atacgtagat gtactgccaa gtaggaaagt cccataaggt  14580
catgtactgg gcataatgcc aggcgggcca tttaccgtca ttgacgtcaa tagggggcgt  14640
acttggcata tgatacactt gatgtactgc caagtgggca gtttaccgta aatactccac  14700
ccattgacgt caatggaaag tccctattgg cgttactatg ggaacatacg tcattattga  14760
cgtcaatggg cgggggtcgt tgggcggtca gccaggcggg ccatttaccg taagttatgt  14820
aacgcggaac tccatatatg ggctatgaac taatgacccc gtaattgatt actattaata  14880
actagtcaat aatcaatgtc aacatggcgg taatgttgga catgagccaa tataaatgta  14940
catattatga tatggataca acgtatgcaa tggccagaat tccgccatag aaatcattta  15000
atgggattgg gttagatttt agtttcaata ggtccatttt ggattgaatg gagagcaaat  15060
attagttttt aattctgggt aacaatgtgt tttctgcctg ttctgctaat ccatcaggac  15120
tgttggatgg gagagaagac tgggaaatat tgctcatgtt ccattgagct tcagttacaa  15180
ccagataatg ggatctttaa gaaaacagaa aaatatggga accttagaga tggaaaacat  15240
aattagcaat tattagttag tgtgcttatt actatggttg tagtaacaga ccagaagtct  15300
```

```
gtttcatttg atccttcttg tatgtacaac gtgcatctga gccatgctag gcaggacata  15360
agtgagaaca agacgtgacc tattattttc ttgacaaaat aggagaaata aagaagcatg  15420
catgtgaagg agccaactga gactagagtg aagagcagac gcactttctt tcctatagtt  15480
ggaatattta aatctatctt tttatgggtg tgaatgcttt ataacaaact tttttttctg  15540
aggatacagc aaaacatagc tccatacaat gcaaaacaat actcaatttc aaatgtgttt  15600
atgatatgaa cttgcagtgt tcctcaaaga tcttccatga ataacttaat ggcctggcag  15660
atgacagagg aattgtgaaa ttcagctgga ggagtgttca tggttcgagg gacaatcata  15720
atatacaata gcaaatatat ttcagttata gaagctattg ttctgtattg aaataataga  15780
attgacaaac agtaaagaaa ccattctgac ctctgtaaag cacacgcgta agcttaaaag  15840
attgaagcac agacacaggc cacaccagag cctacacctg ctgcaataag tggtgctata  15900
gaaaggattc aggaactaac aagtgcataa tttacaaata gagatgcttt atcatacttt  15960
gcccaacatg ggaaaaaaga catcccatga gaatatccaa ctgaggaact tctctgtttc  16020
atagtaactc atctactact gctaagatgg tttgaaaagt acccagcagg tgagatgtgt  16080
tccgggaggt ggctgtgtgg cagcgtgtgg gaacacgaca caaagcaccc cacccctatc  16140
tgcaatgctc actgcaaggc agtgccgtaa acagctgcaa caggcatcca ggcatcactt  16200
ctgcataaac gctgtgactc gttagcatgc tgcaactgtg tttaaaacct atgcactccg  16260
ttaccaaaat aatttaagtc ccaaacaaat ccatgcagct tgcttcctat gccaaaatat  16320
tttagaaagt attcattctt ctttaagaat atgcacgtgg atctgcactt ccctgggatc  16380
tgaagcgatt tatacctcag tgcagaagca gtttagtgtc ctggatctcg ggaaggcagc  16440
agccaaacgt gcccgtttta catttaaacc catgtgacaa cccgccttac tgagcatcgc  16500
tctaggaaat ttaaggctgt atccttacaa cacaagaacc aacgacagac tgcatataaa  16560
attctataaa taaaaatagg agtgaagtct gtttgacctg tacacacaga gcatagagat  16620
aaaaaaaaaa ggaaatcagg aattacgtat ttctataaat gccatatatt tttactagaa  16680
acacagatga caagtatata caacatgtaa atccgaagtt atcaacatgt taactaggaa  16740
aacatttaca agcatttggg tatgcaacta gatcatcagg taaaaaatcc cattagaaaa  16800
atctaagcct caccagtttc aaaggaaaaa aaccagagaa cgctcactac ttcaaaggga  16860
aaaaataaag catcaagctg gcctaaactt aataaggtat ctcgtgtaac aacagctatc  16920
caagctttca agccacacta taaataaaaa cctcaagttc cgatcaacgt tttccataat  16980
gcaatcagaa ccaaaggcat tggcacagaa agcaaaaagg gaatgaaaga aaagggctgt  17040
acagtttcca aaaggttctt cttttgaaga aatgtttctg acctgtcaaa acatacagtc  17100
cagtagaaaa tttactaaga aaaaagaaca ccttacttaa aaaaaaaaaa aaaaaaaaaa  17160
aaaacaggca aaaaaacctc tcctgtcact gagctgccac caccccaacc accacctgct  17220
gtgggctttg tctcccaaga caaaggacac acagccttat ccaatattca acattactta  17280
taaaaacact gatcagaaga aataccaagt atttcctcac agactgttat acagactgtt  17340
atatcctttc atcggcaaga agagatgaaa tacaacagag tgaatatcaa agaaggcggc  17400
aggagccacc gtggcaccat caccgggcag tgcagtgccc agctgccgtt tcctgagcac  17460
gcacaggaag ccgtcagtca catgtaataa accaaaacct ggtacagtta tattatggat  17520
ccgggcccct ccgggatcat atgacaagat gtgtatccac cttaacttaa tgatttttac  17580
caaaatcatt aggggattca tcagtgctca gggtcaacga gaattaacat tccgtcagga  17640
aagcttgaat tcagcttttg ttccctttag tgagggttaa ttgcgcgctt ggcgtaatca  17700
```

```
tggtcatagc tgtttcctgt gtgaaattgt tatccgctca caattccaca caacatacga  17760
gccggaagca taaagtgtaa agcctggggt gcctaatgag tgagctaact cacattaatt  17820
gcgttgcgct cactgcccgc tttccagtcg ggaaacctgt cgtgccagct gcattaatga  17880
atcggccaac gcgcggggag aggcggtttg cgtattgggc gctcttccgc ttcctcgctc  17940
actgactcgc tgcgctcggt cgttcggctg cggcgagcgg tatcagctca ctcaaaggcg  18000
gtaatacggt tatccacaga atcaggggat aacgcaggaa agaacatgtg agcaaaaggc  18060
cagcaaaagg ccaggaaccg taaaaaggcc gcgttgctgg cgtttttcca taggctccgc  18120
ccccctgacg agcatcacaa aaatcgacgc tcaagtcaga ggtggcgaaa cccgacagga  18180
ctataaagat accaggcgtt tccccctgga agctccctcg tgcgctctcc tgttccgacc  18240
ctgccgctta ccggatacct gtccgccttt ctcccttcgg gaagcgtggc gctttctcat  18300
agctcacgct gtaggtatct cagttcggtg taggtcgttc gctccaagct gggctgtgtg  18360
cacgaacccc ccgttcagcc cgaccgctgc gccttatccg gtaactatcg tcttgagtcc  18420
aacccggtaa gacacgactt atcgccactg gcagcagcca ctggtaacag gattagcaga  18480
gcgaggtatg taggcggtgc tacagagttc ttgaagtggt ggcctaacta cggctacact  18540
agaagaacag tatttggtat ctgcgctctg ctgaagccag ttaccttcgg aaaaagagtt  18600
ggtagctctt gatccggcaa acaaaccacc gctggtagcg gtggtttttt tgtttgcaag  18660
cagcagatta cgcgcagaaa aaaaggatct caagaagatc ctttgatctt ttctacgggg  18720
tctgacgctc agtggaacga aaactcacgt taagggattt tggtcatgag attatcaaaa  18780
aggatcttca cctagatcct tttaaattaa aaatgaagtt ttaaatcaat ctaaagtata  18840
tatgagtaaa cttggtctga cagttaccaa tgcttaatca gtgaggcacc tatctcagcg  18900
atctgtctat ttcgttcatc catagttgcc tgactccccg tcgtgtagat aactacgata  18960
cgggagggct taccatctgg ccccagtgct gcaatgatac cgcgagaccc acgctcaccg  19020
gctccagatt tatcagcaat aaaccagcca gccggaaggg ccgagcgcag aagtggtcct  19080
gcaactttat ccgcctccat ccagtctatt aattgttgcc gggaagctag agtaagtagt  19140
tcgccagtta atagtttgcg caacgttgtt gccattgcta caggcatcgt ggtgtcacgc  19200
tcgtcgtttg gtatggcttc attcagctcc ggttcccaac gatcaaggcg agttacatga  19260
tcccccatgt tgtgcaaaaa agcggttagc tccttcggtc ctccgatcgt tgtcagaagt  19320
aagttggccg cagtgttatc actcatggtt atggcagcac tgcataattc tcttactgtc  19380
atgccatccg taagatgctt ttctgtgact ggtgagtact caaccaagtc attctgagaa  19440
tagtgtatgc ggcgaccgag ttgctcttgc ccggcgtcaa tacgggataa taccgcgcca  19500
catagcagaa ctttaaaagt gctcatcatt ggaaaacgtt cttcggggcg aaaactctca  19560
aggatcttac cgctgttgag atccagttcg atgtaaccca ctcgtgcacc caactgatct  19620
tcagcatctt ttactttcac cagcgtttct gggtgagcaa aaacaggaag gcaaaatgcc  19680
gcaaaaaagg gaataagggc gacacggaaa tgttgaatac tcatactctt cctttttcaa  19740
tattattgaa gcatttatca gggttattgt ctcatgagcg gatacatatt tgaatgtatt  19800
tagaaaaata aacaaatagg ggttccgcgc acatttcccc gaaaagtgcc ac          19852
```

<210> SEQ ID NO 24
<211> LENGTH: 16896
<212> TYPE: DNA
<213> ORGANISM: Artificial Sequence
<220> FEATURE:

<223> OTHER INFORMATION: Synthetic construct

<400> SEQUENCE: 24

```
ctgacgcgcc ctgtagcggc gcattaagcg cggcgggtgt ggtggttacg cgcagcgtga     60
ccgctacact tgccagcgcc ctagcgcccg ctcctttcgc tttcttccct tcctttctcg    120
ccacgttcgc cggcatcaga ttggctattg gccattgcat acgttgtatc catatcataa    180
tatgtacatt tatattggct catgtccaac attaccgcca tgttgacatt gattattgac    240
tagttattaa tagtaatcaa ttacggggtc attagttcat agcccatata tggagttccg    300
cgttacataa cttacggtaa atggcccgcc tggctgaccg cccaacgacc cccgcccatt    360
gacgtcaata atgacgtatg ttcccatagt aacgccaata gggactttcc attgacgtca    420
atgggtggag tatttacggt aaactgccca cttggcagta catcaagtgt atcatatgcc    480
aagtacgccc cctattgacg tcaatgacgg taaatggccc gcctggcatt atgcccagta    540
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgacagcgaa aaatcaataa   1800
tcagacaaca agatgtgcga actcgatatt ttacacgact ctctttacca attctgcccc   1860
gaattacact taaaacgact caacagctta acgttggctt gccacgcatt acttgactgt   1920
aaaactctca ctcttaccga acttggccgt aacctgccaa ccaaagcgag aacaaaacat   1980
aacatcaaac gaatcgagcg attgttaggt aatcgtcacc tccacaaaga gcgactcgct   2040
gtataccgtt ggcatgctag ctttatctgt tcgggcaata cgatgcccat tgtacttgtt   2100
gactggtctg atattcgtga gcaaaaacga cttatggtat tgcgagcttc agtcgcacta   2160
cacggtcgtt ctgttactct ttatgagaaa gcgttcccgc tttcagagca atattcaaag   2220
aaagctcatg accaatttct agccgacctt gcgagcattc taccgagtaa caccacaccg   2280
```

```
ctcattgtca gtgatgctgg ctttaaagtg ccatggtata aatccgttga gaagctgggt   2340
tggtactggt taagtcgagt aagaggaaaa gtacaatatg cagacctagg agcggaaaac   2400
tggaaaccta tcagcaactt acatgatatg tcatctagtc actcaaagac tttaggctat   2460
aagaggctga ctaaaagcaa tccaatctca tgccaaattc tattgtataa atctcgctct   2520
aaaggccgaa aaaatcagcg ctcgacacgg actcattatc accacccgtc acctaaaatc   2580
tactcagcgt cggcaaagga gccatgggtt ctagcaacta acttacctgt tgaaattcga   2640
acacccaaac aacttgttaa tatctattcg aagcgaatgc agattgaaga aaccttccga   2700
gacttgaaaa gtcctgccta cggactaggc ctacgccata gccgaacgag cagctcagag   2760
cgttttgata tcatgctgct aatcgccctg atgcttcaac taacatgttg gcttgcgggc   2820
gttcatgctc agaaacaagg ttgggacaag cacttccagg ctaacacagt cagaaatcga   2880
aacgtactct caacagttcg cttaggcatg gaagttttgc ggcattctgg ctacacaata   2940
acaagggaag acttactcgt ggctgcaacc ctactagctc aaaatttatt cacacatggt   3000
tacgctttgg ggaaattatg aggggatcgc tctagagcga tccgggatct cgggaaaagc   3060
gttggtgacc aaaggtgcct tttatcatca ctttaaaaat aaaaaacaat tactcagtgc   3120
ctgttataag cagcaattaa ttatgattga tgcctacatc acaacaaaaa ctgatttaac   3180
aaatggttgg tctgccttag aaagtatatt tgaacattat cttgattata ttattgataa   3240
taataaaaac cttatcccta tccaagaagt gatgcctatc attggttgga atgaacttga   3300
aaaaattagc cttgaataca ttactggtaa ggtaaacgcc attgtcagca aattgatcca   3360
agagaaccaa cttaaagctt tcctgacgga atgttaattc tcgttgaccc tgagcactga   3420
tgaatcccct aatgattttg gtaaaaatca ttaagttaag gtggatacac atcttgtcat   3480
atgatcccgg taatgtgagt tagctcactc attaggcacc ccaggcttta cactttatgc   3540
ttccggctcg tatgttgtgt ggaattgtga gcggataaca atttcacaca ggaaacagct   3600
atgaccatga ttacgccaag cgcgcaatta accctcacta aagggaacaa aagctggagc   3660
tccaccgcgg tggcggccgc tcctggaagg tcctggaagg gggcgtccgc gggagctcac   3720
ggggagagcc cccccccaaa gcccccaggg atgtaattac gtccctcccc cgctaggggg   3780
cagcagcgag ccgcccgggg ctccgctccg gtccggcgct ccccccgcat ccccgagccg   3840
gcagcgtgcg gggacagccc gggcacgggg aaggtggcac gggatcgctt tcctctgaac   3900
gcttctcgct gctctttgag cctgcagaca cctgggggga tacggggaaa aagctttagg   3960
ctgaaagaga gatttagaat gacagaatca cagaatggcc tgggttggaa aggcccacaa   4020
tgctcatcca gttccaaccc ctgctatgtg cagggtcgcc aaccagcagc ccaggctgcc   4080
cagagacaca tccagcctgg cctggaatgc ctgcagggat ggggcatcca cagcctcctt   4140
gggcaacctg ttcagtgcgt caccaccctc tgggggaaaa actgcctctt catatccaac   4200
ccaaacctcc cctgtctaag tgtaaagcca ttcccccttg tcctatcaag gggagtttg    4260
ctgtgacatt gttggtctgg ggtgacacat gtttgccaat tcagtgcatc acggagaggc   4320
agatcttggg gataaggaag agcaggacag catggacgtg ggacatgcag gtgttgaggg   4380
ctctgggaca ctctccaagt cacagcgttc agaacagcct taaggatcag aagataggat   4440
agaaggacaa agagcaagtt aaaacccagc atggagagga gcacaaaaag gccacagaca   4500
ctgctggtcc ctgtgtctga gcctgcatgt ttgatggtgt ctggatgcaa gcagaagggg   4560
tggaagagct tgcctggaga gatacagctg ggtcagtagg actgggacag gcagctggag   4620
```

```
aattgccatg tagatgttca cacaatcgtc aaatcatgaa ggctggaaaa gccctccaag   4680
atccccaaga ccaaccccaa cccacccacc gtgcccactg gccatgtccc tcagtgccac   4740
atccccacag ttcttcatca cctccaggga cggtgacccc cccacctccg tgggcagctg   4800
tgccactgca gcaccgctct ttggagaagg taaatcttgc taaatccagc ccgaccctcc   4860
cctggcacaa cgtaaggcca ttatctctca tcctactcca ggacggagtc agtgagaata   4920
ttctcgaggg cgcgccgaat tcatgccaca atctattgca ctgctgaaag ttgcacctcc   4980
aaaaacatcc tccaatgcag aagaccgcgt gctcttgttc ttgtcgatgc aactgccacc   5040
cacttgcttt ggaggaccaa ctttttgta gggtttacag gaacccgttc attctcttag   5100
ttcactcttt gtttatctcc tatttctgag ggtacctgat gagctgtttc cacactcctg   5160
acgtttctag aacaggcgat tttctgaatg tgttcttgtg ttatcaatat aaatcacagt   5220
tagtgatgaa gttggctgca agcctgcatc agttcagcta cttggctgca ttttgtattt   5280
ggttctgtag gaaatgcaaa agttctagct gacctgcact tctatccctc ttgccttact   5340
gctgagaatc tctgcaggtt ttaattgttc acattttgct cccatttact ttggaagata   5400
aaatatttac agaatgctta tgaaaccttt gttcatttaa aaatattcct ggtcagcgtg   5460
accggagctg aaagaacaca ttgatcccgt gatttcaata aatacatatg ttccatatat   5520
tgtttctcag tagcctctta aatcatgtgc gttggtgcac atatgaatac atgaatagca   5580
aaggtttatc tggattagcc tctggcctgc aggaatggcc ataaaccaaa gctgagggaa   5640
gagggagagt atagtcaatg tagattatac tgattgctga ttgggttatt atcagctaga   5700
taacaacttg ggtcaggtgc caggtcaaca taacctgggc aaaaccagtc tcatctgtgg   5760
caggaccatg taccagcagc cagccgtgac ccaatctagg aaagcaagta gcacatcaat   5820
tttaaattta ttgtaaatgc cgtagtagaa gtgttttact gtgatacatt gaaacttctg   5880
gtcaatcaga aaaaggtttt tttatcagag atgccaaggt attatttgat tttctttatt   5940
cgccgtgaag agaatttatg attgcaaaaa gaggagtgtt tacataaact gataaaaaac   6000
ttgagaattc agcagaaaac agccacgtgt tcctgaacat tcttccataa aagtctcacc   6060
atgcctggca gagcccgagc tcgtttagtg aaccgtcaga tcgcctggag acgccatcca   6120
cgctgttttg acctccatag aagacaccgg gaccgatcca gcctccgcgg ccgggaacgg   6180
tgcattggaa cgcggattcc ccgtgccaag agtgacgtaa gtaccgccta tagactctat   6240
aggcacaccc ctttggctct tatgcatgct atactgtttt tggcttgggg cctatacacc   6300
cccgcttcct tatgctatag gtgatggtat agcttagcct ataggtgtgg gttattgacc   6360
attattgacc actcccctat tggtgacgat actttccatt actaatccat aacatggctc   6420
tttgccacaa ctatctctat tggctatatg ccaatactct gtccttcaga gactgacacg   6480
gactctgtat ttttacagga tggggtccca tttattattt acaaattcac atatacaaca   6540
acgccgtccc ccgtgcccgc agtttttatt aaacatagcg tgggatctcc acgcgaatct   6600
cgggtacgtg ttccggacat gggctcttct ccggtagcgg cggagcttcc acatccgagc   6660
cctggtccca tgcctccagc ggctcatggt cgctcggcag ctccttgctc ctaacagtgg   6720
aggccagact taggcacagc acaatgccca ccaccaccag tgtgccgcac aaggccgtgg   6780
cggtagggta tgtgtctgaa aatgagcgtg gagattgggc tcgcacggct gacgcagatg   6840
gaagacttaa ggcagcggca gaagaagatg caggcagctg agttgttgta ttctgataag   6900
agtcagaggt aactcccgtt gcggtgctgt taacggtgga gggcagtgta gtctgagcag   6960
tactcgttgc tgccgcgcgc gccaccagac ataatagctg acagactaac agactgttcc   7020
```

```
tttccatggg tcttttctgc agtcaccgtc gatatcgcta tgagggggat catactggca   7080
ttagtgctca cccttgtagg cagccagtcc tatgagctca cacagccacc ctcggtgtca   7140
gtgtccccag gacaaacggc caggatcacc tgctctggag atgcattgcc agaaaaatat   7200
gtttattggt accagcagaa gtcaggccag gcccctgtgg tggtcatcta tgaggacagc   7260
aaacgaccct ccgggatccc tgagagattc tctggctcca gctcagggac aatggccacc   7320
ttgactatca gtggggccca ggtggaagat gaaggtgact actactgtta ctcaactgac   7380
agcagtggtt atcataggga ggtgttcggc ggagggacca agctgaccgt cctaggtcag   7440
cccaaggctg ccccctcggt cactctgttc ccaccctcct ctgaggagct tcaagccaac   7500
aaggccacac tggtgtgtct cataagtgac tcctacccgg gagccgtgac agtggcctgg   7560
aaggcagata gcagccccgt caaggcggga gtggagacca ccacaccctc caaacaaagc   7620
aacaacaagt acgcggccag cagctacctg agcctgacgc ctgagcagtg gaagtcccac   7680
aaaagctaca gctgccaggt cacgcatgaa gggagcaccg tggagaagac agtggcccct   7740
gcagaatgtt catgagacgt cagcggtacg ttgcagcact ggagaagaca gaaacatttt   7800
catttttatt gtgtggtgta agaagactca tcttaagaag caatagaaat gttaaattaa   7860
acacttaaag atgcgtggaa ttttcccaag taatttaaag tattaaactt tattattata   7920
gaaactattc taattgccta taattatctg atttcctaat aaatacgtgc atggaaaaac   7980
cgatgaaggc ttccttcttt ctctgactgt ggcaagagga tgtctgcatt gcttctcttc   8040
accccacgtt ttgtagactc gaggctgtgg cagcctgcgg tgtagatgta caccaggcaa   8100
gaatctgtgt caggccccac ctgcgatatg ggttgtgtgg attggcagaa gctgcctacc   8160
aggctccagc ttgtttcccc tgtgcttcct tccctgctgc tgagatcctg ggcaccacag   8220
taggagttgg agcgctgacc acagagatga tcaaggggct ggagcacttc ccctatgagg   8280
acaggctgag ggagctgggc ttattcagcc tggagaagag aaggctgcgc ggtgatccca   8340
ttgcagcctt tcagtccctg aagggagcct ataaacagga agggagtaaa ctctttgaaa   8400
gggtagataa cagcaggaca aggggcaacg gttttaagtt gaaagaggga agatttaggt   8460
tggatgttag ggaaagttc tttaccagga gagtggtgag gtgctggaac aggctgccca   8520
gagaggttgt ggatgctccg tccctggagg tgttcaaggc caggttggat ggggccctgg   8580
gcaacctggt ctagtaaatg gggatgttgg tggccctgcc cagcaggggg gttggagatt   8640
cgtgatcctc gaggtccctt ccaacccagg ccattctgtg attctgtcat ttctgtcatt   8700
tatttttcaa tagagcctgt tttttgtact ggcaagacct acctgtatga ctacttaatt   8760
aagtagtcat acaggtaggt cttgccagta caaaaaacag gctctattga aaaataaatg   8820
acagaaatga cagaatcaca gaatggcctg ggttggaagg gacctcgagg atcacgaatc   8880
tccaaccccc ctgctgggca gggccaccaa catccccatt tactagacca ggttgcccag   8940
ggccccatcc aacctggcct tgaacacctc cagggacgga gcatccacaa cctctctggg   9000
cagcctgttc cagcacctca ccactctcct ggtaaagaac tttcccctaa catccaacct   9060
aaatcttccc tctttcaact taaaaccgtt gccccttgtc ctgctgttat ctaccctttc   9120
aaagagttta ctcccttcct gtttataggc tyccttcagg gactgaaagg ctgcaatggg   9180
atcaccgcgc agccttctct tctccaggct gaataagccc agctccctca gcctgtcctc   9240
ataggggaag tgctccagcc ccttgatcat ctctgtggtc agcgctccaa ctcctactgt   9300
ggtgcccagg atctcagcag cagggaagga agcacagggg aaacaagctg gagcctggta   9360
```

```
ggcagcttct gccaatccac acaacccata tcgcaggtgg ggcctgacac agattcttgc   9420
ctggtgtaca tctacaccgc aggctgccac agcctcgagt ctacaaaacg tggggtgaag   9480
agaagcaatg cagacatcct cttgccacag tcagagaaag aaggaagcct tcatcggttt   9540
ttccatgcac gtatttatta ggaaatcaga taattatagg caattagaat agtttctata   9600
ataataaagt ttaatacttt aaattacttg ggaaaattcc acgcatcttt aagtgtttaa   9660
tttaacattt ctattgcttc ttaagatgag tcttcttaca ccacacaata aaaatgaaaa   9720
tgtttctgtc ttctccagtg ctgcaacgta ccgctgacgt ctcatttacc cggagacagg   9780
gagaggctct tctgcgtgta gtggttgtgc agagcctcat gcatcacgga gcatgagaag   9840
acgttcccct gctgccacct gctcttgtcc acggtgagct tgctgtagag gaagaaggag   9900
ccgtcggagt ccagcacggg aggcgtggtc ttgtagttgt tctccggctg cccattgctc   9960
tcccactcca cggcgatgtc gctgggatag aagcctttga ccaggcaggt caggctgacc  10020
tggttcttgg tcagctcatc ccgggatggg ggcagggtgt acacctgtgg ttctcggggc  10080
tgccctttgg ctttggagat ggttttctcg atgggggctg ggagggcttt gttggagacc  10140
ttgcacttgt actccttgcc attcagccag tcctggtgca ggacggtgag gacgctgacc  10200
acacggtacg tgctgttgta ctgctcctcc cgcggctttg tcttggcatt atgcacctcc  10260
acgccgtcca cgtaccagtt gaacttgacc tcagggtctt cgtggctcac gtccaccacc  10320
acgcatgtga cctcaggggt ccgggagatc atgagggtgt ccttgggttt tggggggaag  10380
aggaagactg acggtccccc caggagttca ggtgctgggc acggtgggca tgtgtgagtt  10440
ttgtcacaag atttgggctc aactttcttg tccaccttgg tgttgctggg cttgtgattc  10500
acgttgcaga tgtaggtctg ggtgcccaag ctgctggagg gcacggtcac cacgctgctg  10560
agggagtaga gtcctgagga ctgtaggaca gccgggaagg tgtgcacgcc gctggtcagg  10620
gcgcctgagt tccacgacac cgtcaccggt tcggggaagt agtccttgac caggcagccc  10680
agggccgctg tgcccccaga ggtgctcttg gaggagggtg ccagggggaa gaccgatggg  10740
cccttggtgg aggctgagga gacggtgacc agggttccct ggccccaatt cgggggaggg  10800
ataactcccc caaatgttat cataatcccc gtggtacagt aatatacggc tgtgtcctcg  10860
gctttcaggc tattcatttg cagatataac gtgtttttg aatcatctct tgagatggtg  10920
aatctgcctt tcacgggtgc agcatagtct gttgtcccac catcaatttt gcttttaata  10980
cggccgaccc actccagccc cttccctgga gcctggcgga cccagctcat ccaggcgttt  11040
ctgaaagtga atccagaggc tgcacaggag actctaaggg acccccccgg ctttaccaag  11100
cctcccccg actcctgcag ctgcacctgc tggctgccta caagggtgag cactaatgcc  11160
agtatgatcc ccctcatagc gatatcgacg gtgactgcag aaaagaccca tggaaaggaa  11220
cagtctgtta gtctgtcagc tattatgtct ggtggcgcgc gcggcagcaa cgagtactgc  11280
tcagactaca ctgccctcca ccgttaacag caccgcaacg ggagttacct ctgactctta  11340
tcagaataca acaactcagc tgcctgcatc ttcttctgcc gctgccttaa gtcttccatc  11400
tgcgtcagcc gtgcgagccc aatctccacg ctcattttca gacacatacc ctaccgccac  11460
ggccttgtgc ggcacactgg tggtggtggg cattgtgctg tgcctaagtc tggcctccac  11520
tgttaggagc aaggagctgc cgagcgacca tgagccgctg gaggcatggg accagggctc  11580
ggatgtggaa gctccgccgc taccggagaa gagcccatgt ccggaacacg tacccgagat  11640
tcgcgtggag atcccacgct atgtttaata aaaactgcgg gcacgggggga cggcgttgtt  11700
gtatatgtga atttgtaaat aataaatggg accccatcct gtaaaaatac agagtccgtg  11760
```

```
tcagtctctg aaggacagag tattggcata tagccaatag agatagttgt ggcaaagagc  11820
catgttatgg attagtaatg gaaagtatcg tcaccaatag gggagtggtc aataatggtc  11880
aataacccac acctataggc taagctatac catcacctat agcataagga agcgggggtg  11940
tataggcccc aagccaaaaa cagtatagca tgcataagag ccaaaggggt gtgcctatag  12000
agtctatagg cggtacttac gtcactcttg gcacggggaa tccgcgttcc aatgcaccgt  12060
tcccggccgc ggaggctgga tcggtcccgg tgtcttctat ggaggtcaaa acagcgtgga  12120
tggcgtctcc aggcgatctg acggttcact aaacgagctc gggctctgcc aggcatggtg  12180
agacttttat ggaagaatgt tcaggaacac gtggctgttt tctgctgaat tctcaagttt  12240
tttatcagtt tatgtaaaca ctcctctttt tgcaatcata aattctcttc acggcgaata  12300
aagaaaatca aataatacct tggcatctct gataaaaaaa ccttttctg attgaccaga  12360
agtttcaatg tatcacagta aaacacttct actacggcat ttacaataaa tttaaaattg  12420
atgtgctact tgctttccta gattgggtca cggctggctg ctggtacatg gtcctgccac  12480
agatgagact ggttttgccc aggttatgtt gacctggcac ctgacccaag ttgttatcta  12540
gctgataata acccaatcag caatcagtat aatctacatt gactatactc tccctcttcc  12600
ctcagctttg gtttatggcc attcctgcag gccagaggct aatccagata aacctttgct  12660
attcatgtat tcatatgtgc accaacgcac atgatttaag aggctactga gaaacaatat  12720
atggaacata tgtatttatt gaaatcacgg gatcaatgtg ttctttcagc tccggtcacg  12780
ctgaccagga atatttttaa atgaacaaag gtttcataag cattctgtaa atattttatc  12840
ttccaaagta aatgggagca aaatgtgaac aattaaaacc tgcagagatt ctcagcagta  12900
aggcaagagg gatagaagtg caggtcagct agaacttttg catttcctac agaaccaaat  12960
acaaaatgca gccaagtagc tgaactgatg caggcttgca gccaacttca tcactaactg  13020
tgatttatat tgataacaca agaacacatt cagaaaatcg cctgttctag aaacgtcagg  13080
agtgtggaaa cagctcatca ggtaccctca gaaataggag ataaacaaag agtgaactaa  13140
gagaatgaac gggttcctgt aaaccctaca aaaaagttgg tcctccaaag caagtgggtg  13200
gcagttgcat cgacaagaac aagagcacgc ggtcttctgc attggaggat gtttttggag  13260
gtgcaacttt cagcagtgca atagattgtg gcatgaattc cgtacgcaat tggtttaaac  13320
gcgtaatatt ctcactgact ccgtcctgga gtaggatgag agataatggc cttacgttgt  13380
gccaggggag ggtcgggctg gatttagcaa gatttacctt ctccaaagag cggtgctgca  13440
gtggcacagc tgcccacgga ggtgggggg tcaccgtccc tggaggtgat gaagaactgt  13500
ggggatgtgg cactgaggga catggccagt gggcacggtg ggtgggttgg ggttggtctt  13560
ggggatcttg gagggctttt ccagccttca tgatttgacg attgtgtgaa catctacatg  13620
gcaattctcc agctgcctgt cccagtccta ctgacccagc tgtatctctc caggcaagct  13680
cttccacccc ttctgcttgc atccagacac catcaaacat gcaggctcag acacagggac  13740
cagcagtgtc tgtggccttt ttgtgctcct ctccatgctg ggttttaact tgctctttgt  13800
ccttctatcc tatcttctga tccttaaggc tgttctgaac gctgtgactt ggagagtgtc  13860
ccagagccct caacacctgc atgtcccacg tccatgctgt cctgctcttc cttatcccca  13920
agatctgcct ctccgtgatg cactgaattg gcaaacatgt gtcaccccag accaacaatg  13980
tcacagcaaa ctccccttg ataggacaag gggaatggc tttacactta gacaggggag  14040
gtttgggttg gatatgaaga ggcagttttt cccccagagg gtggtgacgc actgaacagg  14100
```

```
ttgcccaagg aggctgtgga tgccccatcc ctgcaggcat tccaggccag gctggatgtg  14160
tctctgggca gcctgggctg ctggttggcg accctgcaca tagcaggggt tggaactgga  14220
tgagcattgt gggcctttcc aacccaggcc attctgtgat tctgtcattc taaatctctc  14280
tttcagccta aagctttttc cccgtatccc cccaggtgtc tgcaggctca aagagcagcg  14340
agaagcgttc agaggaaagc gatcccgtgc caccttcccc gtgcccgggc tgtccccgca  14400
cgctgccggc tcggggatgc ggggggagcg ccggaccgga gcggagcccc gggcggctcg  14460
ctgctgcccc ctagcggggg agggacgtaa ttacatccct gggggctttg gggggggggct  14520
ctccccgtga gctcccgcgg acgccccctt ccaggacctt ccaggagggc ccctccggga  14580
tcatatgaca agatgtgtat ccaccttaac ttaatgattt ttaccaaaat cattagggga  14640
ttcatcagtg ctcagggtca acgagaatta acattccgtc aggaaagctt gaattcagct  14700
tttgttccct ttagtgaggg ttaattgcgc gcttggcgta atcatggtca tagctgtttc  14760
ctgtgtgaaa ttgttatccg ctcacaattc cacacaacat acgagccgga agcataaagt  14820
gtaaagcctg gggtgcctaa tgagtgagct aactcacatt aattgcgttg cgctcactgc  14880
ccgctttcca gtcgggaaac ctgtcgtgcc agctgcatta atgaatcggc caacgcgcgg  14940
ggagaggcgg tttgcgtatt gggcgctctt ccgcttcctc gctcactgac tcgctgcgct  15000
cggtcgttcg gctgcggcga gcggtatcag ctcactcaaa ggcggtaata cggttatcca  15060
cagaatcagg ggataacgca ggaaagaaca tgtgagcaaa aggccagcaa aaggccagga  15120
accgtaaaaa ggccgcgttg ctggcgtttt tccataggct ccgcccccct gacgagcatc  15180
acaaaaatcg acgctcaagt cagaggtggc gaaacccgac aggactataa agataccagg  15240
cgtttccccc tggaagctcc ctcgtgcgct ctcctgttcc gaccctgccg cttaccggat  15300
acctgtccgc ctttctccct tcgggaagcg tggcgctttc tcatagctca cgctgtaggt  15360
atctcagttc ggtgtaggtc gttcgctcca agctgggctg tgtgcacgaa ccccccgttc  15420
agcccgaccg ctgcgcctta tccggtaact atcgtcttga gtccaacccg gtaagacacg  15480
acttatcgcc actggcagca gccactggta acaggattag cagagcgagg tatgtaggcg  15540
gtgctacaga gttcttgaag tggtggccta actacggcta cactagaaga acagtatttg  15600
gtatctgcgc tctgctgaag ccagttacct tcggaaaaag agttggtagc tcttgatccg  15660
gcaaacaaac caccgctggt agcggtggtt tttttgtttg caagcagcag attacgcgca  15720
gaaaaaaagg atctcaagaa gatcctttga tcttttctac ggggtctgac gctcagtgga  15780
acgaaaactc acgttaaggg attttggtca tgagattatc aaaaaggatc ttcacctaga  15840
tccttttaaa ttaaaaatga agttttaaat caatctaaag tatatatgag taaacttggt  15900
ctgacagtta ccaatgctta atcagtgagg cacctatctc agcgatctgt ctatttcgtt  15960
catccatagt tgcctgactc cccgtcgtgt agataactac gatacgggag ggcttaccat  16020
ctggccccag tgctgcaatg ataccgcgag acccacgctc accggctcca gatttatcag  16080
caataaacca gccagccgga agggccgagc gcagaagtgg tcctgcaact ttatccgcct  16140
ccatccagtc tattaattgt tgccgggaag ctagagtaag tagttcgcca gttaatagtt  16200
tgcgcaacgt tgttgccatt gctacaggca tcgtggtgtc acgctcgtcg tttggtatgg  16260
cttcattcag ctccggttcc caacgatcaa ggcgagttac atgatccccc atgttgtgca  16320
aaaaagcggt tagctccttc ggtcctccga tcgttgtcag aagtaagttg gccgcagtgt  16380
tatcactcat ggttatggca gcactgcata attctcttac tgtcatgcca tccgtaagat  16440
gcttttctgt gactggtgag tactcaacca agtcattctg agaatagtgt atgcggcgac  16500
```

```
cgagttgctc ttgcccggcg tcaatacggg ataataccgc gccacatagc agaactttaa  16560

aagtgctcat cattggaaaa cgttcttcgg ggcgaaaact ctcaaggatc ttaccgctgt  16620

tgagatccag ttcgatgtaa cccactcgtg cacccaactg atcttcagca tcttttactt  16680

tcaccagcgt ttctgggtga gcaaaaacag gaaggcaaaa tgccgcaaaa aagggaataa  16740

gggcgacacg gaaatgttga atactcatac tcttcctttt tcaatattat tgaagcattt  16800

atcagggtta ttgtctcatg agcggataca tatttgaatg tatttagaaa aataaacaaa  16860

taggggttcc gcgcacattt ccccgaaaag tgccac                            16896
```

<210> SEQ ID NO 25
<211> LENGTH: 19714
<212> TYPE: DNA
<213> ORGANISM: Artificial Sequence
<220> FEATURE:
<223> OTHER INFORMATION: Synthetic construct

<400> SEQUENCE: 25

```
ctgacgcgcc ctgtagcggc gcattaagcg cggcgggtgt ggtggttacg cgcagcgtga     60

ccgctacact tgccagcgcc ctagcgcccg ctcctttcgc tttcttccct tcctttctcg    120

ccacgttcgc cggcatcaga ttggctattg gccattgcat acgttgtatc catatcataa    180

tatgtacatt tatattggct catgtccaac attaccgcca tgttgacatt gattattgac    240

tagttattaa tagtaatcaa ttacggggtc attagttcat agcccatata tggagttccg    300

cgttacataa cttacggtaa atggcccgcc tggctgaccg cccaacgacc cccgcccatt    360

gacgtcaata atgacgtatg ttcccatagt aacgccaata gggactttcc attgacgtca    420

atgggtggag tatttacggt aaactgccca cttggcagta catcaagtgt atcatatgcc    480

aagtacgccc cctattgacg tcaatgacgg taaatggccc gcctggcatt atgcccagta    540

catgacctta tgggactttc ctacttggca gtacatctac gtattagtca tcgctattac    600

catggtgatg cggttttggc agtacatcaa tgggcgtgga tagcggtttg actcacgggg    660

atttccaagt ctccacccca ttgacgtcaa tgggagtttg ttttggcacc aaaatcaacg    720

ggactttcca aaatgtcgta acaactccgc cccattgacg caaatgggcg gtaggcgtgt    780

acggtgggag gtctatataa gcagagctcg tttagtgaac cgtcagatcg cctggagacg    840

ccatccacgc tgttttgacc tccatagaag acaccgggac cgatccagcc tccgcggccg    900

ggaacggtgc attggaacgc ggattccccg tgccaagagt gacgtaagta ccgcctatag    960

actctatagg cacacccctt tggctcttat gcatgctata ctgtttttgg cttggggcct   1020

atacaccccc gcttccttat gctataggtg atggtatagc ttagcctata ggtgtgggtt   1080

attgaccatt attgaccact cccctattgg tgacgatact ttccattact aatccataac   1140

atggctcttt gccacaacta tctctattgg ctatatgcca atactctgtc cttcagagac   1200

tgacacggac tctgtatttt tacaggatgg ggtcccattt attatttaca aattcacata   1260

tacaacaacg ccgtcccccg tgcccgcagt ttttattaaa catagcgtgg gatctccacg   1320

cgaatctcgg gtacgtgttc cggacatggg ctcttctccg gtagcggcgg agcttccaca   1380

tccgagccct ggtcccatgc ctccagcggc tcatggtcgc tcggcagctc cttgctccta   1440

acagtggagg ccagacttag gcacagcaca atgcccacca ccaccagtgt gccgcacaag   1500

gccgtggcgg tagggtatgt gtctgaaaat gagcgtggag attgggctcg cacggctgac   1560

gcagatggaa gacttaaggc agcggcagaa gaagatgcag gcagctgagt tgttgtattc   1620
```

-continued

```
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
```

```
ttttttttgcc tgtttttttt tttttttttt tttttttttaa gtaaggtgtt ctttttttctt   4080
agtaaatttt ctactggact gtatgttttg acaggtcaga aacatttctt caaaagaaga   4140
accttttgga aactgtacag cccttttctt tcattccctt tttgctttct gtgccaatgc   4200
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt atttttccc tttgaagtag tgagcgttct ctggtttttt tcctttgaaa   4380
ctggtgaggc ttagattttt ctaatgggat tttttacctg atgatctagt tgcataccca   4440
aatgcttgta aatgttttcc tagttaacat gttgataact tcggatttac atgttgtata   4500
tacttgtcat ctgtgtttct agtaaaaata tatggcattt atagaaatac gtaattcctg   4560
atttcctttt ttttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
gttcctgaat cctttctata gcaccactta ttgcagcagg tgtaggctct ggtgtggcct   5340
gtgtctgtgc ttcaatcttt taagcttctc gagggcgcgc cgtgctttac agaggtcaga   5400
atggtttctt tactgtttgt caattctatt atttcaatac agaacaatag cttctataac   5460
tgaaatatat ttgctattgt atattatgat tgtccctcga accatgaaca ctcctccagc   5520
tgaatttcac aattcctctg tcatctgcca ggccattaag ttattcatgg aagatctttg   5580
aggaacactg caagttcata tcataaacac atttgaaatt gagtattgtt ttgcattgta   5640
tggagctatg ttttgctgta tcctcagaaa aaaaagtttg ttataaagca ttcacaccca   5700
taaaaagata gatttaaata ttccaactat aggaaagaaa gtgcgtctgc tcttcactct   5760
agtctcagtt ggctccttca catgcatgct tctttatttc tcctattttg tcaagaaaat   5820
aataggtcac gtcttgttct cacttatgtc ctgcctagca tggctcagat gcacgttgta   5880
catacaagaa ggatcaaatg aaacagactt ctggtctgtt actacaacca tagtaataag   5940
cacactaact aataattgct aattatgttt tccatctcta aggttcccat atttttctgt   6000
tttcttaaag atcccattat ctggttgtaa ctgaagctca atggaacatg agcaatattt   6060
cccagtcttc tctcccatcc aacagtcctg atggattagc agaacaggca gaaaacacat   6120
tgttacccag aattaaaaac taatatttgc tctccattca atccaaaatg gacctattga   6180
aactaaaatc taacccaatc ccattaaatg atttctatgg cggaattctg gccattgcat   6240
acgttgtatc catatcataa tatgtacatt tatattggct catgtccaac attaccgcca   6300
tgttgacatt gattattgac tagttattaa tagtaatcaa ttacggggtc attagttcat   6360
```

-continued

```
agcccatata tggagttccg cgttacataa cttacggtaa atggcccgcc tggctgaccg   6420
cccaacgacc cccgcccatt gacgtcaata atgacgtatg ttcccatagt aacgccaata   6480
gggactttcc attgacgtca atgggtggag tatttacggt aaactgccca cttggcagta   6540
catcaagtgt atcatatgcc aagtacgccc cctattgacg tcaatgacgg taaatggccc   6600
gcctggcatt atgcccagta catgacctta tgggactttc ctacttggca gtacatctac   6660
gtattagtca tcgctattac catggtgatg cggttttggc agtacatcaa tgggcgtgga   6720
tagcggtttg actcacgggg atttccaagt ctccacccca ttgacgtcaa tgggagtttg   6780
ttttggcacc aaaatcaacg ggactttcca aaatgtcgta acaactccgc cccattgacg   6840
caaatgggcg gtaggcgtgt acggtgggag gtctatataa gcactcgagc tcgtttagtg   6900
aaccgtcaga tcgcctggag acgccatcca cgctgttttg acctccatag aagacaccgg   6960
gaccgatcca gcctccgcgg ccgggaacgg tgcattggaa cgcggattcc ccgtgccaag   7020
agtgacgtaa gtaccgccta tagactctat aggcacaccc ctttggctct tatgcatgct   7080
atactgtttt tggcttgggg cctatacacc cccgcttcct tatgctatag gtgatggtat   7140
agcttagcct ataggtgtgg gttattgacc attattgacc actcccctat tggtgacgat   7200
actttccatt actaatccat aacatggctc tttgccacaa ctatctctat tggctatatg   7260
ccaatactct gtccttcaga gactgacacg gactctgtat ttttacagga tggggtccca   7320
tttattattt acaaattcac atatacaaca acgccgtccc ccgtgcccgc agtttttatt   7380
aaacatagcg tgggatctcc acgcgaatct cgggtacgtg ttccggacat gggctcttct   7440
ccggtagcgg cggagcttcc acatccgagc cctggtccca tgcctccagc ggctcatggt   7500
cgctcggcag ctccttgctc ctaacagtgg aggccagact taggcacagc acaatgccca   7560
ccaccaccag tgtgccgcac aaggccgtgg cggtagggta tgtgtctgaa aatgagcgtg   7620
gagattgggc tcgcacggct gacgcagatg gaagacttaa ggcagcggca gaagaagatg   7680
caggcagctg agttgttgta ttctgataag agtcagaggt aactcccgtt gcggtgctgt   7740
taacggtgga gggcagtgta gtctgagcag tactcgttgc tgccgcgcgc gccaccagac   7800
ataatagctg acagactaac agactgttcc tttccatggg tcttttctgc agtcaccgtc   7860
gtcgacaaca tgaagctcat cctctgcacc gtgctgtcct tggggatagc ggctgtgtgt   7920
ttcgccgagg ttcagctggt ggagtctggc ggtggcctgg tgcagcccgg gggctctctc   7980
cgtttgtcct gtgcagcttc tggcttcaac attaaagaca cctatatcca ctgggtgcgt   8040
caggctccgg gtaagggcct ggagtgggtt gcaaggattt atcctacgaa tggttatact   8100
cgttatgccg atagcgtcaa gggccgtttc actataagcg cagacacttc gaaaaacaca   8160
gcctacctcc agatgaacag cctgcgtgct gaggacactg ccgtctatta ttgtagcaga   8220
tggggtgggg acggcttcta tgctatggac tactggggtc aaggtacact agtcaccgtc   8280
agcagcgcta gcaccaaggg cccatccgtc ttcccccctgg cgccctcctc caagagcacc   8340
tctgggggca cagcggccct gggctgcctg gtcaaggact acttccccga accggtgacg   8400
gtgtcgtgga actcaggcgc cctgaccagc ggcgtgcaca ccttcccggc tgtcctacag   8460
tcctcaggac tctactccct cagcagcgtg gtgaccgtgc cctccagcag cttgggcacc   8520
cagacctaca tctgcaacgt gaatcacaag cccagcaaca ccaaggtgga caagaaagtt   8580
gagcccaaat cttgtgacaa aactcacaca tgcccaccgt gcccagcacc tgaactcctg   8640
gggggaccgt cagtcttcct cttcccccca aaacccaagg acaccctcat gatctcccgg   8700
acccctgagg tcacatgcgt ggtggtggac gtgagccacg aagaccctga ggtcaagttc   8760
```

```
aactggtacg tggacggcgt ggaggtgcat aatgccaaga caaagccgcg ggaggagcag   8820
tacaacagca cgtaccgtgt ggtcagcgtc ctcaccgtcc tgcaccagga ctggctgaat   8880
ggcaaggagt acaagtgcaa ggtctccaac aaagccctcc cagcccccat cgagaaaacc   8940
atctccaaag ccaaagggca gccccgagaa ccacaggtgt acaccctgcc cccatcccgg   9000
gatgagctga ccaagaacca ggtcagcctg acctgcctgg tcaaaggctt ctatcccagc   9060
gacatcgccg tggagtggga gagcaatggg cagccggaga acaactacaa gaccacgcct   9120
cccgtgctgg actccgacgg ctccttcttc ctctacagca agctcaccgt ggacaagagc   9180
aggtggcagc aggggaacgt cttctcatgc tccgtgatgc atgaggctct gcacaaccac   9240
tacacgcaga agagcctctc cctgtctccg ggtaaatgag gatccaaaga agaaagctga   9300
aaaactctgt cccttccaac aagacccaga gcactgtagt atcaggggta aaatgaaaag   9360
tatgttatct gctgcatcca gacttcataa aagctggagc ttaatctaga aaaaaaatca   9420
gaaagaaatt acactgtgag aacaggtgca attcactttt cctttacaca gagtaatact   9480
ggtaactcat ggatgaaggc ttaagggaat gaaattggac tcacagtact gagtcatcac   9540
actgaaaaat gcaacctgat acatcagcag aaggtttatg ggggaaaaat gcagccttcc   9600
aattaagcca gatatctgta tgaccaagct gctccagaat tagtcactca aaatctctca   9660
gattaaatta tcaactgtca ccaaccattc ctatgctgac aaggcaattg cttgttctct   9720
gtgttcctga tactacaagg ctcttcctga cttcctaaag atgcattata aaaatcttat   9780
aattcacatt tctccctaaa ctttgactca atcatggtat gttggcaaat atggtatatt   9840
actattcaaa ttgttttcct tgtacccata tgtaatgggt cttgtgaatg tgctcttttg   9900
ttcctttaat cataataaaa acatgtttaa gcaaacactt ttcacttgta gtatttgaag   9960
tacagcaagg ttgtgtagca gggaaagaat gacatgcaga ggaataagta tggacacaca  10020
ggctagcagc gactgtagaa caagtactaa tgggtgagaa gttgaacaag agtcccctac  10080
agcaacttaa tctaataagc tagtggtcta catcagctaa aagagcatag tgagggatga  10140
aattggttct cctttctaag catcacctgg gacaactcat ctggagcagt gtgtccaatc  10200
ttgcgatcgc agatctttaa ttaaggcgcc tgcaggaaga ttggacacac tgctccagat  10260
gagttgtccc aggtgatgct tagaaaggag aaccaatttc atccctcact atgctctttt  10320
agctgatgta gaccactagc ttattagatt aagttgctgt aggggactct tgttcaactt  10380
ctcacccatt agtacttgtt ctacagtcgc tgctagcctg tgtgtccata cttattcctc  10440
tgcatgtcat tctttccctg ctacacaacc ttgctgtact tcaaatacta caagtgaaaa  10500
gtgtttgctt aaacatgttt ttattatgat taaaggaaca aaagagcaca ttcacaagac  10560
ccattacata tgggtacaag gaaaacaatt tgaatagtaa tataccatat ttgccaacat  10620
accatgattg agtcaaagtt tagggagaaa tgtgaattat aagattttta taatgcatct  10680
ttaggaagtc aggaagagcc ttgtagtatc aggaacacag agaacaagca attgccttgt  10740
cagcatagga atggttggtg acagttgata atttaatctg agagattttg agtgactaat  10800
tctggagcag cttggtcata cagatatctg gcttaattgg aaggctgcat tttcccccca  10860
taaaccttct gctgatgtat caggttgcat tttcagtgt gatgactcag tactgtgagt  10920
ccaatttcat tcccttaagc cttcatccat gagttaccag tattactctg tgtaaaggaa  10980
aagtgaattg cacctgttct cacagtgtaa tttctttctg atttttttttc tagattaagc  11040
tccagctttt atgaagtctg gatgcagcag ataacatact tttcatttta cccctgatac  11100
```

```
tacagtgctc tgggtcttgt tggaagggac agagtttttc agctttcttc tttggatccc  11160
taacactctc ccctgttgaa gctctttgtg acgggcgaac tcaggccctg atgggtgact  11220
tcgcaggcgt agactttgtg tttctcgtag tctgctttgc tcagcgtcag ggtgctgctg  11280
aggctgtagg tgctgtcctt gctgtcctgc tctgtgacac tctcctggga gttacccgat  11340
tggagggcgt tatccacctt ccactgtact ttggcctctc tgggatagaa gttattcagc  11400
aggcacacaa cagaggcagt tccagatttc aactgctcat cagatggcgg gaagatgaag  11460
acagatggtg cagccgcggc ccgtttgatc tccaccttgg taccctgtcc gaacgtcgga  11520
ggagtagtat agtgttgctg acagtaataa gttgcgaagt cttccggctg cagggagctg  11580
atggtcagag tgaaatccgt cccagagcgg gaaccagaga agcgagaagg gactccagag  11640
tagaggaagg atgccgagta aatcagcagt ttcggggcct ttccgggttt ctgttgatac  11700
caggctacag cagtattcac atcctgactg gcacggcagg tgatagtgac cctatcgccc  11760
acagaggcgg acagggagct cggggactgg gtcatctgga tatcggcgaa acacacagcc  11820
gctatcccca aggacagcac ggtgcagagg atgagcttca tgttgtcgac gacggtgact  11880
gcagaaaaga cccatggaaa ggaacagtct gttagtctgt cagctattat gtctggtggc  11940
gcgcgcggca gcaacgagta ctgctcagac tacactgccc tccaccgtta acagcaccgc  12000
aacgggagtt acctctgact cttatcagaa tacaacaact cagctgcctg catcttcttc  12060
tgccgctgcc ttaagtcttc catctgcgtc agccgtgcga gcccaatctc cacgctcatt  12120
ttcagacaca taccctaccg ccacggcctt gtgcggcaca ctggtggtgg tgggcattgt  12180
gctgtgccta agtctggcct ccactgttag gagcaaggag ctgccgagcg accatgagcc  12240
gctggaggca tgggaccagg gctcggatgt ggaagctccg ccgctaccgg agaagagccc  12300
atgtccggaa cacgtacccg agattcgcgt ggagatccca cgctatgttt aataaaaact  12360
gcgggcacgg gggacggcgt tgttgtatat gtgaatttgt aaataataaa tgggacccca  12420
tcctgtaaaa atacagagtc cgtgtcagtc tctgaaggac agagtattgg catatagcca  12480
atagagatag ttgtggcaaa gagccatgtt atggattagt aatggaaagt atcgtcacca  12540
ataggggagt ggtcaataat ggtcaataac ccacacctat aggctaagct ataccatcac  12600
ctatagcata aggaagcggg ggtgtatagg ccccaagcca aaaacagtat agcatgcata  12660
agagccaaag ggtgtgcct atagagtcta taggcggtac ttacgtcact cttggcacgg  12720
ggaatccgcg ttccaatgca ccgttcccgg ccgcggaggc tggatcggtc ccggtgtctt  12780
ctatggaggt caaaacagcg tggatggcgt ctccaggcga tctgacggtt cactaaacga  12840
gctcgagtgc ttatatagac ctcccaccgt acacgcctac cgcccatttg cgtcaatggg  12900
gcggagttgt tacgacattt tggaaagtcc cgttgatttt ggtgccaaaa caaactccca  12960
ttgacgtcaa tggggtggag acttggaaat ccccgtgagt caaaccgcta tccacgccca  13020
ttgatgtact gccaaaaccg catcaccatg gtaatagcga tgactaatac gtagatgtac  13080
tgccaagtag gaaagtccca taaggtcatg tactgggcat aatgccaggc gggccattta  13140
ccgtcattga cgtcaatagg gggcgtactt ggcatatgat acacttgatg tactgccaag  13200
tgggcagttt accgtaaata ctccacccat tgacgtcaat ggaaagtccc tattggcgtt  13260
actatgggaa catacgtcat tattgacgtc aatgggcggg ggtcgttggg cggtcagcca  13320
ggcgggccat ttaccgtaag ttatgtaacg cggaactcca tatatgggct atgaactaat  13380
gaccccgtaa ttgattacta ttaataacta gtcaataatc aatgtcaaca tggcggtaat  13440
gttggacatg agccaatata aatgtacata ttatgatatg gatacaacgt atgcaatggc  13500
```

```
cagaattccg ccatagaaat catttaatgg gattgggtta gattttagtt tcaataggtc  13560
cattttggat tgaatggaga gcaaatatta gtttttaatt ctgggtaaca atgtgttttc  13620
tgcctgttct gctaatccat caggactgtt ggatgggaga gaagactggg aaatattgct  13680
catgttccat tgagcttcag ttacaaccag ataatgggat ctttaagaaa acagaaaaat  13740
atgggaacct tagagatgga aaacataatt agcaattatt agttagtgtg cttattacta  13800
tggttgtagt aacagaccag aagtctgttt catttgatcc ttcttgtatg tacaacgtgc  13860
atctgagcca tgctaggcag gacataagtg agaacaagac gtgacctatt attttcttga  13920
caaaatagga gaaataaaga agcatgcatg tgaaggagcc aactgagact agagtgaaga  13980
gcagacgcac tttctttcct atagttggaa tatttaaatc tatcttttta tgggtgtgaa  14040
tgctttataa caaacttttt tttctgagga tacagcaaaa catagctcca tacaatgcaa  14100
aacaatactc aatttcaaat gtgtttatga tatgaacttg cagtgttcct caaagatctt  14160
ccatgaataa cttaatggcc tggcagatga cagaggaatt gtgaaattca gctggaggag  14220
tgttcatggt tcgagggaca atcataatat acaatagcaa atatatttca gttatagaag  14280
ctattgttct gtattgaaat aatagaattg acaaacagta aagaaaccat tctgacctct  14340
gtaaagcacc gtacggtaac ctgaggctat ggcagggcct gccgccccga cgttggctgc  14400
gagccctggg ccttcacccg aacttggggg gtggggtggg gaaaaggaag aaacgcgggc  14460
gtattggccc caatggggtc tcggtggggt atcgacagag tgccagccct gggaccgaac  14520
cccgcgttta tgaacaaacg acccaacacc gtgcgtttta ttctgtcttt ttattgccgt  14580
catagcgcgg gttccttccg gtattgtctc cttccgtgtt tcagttagcc tcccccctagg  14640
gtgggcgaag aactccagca tgagatccga gctcaggatc cgctagcgaa ttcaggttta  14700
agcacctggt ttgcgagtca tgcaccaagt gcgtgggcct tctggcactt ccacatcagc  14760
agtcacagtg aagcccaggc gttcatagaa aggcaggttg cgtggagctg aggtctccag  14820
gaaagcaggc acacctgcac gttcagctgc ttccacacca ggcagcacca ctgcagagcc  14880
caggccctta ccctggtggt cagggctcac acccacagtt gccaggaacc aagcaggttc  14940
ttttgggcgg tgtggtgcca gcagaccttc catctgctgt tgtgctgcca ggcggctgcc  15000
agacagttct gccatgcgtg ggccaatctc agcaaacact gcaccagctt caacagattc  15060
aggggtggtc cacactgcca cagcagcacc atcatctgcc acccacactt tgccaatgtc  15120
caggcccaca cgggtcagga acagctcctg cagttcagtc acacgttcaa tgtggcggtc  15180
tgggtccaca gtgtgacggg ttgcagggta gtcagcaaat gcagcagcca gggtgcgaac  15240
tgcacgtgga acatcatcac gagttgccag gcgaacagtt ggtttgtatt cagtcatgac  15300
gatcctcatc ctgtctcttg atcgatcttt gcaaaagcct aggcctccaa aaaagcctcc  15360
tcactacttc tggaatagct cagaggccga ggcggcctcg gcctctgcat aaataaaaaa  15420
aattagtcag ccatggggcg gagaatgggc ggaactgggc ggagttaggg gcgggatggg  15480
cggagttagg ggcgggacta tggttgctga ctaattgaga tgcatgcttt gcatacttct  15540
gcctgctggg gagcctgggg actttccaca cctggttgct gactaattga gatgcatgct  15600
ttgcatactt ctgcctgctg gggagcctgg ggactttcca caccctaact gacacacatt  15660
ccacagctgg ttctttccgc ctcagacgcg taagcttaaa agattgaagc acagacacag  15720
gccacaccag agcctacacc tgctgcaata agtggtgcta tagaaaggat tcaggaacta  15780
acaagtgcat aatttacaaa tagagatgct ttatcatact ttgcccaaca tgggaaaaaa  15840
```

```
gacatcccat gagaatatcc aactgaggaa cttctctgtt tcatagtaac tcatctacta  15900
ctgctaagat ggtttgaaaa gtacccagca ggtgagatgt gttccgggag gtggctgtgt  15960
ggcagcgtgt gggaacacga cacaaagcac cccaccccta tctgcaatgc tcactgcaag  16020
gcagtgccgt aaacagctgc aacaggcatc caggcatcac ttctgcataa acgctgtgac  16080
tcgttagcat gctgcaactg tgtttaaaac ctatgcactc cgttaccaaa ataatttaag  16140
tcccaaacaa atccatgcag cttgcttcct atgccaaaat attttagaaa gtattcattc  16200
ttctttaaga atatgcacgt ggatctgcac ttccctggga tctgaagcga tttatacctc  16260
agtgcagaag cagtttagtg tcctggatct cgggaaggca gcagccaaac gtgcccgttt  16320
tacatttaaa cccatgtgac aacccgcctt actgagcatc gctctaggaa atttaaggct  16380
gtatccttac aacacaagaa ccaacgacag actgcatata aaattctata aataaaaata  16440
ggagtgaagt ctgtttgacc tgtacacaca gagcatagag ataaaaaaaa aaggaaatca  16500
ggaattacgt atttctataa atgccatata tttttactag aaacacagat gacaagtata  16560
tacaacatgt aaatccgaag ttatcaacat gttaactagg aaaacattta caagcatttg  16620
ggtatgcaac tagatcatca ggtaaaaaat cccattagaa aaatctaagc ctcaccagtt  16680
tcaaaggaaa aaaaccagag aacgctcact acttcaaagg gaaaaaataa agcatcaagc  16740
tggcctaaac ttaataaggt atctcgtgta acaacagcta tccaagcttt caagccacac  16800
tataaataaa aacctcaagt tccgatcaac gttttccata atgcaatcag aaccaaaggc  16860
attggcacag aaagcaaaaa gggaatgaaa gaaaagggct gtacagtttc caaaaggttc  16920
ttcttttgaa gaaatgtttc tgacctgtca aaacatacag tccagtagaa aatttactaa  16980
gaaaaaagaa caccttactt aaaaaaaaaa aaaaaaaaaa aaaaaacagg caaaaaaacc  17040
tctcctgtca ctgagctgcc accaccccaa ccaccacctg ctgtgggctt tgtctcccaa  17100
gacaaaggac acacagcctt atccaatatt caacattact tataaaaaca ctgatcagaa  17160
gaaataccaa gtatttcctc acagactgtt atacagactg ttatatcctt tcatcggcaa  17220
gaagagatga aatacaacag agtgaatatc aaagaaggcg gcaggagcca ccgtggcacc  17280
atcaccgggc agtgcagtgc ccagctgccg tttcctgagc acgcacagga agccgtcagt  17340
cacatgtaat aaaccaaaac ctggtacagt tatattatgg atccgggccc ctccgggatc  17400
atatgacaag atgtgtatcc accttaactt aatgattttt accaaaatca ttaggggatt  17460
catcagtgct cagggtcaac gagaattaac attccgtcag gaaagcttga attcagcttt  17520
tgttcccttt agtgagggtt aattgcgcgc ttggcgtaat catggtcata gctgtttcct  17580
gtgtgaaatt gttatccgct cacaattcca cacaacatac gagccggaag cataaagtgt  17640
aaagcctggg gtgcctaatg agtgagctaa ctcacattaa ttgcgttgcg ctcactgccc  17700
gctttccagt cgggaaacct gtcgtgccag ctgcattaat gaatcggcca acgcgcgggg  17760
agaggcggtt tgcgtattgg gcgctcttcc gcttcctcgc tcactgactc gctgcgctcg  17820
gtcgttcggc tgcggcgagc ggtatcagct cactcaaagg cggtaatacg gttatccaca  17880
gaatcagggg ataacgcagg aaagaacatg tgagcaaaag gccagcaaaa ggccaggaac  17940
cgtaaaaagg ccgcgttgct ggcgtttttc cataggctcc gcccccctga cgagcatcac  18000
aaaaatcgac gctcaagtca gaggtggcga aacccgacag gactataaag ataccaggcg  18060
tttccccctg gaagctccct cgtgcgctct cctgttccga ccctgccgct taccggatac  18120
ctgtccgcct ttctcccttc gggaagcgtg gcgctttctc atagctcacg ctgtaggtat  18180
ctcagttcgg tgtaggtcgt tcgctccaag ctgggctgtg tgcacgaacc ccccgttcag  18240
```

cccgaccgct gcgccttatc cggtaactat cgtcttgagt ccaacccggt aagacacgac 18300
ttatcgccac tggcagcagc cactggtaac aggattagca gagcgaggta tgtaggcggt 18360
gctacagagt tcttgaagtg gtggcctaac tacggctaca ctagaagaac agtatttggt 18420
atctgcgctc tgctgaagcc agttaccttc ggaaaaagag ttggtagctc ttgatccggc 18480
aaacaaacca ccgctggtag cggtggtttt tttgtttgca agcagcagat tacgcgcaga 18540
aaaaaaggat ctcaagaaga tcctttgatc ttttctacgg ggtctgacgc tcagtggaac 18600
gaaaactcac gttaagggat tttggtcatg agattatcaa aaaggatctt cacctagatc 18660
cttttaaatt aaaaatgaag ttttaaatca atctaaagta tatatgagta aacttggtct 18720
gacagttacc aatgcttaat cagtgaggca cctatctcag cgatctgtct atttcgttca 18780
tccatagttg cctgactccc cgtcgtgtag ataactacga tacgggaggg cttaccatct 18840
ggccccagtg ctgcaatgat accgcgagac ccacgctcac cggctccaga tttatcagca 18900
ataaaccagc cagccggaag ggccgagcgc agaagtggtc ctgcaacttt atccgcctcc 18960
atccagtcta ttaattgttg ccgggaagct agagtaagta gttcgccagt taatagtttg 19020
cgcaacgttg ttgccattgc tacaggcatc gtggtgtcac gctcgtcgtt tggtatggct 19080
tcattcagct ccggttccca acgatcaagg cgagttacat gatcccccat gttgtgcaaa 19140
aaagcggtta gctccttcgg tcctccgatc gttgtcagaa gtaagttggc cgcagtgtta 19200
tcactcatgg ttatggcagc actgcataat tctcttactg tcatgccatc cgtaagatgc 19260
ttttctgtga ctggtgagta ctcaaccaag tcattctgag aatagtgtat gcggcgaccg 19320
agttgctctt gcccggcgtc aatacgggat aataccgcgc cacatagcag aactttaaaa 19380
gtgctcatca ttggaaaacg ttcttcgggg cgaaaactct caaggatctt accgctgttg 19440
agatccagtt cgatgtaacc cactcgtgca cccaactgat cttcagcatc ttttactttc 19500
accagcgttt ctgggtgagc aaaaacagga aggcaaaatg ccgcaaaaaa gggaataagg 19560
gcgacacgga aatgttgaat actcatactc ttcctttttc aatattattg aagcatttat 19620
cagggttatt gtctcatgag cggatacata tttgaatgta tttagaaaaa taaacaaata 19680
ggggttccgc gcacatttcc ccgaaaagtg ccac 19714

<210> SEQ ID NO 26
<211> LENGTH: 19400
<212> TYPE: DNA
<213> ORGANISM: Artificial Sequence
<220> FEATURE:
<223> OTHER INFORMATION: Synthetic construct

<400> SEQUENCE: 26
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggcatcaga ttggctattg gccattgcat acgttgtatc catatcataa 180
tatgtacatt tatattggct catgtccaac attaccgcca tgttgacatt gattattgac 240
tagttattaa tagtaatcaa ttacggggtc attagttcat agcccatata tggagttccg 300
cgttacataa cttacggtaa atggcccgcc tggctgaccg cccaacgacc cccgcccatt 360
gacgtcaata atgacgtatg ttcccatagt aacgccaata gggactttcc attgacgtca 420
atgggtggag tatttacggt aaactgccca cttggcagta catcaagtgt atcatatgcc 480
aagtacgccc cctattgacg tcaatgacgg taaatggccc gcctggcatt atgcccagta 540

```
catgacctta tgggactttc ctacttggca gtacatctac gtattagtca tcgctattac    600
catggtgatg cggttttggc agtacatcaa tgggcgtgga tagcggtttg actcacgggg    660
atttccaagt ctccacccca ttgacgtcaa tgggagtttg ttttggcacc aaaatcaacg    720
ggactttcca aaatgtcgta acaactccgc cccattgacg caaatgggcg gtaggcgtgt    780
acggtgggag gtctatataa gcagagctcg tttagtgaac cgtcagatcg cctggagacg    840
ccatccacgc tgttttgacc tccatagaag acaccgggac cgatccagcc tccgcggccg    900
ggaacggtgc attggaacgc ggattccccg tgccaagagt gacgtaagta ccgcctatag    960
actctatagg cacacccctt tggctcttat gcatgctata ctgtttttgg cttggggcct   1020
atacaccccc gcttccttat gctataggtg atggtatagc ttagcctata ggtgtgggtt   1080
attgaccatt attgaccact cccctattgg tgacgatact ttccattact aatccataac   1140
atggctcttt gccacaacta tctctattgg ctatatgcca atactctgtc cttcagagac   1200
tgacacggac tctgtatttt tacaggatgg ggtcccattt attatttaca aattcacata   1260
tacaacaacg ccgtcccccg tgcccgcagt ttttattaaa catagcgtgg gatctccacg   1320
cgaatctcgg gtacgtgttc cggacatggg ctcttctccg gtagcggcgg agcttccaca   1380
tccgagccct ggtcccatgc ctccagcggc tcatggtcgc tcggcagctc cttgctccta   1440
acagtggagg ccagacttag gcacagcaca atgcccacca ccaccagtgt gccgcacaag   1500
gccgtggcgg tagggtatgt gtctgaaaat gagcgtggag attgggctcg cacggctgac   1560
gcagatggaa gacttaaggc agcggcagaa gaagatgcag gcagctgagt tgttgtattc   1620
tgataagagt cagaggtaac tcccgttgcg gtgctgttaa cggtggaggg cagtgtagtc   1680
tgagcagtac tcgttgctgc cgcgcgcgcc accagacata atagctgaca gactaacaga   1740
ctgttccttt ccatgggtct tttctgcagt caccgtctcg cgaaaaatca ataatcagac   1800
aacaagatgt gcgaactcga tattttacac gactctcttt accaattctg ccccgaatta   1860
cacttaaaac gactcaacag cttaacgttg gcttgccacg cattacttga ctgtaaaact   1920
ctcactctta ccgaacttgg ccgtaacctg ccaaccaaag cgagaacaaa acataacatc   1980
aaacgaatcg accgattgtt aggtaatcgt cacctccaca aagagcgact cgctgtatac   2040
cgttggcatg ctagctttat ctgttcgggc aatacgatgc ccattgtact tgttgactgg   2100
tctgatattc gtgagcaaaa acgacttatg gtattgcgag cttcagtcgc actacacggt   2160
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
```

```
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
tttttttgcc tgtttttttt tttttttttt ttttttttaa gtaaggtgtt ctttttttctt  4080
agtaaatttt ctactggact gtatgttttg acaggtcaga aacatttctt caaaagaaga   4140
accttttgga aactgtacag ccctttttctt tcattccctt tttgctttct gtgccaatgc  4200
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt atttttttccc tttgaagtag tgagcgttct ctggtttttt tcctttgaaa  4380
ctggtgaggc ttagattttt ctaatgggat tttttacctg atgatctagt tgcataccca   4440
aatgcttgta aatgttttcc tagttaacat gttgataact tcggatttac atgttgtata   4500
tacttgtcat ctgtgtttct agtaaaaata tatggcattt atagaaatac gtaattcctg   4560
atttcctttt ttttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
```

```
gttcctgaat cctttctata gcaccactta ttgcagcagg tgtaggctct ggtgtggcct   5340
gtgtctgtgc ttcaatcttt taagcttctc gagggcgcgc cgtgctttac agaggtcaga   5400
atggtttctt tactgtttgt caattctatt atttcaatac agaacaatag cttctataac   5460
tgaaatatat ttgctattgt atattatgat tgtccctcga accatgaaca ctcctccagc   5520
tgaatttcac aattcctctg tcatctgcca ggccattaag ttattcatgg aagatctttg   5580
aggaacactg caagttcata tcataaacac atttgaaatt gagtattgtt ttgcattgta   5640
tggagctatg ttttgctgta tcctcagaaa aaaaagtttg ttataaagca ttcacaccca   5700
taaaaagata gatttaaata ttccaactat aggaaagaaa gtgcgtctgc tcttcactct   5760
agtctcagtt ggctccttca catgcatgct tctttatttc tcctattttg tcaagaaaat   5820
aataggtcac gtcttgttct cacttatgtc ctgcctagca tggctcagat gcacgttgta   5880
catacaagaa ggatcaaatg aaacagactt ctggtctgtt actacaacca tagtaataag   5940
cacactaact aataattgct aattatgttt tccatctcta aggttcccat atttttctgt   6000
tttcttaaag atcccattat ctggttgtaa ctgaagctca atggaacatg agcaatattt   6060
cccagtcttc tctcccatcc aacagtcctg atggattagc agaacaggca gaaaacacat   6120
tgttacccag aattaaaaac taatatttgc tctccattca atccaaaatg gacctattga   6180
aactaaaatc taacccaatc ccattaaatg atttctatgg cggaattctg gccattgcat   6240
acgttgtatc catatcataa tatgtacatt tatattggct catgtccaac attaccgcca   6300
tgttgacatt gattattgac tagttattaa tagtaatcaa ttacggggtc attagttcat   6360
agcccatata tggagttccg cgttacataa cttacggtaa atggcccgcc tggctgaccg   6420
cccaacgacc cccgcccatt gacgtcaata atgacgtatg ttcccatagt aacgccaata   6480
gggactttcc attgacgtca atgggtggag tatttacggt aaactgccca cttggcagta   6540
catcaagtgt atcatatgcc aagtacgccc cctattgacg tcaatgacgg taaatggccc   6600
gcctggcatt atgcccagta catgacctta tgggactttc ctacttggca gtacatctac   6660
gtattagtca tcgctattac catggtgatg cggttttggc agtacatcaa tgggcgtgga   6720
tagcggtttg actcacgggg atttccaagt ctccacccca ttgacgtcaa tgggagtttg   6780
ttttggcacc aaaatcaacg ggactttcca aaatgtcgta acaactccgc cccattgacg   6840
caaatgggcg gtaggcgtgt acggtgggag gtctatataa gcactcgagc tcgtttagtg   6900
aaccgtcaga tcgcctggag acgccatcca cgctgttttg acctccatag aagacaccgg   6960
gaccgatcca gcctccgcgg ccgggaacgg tgcattggaa cgcggattcc ccgtgccaag   7020
agtgacgtaa gtaccgccta tagactctat aggcacaccc ctttggctct tatgcatgct   7080
atactgtttt tggcttgggg cctatacacc cccgcttcct tatgctatag gtgatggtat   7140
agcttagcct ataggtgtgg gttattgacc attattgacc actcccctat tggtgacgat   7200
actttccatt actaatccat aacatggctc tttgccacaa ctatctctat tggctatatg   7260
ccaatactct gtccttcaga gactgacacg gactctgtat ttttacagga tggggtccca   7320
tttattattt acaaattcac atatacaaca acgccgtccc ccgtgcccgc agtttttatt   7380
aaacatagcg tgggatctcc acgcgaatct cgggtacgtg ttccggacat gggctcttct   7440
ccggtagcgg cggagcttcc acatccgagc cctggtccca tgcctccagc ggctcatggt   7500
cgctcggcag ctccttgctc ctaacagtgg aggccagact taggcacagc acaatgccca   7560
ccaccaccag tgtgccgcac aaggccgtgg cggtagggta tgtgtctgaa aatgagcgtg   7620
gagattgggc tcgcacggct gacgcagatg gaagacttaa ggcagcggca gaagaagatg   7680
```

```
caggcagctg agttgttgta ttctgataag agtcagaggt aactcccgtt gcggtgctgt   7740
taacggtgga gggcagtgta gtctgagcag tactcgttgc tgccgcgcgc gccaccagac   7800
ataatagctg acagactaac agactgttcc tttccatggg tcttttctgc agtcaccgtc   7860
gtcgacaaca tgaagctcat cctctgcacc gtgctgtcct tggggatagc ggctgtgtgt   7920
ttcgccgaca tcgtgatgag ccagtctcca gactccctgg ccgtgtccct gggcgagagg   7980
gtgactctga attgcaagtc cagccagtcc ctgctctata gcagcaatag caagaactat   8040
ctcgcctggt atcagcagaa accagggcag agccctaaac tgctgattta ctgggcatcc   8100
accagggaat ccggcgtacc tgatcgcttc agcggcagcg gatctgggac agacttcact   8160
ctgacaatca gcagcgtgca ggcagaagac gtggcagtct attattgtca gcagccctat   8220
agctatcccc tcagcttcgg cgctggcacc aagctggaac tgaaaagagc cgcagctgca   8280
ccatctgtct tcatcttccc accatctgat gagcagttga aatctggaac tgcctctgtt   8340
gtgtgcctgc tgaataactt ctatcccaga gaggccaaag tacagtggaa ggtggataac   8400
gccctccaat cgggtaactc ccaggagagt gtcacagagc aggacagcaa ggacagcacc   8460
tacagcctca gcagcaccct gacactgagc aaagcagact acgagaaaca caaagtctac   8520
gcctgcgaag tcacccatca gggcctgagc tcgcccgtca caaagagctt caacagggga   8580
gagtgttaga ccggtaaaga agaaagctga aaaactctgt cccttccaac aagacccaga   8640
gcactgtagt atcaggggta aaatgaaaag tatgttatct gctgcatcca gacttcataa   8700
aagctggagc ttaatctaga aaaaaaatca gaaagaaatt acactgtgag aacaggtgca   8760
attcactttt cctttacaca gagtaatact ggtaactcat ggatgaaggc ttaagggaat   8820
gaaattggac tcacagtact gagtcatcac actgaaaaat gcaacctgat acatcagcag   8880
aaggtttatg ggggaaaaat gcagccttcc aattaagcca gatatctgta tgaccaagct   8940
gctccagaat tagtcactca aaatctctca gattaaatta tcaactgtca ccaaccattc   9000
ctatgctgac aaggcaattg cttgttctct gtgttcctga tactacaagg ctcttcctga   9060
cttcctaaag atgcattata aaaatcttat aattcacatt tctccctaaa ctttgactca   9120
atcatggtat gttggcaaat atggtatatt actattcaaa ttgttttcct tgtacccata   9180
tgtaatgggt cttgtgaatg tgctcttttg ttcctttaat cataataaaa acatgtttaa   9240
gcaaacactt ttcacttgta gtatttgaag tacagcaagg ttgtgtagca gggaaagaat   9300
gacatgcaga ggaataagta tggacacaca ggctagcagc gactgtagaa caagtactaa   9360
tgggtgagaa gttgaacaag agtcccctac agcaacttaa tctaataagc tagtggtcta   9420
catcagctaa aagagcatag tgagggatga aattggttct cctttctaag catcacctgg   9480
gacaactcat ctggagcagt gtgtccaatc tttaattaag gcgcctgcag ggtaacctga   9540
ggctatggca gggcctgccg ccccgacgtt ggctgcgagc cctgggcctt cacccgaact   9600
tggggggtgg ggtggggaaa aggaagaaac gcgggcgtat tggccccaat ggggtctcgg   9660
tggggtatcg acagagtgcc agccctggga ccgaaccccg cgtttatgaa caaacgaccc   9720
aacaccgtgc gttttattct gtctttttat tgccgtcata gcgcgggttc cttccggtat   9780
tgtctccttc cgtgtttcag ttagcctccc cctagggtgg gcgaagaact ccagcatgag   9840
atccgagctc aggatccgct agcgaattca ggtttaagca cctggtttgc gagtcatgca   9900
ccaagtgcgt gggccttctg gcacttccac atcagcagtc acagtgaagc ccaggcgttc   9960
atagaaaggc aggttgcgtg gagctgaggt ctccaggaaa gcaggcacac ctgcacgttc  10020
```

```
agctgcttcc acaccaggca gcaccactgc agagcccagg cccttaccct ggtggtcagg  10080
gctcacaccc acagttgcca ggaaccaagc aggttctttt gggcggtgtg gtgccagcag  10140
accttccatc tgctgttgtg ctgccaggcg gctgccagac agttctgcca tgcgtgggcc  10200
aatctcagca aacactgcac cagcttcaac agattcaggg gtggtccaca ctgccacagc  10260
agcaccatca tctgccaccc acactttgcc aatgtccagg cccacacggg tcaggaacag  10320
ctcctgcagt tcagtcacac gttcaatgtg gcggtctggg tccacagtgt gacgggttgc  10380
agggtagtca gcaaatgcag cagccagggt gcgaactgca cgtggaacat catcacgagt  10440
tgccaggcga acagttggtt tgtattcagt catgacgatc ctcatcctgt ctcttgatcg  10500
atctttgcaa aagcctaggc ctccaaaaaa gcctcctcac tacttctgga atagctcaga  10560
ggccgaggcg gcctcggcct ctgcataaat aaaaaaaatt agtcagccat ggggcggaga  10620
atgggcggaa ctgggcggag ttaggggcgg gatgggcgga gttaggggcg ggactatggt  10680
tgctgactaa ttgagatgca tgctttgcat acttctgcct gctggggagc ctggggactt  10740
tccacacctg gttgctgact aattgagatg catgctttgc atacttctgc ctgctgggga  10800
gcctggggac tttccacacc ctaactgaca cacattccac agctggttct ttccgcctca  10860
gcgtacgaga ttggacacac tgctccagat gagttgtccc aggtgatgct tagaaaggag  10920
aaccaatttc atccctcact atgctctttt agctgatgta gaccactagc ttattagatt  10980
aagttgctgt aggggactct tgttcaactt ctcacccatt agtacttgtt ctacagtcgc  11040
tgctagcctg tgtgtccata cttattcctc tgcatgtcat tctttccctg ctacacaacc  11100
ttgctgtact tcaaatacta caagtgaaaa gtgtttgctt aaacatgttt ttattatgat  11160
taaaggaaca aaagagcaca ttcacaagac ccattacata tggtacaag gaaaacaatt  11220
tgaatagtaa tataccatat ttgccaacat accatgattg agtcaaagtt tagggagaaa  11280
tgtgaattat aagattttta taatgcatct ttaggaagtc aggaagagcc ttgtagtatc  11340
aggaacacag agaacaagca attgccttgt cagcatagga atggttggtg acagttgata  11400
atttaatctg agagattttg agtgactaat tctggagcag cttggtcata cagatatctg  11460
gcttaattgg aaggctgcat ttttccccca taaaccttct gctgatgtat caggttgcat  11520
ttttcagtgt gatgactcag tactgtgagt ccaatttcat tcccttaagc cttcatccat  11580
gagttaccag tattactctg tgtaaaggaa aagtgaattg cacctgttct cacagtgtaa  11640
tttctttctg atttttttc tagattaagc tccagctttt atgaagtctg gatgcagcag  11700
ataacatact tttcatttta cccctgatac tacagtgctc tgggtcttgt tggaagggac  11760
agagtttttc agctttcttc tttgcgatcg ctcatttacc tggagacagg gagaggctct  11820
tctgtgtgta gtggttgtgc agagcctcat gcatcacgga gcatgagaag acgttcccct  11880
gctgccacct gctcttgtcc acggtgagct tgctgtagag gaagaaggag ccgtcggagt  11940
ccagcacggg aggtgtggtc ttgtagttgt tctctggctg cccattgctc tcccactcca  12000
cggcgatgtc gctgggatag aagcctttga ccaggcaggt caggctgacc tggttcttgg  12060
tcagctcatc cctggatggg ggcagggtgt acacctgtgg ttcgcggggc tgccctccgg  12120
atccgcctcc actcgagcca cctccgcaag gtgggcatgt gtgagttttg tcacaagatt  12180
cgggctcaac tttcttgtcc accttggtgt tgctgggctt gtgattcacg ttgcagatgt  12240
aggtctgggt gcccaagctg ctggagggca cggtcaccac gctgctgagg gagtagagtc  12300
ctgaggactg taggacagct gggaaggtgt gcacgccgct ggtcagggcg cctgagttcc  12360
acgacactgt cactggttcg gggaagtagt ccttgaccag gcagcccagg gctgctgtgc  12420
```

```
ccccagaggt gctcttggag gagggtgcca gggggaagac cgatgggccg gtagttttgg  12480
cgctggagac ggtgaccagg gttccctgtc cccagtaggc catattcagg gatcttgtgc  12540
agaagtacac tgcagtatcc tcggatctca ggctggagag ctccacgtag gcagtgctgg  12600
cagatgtgtc tgcagtcagg gtggccttgc cctggaactt ctgtgagtac ttaaaatcat  12660
cgtttccggg agagaaatat ccaatccact ccaggcgctg tccaggattc tgtttcaccc  12720
agtggattgc gtgatcagtg aaggtgtagc cgcttgcctt gcaggaaatc ttcacggaag  12780
ccccaggttt caccacctca gcgccggact gcaccagctg gacctgggcg aaacacacag  12840
ccgctatccc caaggacagc acggtgcaga ggatgagctt catgttgtcg acgacggtga  12900
ctgcagaaaa gacccatgga aaggaacagt ctgttagtct gtcagctatt atgtctggtg  12960
gcgcgcgcgg cagcaacgag tactgctcag actacactgc cctccaccgt taacagcacc  13020
gcaacgggag ttacctctga ctcttatcag aatacaacaa ctcagctgcc tgcatcttct  13080
tctgccgctg ccttaagtct tccatctgcg tcagccgtgc gagcccaatc tccacgctca  13140
ttttcagaca catacctac cgccacggcc ttgtgcggca cactggtggt ggtgggcatt  13200
gtgctgtgcc taagtctggc ctccactgtt aggagcaagg agctgccgag cgaccatgag  13260
ccgctggagg catgggacca gggctcggat gtggaagctc cgccgctacc ggagaagagc  13320
ccatgtccgg aacacgtacc cgagattcgc gtggagatcc cacgctatgt ttaataaaaa  13380
ctgcgggcac gggggacggc gttgttgtat atgtgaattt gtaaataata aatgggaccc  13440
catcctgtaa aaatacagag tccgtgtcag tctctgaagg acagagtatt ggcatatagc  13500
caatagagat agttgtggca aagagccatg ttatggatta gtaatggaaa gtatcgtcac  13560
caatagggga gtggtcaata atggtcaata acccacacct ataggctaag ctataccatc  13620
acctatagca taaggaagcg ggggtgtata ggccccaagc caaaaacagt atagcatgca  13680
taagagccaa aggggtgtgc ctatagagtc tataggcggt acttacgtca ctcttggcac  13740
ggggaatccg cgttccaatg caccgttccc ggccgcggag gctggatcgg tcccggtgtc  13800
ttctatggag gtcaaaacag cgtggatggc gtctccaggc gatctgacgg ttcactaaac  13860
gagctcgagt gcttatatag acctcccacc gtacacgcct accgcccatt tgcgtcaatg  13920
gggcggagtt gttacgacat tttggaaagt cccgttgatt ttggtgccaa aacaaactcc  13980
cattgacgtc aatggggtgg agacttggaa atccccgtga gtcaaaccgc tatccacgcc  14040
cattgatgta ctgccaaaac cgcatcacca tggtaatagc gatgactaat acgtagatgt  14100
actgccaagt aggaaagtcc cataaggtca tgtactgggc ataatgccag gcgggccatt  14160
taccgtcatt gacgtcaata gggggcgtac ttggcatatg atacacttga tgtactgcca  14220
agtgggcagt ttaccgtaaa tactccaccc attgacgtca atggaaagtc cctattggcg  14280
ttactatggg aacatacgtc attattgacg tcaatgggcg ggggtcgttg ggcggtcagc  14340
caggcgggcc atttaccgta agttatgtaa cgcggaactc catatatggg ctatgaacta  14400
atgaccccgt aattgattac tattaataac tagtcaataa tcaatgtcaa catggcggta  14460
atgttggaca tgagccaata taaatgtaca tattatgata tggatacaac gtatgcaatg  14520
gccagaattc cgccatagaa atcatttaat gggattgggt tagattttag tttcaatagg  14580
tccattttgg attgaatgga gagcaaatat tagtttttaa ttctgggtaa caatgtgttt  14640
tctgcctgtt ctgctaatcc atcaggactg ttggatggga gagaagactg ggaaatattg  14700
ctcatgttcc attgagcttc agttacaacc agataatggg atctttaaga aaacagaaaa  14760
```

```
atatgggaac cttagagatg gaaaacataa ttagcaatta ttagttagtg tgcttattac  14820
tatggttgta gtaacagacc agaagtctgt ttcatttgat ccttcttgta tgtacaacgt  14880
gcatctgagc catgctaggc aggacataag tgagaacaag acgtgaccta ttattttctt  14940
gacaaaatag gagaaataaa gaagcatgca tgtgaaggag ccaactgaga ctagagtgaa  15000
gagcagacgc actttctttc ctatagttgg aatatttaaa tctatctttt tatgggtgtg  15060
aatgctttat aacaaacttt tttttctgag gatacagcaa aacatagctc catacaatgc  15120
aaaacaatac tcaatttcaa atgtgtttat gatatgaact tgcagtgttc ctcaaagatc  15180
ttccatgaat aacttaatgg cctggcagat gacagaggaa ttgtgaaatt cagctggagg  15240
agtgttcatg gttcgaggga caatcataat atacaatagc aaatatattt cagttataga  15300
agctattgtt ctgtattgaa ataatagaat tgacaaacag taaagaaacc attctgacct  15360
ctgtaaagca cacgcgtaag cttaaaagat tgaagcacag acacaggcca caccagagcc  15420
tacacctgct gcaataagtg gtgctataga aaggattcag gaactaacaa gtgcataatt  15480
tacaaataga gatgctttat catactttgc ccaacatggg aaaaaagaca tcccatgaga  15540
atatccaact gaggaacttc tctgtttcat agtaactcat ctactactgc taagatggtt  15600
tgaaaagtac ccagcaggtg agatgtgttc cgggaggtgg ctgtgtggca gcgtgtggga  15660
acacgacaca aagcacccca cccctatctg caatgctcac tgcaaggcag tgccgtaaac  15720
agctgcaaca ggcatccagg catcacttct gcataaacgc tgtgactcgt tagcatgctg  15780
caactgtgtt taaaacctat gcactccgtt accaaaataa tttaagtccc aaacaaatcc  15840
atgcagcttg cttcctatgc caaaatattt tagaaagtat tcattcttct ttaagaatat  15900
gcacgtggat ctgcacttcc ctgggatctg aagcgattta tacctcagtg cagaagcagt  15960
ttagtgtcct ggatctcggg aaggcagcag ccaaacgtgc ccgttttaca tttaaaccca  16020
tgtgacaacc cgccttactg agcatcgctc taggaaattt aaggctgtat ccttacaaca  16080
caagaaccaa cgacagactg catataaaat tctataaata aaaataggag tgaagtctgt  16140
ttgacctgta cacacagagc atagagataa aaaaaaaagg aaatcaggaa ttacgtattt  16200
ctataaatgc catatatttt tactagaaac acagatgaca agtatataca acatgtaaat  16260
ccgaagttat caacatgtta actaggaaaa catttacaag catttgggta tgcaactaga  16320
tcatcaggta aaaaatccca ttagaaaaat ctaagcctca ccagtttcaa aggaaaaaaa  16380
ccagagaacg ctcactactt caaagggaaa aaataaagca tcaagctggc ctaaacttaa  16440
taaggtatct cgtgtaacaa cagctatcca agctttcaag ccacactata aataaaaacc  16500
tcaagttccg atcaacgttt tccataatgc aatcagaacc aaaggcattg gcacagaaag  16560
caaaaaggga atgaaagaaa agggctgtac agtttccaaa aggttcttct tttgaagaaa  16620
tgtttctgac ctgtcaaaac atacagtcca gtagaaaatt tactaagaaa aaagaacacc  16680
ttacttaaaa aaaaaaaaaa aaaaaaaaaa aacaggcaaa aaaacctctc ctgtcactga  16740
gctgccacca ccccaaccac cacctgctgt gggctttgtc tcccaagaca aaggacacac  16800
agccttatcc aatattcaac attacttata aaaacactga tcagaagaaa taccaagtat  16860
ttcctcacag actgttatac agactgttat atcctttcat cggcaagaag agatgaaata  16920
caacagagtg aatatcaaag aaggcggcag gagccaccgt ggcaccatca ccgggcagtg  16980
cagtgcccag ctgccgtttc ctgagcacgc acaggaagcc gtcagtcaca tgtaataaac  17040
caaaacctgg tacagttata ttatggatcc gggcccctcc gggatcatat gacaagatgt  17100
gtatccacct taacttaatg atttttacca aaatcattag gggattcatc agtgctcagg  17160
```

```
gtcaacgaga attaacattc cgtcaggaaa gcttgaattc agcttttgtt ccctttagtg  17220

agggttaatt gcgcgcttgg cgtaatcatg gtcatagctg tttcctgtgt gaaattgtta  17280

tccgctcaca attccacaca acatacgagc cggaagcata aagtgtaaag cctggggtgc  17340

ctaatgagtg agctaactca cattaattgc gttgcgctca ctgcccgctt tccagtcggg  17400

aaacctgtcg tgccagctgc attaatgaat cggccaacgc gcggggagag gcggtttgcg  17460

tattgggcgc tcttccgctt cctcgctcac tgactcgctg cgctcggtcg ttcggctgcg  17520

gcgagcggta tcagctcact caaaggcggt aatacggtta tccacagaat caggggataa  17580

cgcaggaaag aacatgtgag caaaaggcca gcaaaaggcc aggaaccgta aaaaggccgc  17640

gttgctggcg tttttccata ggctccgccc ccctgacgag catcacaaaa atcgacgctc  17700

aagtcagagg tggcgaaacc cgacaggact ataaagatac caggcgtttc cccctggaag  17760

ctccctcgtg cgctctcctg ttccgaccct gccgcttacc ggatacctgt ccgcctttct  17820

cccttcggga agcgtggcgc tttctcatag ctcacgctgt aggtatctca gttcggtgta  17880

ggtcgttcgc tccaagctgg gctgtgtgca cgaacccccc gttcagcccg accgctgcgc  17940

cttatccggt aactatcgtc ttgagtccaa cccggtaaga cacgacttat cgccactggc  18000

agcagccact ggtaacagga ttagcagagc gaggtatgta ggcggtgcta cagagttctt  18060

gaagtggtgg cctaactacg gctacactag aagaacagta tttggtatct gcgctctgct  18120

gaagccagtt accttcggaa aaagagttgg tagctcttga tccggcaaac aaaccaccgc  18180

tggtagcggt ggtttttttg tttgcaagca gcagattacg cgcagaaaaa aaggatctca  18240

agaagatcct ttgatctttt ctacggggtc tgacgctcag tggaacgaaa actcacgtta  18300

agggattttg gtcatgagat tatcaaaaag gatcttcacc tagatccttt taaattaaaa  18360

atgaagtttt aaatcaatct aaagtatata tgagtaaact tggtctgaca gttaccaatg  18420

cttaatcagt gaggcaccta tctcagcgat ctgtctattt cgttcatcca tagttgcctg  18480

actccccgtc gtgtagataa ctacgatacg ggagggctta ccatctggcc ccagtgctgc  18540

aatgataccg cgagacccac gctcaccggc tccagattta tcagcaataa accagccagc  18600

cggaagggcc gagcgcagaa gtggtcctgc aactttatcc gcctccatcc agtctattaa  18660

ttgttgccgg gaagctagag taagtagttc gccagttaat agtttgcgca acgttgttgc  18720

cattgctaca ggcatcgtgg tgtcacgctc gtcgtttggt atggcttcat tcagctccgg  18780

ttcccaacga tcaaggcgag ttacatgatc ccccatgttg tgcaaaaaag cggttagctc  18840

cttcggtcct ccgatcgttg tcagaagtaa gttggccgca gtgttatcac tcatggttat  18900

ggcagcactg cataattctc ttactgtcat gccatccgta agatgctttt ctgtgactgg  18960

tgagtactca accaagtcat tctgagaata gtgtatgcgg cgaccgagtt gctcttgccc  19020

ggcgtcaata cgggataata ccgcgccaca tagcagaact ttaaaagtgc tcatcattgg  19080

aaaacgttct tcggggcgaa aactctcaag gatcttaccg ctgttgagat ccagttcgat  19140

gtaacccact cgtgcaccca actgatcttc agcatctttt actttcacca gcgtttctgg  19200

gtgagcaaaa acaggaaggc aaaatgccgc aaaaaaggga ataagggcga cacggaaatg  19260

ttgaatactc atactcttcc tttttcaata ttattgaagc atttatcagg gttattgtct  19320

catgagcgga tacatatttg aatgtattta gaaaaataaa caaatagggg ttccgcgcac  19380

atttccccga aaagtgccac                                              19400
```

<210> SEQ ID NO 27

<211> LENGTH: 19718
<212> TYPE: DNA
<213> ORGANISM: Artificial Sequence
<220> FEATURE:
<223> OTHER INFORMATION: Synthetic construct

<400> SEQUENCE: 27
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggcatcaga ttggctattg gccattgcat acgttgtatc catatcataa 180
tatgtacatt tatattggct catgtccaac attaccgcca tgttgacatt gattattgac 240
tagttattaa tagtaatcaa ttacggggtc attagttcat agcccatata tggagttccg 300
cgttacataa cttacggtaa atggcccgcc tggctgaccg cccaacgacc cccgcccatt 360
gacgtcaata atgacgtatg ttcccatagt aacgccaata gggactttcc attgacgtca 420
atgggtggag tatttacggt aaactgccca cttggcagta catcaagtgt atcatatgcc 480
aagtacgccc cctattgacg tcaatgacgg taaatggccc gcctggcatt atgcccagta 540
catgacctta tgggactttc ctacttggca gtacatctac gtattagtca tcgctattac 600
catggtgatg cggttttggc agtacatcaa tgggcgtgga tagcggtttg actcacgggg 660
atttccaagt ctccacccca ttgacgtcaa tgggagtttg ttttggcacc aaaatcaacg 720
ggactttcca aaatgtcgta acaactccgc cccattgacg caaatgggcg gtaggcgtgt 780
acggtgggag gtctatataa gcagagctcg tttagtgaac cgtcagatcg cctggagacg 840
ccatccacgc tgttttgacc tccatagaag acaccgggac cgatccagcc tccgcggccg 900
ggaacggtgc attggaacgc ggattccccg tgccaagagt gacgtaagta ccgcctatag 960
actctatagg cacacccctt tggctcttat gcatgctata ctgtttttgg cttggggcct 1020
atacaccccc gcttccttat gctataggtg atggtatagc ttagcctata ggtgtgggtt 1080
attgaccatt attgaccact cccctattgg tgacgatact ttccattact aatccataac 1140
atggctcttt gccacaacta tctctattgg ctatatgcca atactctgtc cttcagagac 1200
tgacacggac tctgtatttt tacaggatgg ggtcccattt attatttaca aattcacata 1260
tacaacaacg ccgtcccccg tgcccgcagt ttttattaaa catagcgtgg gatctccacg 1320
cgaatctcgg gtacgtgttc cggacatggg ctcttctccg gtagcggcgg agcttccaca 1380
tccgagccct ggtcccatgc ctccagcggc tcatggtcgc tcggcagctc cttgctccta 1440
acagtggagg ccagacttag gcacagcaca atgcccacca ccaccagtgt gccgcacaag 1500
gccgtggcgg tagggtatgt gtctgaaaat gagcgtggag attgggctcg cacggctgac 1560
gcagatggaa gacttaaggc agcggcagaa gaagatgcag gcagctgagt tgttgtattc 1620
tgataagagt cagaggtaac tcccgttgcg gtgctgttaa cggtggaggg cagtgtagtc 1680
tgagcagtac tcgttgctgc cgcgcgcgcc accagacata atagctgaca gactaacaga 1740
ctgttccttt ccatgggtct tttctgcagt caccgtctcg cgaaaaaatca ataatcagac 1800 aacaagatgt gcgaactcga tattttacac gactctcttt accaattctg ccccgaatta 1860
cacttaaaac gactcaacag cttaacgttg gcttgccacg cattacttga ctgtaaaact 1920
ctcactctta ccgaacttgg ccgtaacctg ccaaccaaag cgagaacaaa acataacatc 1980
aaacgaatcg accgattgtt aggtaatcgt cacctccaca aagagcgact cgctgtatac 2040
cgttggcatg ctagctttat ctgttcgggc aatacgatgc ccattgtact tgttgactgg 2100
tctgatattc gtgagcaaaa acgacttatg gtattgcgag cttcagtcgc actacacggt 2160

```
cgttctgtta ctctttatga gaaagcgttc ccgctttcag agcaatattc aaagaaagct   2220
catgaccaat ttctagccga ccttgcgagc attctaccga gtaacaccac accgctcatt   2280
gtcagtgatg ctggctttaa agtgccatgg tataaatccg ttgagaagct gggttggtac   2340
tggttaagtc gagtaagagg aaaagtacaa tatgcagacc taggagcgga aaactggaaa   2400
cctatcagca acttacatga tatgtcatct agtcactcaa agactttagg ctataagagg   2460
ctgactaaaa gcaatccaat ctcatgccaa attctattgt ataaatctcg ctctaaaggc   2520
cgaaaaaatc agcgctcgac acggactcat tatcaccacc cgtcacctaa aatctactca   2580
gcgtcggcaa aggagccatg ggttctagca actaacttac ctgttgaaat tcgaacaccc   2640
aaacaacttg ttaatatcta ttcgaagcga atgcagattg aagaaacctt ccgagacttg   2700
aaaagtcctg cctacggact aggcctacgc catagccgaa cgagcagctc agagcgtttt   2760
gatatcatgc tgctaatcgc cctgatgctt caactaacat gttggcttgc gggcgttcat   2820
gctcagaaac aaggttggga caagcacttc caggctaaca cagtcagaaa tcgaaacgta   2880
ctctcaacag ttcgcttagg catggaagtt ttgcggcatt ctggctacac aataacaagg   2940
gaagacttac tcgtggctgc aaccctacta gctcaaaatt tattcacaca tggttacgct   3000
ttggggaaat tatgagggga tcgctctaga gcgatccggg atctcgggaa aagcgttggt   3060
gaccaaaggt gccttttatc atcactttaa aaataaaaaa caattactca gtgcctgtta   3120
taagcagcaa ttaattatga ttgatgccta catcacaaca aaaactgatt taacaaatgg   3180
ttggtctgcc ttagaaagta tatttgaaca ttatcttgat tatattattg ataataataa   3240
aaaccttatc cctatccaag aagtgatgcc tatcattggt tggaatgaac ttgaaaaaat   3300
tagccttgaa tacattactg gtaaggtaaa cgccattgtc agcaaattga tccaagagaa   3360
ccaacttaaa gctttcctga cggaatgtta attctcgttg accctgagca ctgatgaatc   3420
ccctaatgat tttggtaaaa atcattaagt taaggtggat acacatcttg tcatatgatc   3480
ccggtaatgt gagttagctc actcattagg caccccaggc tttacacttt atgcttccgg   3540
ctcgtatgtt gtgtggaatt gtgagcggat aacaatttca cacaggaaac agctatgacc   3600
atgattacgc caagcgcgca attaaccctc actaaaggga acaaaagctg gagctccacc   3660
gcggtggcgg ccgcggatcc ataatataac tgtaccaggt tttggtttat tacatgtgac   3720
tgacggcttc ctgtgcgtgc tcaggaaacg gcagctgggc actgcactgc ccggtgatgg   3780
tgccacggtg gctcctgccg ccttctttga tattcactct gttgtatttc atctcttctt   3840
gccgatgaaa ggatataaca gtctgtataa cagtctgtga ggaaatactt ggtatttctt   3900
ctgatcagtg tttttataag taatgttgaa tattggataa ggctgtgtgt cctttgtctt   3960
gggagacaaa gcccacagca ggtggtggtt ggggtggtgg cagctcagtg acaggagagg   4020
tttttttgcc tgtttttttt tttttttttt tttttttaa gtaaggtgtt ctttttttctt   4080
agtaaatttt ctactggact gtatgttttg acaggtcaga aacatttctt caaaagaaga   4140
accttttgga aactgtacag cccttttctt tcattccctt tttgctttct gtgccaatgc   4200
ctttggttct gattgcatta tggaaaacgt tgatcggaac ttgaggtttt tatttatagt   4260
gtggcttgaa agcttggata gctgttgtta cacgagatac cttattaagt ttaggccagc   4320
ttgatgcttt attttttccc tttgaagtag tgagcgttct ctggtttttt tcctttgaaa   4380
ctggtgaggc ttagattttt ctaatgggat tttttacctg atgatctagt tgcataccca   4440
aatgcttgta aatgttttcc tagttaacat gttgataact tcggatttac atgttgtata   4500
```

```
tacttgtcat ctgtgtttct agtaaaaata tatggcattt atagaaatac gtaattcctg   4560
atttcctttt ttttttatct ctatgctctg tgtgtacagg tcaaacagac ttcactccta   4620
tttttattta tagaatttta tatgcagtct gtcgttggtt cttgtgttgt aaggatacag   4680
ccttaaattt cctagagcga tgctcagtaa ggcgggttgt cacatgggtt taaatgtaaa   4740
acgggcacgt ttggctgctg ccttcccgag atccaggaca ctaaactgct tctgcactga   4800
ggtataaatc gcttcagatc ccagggaagt gcagatccac gtgcatattc ttaaagaaga   4860
atgaatactt tctaaaatat tttggcatag gaagcaagct gcatggattt gtttgggact   4920
taaattattt tggtaacgga gtgcataggt tttaaacaca gttgcagcat gctaacgagt   4980
cacagcgttt atgcagaagt gatgcctgga tgcctgttgc agctgtttac ggcactgcct   5040
tgcagtgagc attgcagata ggggtggggt gctttgtgtc gtgttcccac acgctgccac   5100
acagccacct cccggaacac atctcacctg ctgggtactt ttcaaaccat cttagcagta   5160
gtagatgagt tactatgaaa cagagaagtt cctcagttgg atattctcat gggatgtctt   5220
ttttcccatg ttgggcaaag tatgataaag catctctatt tgtaaattat gcacttgtta   5280
gttcctgaat cctttctata gcaccactta ttgcagcagg tgtaggctct ggtgtggcct   5340
gtgtctgtgc ttcaatcttt taagcttctc gagggcgcgc cgtgctttac agaggtcaga   5400
atggtttctt tactgtttgt caattctatt atttcaatac agaacaatag cttctataac   5460
tgaaatatat ttgctattgt atattatgat tgtccctcga accatgaaca ctcctccagc   5520
tgaatttcac aattcctctg tcatctgcca ggccattaag ttattcatgg aagatctttg   5580
aggaacactg caagttcata tcataaacac atttgaaatt gagtattgtt ttgcattgta   5640
tggagctatg ttttgctgta tcctcagaaa aaaaagtttg ttataaagca ttcacaccca   5700
taaaaagata gatttaaata ttccaactat aggaaagaaa gtgcgtctgc tcttcactct   5760
agtctcagtt ggctccttca catgcatgct tctttatttc tcctattttg tcaagaaaat   5820
aataggtcac gtcttgttct cacttatgtc ctgcctagca tggctcagat gcacgttgta   5880
catacaagaa ggatcaaatg aaacagactt ctggtctgtt actacaacca tagtaataag   5940
cacactaact aataattgct aattatgttt tccatctcta aggttcccat atttttctgt   6000
tttcttaaag atcccattat ctggttgtaa ctgaagctca atggaacatg agcaatattt   6060
cccagtcttc tctcccatcc aacagtcctg atggattagc agaacaggca gaaaacacat   6120
tgttacccag aattaaaaac taatatttgc tctccattca atccaaaatg gacctattga   6180
aactaaaatc taacccaatc ccattaaatg atttctatgg cggaattctg gccattgcat   6240
acgttgtatc catatcataa tatgtacatt tatattggct catgtccaac attaccgcca   6300
tgttgacatt gattattgac tagttattaa tagtaatcaa ttacggggtc attagttcat   6360
agcccatata tggagttccg cgttacataa cttacggtaa atggcccgcc tggctgaccg   6420
cccaacgacc cccgcccatt gacgtcaata atgacgtatg ttcccatagt aacgccaata   6480
gggactttcc attgacgtca atgggtggag tatttacggt aaactgccca cttggcagta   6540
catcaagtgt atcatatgcc aagtacgccc cctattgacg tcaatgacgg taaatggccc   6600
gcctggcatt atgcccagta catgacctta tgggactttc ctacttggca gtacatctac   6660
gtattagtca tcgctattac catggtgatg cggttttggc agtacatcaa tgggcgtgga   6720
tagcggtttg actcacgggg atttccaagt ctccacccca ttgacgtcaa tgggagtttg   6780
ttttggcacc aaaatcaacg ggactttcca aaatgtcgta acaactccgc cccattgacg   6840
caaatgggcg gtaggcgtgt acggtgggag gtctatataa gcactcgagc tcgtttagtg   6900
```

```
aaccgtcaga tcgcctggag acgccatcca cgctgttttg acctccatag aagacaccgg   6960
gaccgatcca gcctccgcgg ccgggaacgg tgcattggaa cgcggattcc ccgtgccaag   7020
agtgacgtaa gtaccgccta tagactctat aggcacaccc ctttggctct tatgcatgct   7080
atactgtttt tggcttgggg cctatacacc cccgcttcct tatgctatag gtgatggtat   7140
agcttagcct ataggtgtgg gttattgacc attattgacc actcccctat tggtgacgat   7200
actttccatt actaatccat aacatggctc tttgccacaa ctatctctat tggctatatg   7260
ccaatactct gtccttcaga gactgacacg gactctgtat ttttacagga tggggtccca   7320
tttattattt acaaattcac atatacaaca acgccgtccc ccgtgcccgc agtttttatt   7380
aaacatagcg tgggatctcc acgcgaatct cgggtacgtg ttccggacat gggctcttct   7440
ccggtagcgg cggagcttcc acatccgagc cctggtccca tgcctccagc ggctcatggt   7500
cgctcggcag ctccttgctc ctaacagtgg aggccagact taggcacagc acaatgccca   7560
ccaccaccag tgtgccgcac aaggccgtgg cggtagggta tgtgtctgaa aatgagcgtg   7620
gagattgggc tcgcacggct gacgcagatg gaagacttaa ggcagcggca gaagaagatg   7680
caggcagctg agttgttgta ttctgataag agtcagaggt aactcccgtt gcggtgctgt   7740
taacggtgga gggcagtgta gtctgagcag tactcgttgc tgccgcgcgc gccaccagac   7800
ataatagctg acagactaac agactgttcc tttccatggg tcttttctgc agtcaccgtc   7860
gtcgacaaca tgaagctcat cctctgcacc gtgctgtcct tggggatagc ggctgtgtgt   7920
ttcgcctcct atgagctgac acagccaccc tcggtgtcag tgtccccagg acaaacagcc   7980
aggatcacct gctctggaga tgcattgcca gaaaaatatg tttattggta ccagcagaag   8040
tcaggccagg cccctgtggt ggtcatctat gaggacagca aaagaccctc cgggatccct   8100
gagagattct ctggctccag ctcagggaca atggccacct tgactatcag tggggcccag   8160
gtggaagatg aaggtgacta ctactgttac tcaactgaca gcagtggtta tcatagggag   8220
gtgttcggcg gagggaccaa gctgaccgtc ctaggtcagc ccaaggctgc cccctcggtc   8280
actctgttcc caccctcctc tgaggagctt caagccaaca aggccacact ggtgtgtctc   8340
ataagtgact cctacccagg agccgtgaca gtggcctgga aggcagatag cagccccgtc   8400
aaggcaggag tggagaccac cacaccctcc aaacaaagca acaacaagta cgcagccagc   8460
agctacctga gcctgacacc tgagcagtgg aagtcccaca aaagctacag ctgccaggtc   8520
acacatgaag ggagcaccgt ggagaagaca gtggcccctg cagaatgttc atagaccggt   8580
aaagaagaaa gctgaaaaac tctgtccctt ccaacaagac ccagagcact gtagtatcag   8640
gggtaaaatg aaaagtatgt tatctgctgc atccagactt cataaaagct ggagcttaat   8700
ctagaaaaaa aatcagaaag aaattacact gtgagaacag gtgcaattca cttttccttt   8760
acacagagta atactggtaa ctcatggatg aaggcttaag ggaatgaaat tggactcaca   8820
gtactgagtc atcacactga aaaatgcaac ctgatacatc agcagaaggt ttatggggga   8880
aaaatgcagc cttccaatta agccagatat ctgtatgacc aagctgctcc agaattagtc   8940
actcaaaatc tctcagatta aattatcaac tgtcaccaac cattcctatg ctgacaaggc   9000
aattgcttgt tctctgtgtt cctgatacta caaggctctt cctgacttcc taaagatgca   9060
ttataaaaat cttataattc acatttctcc ctaaactttg actcaatcat ggtatgttgg   9120
caaatatggt atattactat tcaaattgtt ttccttgtac ccatatgtaa tgggtcttgt   9180
gaatgtgctc ttttgttcct ttaatcataa taaaaacatg tttaagcaaa cacttttcac   9240
```

-continued

```
ttgtagtatt tgaagtacag caaggttgtg tagcagggaa agaatgacat gcagaggaat   9300
aagtatggac acacaggcta gcagcgactg tagaacaagt actaatgggt gagaagttga   9360
acaagagtcc cctacagcaa cttaatctaa taagctagtg gtctacatca gctaaaagag   9420
catagtgagg gatgaaattg gttctccttt ctaagcatca cctgggacaa ctcatctgga   9480
gcagtgtgtc caatctttaa ttaaggcgcc tgcagggtaa cctgaggcta tggcagggcc   9540
tgccgccccg acgttggctg cgagccctgg gccttcaccc gaacttgggg ggtggggtgg   9600
ggaaaaggaa gaaacgcggg cgtattggcc ccaatggggt ctcggtgggg tatcgacaga   9660
gtgccagccc tgggaccgaa ccccgcgttt atgaacaaac gacccaacac cgtgcgtttt   9720
attctgtctt tttattgccg tcatagcgcg ggttccttcc ggtattgtct ccttccgtgt   9780
ttcagttagc ctcccccctag ggtgggcgaa gaactccagc atgagatccg agctcaggat   9840
ccgctagcga attcaggttt aagcacctgg tttgcgagtc atgcaccaag tgcgtgggcc   9900
ttctggcact tccacatcag cagtcacagt gaagcccagg cgttcataga aaggcaggtt   9960
gcgtggagct gaggtctcca ggaaagcagg cacacctgca cgttcagctg cttccacacc  10020
aggcagcacc actgcagagc ccaggccctt accctggtgg tcagggctca cacccacagt  10080
tgccaggaac caagcaggtt cttttgggcg gtgtggtgcc agcagacctt ccatctgctg  10140
ttgtgctgcc aggcggctgc cagacagttc tgccatgcgt gggccaatct cagcaaacac  10200
tgcaccagct tcaacagatt caggggtggt ccacactgcc acagcagcac catcatctgc  10260
cacccacact ttgccaatgt ccaggcccac acgggtcagg aacagctcct gcagttcagt  10320
cacacgttca atgtggcggt ctgggtccac agtgtgacgg gttgcagggt agtcagcaaa  10380
tgcagcagcc agggtgcgaa ctgcacgtgg aacatcatca cgagttgcca ggcgaacagt  10440
tggtttgtat tcagtcatga cgatcctcat cctgtctctt gatcgatctt tgcaaaagcc  10500
taggcctcca aaaaagcctc ctcactactt ctggaatagc tcagaggccg aggcggcctc  10560
ggcctctgca taaataaaaa aaattagtca gccatggggc ggagaatggg cggaactggg  10620
cggagttagg ggcgggatgg gcggagttag gggcgggact atggttgctg actaattgag  10680
atgcatgctt tgcatacttc tgcctgctgg ggagcctggg gactttccac acctggttgc  10740
tgactaattg agatgcatgc tttgcatact tctgcctgct ggggagcctg gggactttcc  10800
acaccctaac tgacacacat tccacagctg gttctttccg cctcagcgta cgagattgga  10860
cacactgctc cagatgagtt gtcccaggtg atgcttagaa aggagaacca atttcatccc  10920
tcactatgct cttttagctg atgtagacca ctagcttatt agattaagtt gctgtagggg  10980
actcttgttc aacttctcac ccattagtac ttgttctaca gtcgctgcta gcctgtgtgt  11040
ccatacttat tcctctgcat gtcattcttt ccctgctaca caaccttgct gtacttcaaa  11100
tactacaagt gaaaagtgtt tgcttaaaca tgtttttatt atgattaaag gaacaaaaga  11160
gcacattcac aagacccatt acatatgggt acaaggaaaa caatttgaat agtaatatac  11220
catatttgcc aacataccat gattgagtca aagtttaggg agaaatgtga attataagat  11280
ttttataatg catctttagg aagtcaggaa gagccttgta gtatcaggaa cacagagaac  11340
aagcaattgc cttgtcagca taggaatggt tggtgacagt tgataattta atctgagaga  11400
ttttgagtga ctaattctgg agcagcttgg tcatacagat atctggctta attggaaggc  11460
tgcatttttc ccccataaac cttctgctga tgtatcaggt tgcatttttc agtgtgatga  11520
ctcagtactg tgagtccaat ttcattccct taagccttca tccatgagtt accagtatta  11580
ctctgtgtaa aggaaaagtg aattgcacct gttctcacag tgtaatttct ttctgatttt  11640
```

```
ttttctagat taagctccag cttttatgaa gtctggatgc agcagataac atacttttca  11700
ttttacccct gatactacag tgctctgggt cttgttggaa gggacagagt tttcagctt   11760
tcttctttgc gatcgctcat ttacctggag acagggagag gctcttctgt gtgtagtggt  11820
tgtgcagagc ctcatgcatc acggagcatg agaagacgtt cccctgctgc cacctgctct  11880
tgtccacggt gagcttgctg tagaggaaga aggagccgtc ggagtccagc acgggaggtg  11940
tggtcttgta gttgttctct ggctgcccat tgctctccca ctccacggcg atgtcgctgg  12000
gatagaagcc tttgaccagg caggtcaggc tgacctggtt cttggtcagc tcatccctgg  12060
atgggggcag ggtgtacacc tgtggttcgc ggggctgccc tttggctttg gagatggttt  12120
tctcgatggg ggctgggagg gctttgttgg agaccttgca cttgtactcc ttgccattca  12180
gccagtcctg gtgcaggacg gtgaggacgc tgaccacgcg gtatgtgctg ttgtactgct  12240
cctccctagg ctttgtcttg gcattatgca cctccacgcc gtccacgtac cagttgaact  12300
tgacctcagg gtcttcgtgg ctcacgtcca ccaccacgca tgtgacctca ggggtcctgg  12360
agatcatgag ggtgtccttg ggttttgggg ggaagaggaa gactgatggt cccccccagga 12420
gttcaggtgc tgggcatggt gggcatgtgt gagttttgtc acaagatttg ggctcaactt  12480
tcttgtccac cttggtgttg ctgggcttgt gattcacgtt gcagatgtag gtctgggtgc  12540
ccaagctgct ggagggcacg gtcaccacgc tgctgaggga gtagagtcct gaggactgta  12600
ggacagctgg gaaggtgtgc acgccgctgg tcagggcgcc tgagttccac gacactgtca  12660
ctggttcggg gaagtagtcc ttgaccaggc agcccagggc tgctgtgccc ccagaggtgc  12720
tcttggagga gggtgccagg gggaagaccg atgggccctt ggtggaggct gaggagacgg  12780
tgaccagggt tccctggccc caatttgggg gagggataac tcccccaaat gttatcataa  12840
tcccagtggt acagtaatat acggctgtgt cctcggcttt caggctattc atttgcagat  12900
ataatgtgtt ttttgaatca tctcttgaga tggtgaatct gcctttcacg ggtgcagcat  12960
agtctgttgt cccaccatca attttgcttt taatgcggcc gacccactcc agccccttcc  13020
ctggagcctg gcggacccag ctcatccagg cgtttctgaa agtgaatcca gaggctgcac  13080
aggagactct aagggacccg cctggcttta ccaagcctcc gccagactcc tgcagctgca  13140
cctgggcgaa acacacagcc gctatcccca aggacagcac ggtgcagagg atgagcttca  13200
tgttgtcgac gacggtgact gcagaaaaga cccatggaaa ggaacagtct gttagtctgt  13260
cagctattat gtctggtggc gcgcgcggca gcaacgagta ctgctcagac tacactgccc  13320
tccaccgtta acagcaccgc aacgggagtt acctctgact cttatcagaa tacaacaact  13380
cagctgcctg catcttcttc tgccgctgcc ttaagtcttc catctgcgtc agccgtgcga  13440
gcccaatctc cacgctcatt ttcagacaca taccctaccg ccacggcctt gtgcggcaca  13500
ctggtggtgg tgggcattgt gctgtgccta agtctggcct ccactgttag gagcaaggag  13560
ctgccgagcg accatgagcc gctggaggca tgggaccagg gctcggatgt ggaagctccg  13620
ccgctaccgg agaagagccc atgtccggaa cacgtacccg agattcgcgt ggagatccca  13680
cgctatgttt aataaaaact gcgggcacgg gggacggcgt tgttgtatat gtgaatttgt  13740
aaataataaa tgggacccca tcctgtaaaa atacagagtc cgtgtcagtc tctgaaggac  13800
agagtattgg catatagcca atagagatag ttgtggcaaa gagccatgtt atggattagt  13860
aatggaaagt atcgtcacca ataggggagt ggtcaataat ggtcaataac ccacacctat  13920
aggctaagct ataccatcac ctatagcata aggaagcggg ggtgtatagg ccccaagcca  13980
```

```
aaaacagtat agcatgcata agagccaaag gggtgtgcct atagagtcta taggcggtac  14040
ttacgtcact cttggcacgg ggaatccgcg ttccaatgca ccgttcccgg ccgcggaggc  14100
tggatcggtc ccggtgtctt ctatggaggt caaaacagcg tggatggcgt ctccaggcga  14160
tctgacggtt cactaaacga gctcgagtgc ttatatagac ctcccaccgt acacgcctac  14220
cgcccatttg cgtcaatggg gcggagttgt tacgacattt tggaaagtcc cgttgatttt  14280
ggtgccaaaa caaactccca ttgacgtcaa tggggtggag acttggaaat ccccgtgagt  14340
caaaccgcta tccacgccca ttgatgtact gccaaaaccg catcaccatg gtaatagcga  14400
tgactaatac gtagatgtac tgccaagtag gaaagtccca taaggtcatg tactgggcat  14460
aatgccaggc gggccattta ccgtcattga cgtcaatagg gggcgtactt ggcatatgat  14520
acacttgatg tactgccaag tgggcagttt accgtaaata ctccacccat tgacgtcaat  14580
ggaaagtccc tattggcgtt actatgggaa catacgtcat tattgacgtc aatgggcggg  14640
ggtcgttggg cggtcagcca ggcgggccat ttaccgtaag ttatgtaacg cggaactcca  14700
tatatgggct atgaactaat gaccccgtaa ttgattacta ttaataacta gtcaataatc  14760
aatgtcaaca tggcggtaat gttggacatg agccaatata aatgtacata ttatgatatg  14820
gatacaacgt atgcaatggc cagaattccg ccatagaaat catttaatgg gattgggtta  14880
gattttagtt tcaataggtc cattttggat tgaatggaga gcaaatatta gtttttaatt  14940
ctgggtaaca atgtgttttc tgcctgttct gctaatccat caggactgtt ggatgggaga  15000
gaagactggg aaatattgct catgttccat tgagcttcag ttacaaccag ataatgggat  15060
ctttaagaaa acagaaaaat atgggaacct tagagatgga aaacataatt agcaattatt  15120
agttagtgtg cttattacta tggttgtagt aacagaccag aagtctgttt catttgatcc  15180
ttcttgtatg tacaacgtgc atctgagcca tgctaggcag gacataagtg agaacaagac  15240
gtgacctatt attttcttga caaaatagga gaaataaaga agcatgcatg tgaaggagcc  15300
aactgagact agagtgaaga gcagacgcac tttctttcct atagttggaa tatttaaatc  15360
tatcttttta tgggtgtgaa tgctttataa caaacttttt tttctgagga tacagcaaaa  15420
catagctcca tacaatgcaa aacaatactc aatttcaaat gtgtttatga tatgaacttg  15480
cagtgttcct caaagatctt ccatgaataa cttaatggcc tggcagatga cagaggaatt  15540
gtgaaattca gctggaggag tgttcatggt tcgagggaca atcataatat acaatagcaa  15600
atatatttca gttatagaag ctattgttct gtattgaaat aatagaattg acaaacagta  15660
aagaaaccat tctgacctct gtaaagcaca cgcgtaagct taaaagattg aagcacagac  15720
acaggccaca ccagagccta cacctgctgc aataagtggt gctatagaaa ggattcagga  15780
actaacaagt gcataattta caaatagaga tgctttatca tactttgccc aacatgggaa  15840
aaaagacatc ccatgagaat atccaactga ggaacttctc tgtttcatag taactcatct  15900
actactgcta agatggtttg aaaagtaccc agcaggtgag atgtgttccg ggaggtggct  15960
gtgtggcagc gtgtgggaac acgacacaaa gcaccccacc cctatctgca atgctcactg  16020
caaggcagtg ccgtaaacag ctgcaacagg catccaggca tcacttctgc ataaacgctg  16080
tgactcgtta gcatgctgca actgtgttta aaacctatgc actccgttac caaaataatt  16140
taagtcccaa acaaatccat gcagcttgct tcctatgcca aaatatttta gaaagtattc  16200
attcttcttt aagaatatgc acgtggatct gcacttccct gggatctgaa gcgatttata  16260
cctcagtgca gaagcagttt agtgtcctgg atctcgggaa ggcagcagcc aaacgtgccc  16320
gttttacatt taaacccatg tgacaacccg ccttactgag catcgctcta ggaaatttaa  16380
```

```
ggctgtatcc ttacaacaca agaaccaacg acagactgca tataaaattc tataaataaa  16440
aataggagtg aagtctgttt gacctgtaca cacagagcat agagataaaa aaaaaaggaa  16500
atcaggaatt acgtatttct ataaatgcca tatattttta ctagaaacac agatgacaag  16560
tatatacaac atgtaaatcc gaagttatca acatgttaac taggaaaaca tttacaagca  16620
tttgggtatg caactagatc atcaggtaaa aaatcccatt agaaaaatct aagcctcacc  16680
agtttcaaag gaaaaaaacc agagaacgct cactacttca aagggaaaaa ataaagcatc  16740
aagctggcct aaacttaata aggtatctcg tgtaacaaca gctatccaag ctttcaagcc  16800
acactataaa taaaaacctc aagttccgat caacgttttc cataatgcaa tcagaaccaa  16860
aggcattggc acagaaagca aaaagggaat gaaagaaaag ggctgtacag tttccaaaag  16920
gttcttcttt tgaagaaatg tttctgacct gtcaaaacat acagtccagt agaaaattta  16980
ctaagaaaaa agaacacctt acttaaaaaa aaaaaaaaaa aaaaaaaaaa caggcaaaaa  17040
aacctctcct gtcactgagc tgccaccacc ccaaccacca cctgctgtgg gctttgtctc  17100
ccaagacaaa ggacacacag ccttatccaa tattcaacat tacttataaa aacactgatc  17160
agaagaaata ccaagtattt cctcacagac tgttatacag actgttatat cctttcatcg  17220
gcaagaagag atgaaataca acagagtgaa tatcaaagaa ggcggcagga gccaccgtgg  17280
caccatcacc gggcagtgca gtgcccagct gccgtttcct gagcacgcac aggaagccgt  17340
cagtcacatg taataaacca aaacctggta cagttatatt atggatccgg gcccctccgg  17400
gatcatatga caagatgtgt atccacctta acttaatgat tttaccaaa atcattaggg  17460
gattcatcag tgctcagggt caacgagaat taacattccg tcaggaaagc ttgaattcag  17520
cttttgttcc ctttagtgag ggttaattgc gcgcttggcg taatcatggt catagctgtt  17580
tcctgtgtga aattgttatc cgctcacaat tccacacaac atacgagccg gaagcataaa  17640
gtgtaaagcc tggggtgcct aatgagtgag ctaactcaca ttaattgcgt tgcgctcact  17700
gcccgctttc cagtcgggaa acctgtcgtg ccagctgcat taatgaatcg gccaacgcgc  17760
ggggagaggc ggtttgcgta ttgggcgctc ttccgcttcc tcgctcactg actcgctgcg  17820
ctcggtcgtt cggctgcggc gagcggtatc agctcactca aaggcggtaa tacggttatc  17880
cacagaatca ggggataacg caggaaagaa catgtgagca aaaggccagc aaaaggccag  17940
gaaccgtaaa aaggccgcgt tgctggcgtt tttccatagg ctccgccccc ctgacgagca  18000
tcacaaaaat cgacgctcaa gtcagaggtg gcgaaacccg acaggactat aaagatacca  18060
ggcgtttccc cctggaagct ccctcgtgcg ctctcctgtt ccgaccctgc cgcttaccgg  18120
atacctgtcc gcctttctcc cttcgggaag cgtggcgctt tctcatagct cacgctgtag  18180
gtatctcagt tcggtgtagg tcgttcgctc caagctgggc tgtgtgcacg aaccccccgt  18240
tcagcccgac cgctgcgcct tatccggtaa ctatcgtctt gagtccaacc cggtaagaca  18300
cgacttatcg ccactggcag cagccactgg taacaggatt agcagagcga ggtatgtagg  18360
cggtgctaca gagttcttga agtggtggcc taactacggc tacactagaa gaacagtatt  18420
tggtatctgc gctctgctga agccagttac cttcggaaaa agagttggta gctcttgatc  18480
cggcaaacaa accaccgctg gtagcggtgg tttttttgtt tgcaagcagc agattacgcg  18540
cagaaaaaaa ggatctcaag aagatccttt gatcttttct acggggtctg acgctcagtg  18600
gaacgaaaac tcacgttaag ggattttggt catgagatta tcaaaaagga tcttcaccta  18660
gatcctttta aattaaaaat gaagttttaa atcaatctaa agtatatatg agtaaacttg  18720
```

```
gtctgacagt taccaatgct taatcagtga ggcacctatc tcagcgatct gtctatttcg  18780

ttcatccata gttgcctgac tccccgtcgt gtagataact acgatacggg agggcttacc  18840

atctggcccc agtgctgcaa tgataccgcg agacccacgc tcaccggctc cagatttatc  18900

agcaataaac cagccagccg gaagggccga gcgcagaagt ggtcctgcaa ctttatccgc  18960

ctccatccag tctattaatt gttgccggga agctagagta agtagttcgc cagttaatag  19020

tttgcgcaac gttgttgcca ttgctacagg catcgtggtg tcacgctcgt cgtttggtat  19080

ggcttcattc agctccggtt cccaacgatc aaggcgagtt acatgatccc ccatgttgtg  19140

caaaaaagcg gttagctcct tcggtcctcc gatcgttgtc agaagtaagt tggccgcagt  19200

gttatcactc atggttatgg cagcactgca taattctctt actgtcatgc catccgtaag  19260

atgcttttct gtgactggtg agtactcaac caagtcattc tgagaatagt gtatgcggcg  19320

accgagttgc tcttgcccgg cgtcaatacg ggataatacc gcgccacata gcagaacttt  19380

aaaagtgctc atcattggaa aacgttcttc ggggcgaaaa ctctcaagga tcttaccgct  19440

gttgagatcc agttcgatgt aacccactcg tgcacccaac tgatcttcag catcttttac  19500

tttcaccagc gtttctgggt gagcaaaaac aggaaggcaa aatgccgcaa aaaagggaat  19560

aagggcgaca cggaaatgtt gaatactcat actcttcctt tttcaatatt attgaagcat  19620

ttatcagggt tattgtctca tgagcggata catatttgaa tgtatttaga aaaataaaca  19680

aataggggtt ccgcgcacat ttccccgaaa agtgccac                          19718
```

<210> SEQ ID NO 28
<211> LENGTH: 6
<212> TYPE: DNA
<213> ORGANISM: Artificial Sequence
<220> FEATURE:
<223> OTHER INFORMATION: Kozak sequence

<400> SEQUENCE: 28 accatg 6

<210> SEQ ID NO 29
<211> LENGTH: 7
<212> TYPE: DNA
<213> ORGANISM: Artificial Sequence
<220> FEATURE:
<223> OTHER INFORMATION: Kozak sequence

<400> SEQUENCE: 29 accatgg 7

<210> SEQ ID NO 30
<211> LENGTH: 7
<212> TYPE: DNA
<213> ORGANISM: Artificial Sequence
<220> FEATURE:
<223> OTHER INFORMATION: Kozak sequence

<400> SEQUENCE: 30 accatgt 7

<210> SEQ ID NO 31
<211> LENGTH: 7
<212> TYPE: DNA
<213> ORGANISM: Artificial Sequence
<220> FEATURE:
<223> OTHER INFORMATION: Kozak sequence

<400> SEQUENCE: 31 aagatgt 7

<210> SEQ ID NO 32
<211> LENGTH: 7
<212> TYPE: DNA
<213> ORGANISM: Artificial Sequence
<220> FEATURE:
<223> OTHER INFORMATION: Kozak sequence

<400> SEQUENCE: 32 acgatga 7

<210> SEQ ID NO 33
<211> LENGTH: 7
<212> TYPE: DNA
<213> ORGANISM: Artificial Sequence
<220> FEATURE:
<223> OTHER INFORMATION: Kozak sequence

<400> SEQUENCE: 33 aagatgg 7

<210> SEQ ID NO 34
<211> LENGTH: 7
<212> TYPE: DNA
<213> ORGANISM: Artificial Sequence
<220> FEATURE:
<223> OTHER INFORMATION: Kozak sequence

<400> SEQUENCE: 34 gacatga 7

<210> SEQ ID NO 35
<211> LENGTH: 7
<212> TYPE: DNA
<213> ORGANISM: Artificial Sequence
<220> FEATURE:
<223> OTHER INFORMATION: Kozak sequence

<400> SEQUENCE: 35 accatga 7

<210> SEQ ID NO 36
<211> LENGTH: 7
<212> TYPE: DNA
<213> ORGANISM: Artificial Sequence
<220> FEATURE:
<223> OTHER INFORMATION: Kozak sequence

<400> SEQUENCE: 36 accatgt 7

<210> SEQ ID NO 37
<211> LENGTH: 6
<212> TYPE: DNA
<213> ORGANISM: Artificial Sequence
<220> FEATURE:
<223> OTHER INFORMATION: Kozak sequence

<400> SEQUENCE: 37 gggatg 6

<210> SEQ ID NO 38
<211> LENGTH: 680
<212> TYPE: DNA

```
<213> ORGANISM: Gallus sp.

<400> SEQUENCE: 38

ccgggctgca gaaaaatgcc aggtggacta tgaactcaca tccaaaggag cttgacctga     60

tacctgattt tcttcaaact ggggaaacaa cacaatccca caaaacagct cagagagaaa    120

ccatcactga tggctacagc accaaggtat gcaatggcaa tccattcgac attcatctgt    180

gacctgagca aaatgattta tctctccatg aatggttgct tctttccctc atgaaaaggc    240

aatttccaca ctcacaatat gcaacaaaga caaacagaga acaattaatg tgctccttcc    300

taatgtcaaa attgtagtgg caaagaggag aacaaaatct caagttctga gtaggtttta    360

gtgattggat aagaggcttt gacctgtgag ctcacctgga cttcatatcc ttttggataa    420

aaagtgcttt tataactttc aggtctccga gtctttattc atgagactgt tggtttaggg    480

acagacccac aatgaaatgc ctggcatagg aaagggcagc agagccttag ctgacctttt    540

cttgggacaa gcattgtcaa acaatgtgtg acaaaactat ttgtactgct ttgcacagct    600

gtgctgggca gggcaatcca ttgccaccta tcccaggtaa ccttccaact gcaagaagat    660

tgttgcttac tctctctaga                                                680


<210> SEQ ID NO 39
<211> LENGTH: 72
<212> TYPE: DNA
<213> ORGANISM: Artificial Sequence
<220> FEATURE:
<223> OTHER INFORMATION: Synthetic construct

<400> SEQUENCE: 39

gtggatcaac atacagctag aaagctgtat tgcctttagc actcaagctc aaaagacaac     60

tcagagttca cc                                                         72


<210> SEQ ID NO 40
<211> LENGTH: 62
<212> TYPE: DNA
<213> ORGANISM: Artificial Sequence
<220> FEATURE:
<223> OTHER INFORMATION: Synthetic construct

<400> SEQUENCE: 40

acatacagct agaaagctgt attgccttta gcactcaagc tcaaaagaca actcagagtt     60

ca                                                                    62
```